United States Patent
Boehm et al.

(10) Patent No.: US 8,507,538 B2
(45) Date of Patent: Aug. 13, 2013

(54) SELECTIVE HETEROCYCLIC SPHINGOSINE 1 PHOSPHATE RECEPTOR MODULATORS

(75) Inventors: Marcus F. Boehm, San Diego, CA (US); Esther Martinborough, San Diego, CA (US); Enugurthi Brahmachary, San Diego, CA (US); Manisha Moorjani, San Diego, CA (US); Junko Tamiya, Carlsbad, CA (US); Liming Huang, San Diego, CA (US); Adam Richard Yeager, San Diego, CA (US)

(73) Assignee: Receptos, Inc., San Diego, CA (US)

( * ) Notice: Subject to any disclaimer, the term of this patent is extended or adjusted under 35 U.S.C. 154(b) by 196 days.

(21) Appl. No.: 12/946,828

(22) Filed: Nov. 15, 2010

(65) Prior Publication Data

US 2011/0183953 A1 Jul. 28, 2011

Related U.S. Application Data

(60) Provisional application No. 61/261,295, filed on Nov. 13, 2009, provisional application No. 61/262,474, filed on Nov. 18, 2009.

(51) Int. Cl.

| | | |
|---|---|---|
| *A61K 31/5377* | (2006.01) | |
| *A61K 31/496* | (2006.01) | |
| *A61K 31/454* | (2006.01) | |
| *A61K 31/433* | (2006.01) | |
| *A61K 31/427* | (2006.01) | |
| *A61K 31/426* | (2006.01) | |
| *A61K 31/425* | (2006.01) | |
| *A61K 31/381* | (2006.01) | |
| *C07D 417/12* | (2006.01) | |
| *C07D 417/10* | (2006.01) | |
| *C07D 333/24* | (2006.01) | |
| *C07D 333/22* | (2006.01) | |
| *C07D 333/20* | (2006.01) | |
| *C07D 333/16* | (2006.01) | |
| *C07D 277/30* | (2006.01) | |
| *C07D 277/28* | (2006.01) | |
| *C07D 277/24* | (2006.01) | |
| *C07D 285/12* | (2006.01) | |
| *C07D 285/10* | (2006.01) | |
| *C07D 285/08* | (2006.01) | |

(52) U.S. Cl.
USPC ........ 514/363; 514/236.8; 514/319; 514/365; 514/254.02; 514/438; 544/367; 544/369; 544/133; 544/134; 546/205; 546/206; 548/136; 548/203; 548/204; 548/205; 549/75; 549/78

(58) Field of Classification Search
USPC ............... 514/363, 236.8, 319, 365, 254.02, 514/438; 544/367, 369, 133, 134; 546/205, 546/206; 548/136, 203, 204, 205; 549/75, 549/78
See application file for complete search history.

(56) References Cited

U.S. PATENT DOCUMENTS

| | | |
|---|---|---|
| 6,511,975 B1 | 1/2003 | Nishi et al. |
| 2006/0161005 A1 | 7/2006 | Doherty et al. |
| 2007/0293545 A1 | 12/2007 | Edwards et al. |
| 2008/0009534 A1 | 1/2008 | Cheng et al. |
| 2008/0249093 A1 | 10/2008 | Colandrea et al. |
| 2008/0280876 A1 | 11/2008 | Hobson et al. |
| 2010/0010001 A1* | 1/2010 | Roberts et al. ........... 514/252.05 |

FOREIGN PATENT DOCUMENTS

| | | |
|---|---|---|
| WO | WO 2005/032465 A2 | 4/2005 |
| WO | WO 2006/120577 A1 | 11/2006 |
| WO | WO 2008/076356 A1 | 6/2008 |

OTHER PUBLICATIONS

Zanotti-Gerosa et al., Ruthenium-Catalysed Asymmetric Reduction of Ketones, Platinum Metals Rev, 2005, vol. 49(4), pp. 158-165.
Fujiwara et al., Identification of the Hydrophobic Ligand Binding Pocket of the S1P1 Receptor, The Journal of Biological chemistry, 2007, vol. 282(4), pp. 2374-2385.
International Search Report for PCT/US10/56757, PCT/ISA/210, Jan. 14, 2011, pp. 1-3.
International Search Report for PCT/US10/56760, PCT/ISA/210, Jan. 19, 2011, pp. 1-3.
International Search Report for PCT/US10/56759, PCT/ISA/210, Jan. 12, 2011, pp. 1-3.

* cited by examiner

*Primary Examiner* — Joseph Kosack
*Assistant Examiner* — Matthew Coughlin
(74) *Attorney, Agent, or Firm* — Seed IP Law Group PLLC

(57) ABSTRACT

Compounds that selectively modulate the sphingosine 1 phosphate receptor are provided including compounds which modulate subtype 1 of the S1P receptor. Methods of chiral synthesis of such compounds is provided. Uses, methods of treatment or prevention and methods of preparing inventive compositions including inventive compounds are provided in connection with the treatment or prevention of diseases, malconditions, and disorders for which modulation of the sphingosine 1 phosphate receptor is medically indicated.

59 Claims, No Drawings

SELECTIVE HETEROCYCLIC SPHINGOSINE 1 PHOSPHATE RECEPTOR MODULATORS

CROSS-REFERENCE TO RELATED APPLICATIONS

This application claims the priority of U.S. Ser. No. 61/261,295, filed Nov. 13, 2009 and U.S. Ser. No. 61/262,474, filed Nov. 18, 2009, the disclosures of which are incorporated herein in their entireties.

FIELD OF THE INVENTION

The invention relates to compounds which are agonists of the sphingosine 1-phosphate receptor subtype 1, methods of their synthesis and methods of their therapeutic and/or prophylactic use.

BACKGROUND

The $S1P_1/EDG_1$ receptor is a G-protein coupled receptor (GPCR) and is a member of the endothelial cell differentiation gene (EDG) receptor family. Endogenous ligands for EDG receptors include lysophospholipids, such as sphingosine-1-phosphate (S1P). Like all GPCRs, ligation of the receptor propagates second messenger signals via activation of G-proteins (alpha, beta and gamma).

Development of small molecule $S1P_1$ agonists and antagonists has provided insight into some physiological roles of the $S1P_1/S1P$-receptor signaling system. Agonism of the $S1P_1$ receptor perturbs lymphocyte trafficking, sequestering them in lymph nodes and other secondary lymphoid tissue. This leads to rapid and reversible lymphopenia, and is probably due to receptor ligation on both lymphatic endothelial cells and lymphocytes themselves (Rosen et al, *Immunol. Rev.*, 195:160-177, 2003). A clinically valuable consequence of lymphocyte sequestration is exclusion of them from sights of inflammation and/or auto-immune reactivity in peripheral tissues.

Agonism of $S1P_1$ has also been reported to promote survival of oligodendrocyte progenitors (Miron et al, *Ann. Neurol.*, 63:61-71, 2008). This activity, in conjunction with lymphocyte sequestration would be useful in treating inflammatory and autoimmune conditions of the central nervous system.

SUMMARY OF THE INVENTION

The present invention is directed to heterocyclic compounds adapted to act as agonists of S1P receptor subtype 1, $S1P_1$; methods of preparation and methods of use, such as in treatment of a malcondition mediated by $S1P_1$ activation, or when activation of $S1P_1$ is medically indicated.

Certain embodiments of the present invention comprise a compound having the structure of Formula (I) or a pharmaceutically acceptable salt, ester, prodrug, homolog, tautomer, stereoisomer, or hydrate, or solvate thereof:

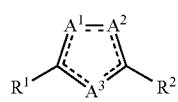

(I)

A dashed line signifies that a single bond or a double bond can be present, provided that there are two double bonds and three single bonds in the ring comprising $A^1$, $A^2$, and $A^3$. $A^1$, $A^2$, and $A^3$ each independently can be C or S or N; provided that one of $A^1$, $A^2$, and $A^3$ is S.

$R^1$ can be di-substituted phenyl or di-substituted pyridinyl where the phenyl and pyridinyl substituents ca each be independently any of halo, nitro, cyano, perfluromethyl, fluorinated methyl, and $C_{1-4}$-alkoxy. When $R^1$ is di-substituted phenyl, such phenyl is para-substituted with $R^2$ can be

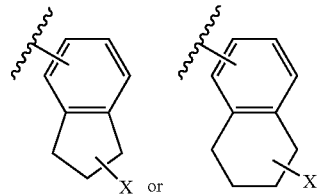

wherein a wavy line indicates a point of attachment.

X can be —NR'R" or —OR'''; R' can be H, $C_{1-4}$ alkyl, n-hydroxy $C_{1-4}$ alkyl, —$SO_2$—$R^3$, or —CO—$R^3$. R" can be H, —$SO_2$—$R^5$, $C_{1-4}$ alkyl optionally substituted with 1 or more $R^4$, or a ring moiety optionally substituted with $R^6$ wherein such ring moiety is piperidinyl, cyclohexyl, morpholinyl, thiazolyl, pyrazolyl, pyrrolidinyl, imidazolyl, or phenyl. R''' can be H, $C_{1-4}$ alkyl, or —CO—$R^3$. R' and R" taken together with the nitrogen atom to which they are bound can form a 4, 5, or 6 membered saturated heterocyclic ring containing 0 or 1 additional heteroatoms where such additional heteroatom is O or N wherein such heterocycle is optionally singly or multiply substituted with substituents independently selected from the group consisting of —OH, oxo, —$NH_2$, n-hydroxy-$C_{1-4}$ alkyl, —COOH, —$(CH_2)_m$—COOH, —$(CH_2)_m$—COOR$^3$, —$N(R^3R^3)$, and —$(CH_2)_m$—CO—$N(R^7R^7)$. Each $R^3$ can be independently $C_{1-4}$ alkyl or H. Each $R^4$ can be independently H, halo, OH, oxo, =NH, $NH_2$, —COOH, F, —NHR$^3$, —$N(R^7R^7)$, —$SO_2$—$R^3$, —$SO_2$—$N(R^7R^7)$, —$N(R^3)$—$SO_2$—$R^3$, —COOR$^3$, —OCO—$R^3$, —CO—$N(R^7R^7)$, —$N(R^3)$—COR$^3$, $C_{1-3}$ alkyl, $C_{1-3}$ alkoxy, and a ring moiety optionally substituted with $R^6$ wherein such ring moiety is piperazinyl, piperidinyl, morpholinyl, pyrrolidinyl, pyrazolyl, imidazolyl, benzimidazolyl, azetidinyl, cyclobutinyl, or phenyl. Each $R^5$ can be independently $R^4$, $C_{1-4}$ alkyl, $C_{3-6}$ cycloalkyl, or $C_{1-4}$ alkyl optionally substituted with 1 or more $R^4$. Each $R^6$ can be independently halo, OH, —$NH_2$, —NHR$^3$, —$N(R^3R^3)$, —COOH, —COOR$^3$, —NHCO—$R^3$. Each $R^7$ can be independently $C_{1-4}$ alkyl or H, or two $R^7$ taken together with the nitrogen atom to which they are bound can form a 4, 5, or 6 membered saturated heterocyclic ring containing 0 or 1 additional heteroatoms where such additional heteroatom is O or N wherein such heterocycle can be optionally substituted with —OH, —$NH_2$, —$N(R^3R^3)$, n-hydroxy $C_{1-4}$ alkyl, —$(CH_2)_m$—COOH, —$(CH_2)_m$—COOR$^3$. Each m can be independently 0, 1, 2, or 3.

In certain embodiments, a pharmaceutical composition comprising a compound of the invention and a suitable excipient is provided.

In certain embodiments a method of use of an inventive compound comprising preparation of a medicament is provided.

In certain combinations a pharmaceutical combination comprising a compound of the invention and a second medicament is provided. In various embodiments the second medicament is medically indicated for the treatment of multiple sclerosis, transplant rejection, acute respiratory distress syndrome or adult respiratory distress syndrome.

In certain embodiments, a method of activation or agonism of a sphingosine-1-phosphate receptor subtype 1 comprising contacting the receptor subtype 1 with a compound of claim 1 is provided. In various embodiments, the compound of claim 1 activates or agonizes the sphingosine-1-phosphate receptor subtype 1 to a greater degree than the compound activates or agonizes a sphingosin-1-phosphate receptor subtype 3.

In certain embodiments a method of treatment of a malcondition in a patient for which activation or agonism of an $S1P_1$ receptor is medically indicated, is provided. In various embodiment, selective activation or agonism of an $S1P_1$ receptor, such as with respect to an $S1P_3$ receptor, is medically indicated. In various embodiments, the malcondition comprises multiple sclerosis, transplant rejection, or acute respiratory distress syndrome.

In certain embodiments, a method is provided for chiral synthesis of certain compounds including compounds of the invention. In certain other embodiments the invention provides certain intermediate compounds associated with such methods of chiral synthesis.

DETAILED DESCRIPTION OF THE INVENTION

Certain embodiments of the present invention comprise a compound having the structure of Formula (I) or a pharmaceutically acceptable salt, ester, prodrug, homolog, tautomer, stereoisomer, or hydrate, or solvate thereof:

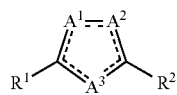

(I)

A dashed line signifies that a single bond or a double bond can be present, provided that there are two double bonds and three single bonds in the ring comprising $A^1$, $A^2$, and $A^3$. $A^1$, $A^2$, and $A^3$ each independently can be C or S or N; provided that one of $A^1$, $A^2$, and $A^3$ is S.

$R^1$ can be di-substituted phenyl or di-substituted pyridinyl where the phenyl and pyridinyl substituents ca each be independently any of halo, nitro, cyano, perfluromethyl, fluorinated methyl, and $C_{1-4}$-alkoxy. When $R^1$ is di-substituted phenyl, such phenyl is para-substituted with $C_{1-4}$-alkoxy.

$R^2$ can be

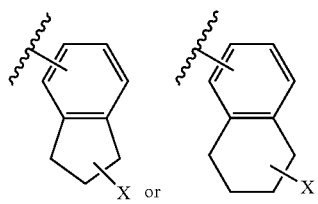

wherein a wavy line indicates a point of attachment.

X can be —NR'R" or —OR'''; R' can be H, $C_{1-4}$ alkyl, n-hydroxy $C_{1-4}$ alkyl, —$SO_2$—$R^3$, or —CO—$R^3$. R" can be H, —$SO_2$—$R^5$, $C_{1-4}$ alkyl optionally substituted with 1 or more $R^4$, or a ring moiety optionally substituted with $R^6$ wherein such ring moiety is piperidinyl, cyclohexyl, morpholinyl, thiazolyl, pyrazolyl, pyrrolidinyl, imidazolyl, or phenyl. R''' can be H, $C_{1-4}$ alkyl, or —CO—$R^3$. R' and R'' taken together with the nitrogen atom to which they are bound can form a 4, 5, or 6 membered saturated heterocyclic ring containing 0 or 1 additional heteroatoms where such additional heteroatom is O or N wherein such heterocycle is optionally singly or multiply substituted with substituents independently selected from the group consisting of —OH, oxo, —$NH_2$, n-hydroxy-$C_{1-4}$ alkyl, —COOH, —$(CH_2)_m$—COOH, —$(CH_2)_m$—COOR$^3$, —N($R^3R^3$), and —$(CH_2)_m$—CO—N($R^7R^7$). Each $R^3$ can be independently $C_{1-4}$ alkyl or H. Each $R^4$ can be independently H, halo, OH, oxo, =NH, $NH_2$, —COOH, F, —NHR$^3$, —N($R^7R^7$), —$SO_2$—$R^3$, —$SO_2$—N($R^7R^7$), —N($R^3$)—$SO_2$—$R^3$, —COOR$^3$, —OCO—$R^3$, —CO—N($R^7R^7$), —N($R^3$)—COR$^3$, $C_{1-3}$ alkyl, $C_{1-3}$ alkoxy, and a ring moiety optionally substituted with $R^6$ wherein such ring moiety is piperazinyl, piperidinyl, morpholinyl, pyrrolidinyl, pyrazolyl, imidazolyl, benzimidazolyl, azetidinyl, cyclobutinyl, or phenyl. Each $R^5$ can be independently $R^4$, $C_{1-4}$ alkyl, $C_{3-6}$ cycloalkyl, or $C_{1-4}$ alkyl optionally substituted with 1 or more $R^4$. Each $R^6$ can be independently halo, OH, —$NH_2$, —NHR$^3$, —N($R^3R^3$), —COOH, —COOR$^3$, —NHCO—$R^3$. Each $R^7$ can be independently $C_{1-4}$ alkyl or H, or two $R^7$ taken together with the nitrogen atom to which they are bound can form a 4, 5, or 6 membered saturated heterocyclic ring containing 0 or 1 additional heteroatoms where such additional heteroatom is O or N wherein such heterocycle can be optionally substituted with —OH, —$NH_2$, —N($R^3R^3$), n-hydroxy $C_{1-4}$ alkyl, —$(CH_2)_m$—COOH, —$(CH_2)_m$—COOR$^3$. Each m can be independently 0, 1, 2, or 3.

In certain embodiments, the compounds of the invention have the structure of a specific of Formula I or a pharmaceutically acceptable salt, ester, prodrug, homolog, hydrate or solvate thereof. In certain embodiments the invention provides compounds which are substantially enantiomerically pure. In certain such embodiments, the compounds are enantiomerically pure with respect to a chiral carbon on an indanyl or tetrahydronaphthalenyl moiety.

In certain embodiments the invention provides compounds which have an $EC_{50}$ as an agonist of the wild type S1P receptor subtype 1 which is at least ten times smaller than the $EC_{50}$ of such compound as an agonist of a mutant S1P receptor subtype 1 having a single mutation with respect to wild type SP receptor subtype 1 such that the 101$^{st}$ amino acid residue is changed from asparagine to alanine.

In certain embodiments the invention provides compounds which have an $EC_{50}$ as an agonist of the wild type S1P receptor subtype 1 which is at least twenty times smaller than the $EC_{50}$ of such compound as an agonist of a mutant S1P receptor subtype 1 having a single mutation with respect to wild type S1P receptor subtype 1 such that the 101$^{st}$ amino acid residue is changed from asparagine to alanine.

In certain embodiments the invention provides compounds which have a therapeutic index of at least 5 as measured in rats following 5 or 14 days of dosing of rats with the compound where the therapeutic index is calculated as a ratio of (i) the highest dose of such compound which achieves less than or equal to a ten percent increase in the ratio of lung to terminal body weight at the conclusion of such 5 or 14 days of dosing, to (ii) the dose of such compound achieving 50% lymphopenia in rats. In certain embodiments, such therapeutic index is at least 10 and in certain embodiments the therapeutic index is at least 20. In certain embodiments, the therapeutic index for a compound is at least five times greater than the therapeutic index for the enantiomer of such compound.

In certain embodiments the invention provides compounds which have a therapeutic index of at least 5 as measured in rats following 5 or 14 days of dosing of rats with the compound where the therapeutic index is calculated as a ratio of (i) the highest dose of such compound which achieves less than or equal to a ten percent increase in the ratio of lung to terminal body weight at the conclusion of such 5 or 14 days of dosing, to (ii) the dose of such compound achieving 50% lymphopenia in rats. In certain embodiments, such therapeutic index is at least 10 and in certain embodiments the therapeutic index is at least 20. In certain embodiments, the therapeutic index for a compound is greater than the therapeutic index for the enantiomer of such compound. In certain embodiments, the therapeutic index for a compound is at least 150% of the therapeutic index for the enantiomer of such compound.

In certain embodiments the invention provides compounds where the structure of Formula I is selected from the group consisting of formulas a-i through a-x:

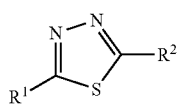
a-i

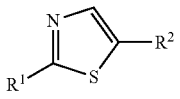
a-ii

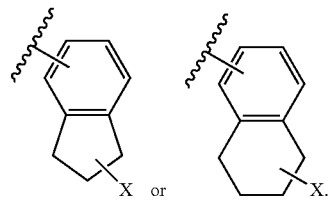
a-iii a-iv

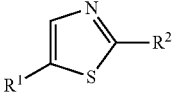
a-v

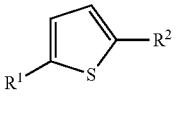
a-vi

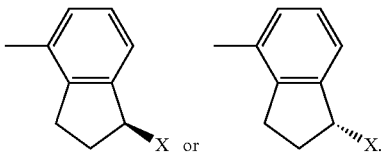
a-vii

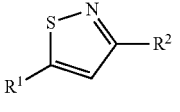
a-viii

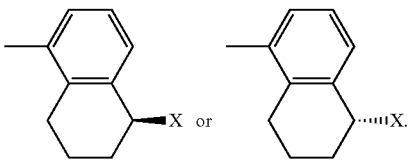

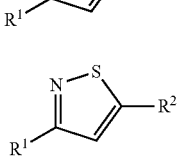
a-ix

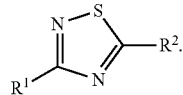
a-x

In certain embodiments the invention provides compounds where $A^1$ is S, in other embodiments the invention provides compounds where $A^2$ is S and in other embodiments the invention provides compounds where $A^3$ is S. In certain embodiments $A^1$ is N and $A^2$ is C or N; in certain such embodiments $A^2$ is C and in others $A^2$ is N.

In certain embodiments the invention provides compounds where $R^1$ is

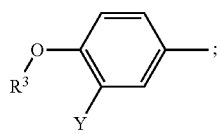

$R^3$ is $C_{2-4}$ alkyl; and Y is —CN, —Cl, —O—$R^3$, or —CF$_3$. In certain such embodiments $R^3$ is isopropyl or ethyl. In certain embodiments Y is —CN or —O—$C_2H_5$.

In certain embodiments the invention provides compounds where $R^2$ is

In certain of such embodiments the invention provides compounds where $R^2$ is

In other embodiments the invention provides compounds where $R^2$ is

In certain of such embodiments the compound is substantially enantiomerically pure.

In certain embodiments the invention provides compounds where Y is Cl, in other embodiments the invention provides compounds where Y is CF$_3$ and in other embodiments the invention provides compounds where Y is CN.

In certain embodiments the invention provides compounds where X is —NR'R", in other embodiments the invention provides compounds where X is —OR'". In certain embodiments the invention provides compounds where X is —OR'". In certain embodiments the invention provides compounds where X is —OH and in other embodiments the invention provides compounds where X is —OCO—$R^3$.

In certain embodiments the invention provides compounds where $R^3$ is $C_{1-3}$ alkyl; in other embodiments the invention provides compounds where R' is H.

In certain embodiments the invention provides compounds where R' is —$COR^3$; in other embodiments the invention provides compounds where R' is $SO_2$—$R^3$. In certain embodiments the invention provides compounds where R" is H.

In certain embodiments the invention provides compounds where R" is —$SO_2$—$R^5$; in other embodiments the invention provides compounds where R" is $C_{1-4}$ alkyl where the $C_{1-4}$ alkyl is optionally substituted with 1 or more substituents defined by $R^4$. In certain embodiments the invention provides compounds where R" is —$(CR^aR^b)_n$—$R^4$ and each $R^a$ and each $R^b$ can be independently any of H, hydroxyl and methyl or where $R^a$ and $R^b$ are bound to the same carbon they can be taken together to form oxo (i.e. with the carbon to which they are bound forming a carbonyl moiety). In certain such embodiments n can be 0, 1, 2, or 3 and in certain embodiments n is 2. In certain such embodiments $R^2$ can be —OH, —$NH_2$, —$NHR^3$, —$N(R^7R^7)$, or —COOH.

In certain embodiments the invention provides compounds where $R^5$ is $C_{1-4}$ alkyl optionally substituted with 1 or more $R^4$. In certain embodiments the invention provides compounds where $R^4$ is OH; in other embodiments the invention provides compounds where $R^4$ is $C_{1-3}$ alkoxy. In certain embodiments the invention provides compounds where $R^5$ is $(CH_2)_2$—$OR^3$.

In certain embodiments the invention provides compounds where Y is CN and X is —NH—$SO_2$—$R^5$. In certain embodiments the invention provides compounds where $R^5$ is —$C_2H_5$—$N((R^7R^7)$ or —$CH_2$—CO—$N(R^7R^7)$. In certain embodiments the invention provides compounds where Y is CN and X is —NH—CO—$N(R^7R^7)$.

In certain embodiments X is —$NH_2$ and in certain of such embodiments Y is CN.

In certain embodiments the invention provides one or more of compounds 1-227:

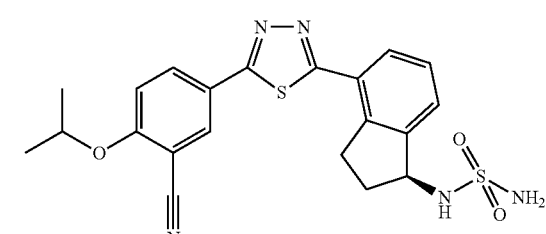

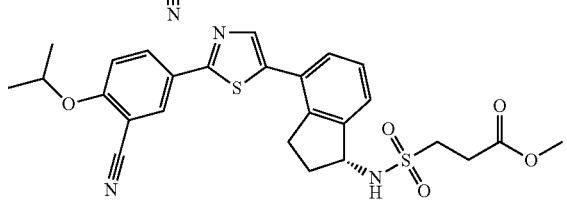

-continued

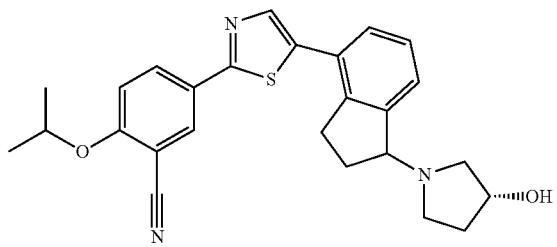

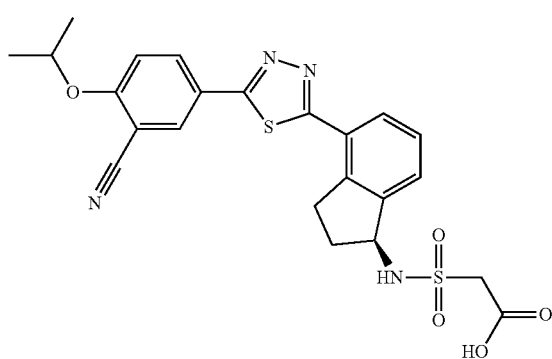

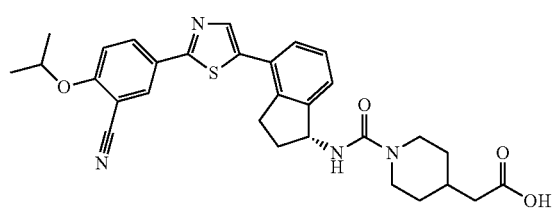

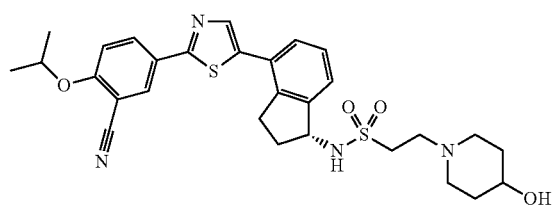

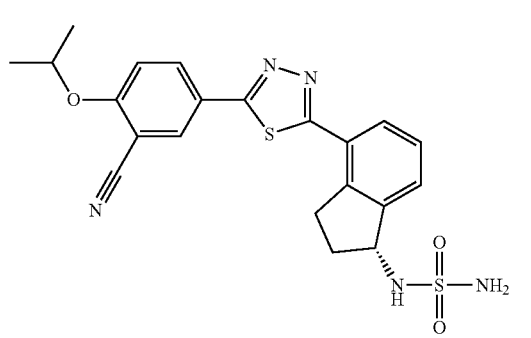

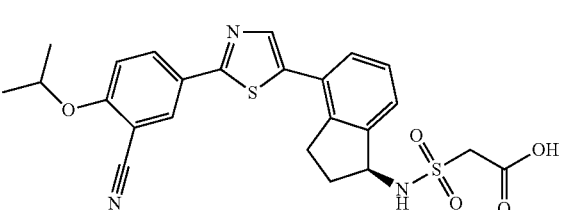

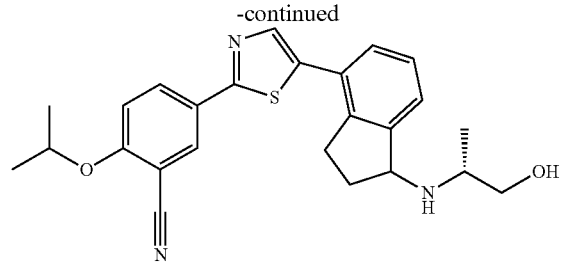
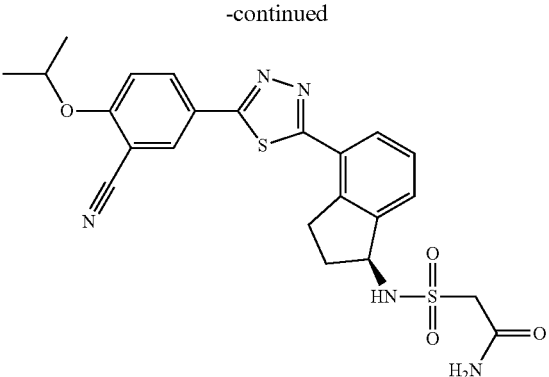

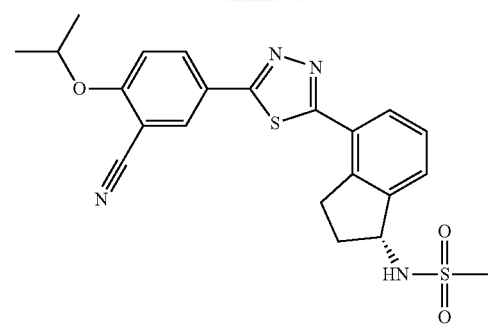
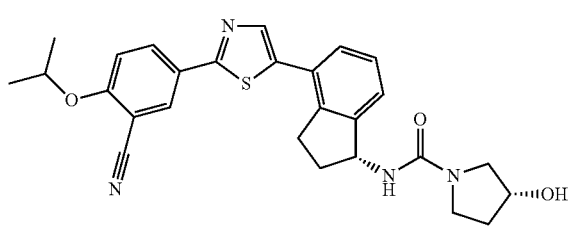
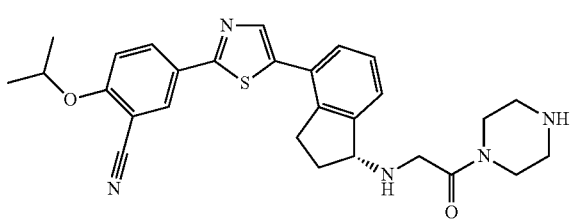
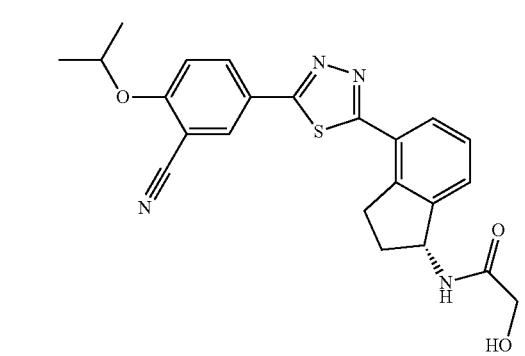
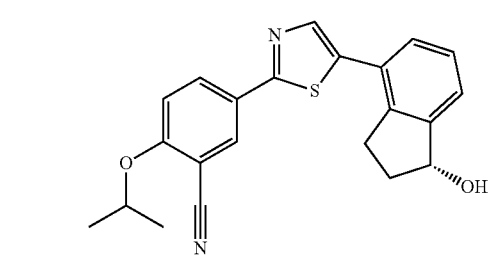
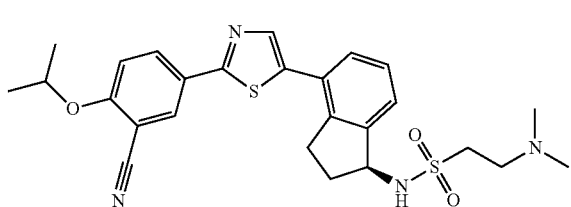
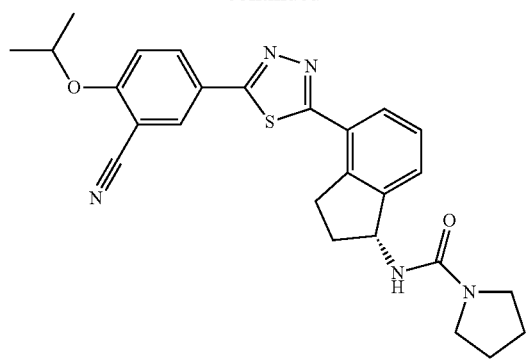
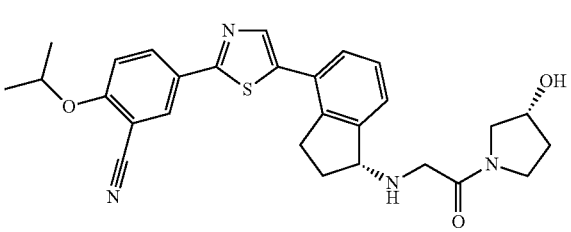
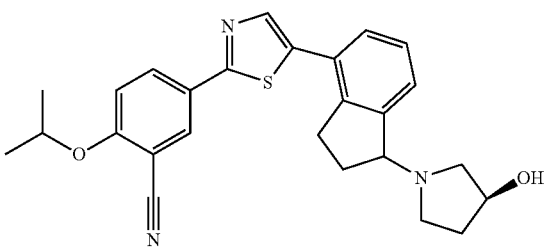
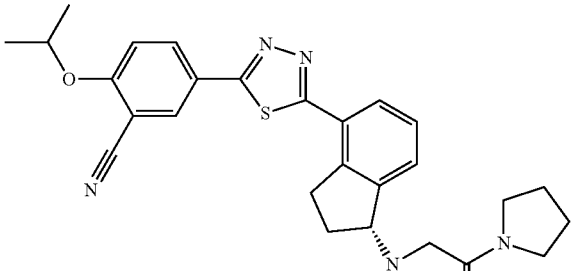
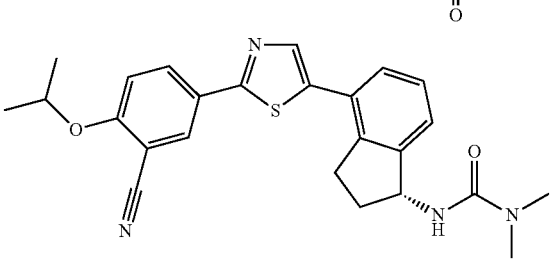
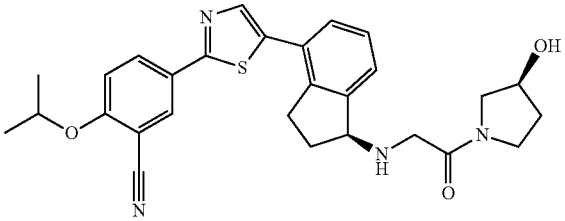

13
-continued
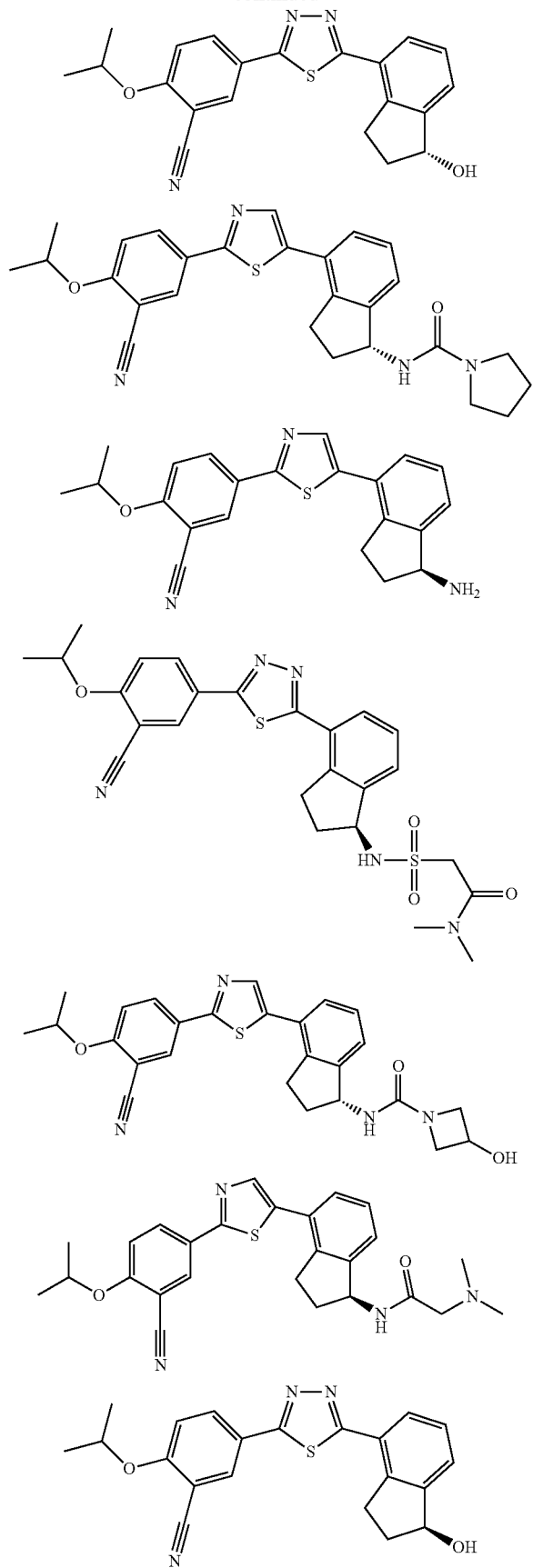
14
-continued
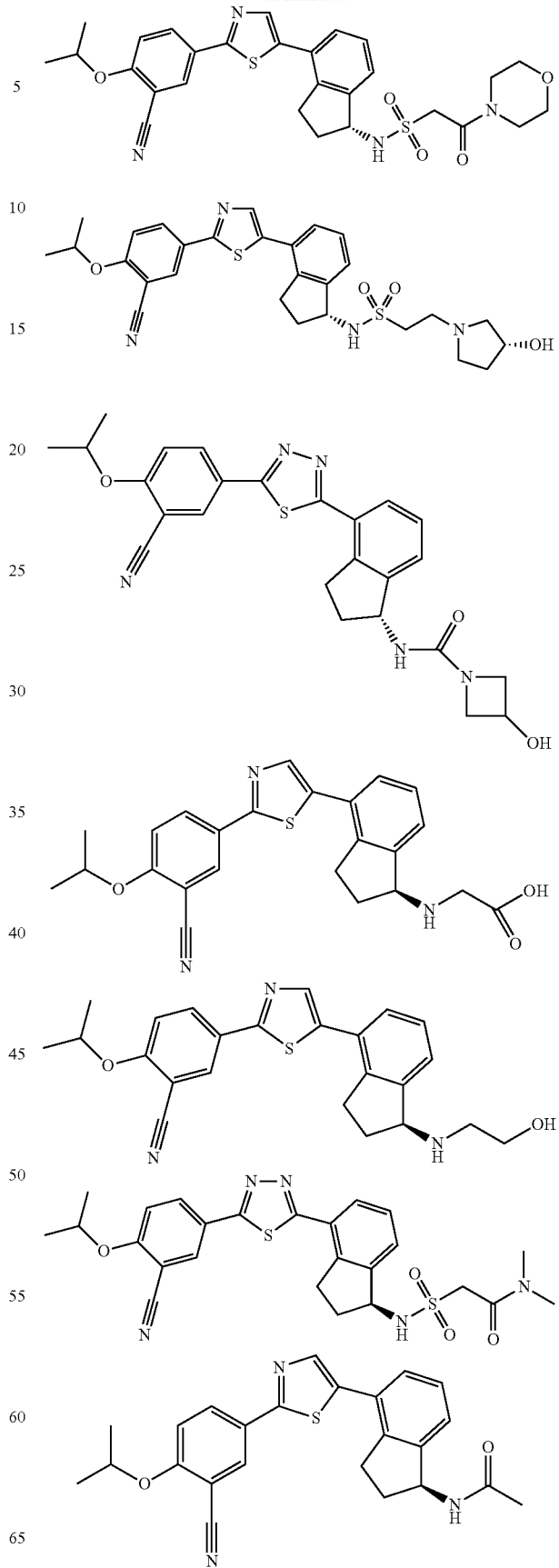

-continued
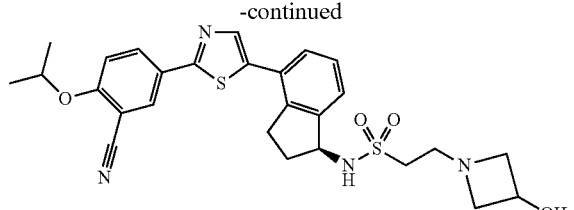
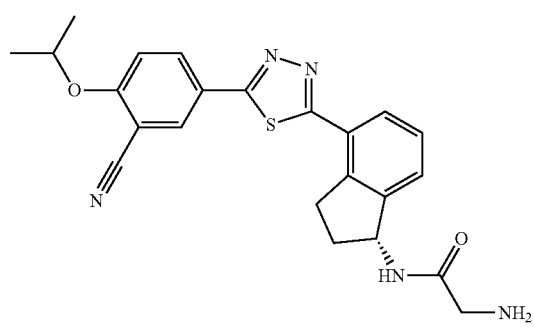
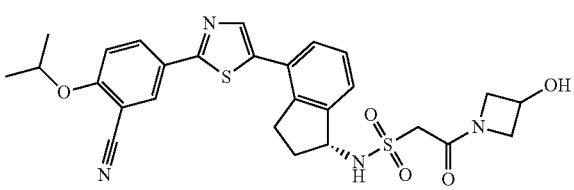
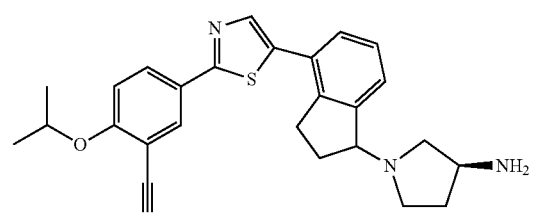
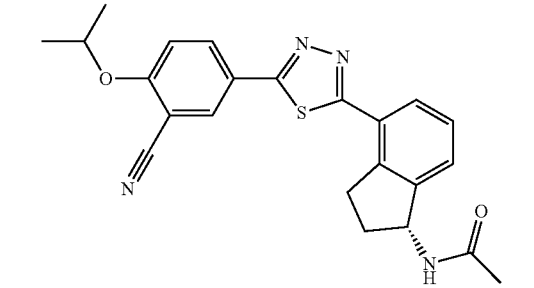
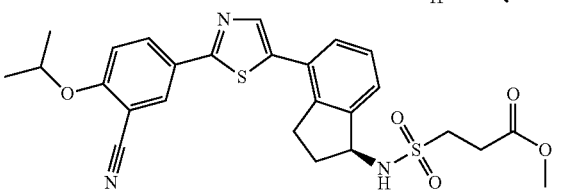
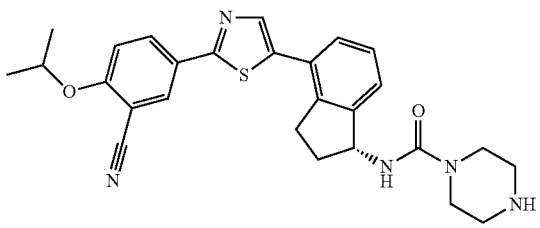
-continued
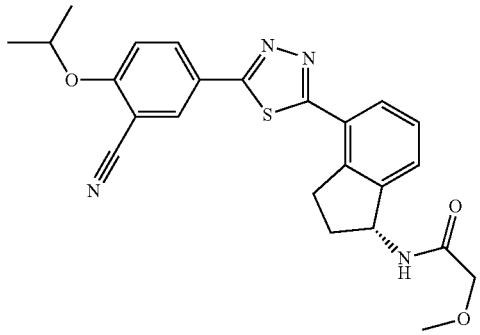
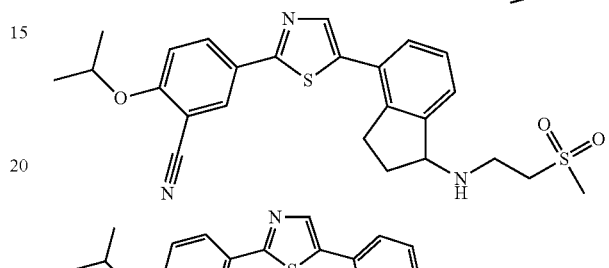
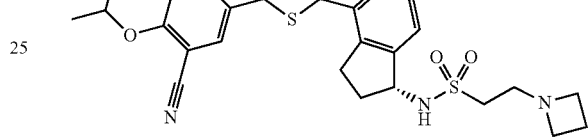
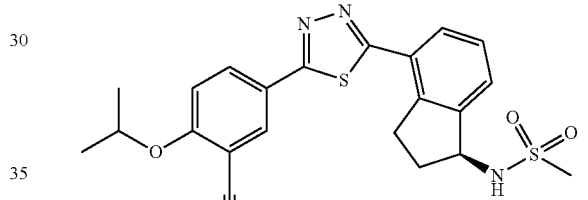
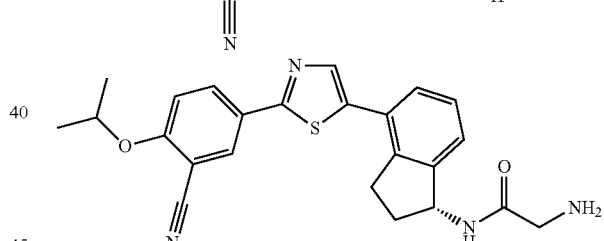
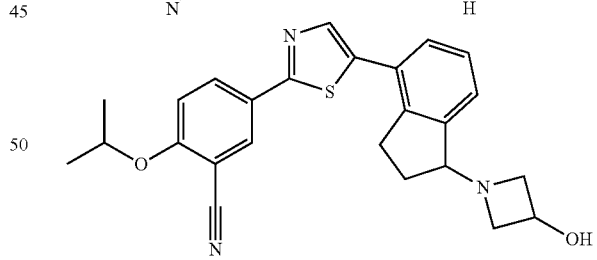
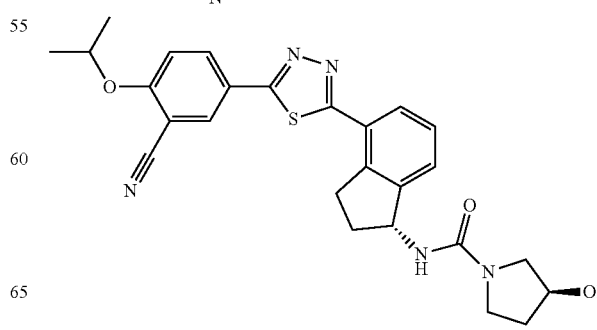

17
-continued
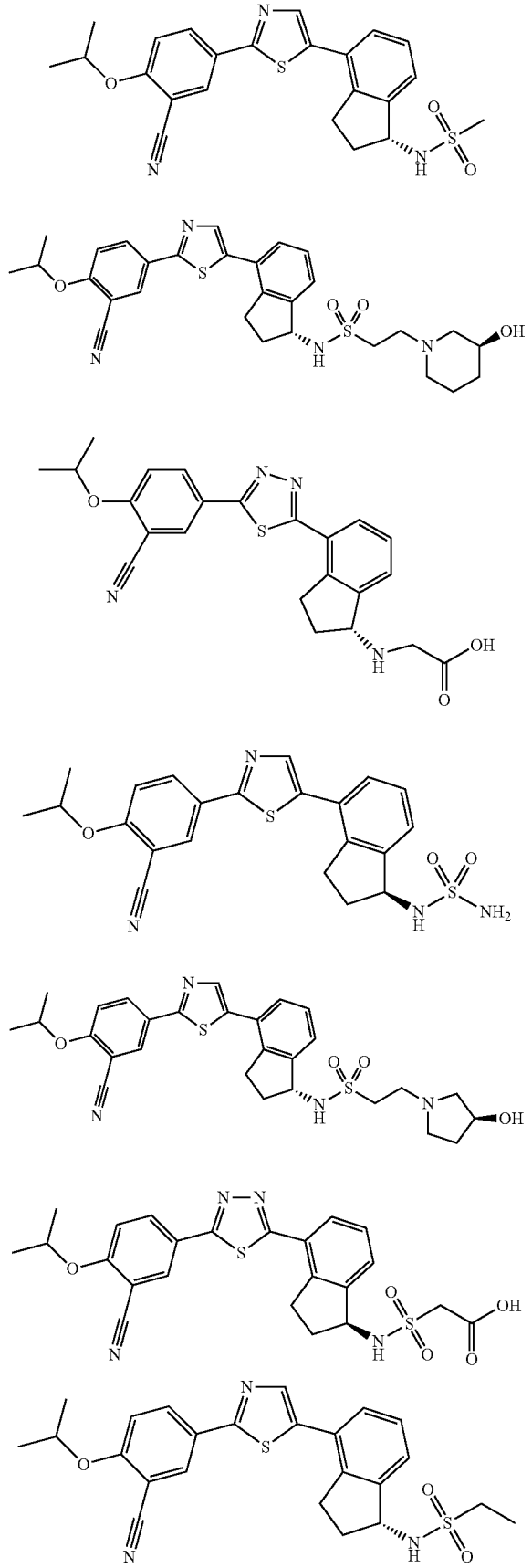
18
-continued
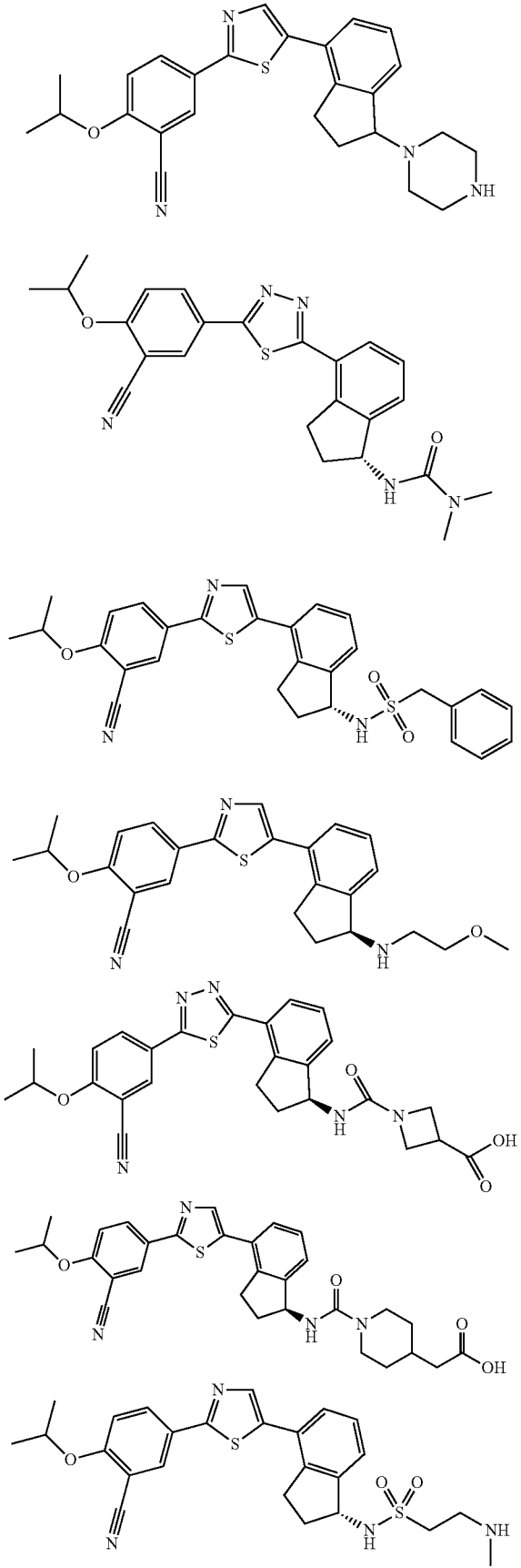

-continued
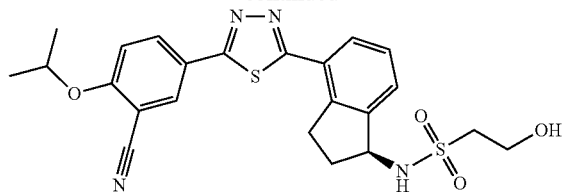
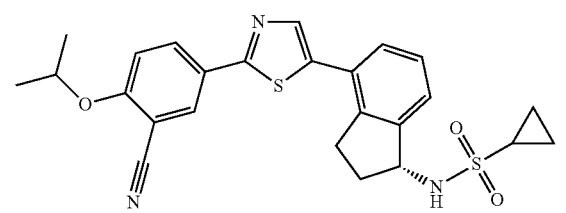
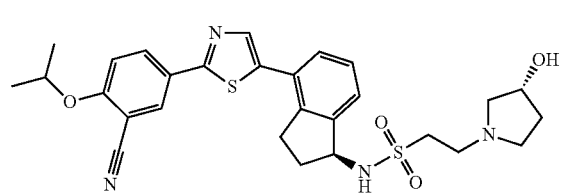
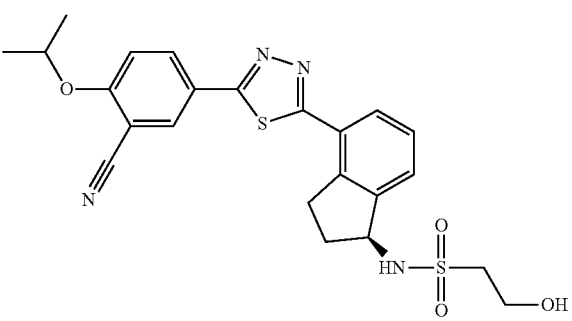
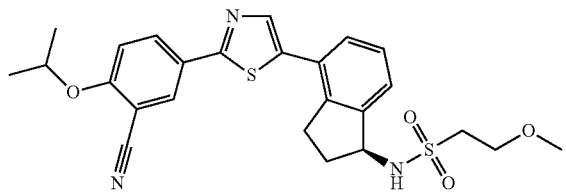
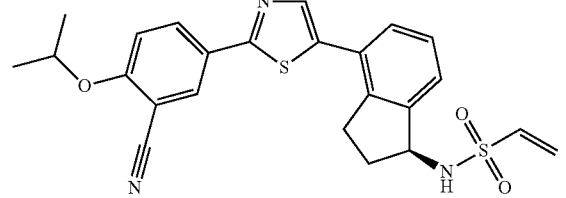
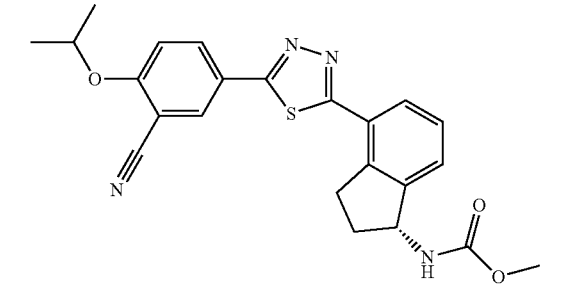
-continued
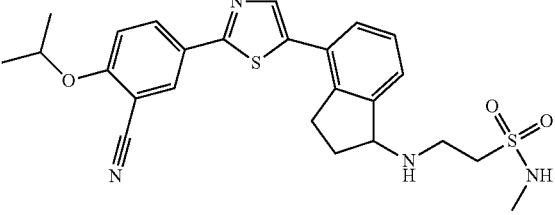
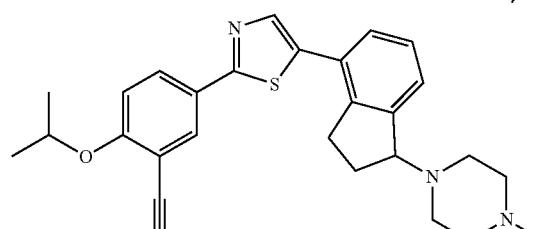
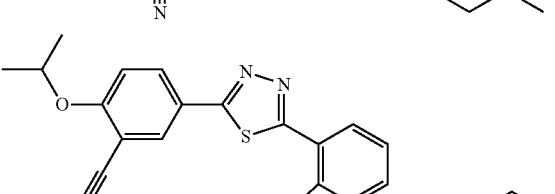
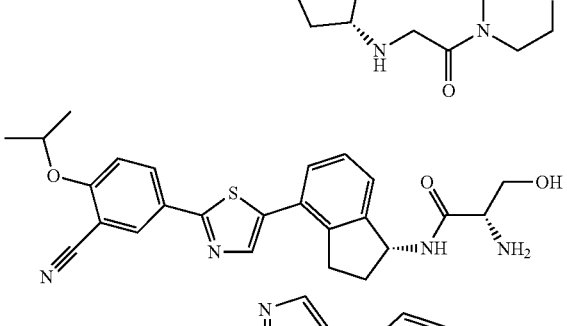
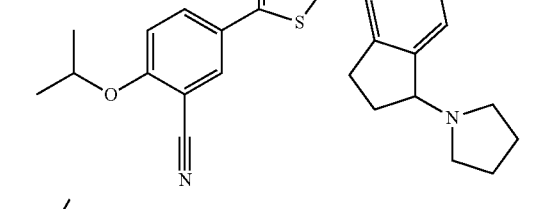
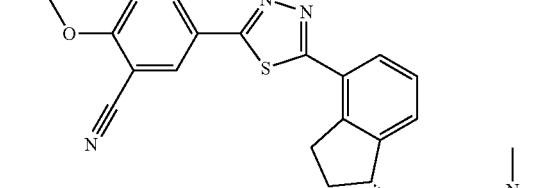
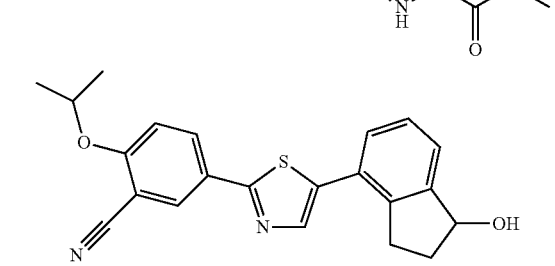

21
-continued
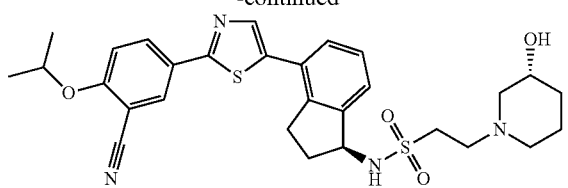
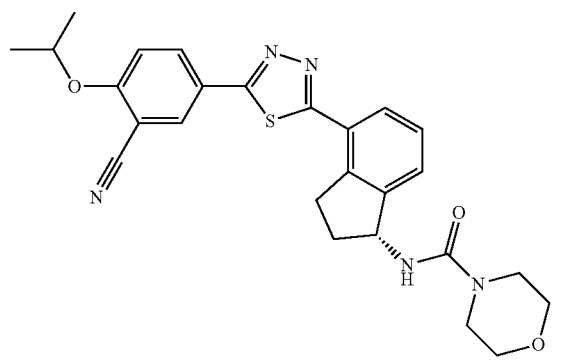
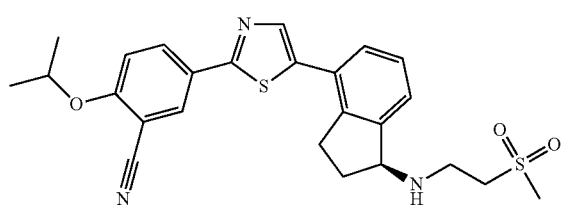
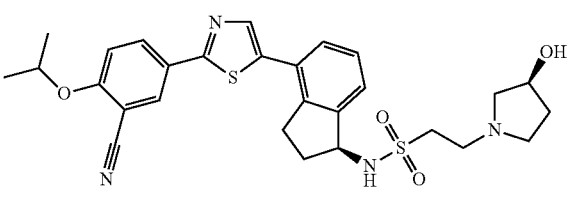
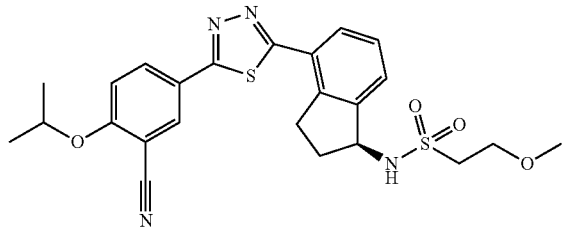
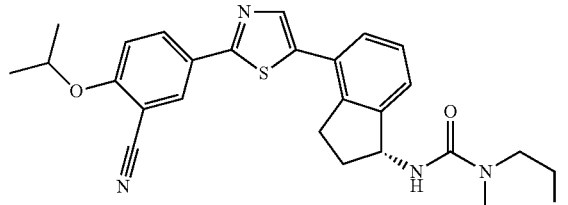
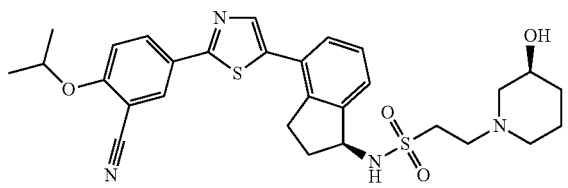
22
-continued
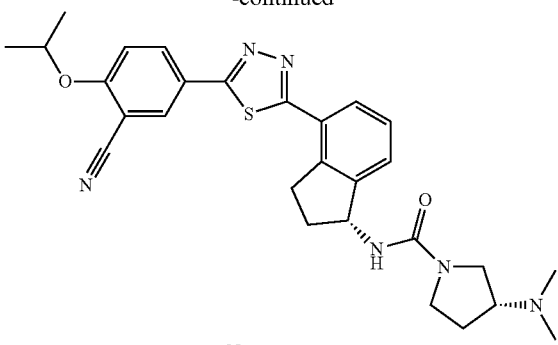
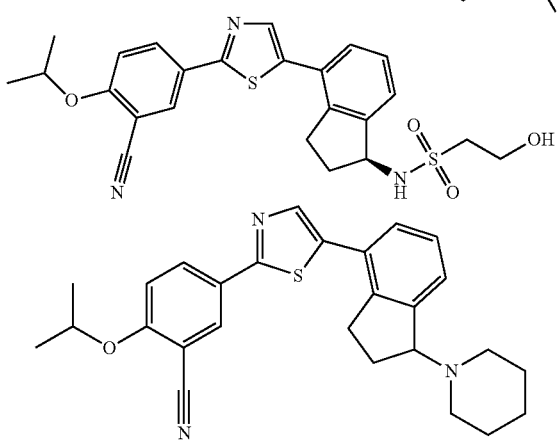
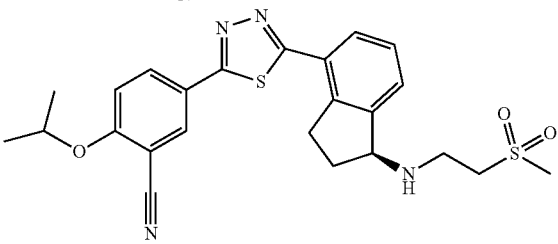
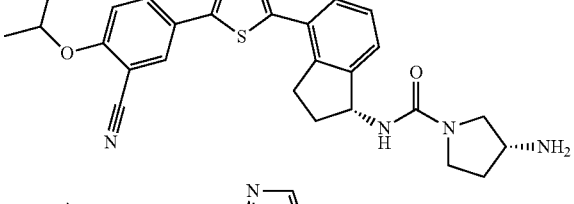
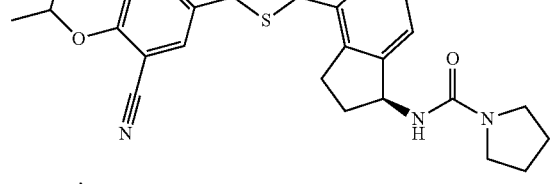
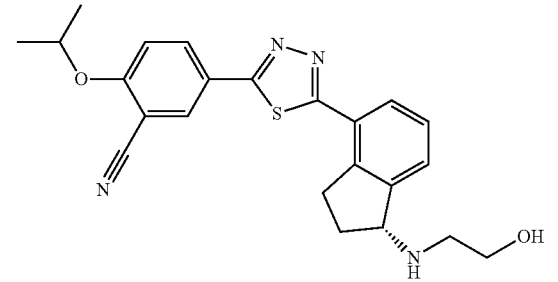

23
-continued
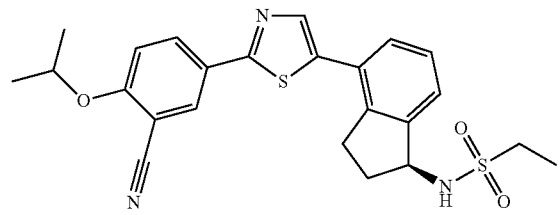
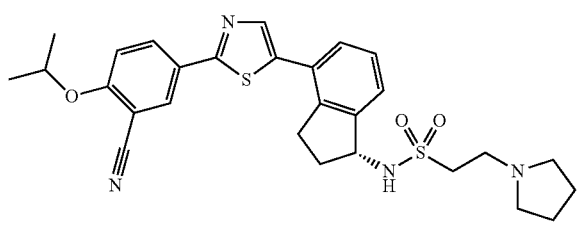
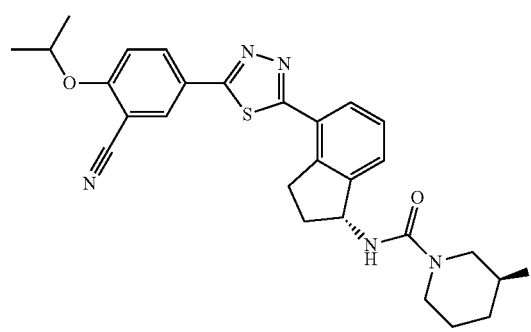
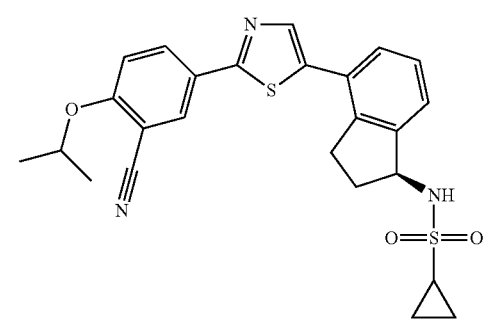
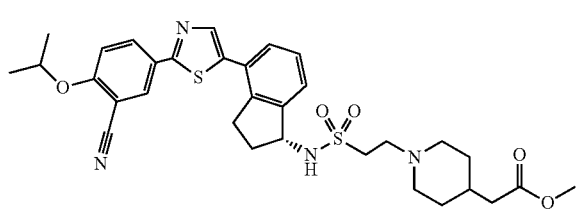
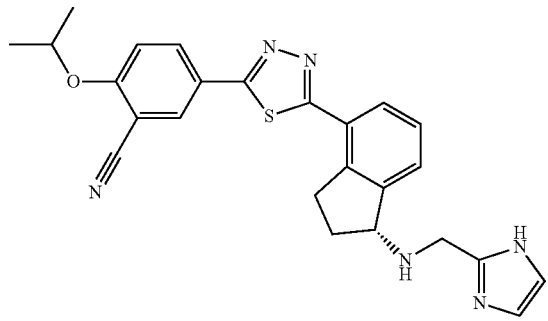
24
-continued
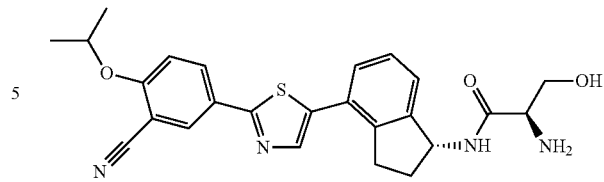
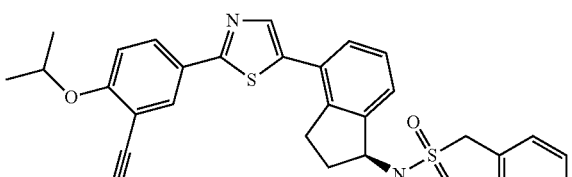
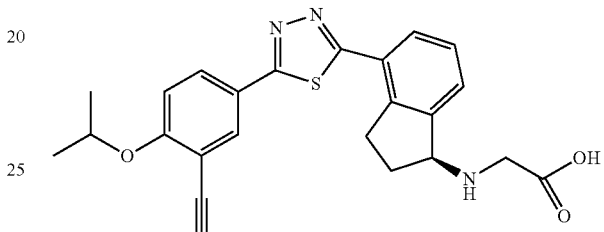
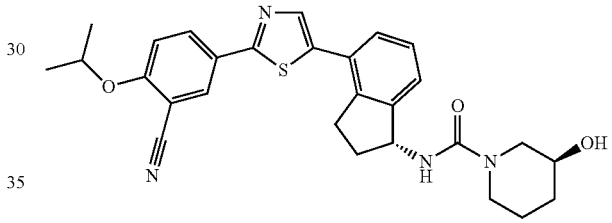
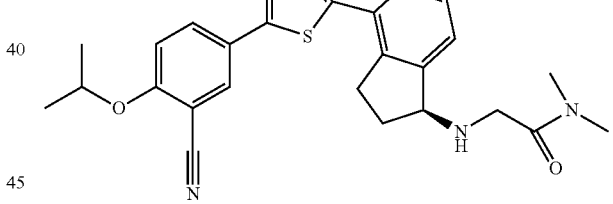
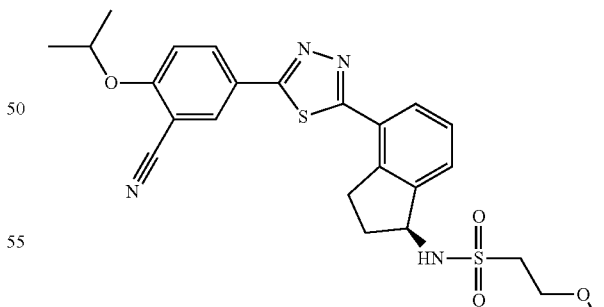
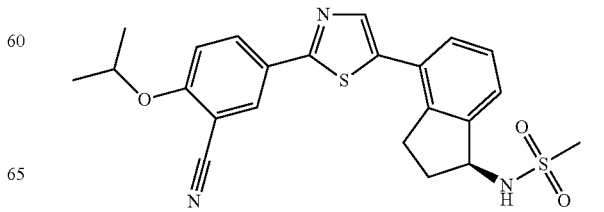

25
-continued
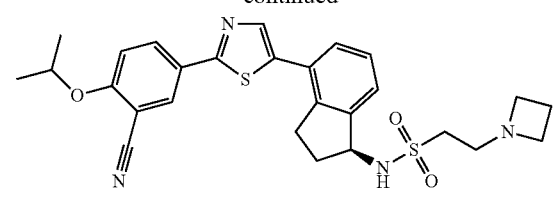
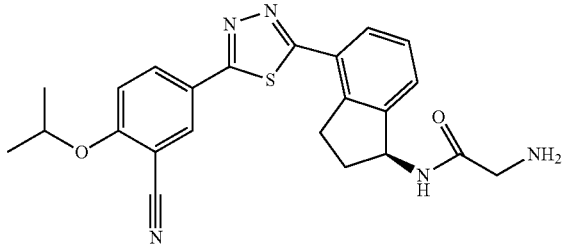
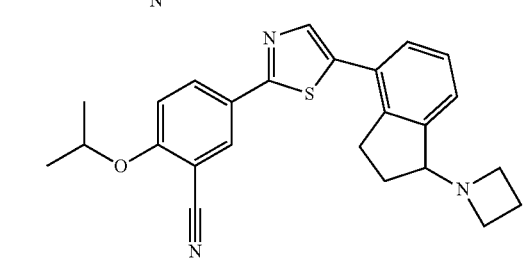
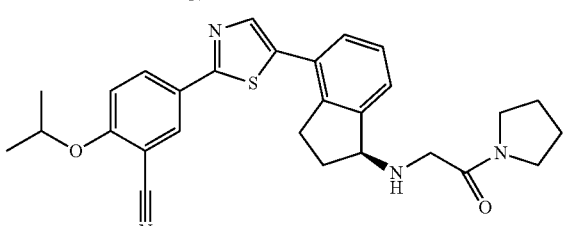
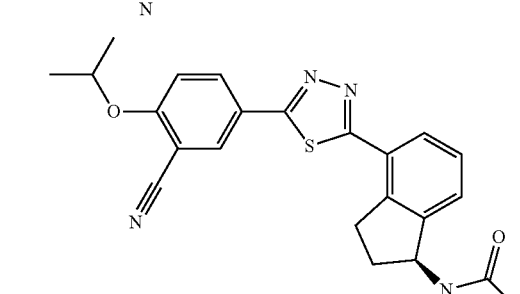
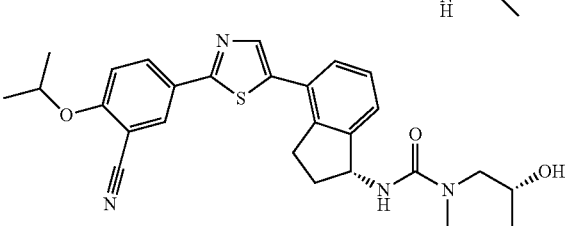
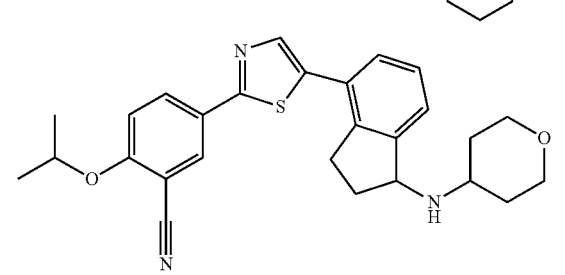
26
-continued
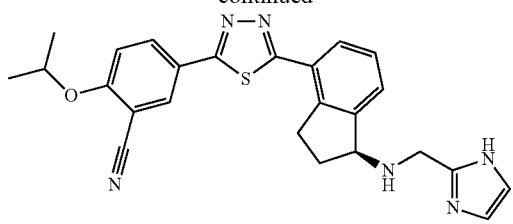
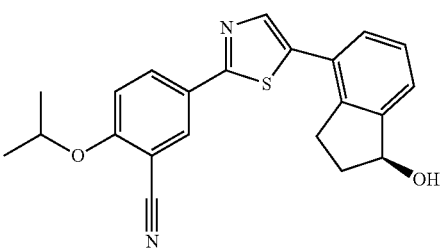
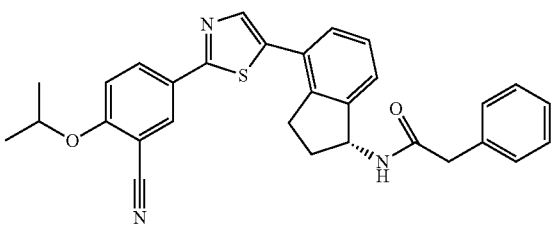
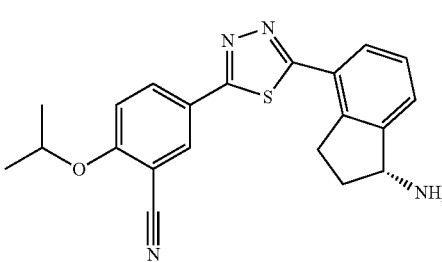
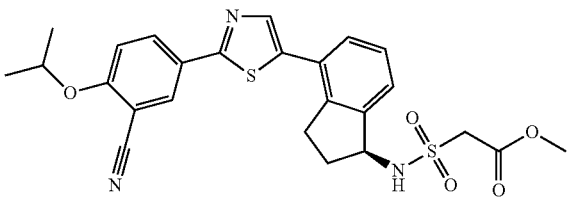
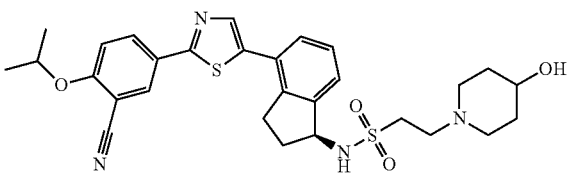
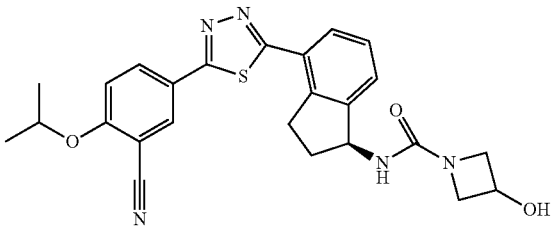

27
-continued
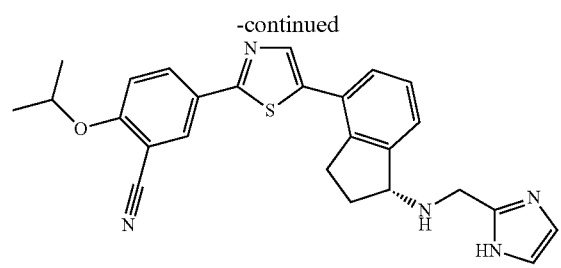
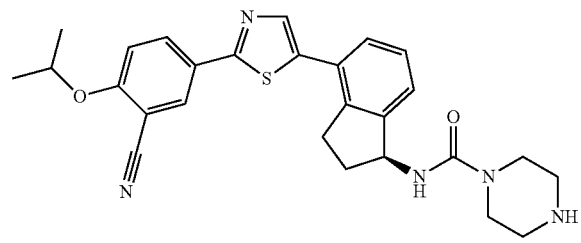
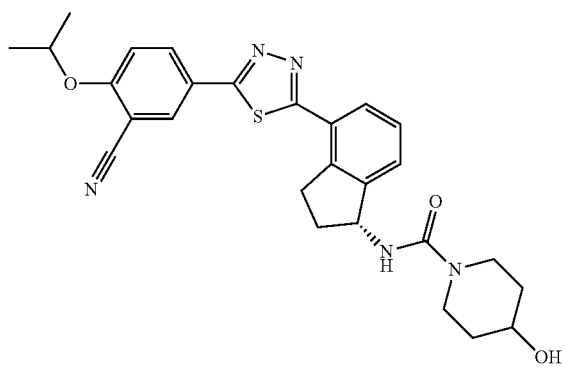
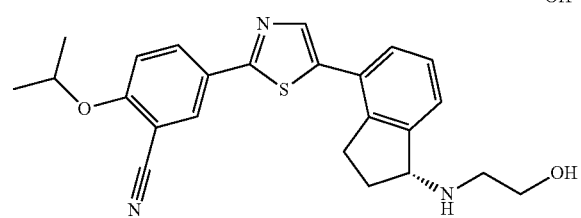
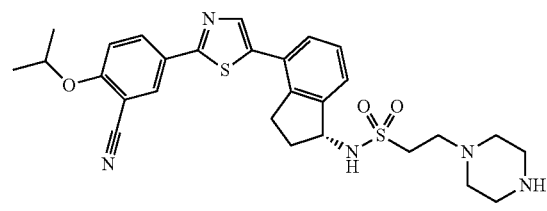
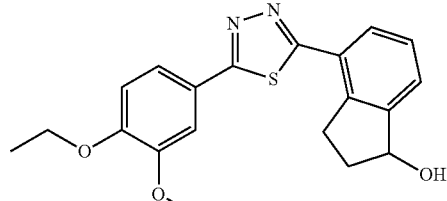
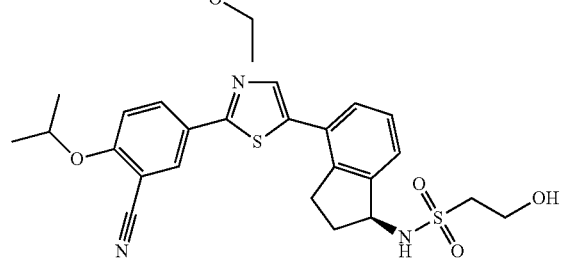
28
-continued
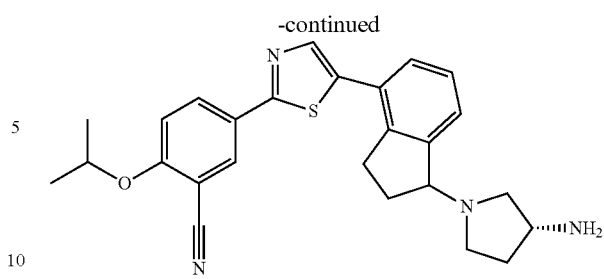
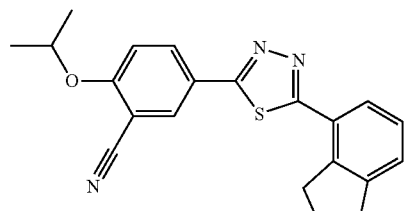
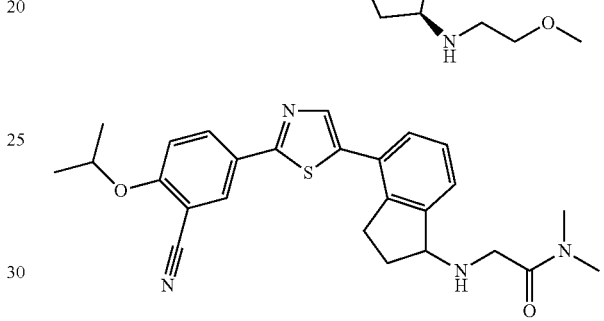
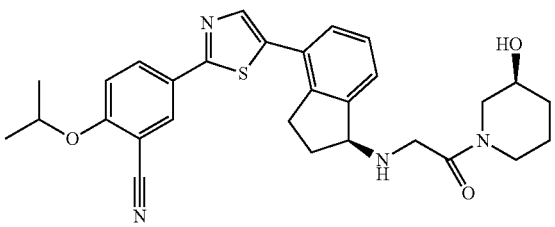
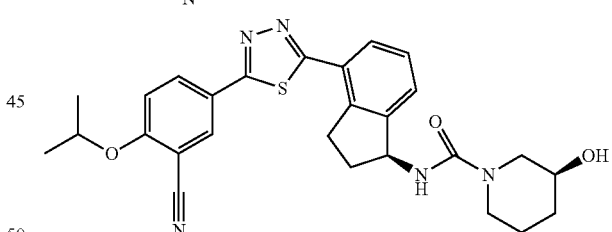
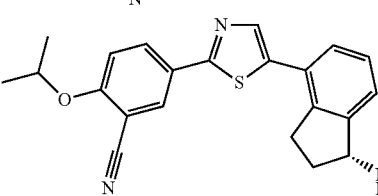
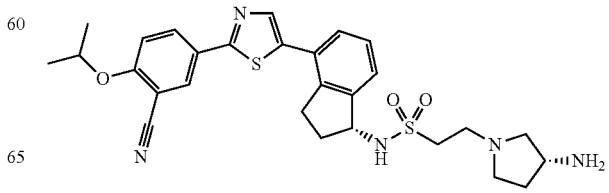

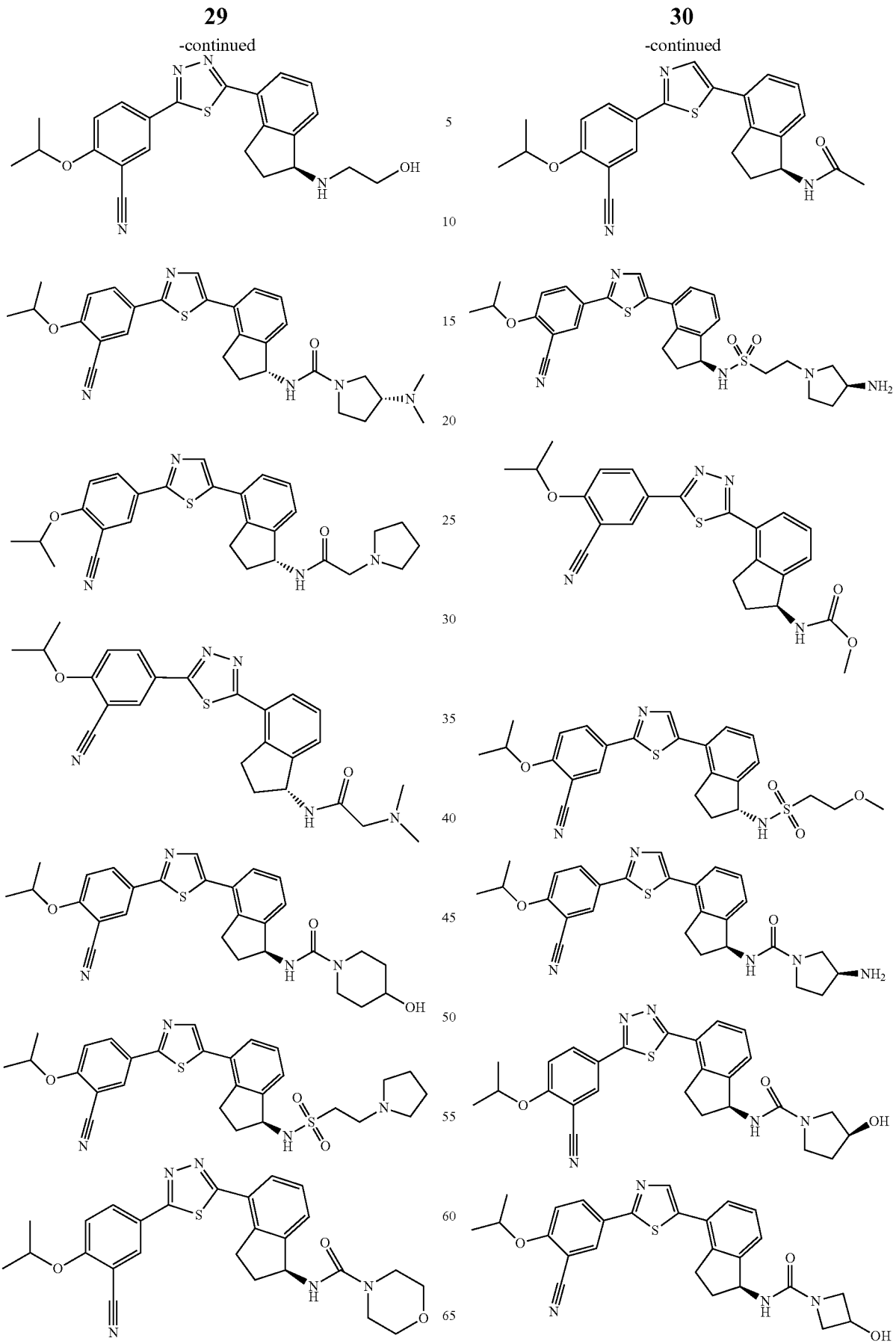

31
-continued
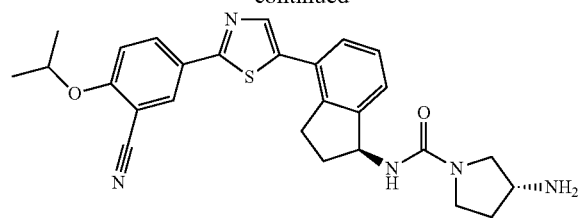
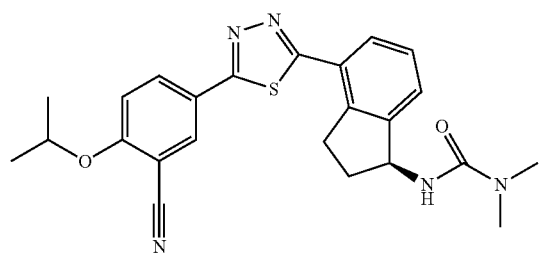
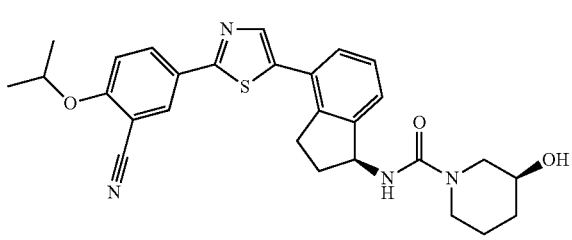
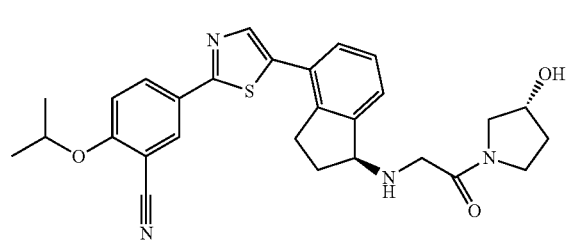
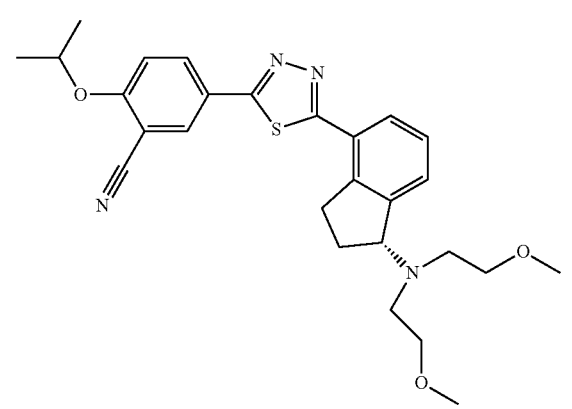
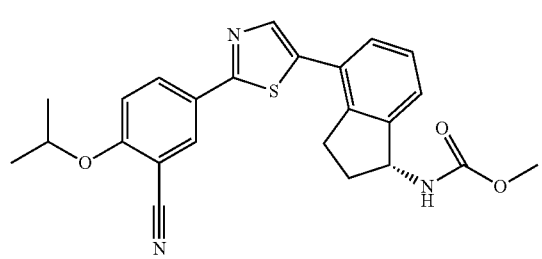
32
-continued
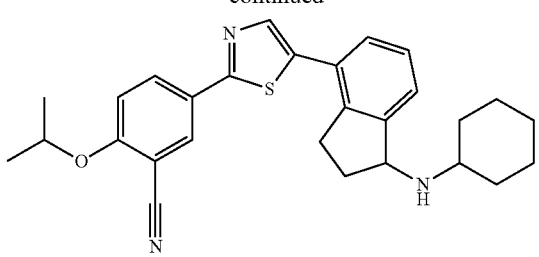
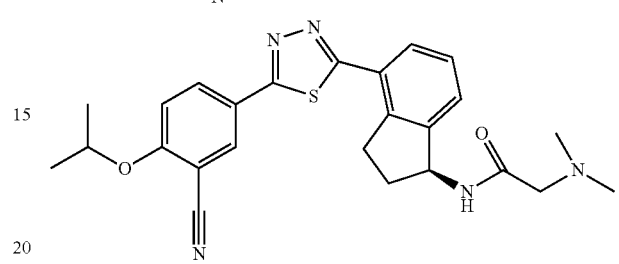
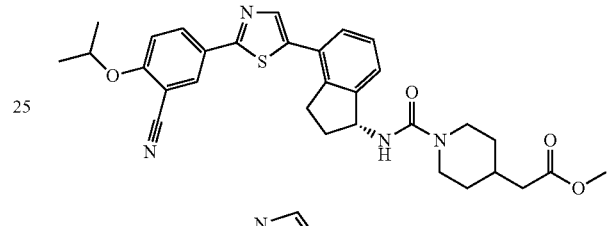
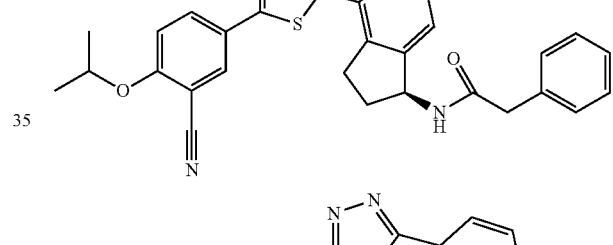
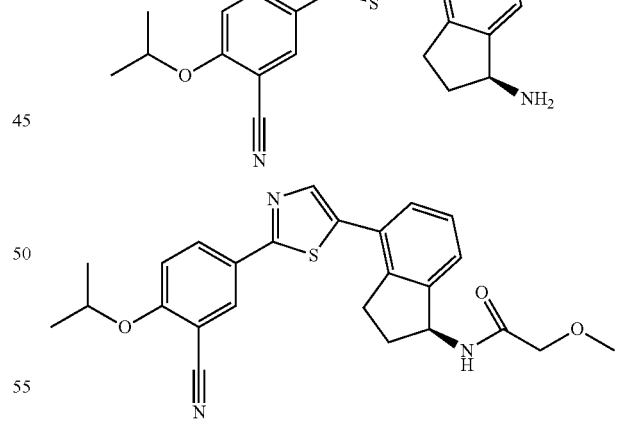
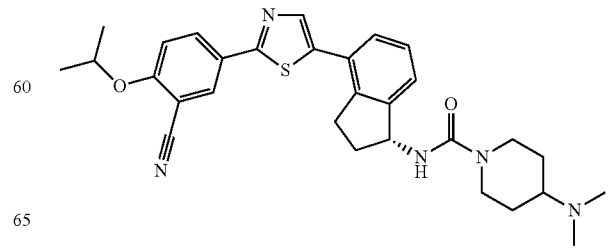

33
-continued
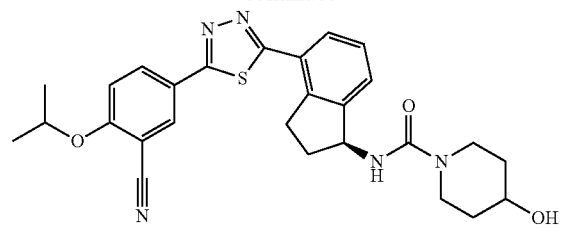
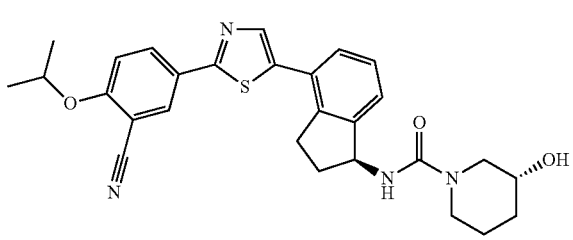
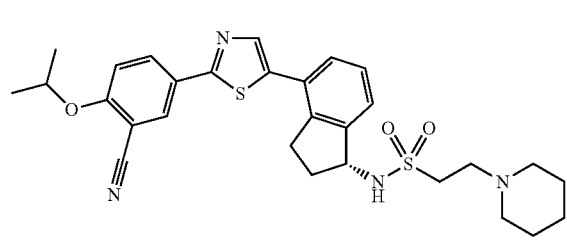
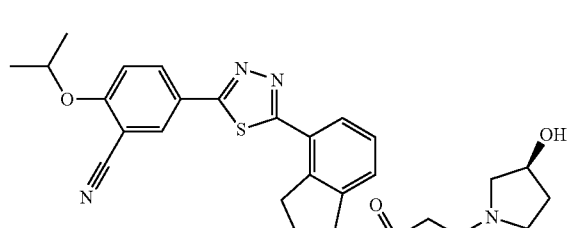
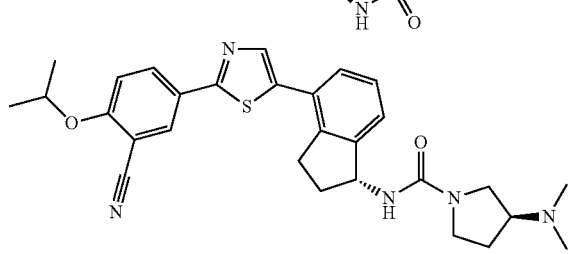
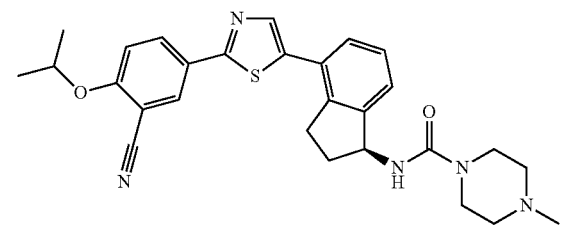
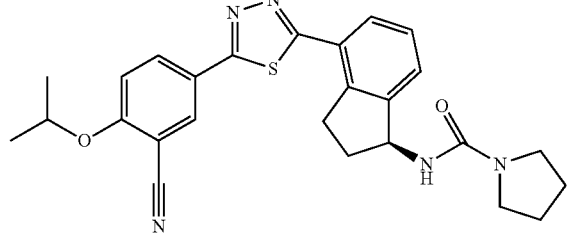
34
-continued
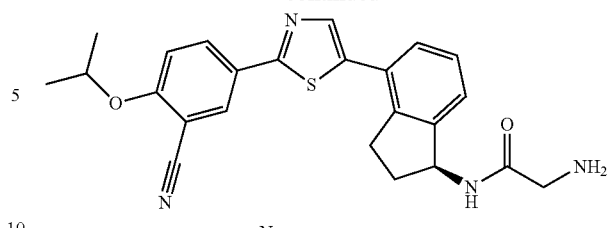
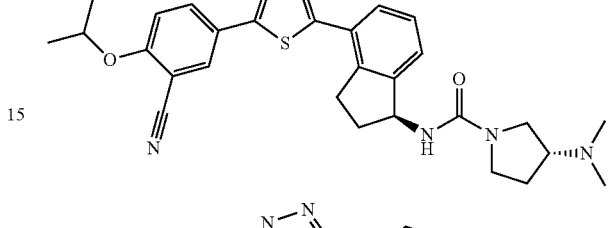
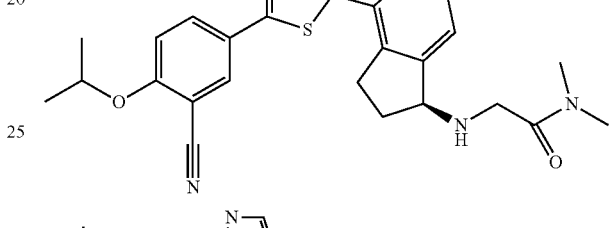
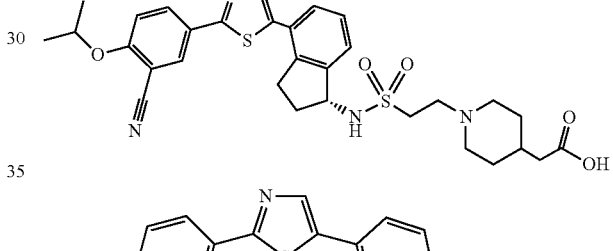
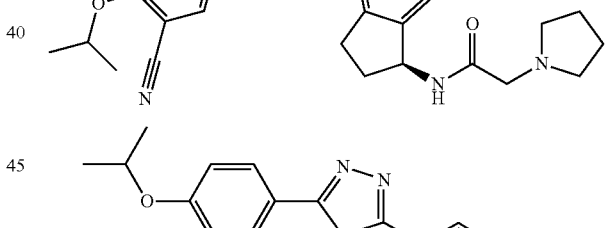
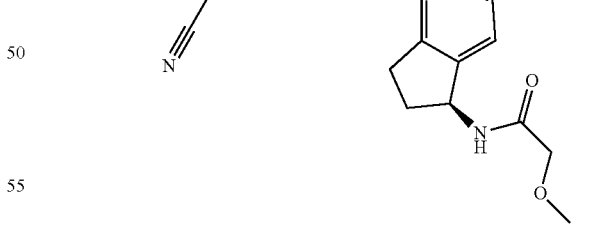
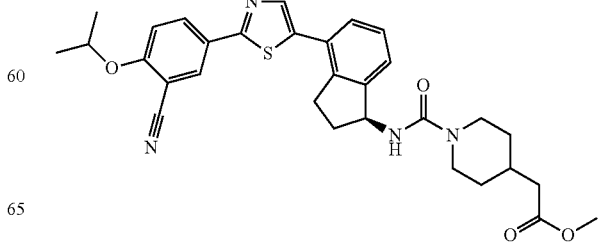

35
-continued
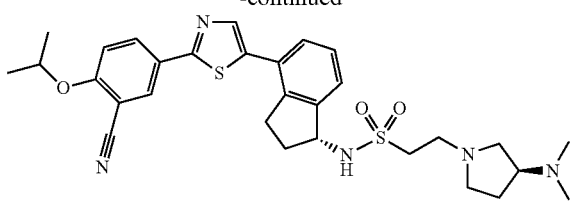
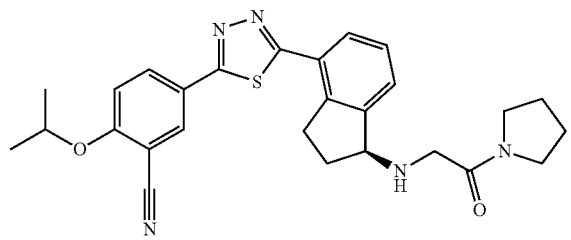
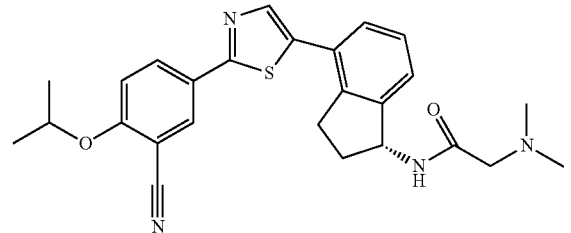
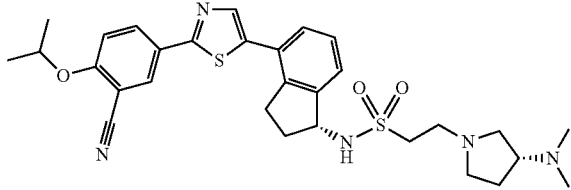
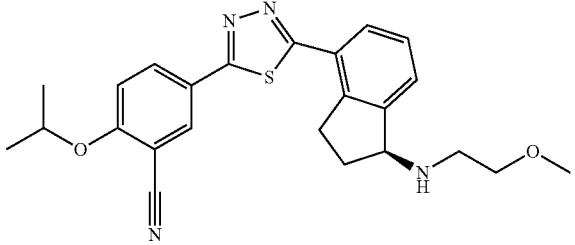
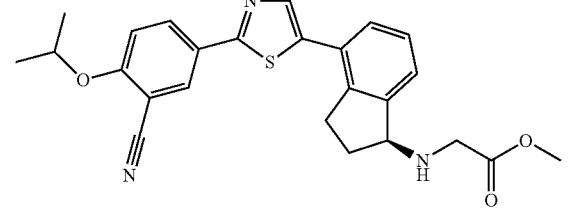
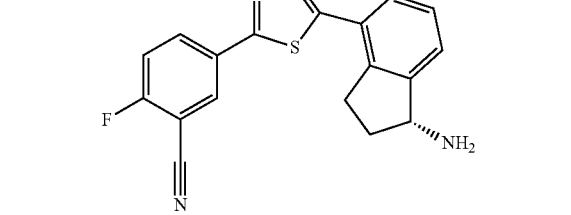
36
-continued
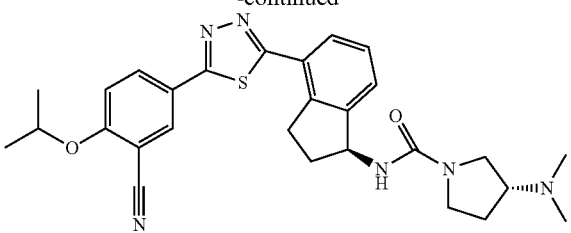
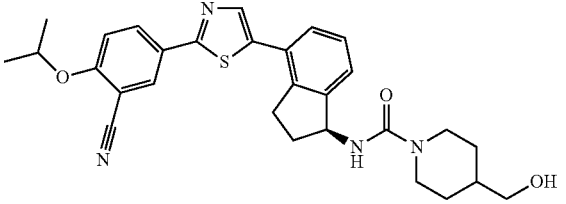
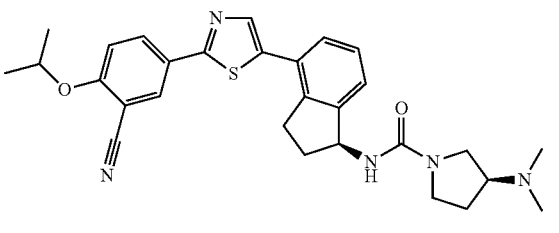
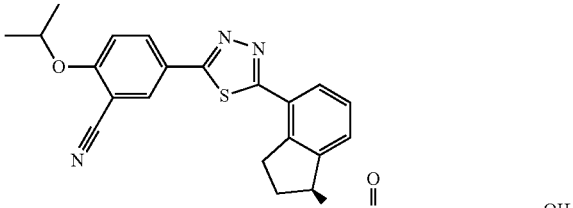
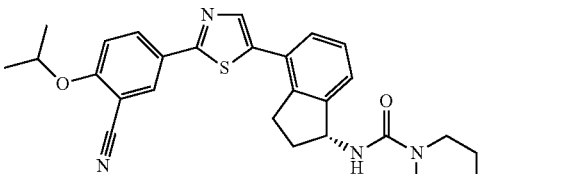
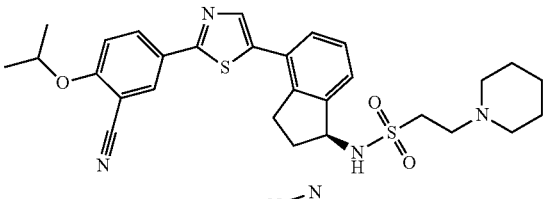
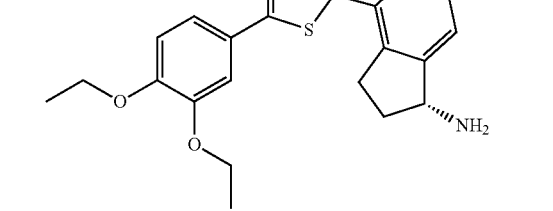

37
-continued

38
-continued
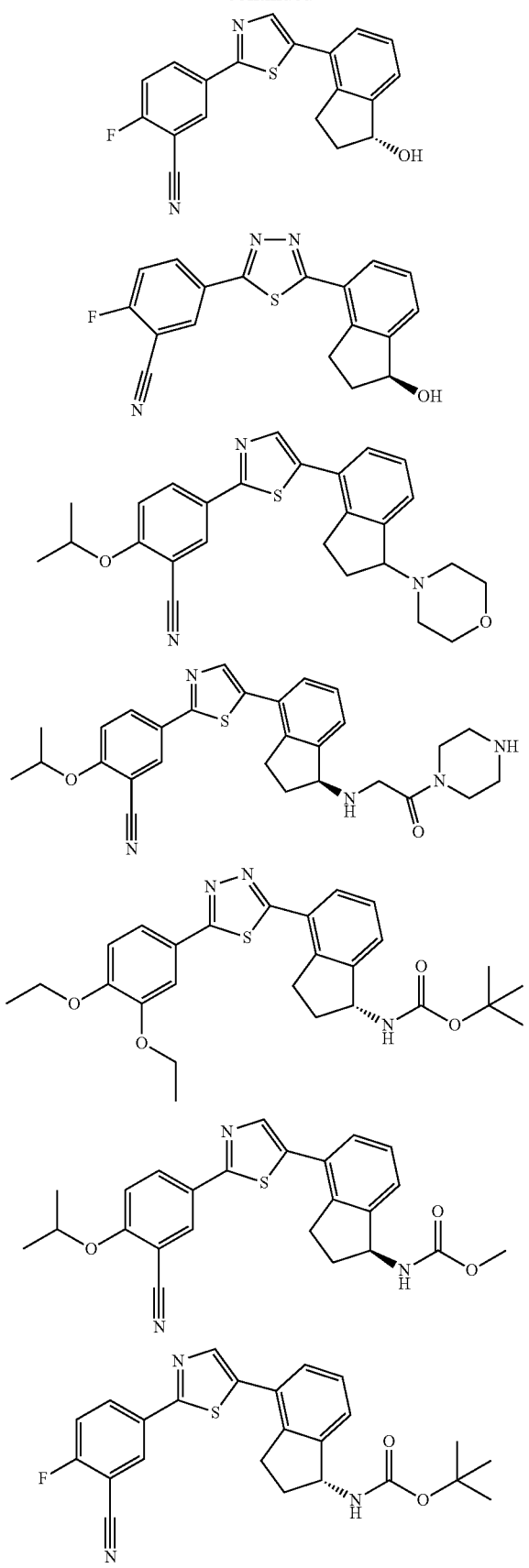

-continued
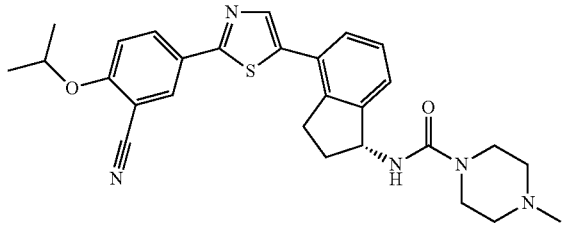
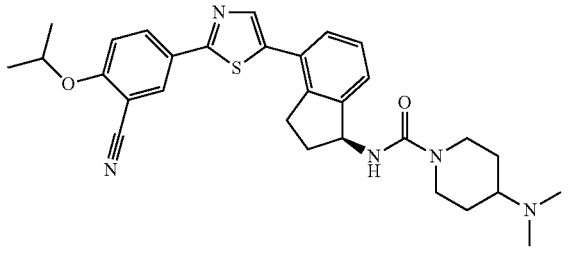
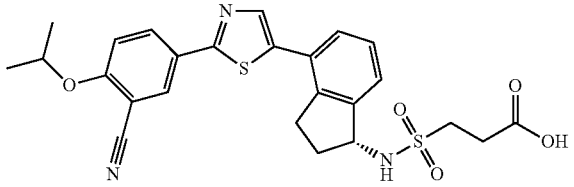
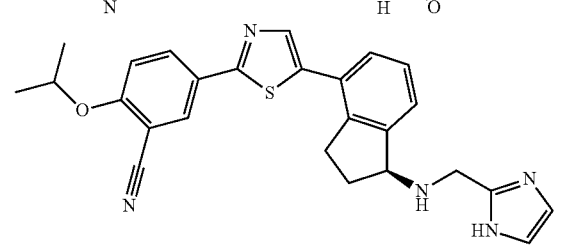
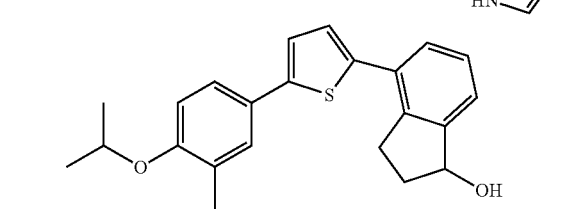
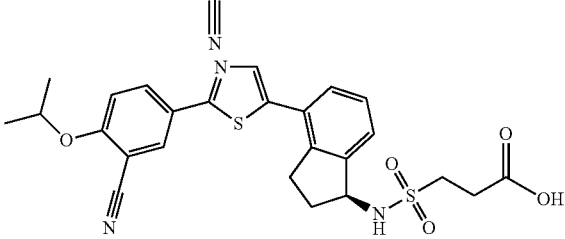
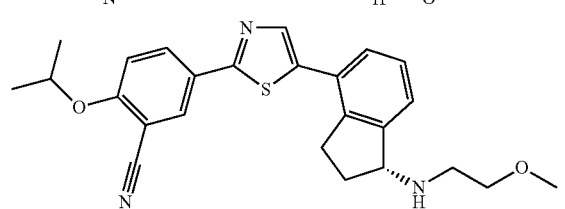
-continued
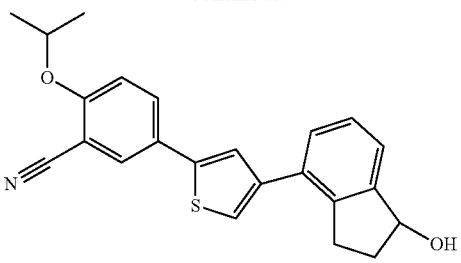
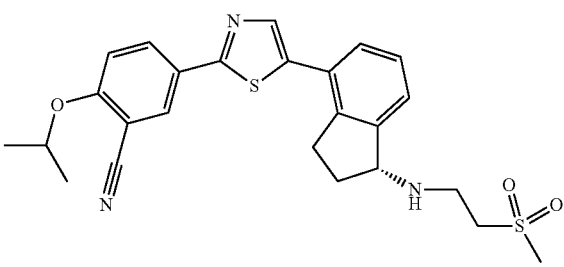
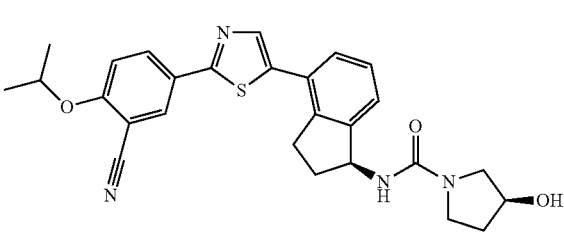
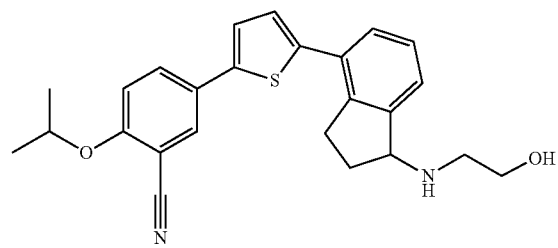
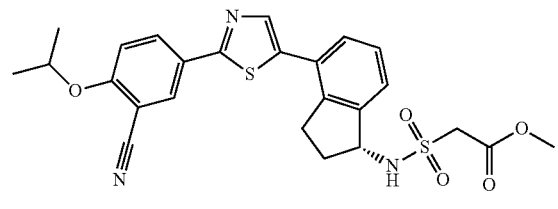
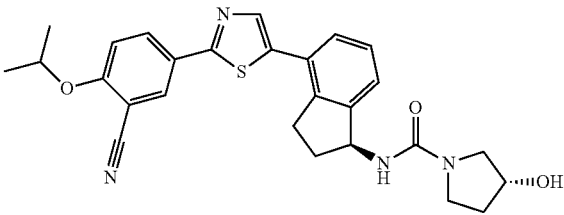

-continued

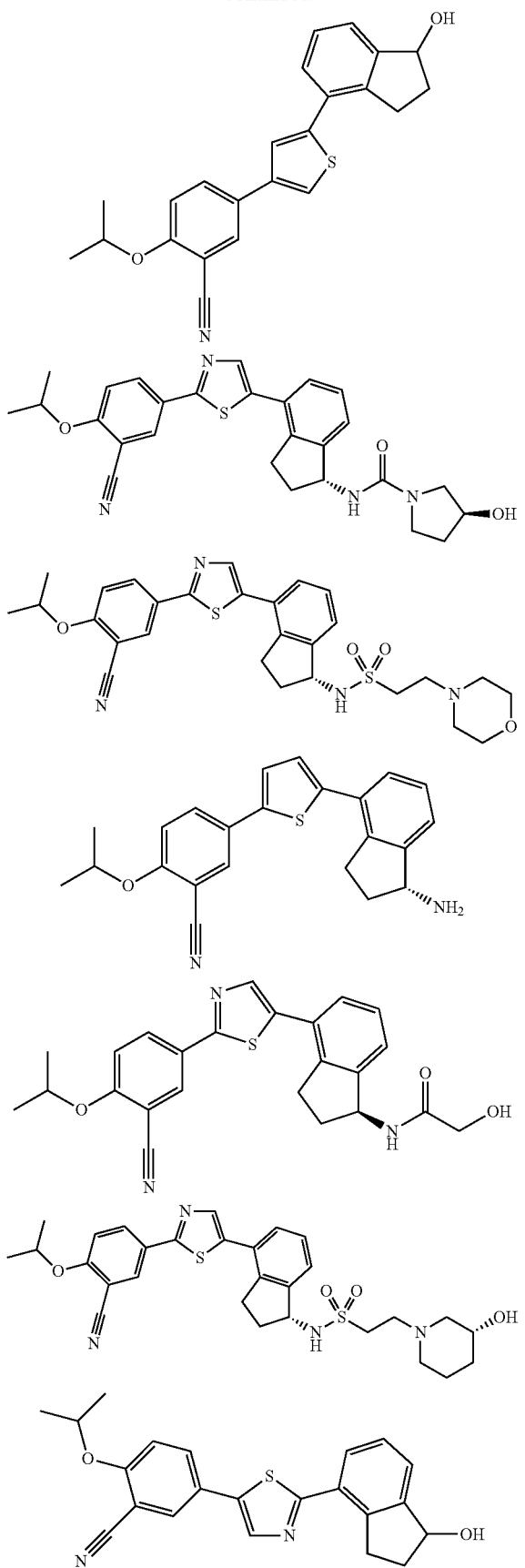

-continued

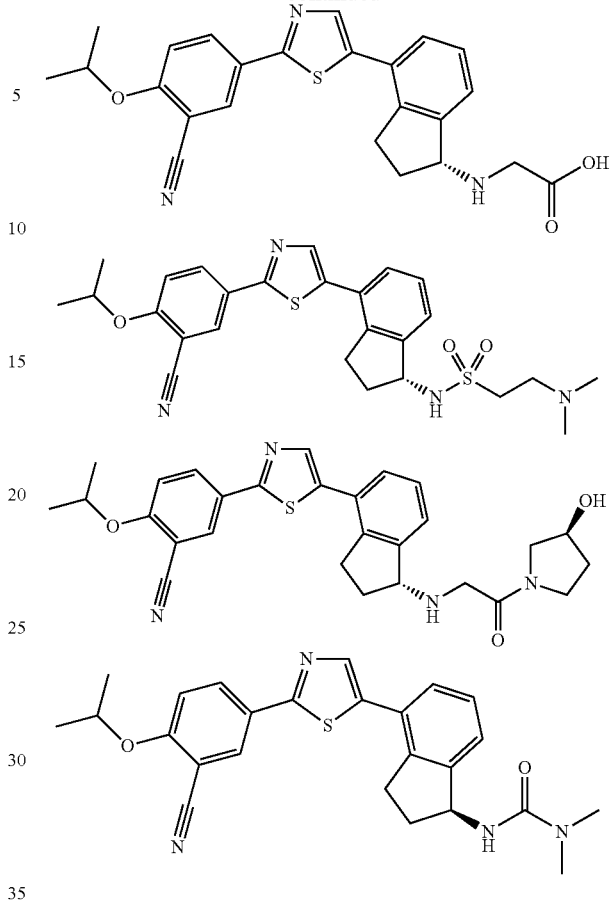

or any pharmaceutically acceptable salt, tautomer, stereoisomer, solvate, hydrate, or prodrug thereof. In certain of such embodiments, the invention provides a compound selected from compounds 43, 46, 47, 56, 58, 166, 172, and 186 or any pharmaceutically acceptable salt, ester, tautomer, stereoisomer, solvate, hydrate, homolog, or prodrug thereof. In certain of such embodiments, the invention provides compound 43, 46, or 166 or any pharmaceutically acceptable salt, ester, tautomer, solvate, hydrate, homolog, or prodrug thereof.

In certain embodiments, an invention compound of Formula I is provided wherein the compound has at least one chiral center and is substantially enantiomerically pure.

In other embodiments, a pharmaceutical composition comprising an invention compound of Formula I and a suitable excipient is provided.

In other embodiments, a pharmaceutical combination comprising an invention compound and a second medicament is provided. In still other embodiments, a pharmaceutical combination comprising an invention compound and a second medicament is provided wherein the second medicament is medically indicated for the treatment of multiple sclerosis, transplant rejection, or adult respiratory distress syndrome.

In certain embodiments, a method of use of an invention compound for preparation of a medicament is provided.

In certain embodiments a method of activation or agonism of a sphingosine-1-phosphate receptor subtype 1 by contacting the receptor subtype 1 with an effective amount of an invention compound. In further embodiments, a method of activation or agonism of a sphingosine-1-phosphate receptor subtype 1 by contacting the receptor subtype 1 with an effective amount of an invention compound is provided, wherein the compound activates or agonizes the sphingosine-1-phosphate receptor subtype 1 to a greater extent than the compound activates or agonizes a sphingosine-1-phosphate receptor subtype 3. In further embodiments, a method of activation or agonism of a sphingosine-1-phosphate receptor subtype 1 by contacting the receptor subtype 1 with an effective amount of an invention compound is provided, wherein the sphingosine-1-phosphate receptor subtype 1 is disposed within a living mammal.

In certain embodiments, a method is provided for treatment of a malcondition in a patient for which activation or agonism of an sphingosine-1-phosphate receptor subtype 1 is medically indicated, by administering an effective amount of an invention compound to the patient at a frequency and for a duration of time sufficient to provide a beneficial effect to the patient. In further embodiments, a method is provided for treatment of a malcondition in a patient for which activation or agonism of an sphingosine-1-phosphate receptor subtype 1 is medically indicated, by administering an effective amount of an invention compound to the patient at a frequency and for a duration of time sufficient to provide a beneficial effect to the patient, wherein selective activation or agonism of an S1P subtype 1 receptor with respect to other subtypes of S1P receptor is medically indicated. In yet further embodiments, a method is provided for treatment of a malcondition in a patient for which activation or agonism of an sphingosine-1-phosphate receptor subtype 1 is medically indicated, by administering an effective amount of an invention compound to the patient at a frequency and for a duration of time sufficient to provide a beneficial effect to the patient, wherein the malcondition comprises rejection of transplanted organs or tissue; graft-versus-host diseases brought about by transplantation; autoimmune syndromes including rheumatoid arthritis; acute respiratory distress syndrome; adult respiratory distress syndrome; influenza; cancer; systemic erythematosus; Hashimoto's thyroiditis; lymphocytic thyroiditis; multiple sclerosis; myasthenia gravis; type I and II diabetes; uveitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; cutaneous manifestations of immunologically-mediated disorders; psoriasis; atopic dermatitis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchitis; gastric ulcers; ischemic bowel diseases; inflammatory bowel diseases; necrotizing enterocolitis; intestinal lesions associated with thermal burns; celiac diseases; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; arteriosclerosis; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; multiple myositis; Guillain-Barre syndrome; Meniere's disease; polyneuritis; multiple neuritis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; agranulocytosis; pernicious anemia; megaloblastic anemia; anerythroplasia; osteoporosis; sarcoidosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic; leukemias; lymphoma; psoriasis; inflammatory lung injury, pulmonary emphysema; cataracta; dieresis; retinitis pigmentosa; senile macular degeneration; vitreal scarring; inflammatory eye disease; corneal alkali burn; dermatitis erythema; ballous dermatitis; cement dermatitis; gingivitis; periodontitis; sepsis; pancreatitis; carcinogenesis; metastasis of carcinoma; hypobaropathy; autoimmune hepatitis; primary biliary cirrhosis; sclerosing cholangitis; partial liver resection; acute liver necrosis; cirrhosis; alcoholic cirrhosis; hepatic failure; fulminant hepatic failure; late-onset hepatic failure; "acute-on-chronic" liver failure. In yet further embodiments, the malcondition is one or more of rejection of transplanted organs or tissue; graft-versus-host diseases brought about by transplantation; autoimmune syndromes including rheumatoid arthritis, multiple sclerosis, myasthenia gravis; pollen allergies; type I diabetes; prevention of psoriasis; Crohn's disease; ulcerative colitis, acute respiratory distress syndrome; adult respiratory distress syndrome; influenza; post-infectious autoimmune diseases including rheumatic fever and post-infectious glomerulonephritis; and metastasis of carcinoma. In yet further empbodiments the malcondition is one of influenza, ulcerative colitis, multiple sclerosis, transplant rejection, acute respiratory distress syndrome or adult respiratory distress syndrome.

In certain embodiments, methods are provided for use of an invention compound for preparation of a medicament adapted for treatment of a disorder or a malcondition wherein activation or inhibition of a sphingosine-1-phosphate receptor subtype 1 is medically indicated.

In certain embodiments the invention provides a method for the chiral synthesis of a compound comprising an indane moiety having a chiral carbon in the five-membered ring of the indane moiety where the compound is enantiomerically enriched with respect to the chiral carbon. In such embodiments, the method of the invention provides the steps of
(i) providing a compound comprising an indane moiety where the ring carbon of the five-membered ring of the indane moiety where chiral substitution is desired is oxo substituted at such carbon, and wherein a carbon of the phenyl ring is halo substituted;

(ii) reacting such compound with a chiral reagent selected from the group consisting of a Corey Bakshita Shibata-oxazaborolidine and a chiral sulfinamide of the form RS(=O)NH$_2$ where R is selected from the group consisting of t-butyl, branched C$_{2-6}$ alkyl and C$_{3-8}$ cycloalkyl; and (iii) forming the chiral center at the indane moiety carbon previously bound to the oxo group by either reacting such compound with a suitable reducing agent along with the chiral reagent in step (ii) or reacting the result of the reaction of such compound with a suitable reducing agent.

In certain embodiments R is t-butyl, sec-butyl, isopropyl, cyclopropyl, adamantyl, C$_{3-6}$ branched alkyl, or optionally bridged C$_{3-8}$ cycloalkyl. In certain of such embodiments the chiral reagent is the Corey Bakshita Shibata-oxazaborolidine and the compound comprising an indane moiety is enantiomerically enriched with respect to a carbon-oxygen bond on a ring carbon of the five-membered ring of the indane moiety. In certain of such embodiments a suitable reducing reagent includes a borohydride such as BH$_3$-DMS or NaBH$_4$.

In further embodiments, the chiral reagent is (R)-(−)-(2)-methyl-CBS-oxazaborolidine or (S)-(−)-(2)-methyl-CBS-oxazaborolidine.

In certain of such embodiments the compound comprising an indane moiety provided in step (i) is contacted with the chiral reagent to form in step (ii) Formula VI-R or VI-S:

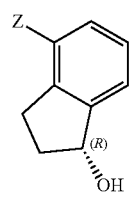

VI-R

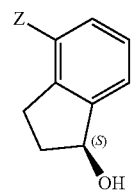

VI-S wherein Z is Cl, Br or I.

In certain embodiments the method further comprises the step of protecting the hydroxy group of Formula VI-R or VI-S by treating Formula VI-R or VI-S with a protecting agent to form Formula VIa-R or VIa-S:

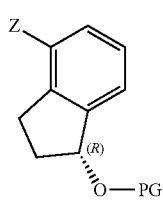

VIa-R

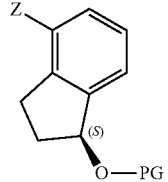

VIa-S wherein PG is a protecting group.

Protecting groups can render chemical functionality inert to specific reaction conditions and can be appended to and removed from such functionality in a molecule without substantially damaging the remainder of the molecule. Practitioners in the art would be familiar with suitable protecting groups for use in the synthetic methods of the invention. See, e.g., Greene and Wuts, *Protective Groups in Organic Synthesis*, 2$^{nd}$ ed., John Wiley & Sons, New York, 1991. In certain embodiments such protecting agent is t-butyldimethylsilyl chloride (TBSCl).

In certain embodiments the method further comprises the step of reacting Formula VIa-R or VIa-S with boronic acid or bis(pinacolato)diboron to form a boronic acid or boronate ester of Formula VIb-R or VIb-S:

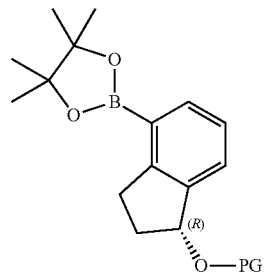

VIb-R

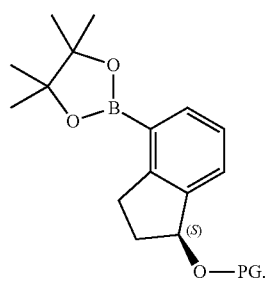

VIb-S

In certain embodiments the chiral reagent is RS(=O)NH$_2$ and the compound comprising an indane moiety is enantiomerically enriched with respect to a carbon-nitrogen bond on a ring carbon of the five-membered ring of the indane moiety. In further embodiments the chiral reagent is t-Bu-S(=O)NH$_2$.

In certain embodiments the compound comprising an indane moiety provided in step (i) is contacted with the chiral reagent to form in step (ii) Formula VII-R or VII-S:

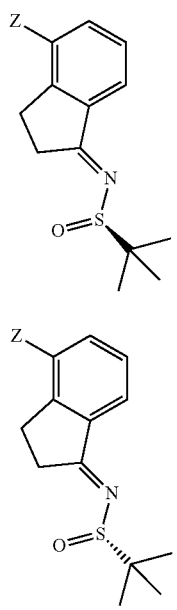

wherein Z is Cl, Br or I.

In certain embodiments a compound of Formula or VIII-S is formed in step (iii):

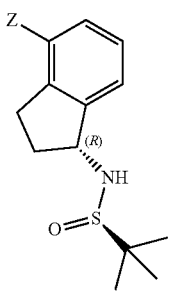

VIII-R

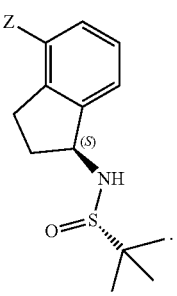

VIII-S

In certain embodiments the method further comprises the step of contacting Formula VIII-R or VIII-S with 1,4-dioxane in the presence of an acid to form Formula VIb-R or VIb-S or Formula IX-R or IX-S:

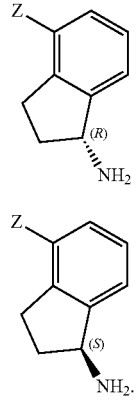

In certain embodiments the method further comprises the step of protecting the amino group by treating Formula IX-R or IX-S with a protecting agent to form Formula IXa-R or IXa-S:

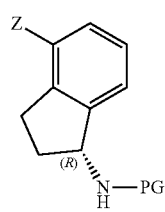

IXa-R

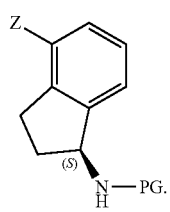

IXa-S

In certain of such embodiments the protecting agent is di-tert-butyldicarbonate.

In certain embodiments the method further comprises the step of reacting Formula IXa-R or IXa-S with boronic acid or bis(pinacolato)diboron to form a boronic acid or boronate ester of Formula IXb-R or IXb-S:

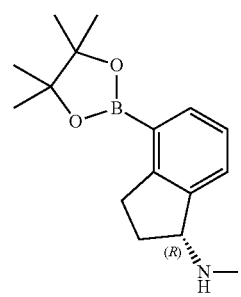

IXb-R

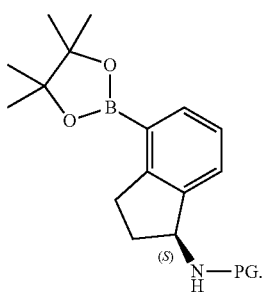

IXb-S


XIII-R


XIII-S

In certain embodiments the method further comprises the step of reacting Formula VIb-R, Formula VIb-S, Formula IXb-R or Formula IXb-S with Formula XI:

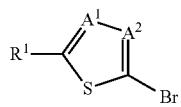

XI to form Formula XII-R or XII-S:

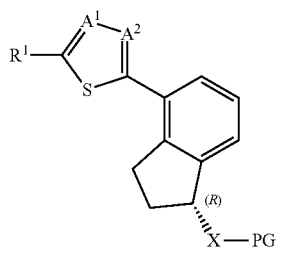

XII-R

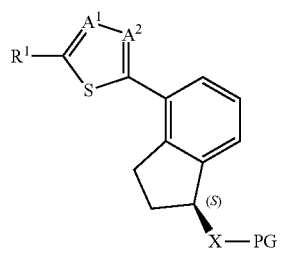

XII-S wherein each $A^1$ and each $A^2$ is independently N, or CH; $R^1$ is di-substituted phenyl or di-substituted pyridinyl where the phenyl and pyridinyl substituents are each independently selected from the group consisting of halo, nitro, cyano, perfluromethyl, fluorinated methyl, and $C_{1\text{-}4}$-alkoxy; provided that if $R^1$ is di-substituted phenyl, such phenyl is para-substituted with $C_{1\text{-}4}$-alkoxy; and X is NH or O.

In further embodiments $R^1$ is di-substituted phenyl where the phenyl substituents are F and Y, wherein Y is —CN, —Cl, or —CF$_3$. In still further embodiment Y is —CN.

In certain embodiments the method further comprises the step of reacting Formula XII-R or XII-S with IPrOH in the presence of NaOiPr to from Formula XIII-R or XIII-S:

In certain embodiments the method further comprises the step of deprotecting the hydroxyl group wherein X is O, or the amino group wherein X is NH, by treating Formula XIII-R or XIII-S with a deprotecting agent. In further embodiments the method further comprises the step of converting the deprotected amino group to a secondary amine.

In certain embodiments $A^1$ is N and $A^2$ is N. In certain of such embodiments Formula XI is prepared following the process comprising the step of
  a) treating a di-substituted benzaldehyde with potassium phosphate monobasic to form a di-substituted benzoic acid;
  b) contacting the di-substituted benzoic acid with H$_2$NNHCSNH$_2$ to form an amino-1,3-4-thiadizole having a di-substituted phenyl group substituted on the thiadiazole moiety; and
  c) treating the amino-1,3-4-thiadizole in step b) with a mixture of copper bromide and isoamylnitrite.

In certain embodiments $A^1$ is N and $A^2$ is CH. In certain of such embodiments Formula XI is prepared following the process comprising the step of
  a) contacting 2-bromothiazole with a (di-substituted phenyl)boronic acid to form a 2-(di-substituted phenyl)thiazole; and
  b) treating the 2-(di-substituted phenyl)thiazole with NBS.

In certain embodiments $A^1$ is CH and $A^2$ is N. In certain of such embodiments Formula XI is prepared following the process comprising the step of
  a) contacting 5-(tributylstannyl)thiazole with an iodobenzene having two other substituents to form a 5-(di-substituted phenyl)thiazole; and
  b) treating the 2-(di-substituted phenyl)thiazole with NBS.

In certain embodiments, the method of the invention provides the steps of (i) providing the compound

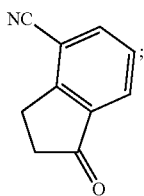 [SMILES: N#Cc1cccc2c1CCC2=O]

and
(ii) reacting such compound with a chiral reagent selected from the group consisting of a Corey Bakshita-oxazaborolidine and a chiral sulfinamide of the form RS(=O)NH₂ where R is a bulky group [e.g. t-butyl, branched alkyl or cycloalkyl]; and
(iii) forming a chiral center at the indane moiety carbon previously bound to the oxo group by either reacting such compound with a suitable reducing agent along with the chiral reagent in step (ii) or reacting the result of the reaction of such compound with a suitable reducing agent.

In certain of such embodiments, the chiral reagent is a Corey Bakshita Shibata-oxazaborolidine and X is —OR'''. In further embodiments, the chiral reagent is (R)-(–)-(2)-methyl-CBS-oxazaborolidine or (S)-(–)-(2)-methyl-CBS-oxazaborolidine.

In certain of such embodiments the chiral reagent is RS(=O)NH₂ where R is branched alkyl or cycloalkyl and X is —NR'R''. In further such embodiments, the chiral reagent is t-Bu-S(=O)NH₂.

In certain of such embodiments a suitable reducing reagent includes a borohydride such as BH₃-DMS or NaBH₄.

Additional steps for the preparation of such compounds can be adapted from the synthetic methods disclosed herein including recrystallization and other processes for purification.

In certain of such embodiments the invention provides a method of synthesizing a chiral compound of the invention by (i) providing a compound comprising an indane moiety where the ring carbon of the five-membered ring of the indane moiety where chiral substitution is desired is oxo substituted at such carbon; (ii) reacting such compound with a chiral reagent selected from the group consisting of a Corey Bakshita Shibata-oxazaborolidine and a chiral sulfinamide of the form RS(=O)NH₂ where R is a bulky group [e.g. t-butyl or other branched alkyl or cycloalkyl]; and (iii) forming a chiral center at the indane moiety carbon previously bound to the oxo group by either reacting such compound with a suitable reducing agent along with the chiral reagent in step (ii) or reacting the result of the reaction of such compound with a suitable reducing agent.

Additional steps for the preparation of such compounds can be adapted from the synthetic methods disclosed herein including recrystallization and other processes for purification.

In certain of such embodiments the invention provides a method of synthesizing a chiral compound of the invention by (i) providing a compound comprising an indane moiety where the ring carbon of the five-membered ring of the indane moiety where chiral substitution is desired is oxo substituted at such carbon; (ii) reacting such compound with a chiral reagent selected from the group consisting of a Corey Bakshita-oxazaborolidine and a chiral sulfinamide of the form RS(=O)NH₂ where R is a bulky group [e.g. t-butyl or other branched alkyl or cycloalkyl]; and (iii) forming a chiral center at the indane moiety carbon previously bound to the oxo group by either reacting such compound with a suitable reducing agent along with the chiral reagent in step (ii) or reacting the result of the reaction of such compound with a suitable reducing agent.

In certain of such embodiments, the invention provides a method for chiral synthesis of a chiral compound comprising an indane moiety having a chiral carbon in the five-membered ring of the indane moiety or a chiral compound comprising an oxadiazole-indane moiety having a chiral carbon in the five-membered ring of the indane moiety where the chiral compound has an enantiomeric enrichment of at least 75%, 85%, 90%, 95%, 98%, or 99%.

In certain of such embodiments, the invention provides a method for synthesis of a chiral compound of the invention having an enantiomeric enrichment of at least 75%, 85%, 90%, 95%, 98%, or 99%.

In certain embodiments, a method for the synthesis of a compound comprising an indane moiety having a chiral carbon in the five-membered ring of the indane moiety where the compound is enantiomerically enriched with respect to the chiral carbon is provided. In certain embodiments, a method comprising a step of providing a compound of the structures described herein is provided.

As used in the specification and the appended claims, the singular forms "a," "an" and "the" include plural referents unless the context clearly dictates otherwise.

As used herein, "individual" (as in the subject of the treatment) means both mammals and non-mammals. Mammals include, for example, humans; non-human primates, e.g. apes and monkeys; cattle; horses; sheep; and goats. Non-mammals include, for example, fish and birds.

The term "S1P₁" as used herein refers to subtype 1 of a sphingosine-1-phosphate receptor, while other sphingosine-1-phosphate receptor subtypes are referred to in a corresponding manner, for example, sphingosine-1-phosphate receptor subtype 3 is referred to as "S1P₃".

A "receptor", as is well known in the art, is a biomolecular entity usually comprising a protein that specifically binds a structural class of ligands or a single native ligand in a living organism, the binding of which causes the receptor to transduce the binding signal into another kind of biological action, such as signaling a cell that a binding event has occurred, which causes the cell to alter its function in some manner. An example of transduction is receptor binding of a ligand causing alteration of the activity of a "G-protein" in the cytoplasm of a living cell. Any molecule, naturally occurring or not, that binds to a receptor and activates it for signal transduction, is referred to as an "agonist" or "activator." Any molecule, naturally occurring or not, that binds to a receptor, but does not cause signal transduction to occur, and which can block the binding of an agonist and its consequent signal transduction, is referred to as an "antagonist."

An "S1P₁ compound" or "S1P₁ agonist" or "S1P₁ activator" or "S1P₁ inhibitor" or "S1P₁ antagonist" as the terms are used herein refer to compounds that interact in some way with the S1P receptor subtype 1. They can be agonist or activators, or they can be antagonists or inhibitors. An "S1P₁ compound" of the invention can be selective for action on subtype 1 of the S1P receptor family; for example a compound of the invention can act at a lower concentration on subtype 1 of the S1P receptor family than on other subtypes of the S1P receptor family; more specifically, an "S1P₁ compound" of the invention can selectively act on subtype 1 receptors compared to its action on subtype 3, or "S1P₃" receptors.

In certain embodiments, compounds of the invention are orthostatic agonists. In certain other embodiments, compounds of the invention are allosteric agonists. Receptor agonists may be classified as either orthosteric or allosteric. An orthosteric agonist binds to a site in the receptor that significantly overlaps with the binding of the natural ligand and replicates the key interactions of the natural ligand with the receptor. An orthosteric agonist will activate the receptor by a molecular mechanism similar to that of the natural ligand, will be competitive for the natural ligand, and will be competitively antagonized by pharmacological agents that are competitive antagonists for the natural ligand. An allosteric agonist binds to a site in the receptor that makes some significant interactions that are partly or wholly non-overlapping with the natural ligand. Allosteric agonists are true agonists and not allosteric potentiators. Consequently, they activate receptor signaling alone and without a requirement for a sub-maximal concentration of the natural ligand. Allosteric agonists may be identified when an antagonist known to be competitive for the orthosteric ligand shows non-competitive antagonism. The allosteric agonist site can also be mapped by receptor mutagenesis. The introduction of single point mutations in receptors that retain receptor activation by allosteric agonist, while diminishing or abolishing signaling induced by orthosteric agonist or vice versa provide formal evidence for differences in binding interactions. Orthosteric agonists may destabilize GPCR structure and conformation, while allosteric agonists may either stabilize or destabilize GPCR structure and conformation. Allosteric agonists, by virtue of their different interactions with receptor, may be pharmaceutically useful because the allosteric site may confer additional opportunities for agonist potency and selectivity within a related family of receptor subtypes that share a similar orthosteric ligand. In addition, the allosteric site may require very different physical and chemical properties of an agonist compared to the orthosteric ligand. These chemico-physical properties, which include hydrophobicity, aromaticity, charge distribution and solubility may also provide advantages in generating agonists of varying pharmacokinetic, oral bioavailability, distributional and metabolism profiles that facilitate the development of effective pharmaceutical substances.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

Substantially enantiomerically pure means a level of enantiomeric enrichment of one enantiomer with respect to the other enantiomer of at least 90%, 95%, 98%, 99%, 99.5% or 99.9%.

"Treating" or "treatment" within the meaning herein refers to an alleviation of symptoms associated with a disorder or disease, or inhibition of further progression or worsening of those symptoms, or prevention or prophylaxis of the disease or disorder.

The expression "effective amount", when used to describe use of a compound of the invention in providing therapy to a patient suffering from a disorder or malcondition mediated by a sphingosine-1-phospate receptor of subtype 1 refers to the amount of a compound of the invention that is effective to bind to as an agonist or as an antagonist a $S1P_1$ receptor in the individual's tissues, wherein the $S1P_1$ is implicated in the disorder, wherein such binding occurs to an extent sufficient to produce a beneficial therapeutic effect on the patient. Similarly, as used herein, an "effective amount" or a "therapeutically effective amount" of a compound of the invention refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result by acting as an agonist of sphingosine-1-phosphate receptor subtype 1 ($S1P_1$) activity. A therapeutically effective amount is also one in which any toxic or detrimental effects of compounds of the invention are outweighed by the therapeutically beneficial effects. For example, in the context of treating a malcondition mediated by activation of $S1P_1$, a therapeutically effective amount of an $S1P_1$ agonist of the invention is an amount sufficient to control the malcondition, to mitigate the progress of the malcondition, or to relieve the symptoms of the malcondition. Examples of malconditions that can be so treated include multiple sclerosis, transplant rejection, adult respiratory distress syndrome.

Diseases, disorders and conditions which may be treated by compounds of the invention include rejection of transplanted organs or tissue; graft-versus-host diseases brought about by transplantation; autoimmune syndromes including rheumatoid arthritis; acute respiratory distress syndrome; adult respiratory distress syndrome; influenza; cancer; systemic erythematosus; Hashimoto's thyroiditis; lymphocytic thyroiditis; multiple sclerosis; myasthenia gravis; type I and II diabetes; uveitis; posterior uveitis; uveitis associated with Behcet's disease; uveomeningitis syndrome; allergic encephalomyelitis; chronic allograft vasculopathy; post-infectious autoimmune diseases including rheumatic fever and post-infectious glomerulonephritis; inflammatory and hyperproliferative skin diseases; cutaneous manifestations of immunologically-mediated disorders; psoriasis; atopic dermatitis; osteomyelitis; contact dermatitis; eczematous dermatitis; seborrhoeic dermatitis; lichen planus; pemphigus; bullous pemphigoid; epidermolysis bullosa; urticaria; angioedema; vasculitis; erythema; cutaneous eosinophilia; acne; alopecia areata; keratoconjunctivitis; vernal conjunctivitis; keratitis; herpetic keratitis; dystrophia epithelialis corneae; corneal leukoma; ocular pemphigus; Mooren's ulcer; ulcerative keratitis; scleritis; Graves' ophthalmopathy; Vogt-Koyanagi-Harada syndrome; sarcoidosis; pollen allergies; reversible obstructive airway disease; bronchial asthma; allergic asthma; intrinsic asthma; extrinsic asthma; dust asthma; chronic or inveterate asthma; late asthma and airway hyper-responsiveness; bronchitis; gastric ulcers; ischemic bowel diseases; inflammatory bowel diseases; necrotizing enterocolitis; intestinal lesions associated with thermal burns; celiac diseases; proctitis; eosinophilic gastroenteritis; mastocytosis; Crohn's disease; ulcerative colitis; vascular damage caused by ischemic diseases and thrombosis; atherosclerosis; fatty heart; myocarditis; cardiac infarction; arteriosclerosis; aortitis syndrome; cachexia due to viral disease; vascular thrombosis; migraine; rhinitis; eczema; interstitial nephritis; IgA-induced nephropathy; Goodpasture's syndrome; hemolytic-uremic syndrome; diabetic nephropathy; glomerulosclerosis; glomerulonephritis; multiple myositis; Guillain-Barre syndrome; Meniere's disease; polyneuritis; multiple neuritis; mononeuritis; radiculopathy; hyperthyroidism; Basedow's disease; thyrotoxicosis; pure red cell aplasia; aplastic anemia; hypoplastic anemia; idiopathic thrombocytopenic purpura; autoimmune hemolytic anemia; agranulocytosis; pernicious anemia; megaloblastic anemia; anerythroplasia; osteoporosis; sarcoidosis; fibroid lung; idiopathic interstitial pneumonia; dermatomyositis; leukoderma vulgaris; ichthyosis vulgaris; photoallergic sensitivity; cutaneous T cell lymphoma; polyarteritis nodosa; Huntington's chorea; Sydenham's chorea; myocardosis; scleroderma; Wegener's granuloma; Sjogren's syndrome; adiposis; eosinophilic fascitis; lesions of gingiva, periodontium, alveolar bone, substantia ossea dentis; male pattern alopecia or alopecia senilis; muscular dystrophy; pyoderma; Sezary's syndrome; chronic adrenal insufficiency; Addison's disease; ischemia-reperfusion injury of organs which occurs upon preservation; endotoxin shock; pseudomembranous colitis; colitis caused by drug or radiation; ischemic acute renal insufficiency; chronic renal insufficiency; lung cancer; malignancy of lymphoid origin; acute or chronic lymphocytic; leukemias; lymphoma; psoriasis; inflammatory lung injury, pulmonary emphysema; cataracta; siderosis; retinitis pigmentosa; senile macular degeneration; vitreal scarring; inflammatory eye disease; corneal alkali bum; dermatitis erythema; ballous dermatitis; cement dermatitis; gingivitis; periodontitis; sepsis; pancreatitis; carcinogenesis; metastasis of carcinoma; hypobaropathy; autoimmune hepatitis; primary biliary cirrhosis;' sclerosing cholangitis; partial liver resection; acute liver necrosis; cirrhosis; alcoholic cirrhosis; hepatic failure; fulminant hepatic failure; late-onset hepatic failure; "acute-on-chronic" liver failure. Particularly preferred diseases and conditions which may be treated with compounds of the invention comprise the group consisting of rejection of transplanted organs or tissue; graft-versus-host diseases brought about by transplantation; autoimmune syndromes including rheumatoid arthritis, multiple sclerosis, myasthenia gravis; pollen allergies; type I diabetes; prevention of psoriasis; Crohn's disease; ulcerative colitis, acute respiratory distress syndrome; adult respiratory distress syndrome; influenza; post-infectious autoimmune diseases including rheumatic fever and post-infectious glomerulonephritis; and metastasis of carcinoma.

Furthermore, compounds of Formula I-R or I-S are also useful, in combination with one or several immunosuppressant agents, for the treatment of diseases, disorders and conditions associated with an activated immune system and selected from the list as above-mentioned. According to a preferred embodiment of the invention, said immunosuppressant agent is selected from the group comprising or consisting of cyclosporin, daclizumab, basiliximab, everolimus, tacrolimus (FK506), azathiopirene, leflunomide, 15-deoxyspergualin, or other immunosuppressant drugs All chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention.

The isomers resulting from the presence of a chiral center comprise a pair of non-superimposable isomers that are called "enantiomers." Single enantiomers of a pure compound are optically active, i.e., they are capable of rotating the plane of plane polarized light. Single enantiomers are designated according to the Cahn-Ingold-Prelog system. Once the priority ranking of the four groups is determined, the molecule is oriented so that the lowest ranking group is pointed away from the viewer. Then, if the descending rank order of the other groups proceeds clockwise, the molecule is designated (R) and if the descending rank of the other groups proceeds counterclockwise, the molecule is designated (S). In the examples, the Cahn-Ingold-Prelog ranking is A>B>C>D. The lowest ranking atom, D is oriented away from the viewer.

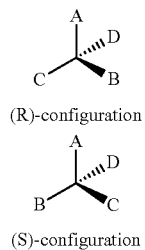

(R)-configuration (S)-configuration

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

Rotational Isomerism

It is understood that due to chemical properties (i.e., resonance lending some double bond character to the C—N bond) of restricted rotation about the amide bond linkage (as illustrated below) it is possible to observe separate rotamer species and even, under some circumstances, to isolate such species, example shown below. It is further understood that certain structural elements, including steric bulk or substituents on the amide nitrogen, may enhance the stability of a rotamer to the extent that a compound may be isolated as, and exist indefinitely, as a single stable rotamer. The present invention therefore includes any possible stable rotamers of compounds of the invention which are biologically active in the treatment of a disease, disorder or condition for which a compound of the invention may be effective as described herein.

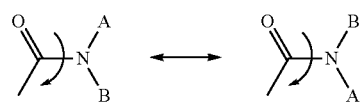

Regioisomerism

The preferred compounds of the present invention have a particular spatial arrangement of substituents on the aromatic rings, which is related to the structure activity relationship demonstrated by the compound class. Often such substitution arrangement is denoted by a numbering system; however, numbering systems are often not consistent between different ring systems. In six-membered aromatic systems, the spatial arrangements are specified by the common nomenclature "para" for 1,4-substitution, "meta" for 1,3-substitution and "ortho" for 1,2-substitution as shown below.

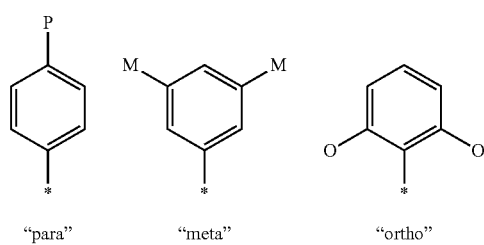

"para"   "meta"   "ortho"

All structures encompassed within a claim are "chemically feasible", by which is meant that the structure depicted by any combination or subcombination of optional substituents meant to be recited by the claim is physically capable of existence with at least some stability as can be determined by the laws of structural chemistry and by experimentation. Structures that are not chemically feasible are not within a claimed set of compounds.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboyxlate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O) CH$_2$C(O)R', C(S)R', C(O)OR', OC(O)R', C(O)N(R')$_2$, OC(O)N(R')$_2$, C(S)N(R')$_2$, (CH$_2$)$_{0-2}$NHC(O)R', (CH$_2$)$_{0-2}$N (R')N(R')$_2$, N(R')N(R')C(O)R', N(R')N(R')C(O)OR', N(R')N (R')CON(R')$_2$, N(R')SO$_2$R', N(R')SO$_2$N(R')$_2$, N(R')C(O) OR', N(R')C(O)R', N(R')C(S)R', N(R')C(O)N(R')$_2$, N(R')C (S)N(R')$_2$, N(COR')COR', N(OR')R', C(=NH)N(R')$_2$, C(O) N(OR')R', or C(=NOR)R' wherein R' can be hydrogen or a carbon-based moiety, and wherein the carbon-based moiety can itself be further substituted.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl(oxo), carboxyl, ester, amide, imide, urethane, and urea groups; and nitrogen in imines, hydroxyimines, oximes, hydrazones, amidines, guanidines, and nitriles. The substituents of the substituted groups can further be substituted with alkyl, alkenyl, cycloalkyl, aryl, heteroaryl, and alkynyl groups as defined herein, which can themselves be further substituted. For example, an C$_{1-4}$ alkyl group can be substituted with an amide, and the amide can further be substituted with another C$_{1-4}$ alkyl, which can further be substituted.

Substituted ring groups such as substituted aryl, heterocyclyl and heteroaryl groups also include rings and fused ring systems in which a bond to a hydrogen atom is replaced with a bond to a carbon atom. Therefore, substituted aryl, heterocyclyl and heteroaryl groups can also be substituted with alkyl, alkenyl, cycloalkyl, aryl, heteroaryl, and alkynyl groups as defined herein, which can themselves be further substituted.

The term "heteroatoms" as used herein refers to non-carbon and non-hydrogen atoms, capable of forming covalent bonds with carbon, and is not otherwise limited. Typical heteroatoms are N, O, and S. When sulfur (S) is referred to, it is understood that the sulfur can be in any of the oxidation states in which it is found, thus including sulfoxides (R—S (O)—R') and sulfones (R—S(O)$_2$—R'), unless the oxidation state is specified; thus, the term "sulfone" encompasses only the sulfone form of sulfur; the term "sulfide" encompasses only the sulfide (R—S—R') form of sulfur. When the phrases such as "heteroatoms selected from the group consisting of O, NH, NR' and S," or "[variable] is O, S . . . " are used, they are understood to encompass all of the sulfide, sulfoxide and sulfone oxidation states of sulfur.

Alkyl groups include straight chain and branched alkyl groups and cycloalkyl groups having from 1 to about 20 carbon atoms (C$_{1-20}$ alkyl), and typically from 1 to 12 carbons (C$_{1-12}$ alkyl)or, in some embodiments, from 1 to 8 carbon atoms (C$_{1-8}$ alkyl) or, in some embodiments, from 1 to 4 carbon atoms (C$_{1-4}$ alkyl) or, in some embodiments, from 1 to 3 carbon atoms (C$_{1-3}$ alkyl). Examples of straight chain alkyl groups include, but are not limited to methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups. The group "n-hydroxy C$_{1-4}$ alkyl" represents an C$_{1-4}$ alkyl substituted with a terminal hydroxy group.

Cycloalkyl groups are alkyl groups forming a ring structure, which can be substituted or unsubstituted. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4- 2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

The terms "carbocyclic" and "carbocycle" denote a ring structure wherein the atoms of the ring are carbon. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, amino, hydroxy, cyano, carboxy, nitro, thio, alkoxy, and halogen groups.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to —CH=CH(CH$_3$), —CH=C(CH$_3$)$_2$, —C(CH$_3$)=CH$_2$, —C(CH$_3$)=CH(CH$_3$), —C(CH$_2$CH$_3$)=CH$_2$, vinyl cyclohexenyl, cyclopentenyl, cyclohexadienyl, butadienyl, pentadienyl, and hexadienyl among others.

The term "cycloalkenyl" alone or in combination denotes a cyclic alkenyl group wherein at least one double bond is present in the ring structure. Cycloalkenyl groups include cycloalkyl groups having at least one double bond between two adjacent carbon atoms. Thus for example, cycloalkenyl groups include but are not limited to cyclohexenyl, cyclopentenyl, and cyclohexadienyl groups.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C($CH_3$), —C≡C($CH_2CH_3$), —$CH_2$C≡CH, —$CH_2$C≡C($CH_3$), and —$CH_2$C≡C($CH_2CH_3$), among others.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like), and also includes substituted aryl groups that have other groups, including but not limited to alkyl, halo, amino, hydroxy, cyano, carboxy, nitro, thio, or alkoxy groups, bonded to one of the ring atoms. Representative substituted aryl groups can be mono-substituted or substituted more than once, such as, but not limited to, 2-, 3-, 4-, 5-, or 6-substituted phenyl or naphthyl groups, which can be substituted with groups including but not limited to those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. The aryl moiety or the alkyl moiety or both are optionally substituted with other groups, including but not limited to alkyl, halo, amino, hydroxy, cyano, carboxy, nitro, thio, or alkoxy groups. Aralkenyl group are alkenyl groups as defined above in which a hydrogen or carbon bond of an alkyl group is replaced with a bond to an aryl group as defined above.

Heterocyclyl groups include aromatic and non-aromatic ring compounds (heterocyclic rings) containing 3 or more ring members, of which one or more is a heteroatom such as, but not limited to, N, O, S, or P. In some embodiments, heterocyclyl groups include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a $C_2$-heterocyclyl can be a 5-membered ring with two carbon atoms and three hetero atoms, a 6-membered ring with two carbon atoms and four heteroatoms and so forth. Likewise a $C_4$-heterocyclyl can be a 5-membered ring with one heteroatom, a 6-membered ring with two heteroatoms, and so forth. The number of carbon atoms plus the number of heteroatoms sums up to equal the total number of ring atoms. A saturated heterocyclic ring refers to a heterocyclic ring containing no unsaturated carbon atoms.

The phrase "heterocyclyl group" includes fused ring species including those having fused aromatic and non-aromatic groups. The phrase also includes polycyclic ring systems containing a heteroatom such as, but not limited to, quinuclidyl and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heterocyclyl groups can be substituted. Representative substituted heterocyclyl groups can be mono-substituted or substituted more than once, including but not limited to, rings containing at least one heteroatom which are mono, di, tri, tetra, penta, hexa, or higher-substituted with substituents such as those listed above, including but not limited to alkyl, halo, amino, hydroxy, cyano, carboxy, nitro, thio, and alkoxy groups.

Heteroaryl groups are aromatic ring compounds containing 5 or more ring members, of which, one or more is a heteroatom such as, but not limited to, N, O, and S. A heteroaryl group designated as a $C_2$-heteroaryl can be a 5-membered ring with two carbon atoms and three heteroatoms, a 6-membered ring with two carbon atoms and four heteroatoms and so forth. Likewise a $C_4$-heteroaryl can be a 5-membered ring with one heteroatom, a 6-membered ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl. The term also includes heteroaryl groups that have other groups bonded to one of the ring members, including but not limited to alkyl, halo, amino, hydroxy, cyano, carboxy, nitro, thio, or alkoxy groups. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N-hydroxyimidazolyl, anthracenyl (1-anthracenyl, 2-anthracenyl, 3-anthracenyl), thiophenyl (2-thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4-imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3-pyridyl, 4-pyridyl), pyrimidinyl (2-pyrimidinyl, 4-pyrimidinyl, 5-pyrimidinyl, 6-pyrimidinyl), pyrazinyl, pyridazinyl (3- pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4(2,3-dihydro-benzo[b]furanyl), 5-(2,3-dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b] thiophenyl), indolyl (1-indolyl 2-indolyl, 3-indolyl, 4-indolyl, 5-indolyl, 6-indolyl, 7-indolyl), indazole (1-indazolyl, 3-indazolyl, 4-indazolyl, 5-indazolyl, 6-indazolyl, 7-indazolyl), benzimidazolyl (1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6-benzothiazolyl, 7-benzothiazolyl), carbazolyl (1-carbazolyl, 2-carbazolyl, 3-carbazolyl, 4-carbazolyl), 5H-dibenz[b,f]azepine (5H-dibenz[b,f]azepin-1-yl, 5H-dibenz[b,f]azepine-2-yl, 5H-dibenz[b,f]azepine-3-yl, 5H-dibenz[b,f]azepine-4-yl, 5H-dibenz[b,f]azepine-5-yl), 10,11-dihydro-5H-dibenz[b,f] azepine (10,11-dihydro-5H-dibenz[b,f]azepine-1-yl, 10,11-dihydro-5H-dibenz[b,f]azepine-2-yl, 10,11-dihydro-5H-dibenz[b,f] azepine-3-yl, 10,11-dihydro-5H-dibenz[b,f] azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-2-yl methyl (α-picolyl), pyridine-3-yl methyl (β-picolyl), pyridine-4-yl methyl (γ-picolyl), tetrahydrofuran-2-yl ethyl, and indol-2-yl propyl. Heterocyclylalkyl groups can be substituted on the heterocyclyl moiety, the alkyl moiety, or both.

Heteroarylalkyl groups are alkyl groups as defined above in which a hydrogen or carbon bond of an alkyl group is replaced with a bond to a heteroaryl group as defined above. Heteroarylalkyl groups can be substituted on the heteroaryl moiety, the alkyl moiety, or both.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic. By "spirocyclic" is meant the class of structures wherein two rings are fused at a single tetrahedral carbon atom, as is well known in the art.

A "monocyclic, bicyclic or polycyclic, aromatic or partially aromatic ring" as the term is used herein refers to a ring system including an unsaturated ring possessing 4n+2 pi electrons, or a partially reduced (hydrogenated) form thereof. The aromatic or partially aromatic ring can include additional fused, bridged, or spiro rings that are not themselves aromatic or partially aromatic. For example, naphthalene and tetrahydronaphthalene are both a "monocyclic, bicyclic or polycyclic, aromatic or partially aromatic ring" within the meaning herein. Also, for example, a benzo-[2.2.2]-bicyclooctane is also a "monocycle, bicyclic or polycyclic, aromatic or partially aromatic ring" within the meaning herein, containing a phenyl ring fused to a bridged bicyclic system. A fully saturated ring has no double bonds therein, and is carbocyclic or heterocyclic depending on the presence of heteroatoms within the meaning herein.

The term "alkoxy" refers to an oxygen atom connected to an alkyl group, including a cycloalkyl group, as are defined above. Examples of linear alkoxy groups include but are not limited to methoxy, ethoxy, n-propoxy, n-butoxy, n-pentyloxy, n-hexyloxy, and the like. Examples of branched alkoxy include but are not limited to isopropoxy, sec-butoxy, tert-butoxy, isopentyloxy, isohexyloxy, and the like. Examples of cyclic alkoxy include but are not limited to cyclopropyloxy, cyclobutyloxy, cyclopentyloxy, cyclohexyloxy, and the like.

The terms "aryloxy" and "arylalkoxy" refer to, respectively, an aryl group bonded to an oxygen atom and an aralkyl group bonded to the oxygen atom at the alkyl moiety. Examples include but are not limited to phenoxy, naphthyloxy, and benzyloxy.

An "acyl" group as the term is used herein refers to a group containing a carbonyl moiety wherein the group is bonded via the carbonyl carbon atom. The carbonyl carbon atom is also bonded to another carbon atom, which can be part of an alkyl, aryl, aralkyl cycloalkyl, cycloalkylalkyl, heterocyclyl, heterocyclylalkyl, heteroaryl, heteroarylalkyl group or the like. In the special case wherein the carbonyl carbon atom is bonded to a hydrogen, the group is a "formyl" group, an acyl group as the term is defined herein. An acyl group can include 0 to about 12-20 additional carbon atoms bonded to the carbonyl group. An acyl group can include double or triple bonds within the meaning herein. An acryloyl group is an example of an acyl group. An acyl group can also include heteroatoms within the meaning here. A nicotinoyl group (pyridyl-3-carbonyl) group is an example of an acyl group within the meaning herein. Other examples include acetyl, benzoyl, phenylacetyl, pyridylacetyl, cinnamoyl, and acryloyl groups and the like. When the group containing the carbon atom that is bonded to the carbonyl carbon atom contains a halogen, the group is termed a "haloacyl" group. An example is a trifluoroacetyl group.

The term "amine" includes primary, secondary, and tertiary amines having, e.g., the formula N(group)$_3$ wherein each group can independently be H or non-H, such as alkyl, aryl, and the like. Amines include but are not limited to $RNH_2$, for example, alkylamines, arylamines, alkylarylamines; $R_2NH$ wherein each R is independently selected, such as dialkylamines, diarylamines, aralkylamines, heterocyclylamines and the like; and $R_3N$ wherein each R is independently selected, such as trialkylamines, dialkylarylamines, alkyldiarylamines, triarylamines, and the like. The term "amine" also includes ammonium ions as used herein.

An "amino" group is a substituent of the form —$NH_2$, —NHR, —$NR_2$, —$NR_3^+$, wherein each R is independently selected, and protonated forms of each. Accordingly, any compound substituted with an amino group can be viewed as an amine.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., —C(O)N R'R", and —NR'C(O)R" groups, respectively. The R' and R" of the C-amide may join together to form a heterocyclic ring with the nitrogen atom. Amide groups therefore include but are not limited to carbamoyl groups (—C(O)NH$_2$) and formamide groups (—NHC(O)H). A "carboxamido" group is a group of the formula C(O)NR$_2$, wherein R can be H, alkyl, aryl, etc.

The term "urethane" (or "carbamyl") includes N- and O-urethane groups, i.e., —NRC(O)OR and —OC(O)NR$_2$ groups, respectively.

The term "sulfonamide" (or "sulfonamido") includes S- and N-sulfonamide groups, i.e., —SO$_2$NR$_2$ and —NRSO$_2$R groups, respectively. Sulfonamide groups therefore include but are not limited to sulfamoyl groups (—SO$_2$NH$_2$).

The term "amidine" or "amidino" includes groups of the formula —C(NR)NR$_2$. Typically, an amidino group is —C(NH)NH$_2$.

The term "guanidine" or "guanidino" includes groups of the formula —NRC(NR)NR$_2$. Typically, a guanidino group is —NHC(NH)NH$_2$.

"Halo," "halogen," and "halide" include fluorine, chlorine, bromine and iodine.

The terms "comprising," "including," "having," "composed of," are open-ended terms as used herein, and do not preclude the existence of additional elements or components. In a claim element, use of the forms "comprising," "including," "having," or "composed of" means that whatever element is comprised, had, included, or composes is not necessarily the only element encompassed by the subject of the clause that contains that word.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as NH$_4^+$ or the cations of various amines, including tetraalkyl ammonium salts such as tetramethylammonium and alkyl ammonium salts such as tromethamine salts, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present invention may take the form of salts. The term "salts" embraces addition salts of free acids or free bases which are compounds of the invention. Salts can be "pharmaceutically-acceptable salts." The term "pharmaceutically-acceptable salt" refers to salts which possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds of the invention.

Suitable pharmaceutically-acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,NT-dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of compounds, for example in their purification by recrystallization. All of these salts may be prepared by conventional means from the corresponding compound by reacting, for example, the appropriate acid or base with the compound. The term "pharmaceutically acceptable salts" refers to nontoxic inorganic or organic acid and/or base addition salts, see, for example, Lit et al., Salt Selection for Basic Drugs (1986), *Int J. Pharm.*, 33, 201-217, incorporated by reference herein Nonlimiting examples of potential salts of this invention include but are not limited to hydrochloride, citrate, glycolate, fumarate, malate, tartrate, mesylate, esylate, cinnamate, isethionate, sulfate, phosphate, diphosphate, nitrate, hydrobromide, hydroiodide, succinate, formate, acetate, dichloroacetate, lactate, p-toluenesulfonate, pamitate, pidolate, pamoate, salicylate, 4-aminosalicylate, benzoate, 4-acetamido benzoate, glutamate, aspartate, glycolate, adipate, alginate, ascorbate, besylate, camphorate, camphorsulfonate, camsylate, caprate, caproate, cyclamate, laurylsulfate, edisylate, gentisate, galactarate, gluceptate, gluconate, glucuronate, oxoglutarate, hippurate, lactobionate, malonate, maleate, mandalate, napsylate, napadisylate, oxalate, oleate, sebacate, stearate, succinate, thiocyanate, undecylenate, and xinafoate.

A "hydrate" is a compound that exists in a composition with water molecules. The composition can include water in stoichiometic quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "homolog" of a compound of the invention is a compound having one or more atoms of the compound replaced by an isotope of such atom. For example, homologs include compounds with deuterium in place of some hydrogen atoms of the compound such as compounds of the invention in which the methyl groups of the isopropoxy moiety of Formulas I—R and I—S are fully or partially deuterated (e.g., (D$_3$C)$_2$C—O—). Isotopic substitutions which may be made in the formation of homologs of the invention include non-radioactive (stable) atoms such as deuterium and carbon 13, as well as radioactive (unstable) atoms such as tritium, carbon 14, iodine 123, iodine 125, etc.

A "solvate" is a similar composition except that a solvent other that water replaces the water. For example, methanol or ethanol can form an "alcoholate", which can again be stoichiometic or non-stoichiometric. As the term is used herein a "solvate" refers to a solid form, i.e., a compound in solution in a solvent, while it may be solvated, is not a solvate as the term is used herein.

A "prodrug" as is well known in the art is a substance that can be administered to a patient where the substance is converted in vivo by the action of biochemicals within the patients body, such as enzymes, to the active pharmaceutical ingredient. Examples of prodrugs include esters of carboxylic acid groups, which can be hydrolyzed by endogenous esterases as are found in the bloodstream of humans and other mammals.

Any compound which can be converted in vivo to the active drug by chemical or biochemical transformations functions as a prodrug. Prodrugs of claimed compounds are covered under this invention.

Some examples of prodrugs within the scope of this invention include:

i. If the compound contains a hydroxyl group, the hydroxyl group may be modified to form an ester, carbonate, or carbamate. Examples include acetate, pivalate, methyl and ethyl carbonates, and dimethylcarbamate. The ester may also be derived from amino acids such as glycine, serine, or lysine.

ii. If the compound contains an amine group, the amine group may be modified to form an amide. Examples include acetamide or derivatization with amino acids such as glycine, serine, or lysine.

Certain compounds of the invention and their salts may exist in more than one crystal form and the present invention includes each crystal form and mixtures thereof. In addition, the compounds of the present invention can exist in unsolvated as well as solvated forms with pharmaceutically acceptable solvents such as water to form hydrates or adducts with alcohols such as $C_{1-4}$-alkanols, and the like. Furthermore, compounds of this invention can be isolated in association with solvent molecules by crystallization from evaporation of an appropriate solvent. Such solvents include but are not limited to toluene, tetrahydrofuran, dioxane, dimethylformamide, acetonitrile, acetates such as methyl acetate, ethyl acetate, butyl acetate, isobutyl acetate, propyl- and isopropyl acetate, ethers such as diethyl ether and ethyl ether, alcohols such as methanol, ethanol, 1- or 2-butanol, 1- or 2-propanol, pentanol, and dimethylsulfoxide. In general, a depiction for the compound by structure or name is considered to embrace the compound in any form (e.g., by itself, as a hydrate, solvate, or otherwise in a mixture).

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described. Moreover, where features or aspects of the invention are described in terms of Markush groups, those skilled in the art will recognize that the invention is also thereby described in terms of any combination of individual members or subgroups of members of Markush groups. Thus, for example, if X is described as selected from the group consisting of bromine, chlorine, and iodine, and Y is described as selected from the group consisting of methyl, ethyl, and propyl, claims for X being bromine and Y being methyl are fully described.

Compositions and Combination Treatments

The $S1P_1$ compounds, their pharmaceutically acceptable salts or hydrolyzable esters of the present invention may be combined with a pharmaceutically acceptable carrier to provide pharmaceutical compositions useful for treating the biological conditions or disorders noted herein in mammalian species, and more preferably, in humans. The particular carrier employed in these pharmaceutical compositions may vary depending upon the type of administration desired (e.g. intravenous, oral, topical, suppository, or parenteral).

In preparing the compositions in oral liquid dosage forms (e.g. suspensions, elixirs and solutions), typical pharmaceutical media, such as water, glycols, oils, alcohols, flavoring agents, preservatives, coloring agents and the like can be employed. Similarly, when preparing oral solid dosage forms (e.g. powders, tablets and capsules), carriers such as starches, sugars, diluents, granulating agents, lubricants, binders, disintegrating agents and the like can be employed.

Another aspect of an embodiment of the invention provides compositions of the compounds of the invention, alone or in combination with another $S1P_1$ inhibitor or another type of therapeutic agent, or both. As set forth herein, compounds of the invention include stereoisomers, tautomers, solvates, hydrates, salts including pharmaceutically acceptable salts, and mixtures thereof. Compositions containing a compound of the invention can be prepared by conventional techniques, e.g. as described in Remington: *The Science and Practice of Pharmacy,* 19th Ed., 1995, incorporated by reference herein. The compositions can appear in conventional forms, for example capsules, tablets, aerosols, solutions, suspensions or topical applications.

Typical compositions include a compound of the invention and a pharmaceutically acceptable excipient which can be a carrier or a diluent. For example, the active compound will usually be mixed with a carrier, or diluted by a carrier, or enclosed within a carrier which can be in the form of an ampoule, capsule, sachet, paper, or other container. When the active compound is mixed with a carrier, or when the carrier serves as a diluent, it can be solid, semi-solid, or liquid material that acts as a vehicle, excipient, or medium for the active compound. The active compound can be adsorbed on a granular solid carrier, for example contained in a sachet. Some examples of suitable carriers are water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent can include any sustained release material known in the, art, such as glyceryl monostearate or glyceryl distearate, alone or mixed with a wax.

The formulations can be mixed with auxiliary agents which do not deleteriously react with the active compounds. Such additives can include wetting agents, emulsifying and suspending agents, salt for influencing osmotic pressure, buffers and/or coloring substances preserving agents, sweetening agents or flavoring agents. The compositions can also be sterilized if desired.

The route of administration can be any route which effectively transports the active compound of the invention which inhibits the enzymatic activity of the focal adhesion kinase to the appropriate or desired site of action, such as oral, nasal, pulmonary, buccal, subdermal, intradermal, transdermal or parenteral, e.g., rectal, depot, subcutaneous, intravenous, intraurethral, intramuscular, intranasal, ophthalmic solution or an ointment, the oral route being preferred.

For parenteral administration, the carrier will typically comprise sterile water, although other ingredients that aid solubility or serve as preservatives can also be included. Furthermore, injectable suspensions can also be prepared, in which case appropriate liquid carriers, suspending agents and the like can be employed.

For topical administration, the compounds of the present invention can be formulated using bland, moisturizing bases such as ointments or creams.

If a solid carrier is used for oral administration, the preparation can be tabletted, placed in a hard gelatin capsule in powder or pellet form or it can be in the form of a troche or lozenge. If a liquid carrier is used, the preparation can be in the form of a syrup, emulsion, soft gelatin capsule or sterile injectable liquid such as an aqueous or non-aqueous liquid suspension or solution.

Injectable dosage forms generally include aqueous suspensions or oil suspensions which can be prepared using a suitable dispersant or wetting agent and a suspending agent Injectable forms can be in solution phase or in the form of a suspension, which is prepared with a solvent or diluent. Acceptable solvents or vehicles include sterilized water, Ringer's solution, or an isotonic aqueous saline solution. Alternatively, sterile oils can be employed as solvents or suspending agents. Preferably, the oil or fatty acid is non-volatile, including natural or synthetic oils, fatty acids, mono-, di- or tri-glycerides.

For injection, the formulation can also be a powder suitable for reconstitution with an appropriate solution as described above. Examples of these include, but are not limited to, freeze dried, rotary dried or spray dried powders, amorphous powders, granules, precipitates, or particulates. For injection, the formulations can optionally contain stabilizers, pH modifiers, surfactants, bioavailability modifiers and combinations of these. The compounds can be formulated for parenteral administration by injection such as by bolus injection or continuous infusion. A unit dosage form for injection can be in ampoules or in multi-dose containers.

The formulations of the invention can be designed to provide quick, sustained, or delayed release of the active ingredient after administration to the patient by employing procedures well known in the art. Thus, the formulations can also be formulated for controlled release or for slow release.

Compositions contemplated by the present invention can include, for example, micelles or liposomes, or some other encapsulated form, or can be administered in an extended release form to provide a prolonged storage and/or delivery effect. Therefore, the formulations can be compressed into pellets or cylinders and implanted intramuscularly or subcutaneously as depot injections. Such implants can employ known inert materials such as silicones and biodegradable polymers, e.g., polylactide-polyglycolide. Examples of other biodegradable polymers include poly(orthoesters) and poly(anhydrides).

For nasal administration, the preparation can contain a compound of the invention which inhibits the enzymatic activity of the focal adhesion kinase, dissolved or suspended in a liquid carrier, preferably an aqueous carrier, for aerosol application. The carrier can contain additives such as solubilizing agents, e.g., propylene glycol, surfactants, absorption enhancers such as lecithin (phosphatidylcholine) or cyclodextrin, or preservatives such as parabens.

For parenteral application, particularly suitable are injectable solutions or suspensions, preferably aqueous solutions with the active compound dissolved in polyhydroxylated castor oil.

Dosage forms can be administered daily, or more than once a day, such as twice or thrice daily. Alternatively dosage forms can be administered less frequently than daily, such as every other day, or weekly, if found to be advisable by a prescribing physician.

An embodiment of the invention also encompasses prodrugs of a compound of the invention which on administration undergo chemical conversion by metabolic or other physiological processes before becoming active pharmacological substances. Conversion by metabolic or other physiological processes includes without limitation enzymatic (e.g, specific enzymatically catalyzed) and non-enzymatic (e.g., general or specific acid or base induced) chemical transformation of the prodrug into the active pharmacological substance. In general, such prodrugs will be functional derivatives of a compound of the invention which are readily convertible in vivo into a compound of the invention. Conventional procedures for the selection and preparation of suitable prodrug derivatives are described, for example, in *Design of Prodrugs*, ed. H. Bundgaard, Elsevier, 1985.

In another embodiment, there are provided methods of making a composition of a compound described herein including formulating a compound of the invention with a pharmaceutically acceptable carrier or diluent. In some embodiments, the pharmaceutically acceptable carrier or diluent is suitable for oral administration. In some such embodiments, the methods can further include the step of formulating the composition into a tablet or capsule. In other embodiments, the pharmaceutically acceptable carrier or diluent is suitable for parenteral administration. In some such embodiments, the methods further include the step of lyophilizing the composition to form a lyophilized preparation.

The compounds of the invention can be used therapeutically in combination with i) one or more other $S1P_1$ inhibitors and/or ii) one or more other types of protein kinase inhibitors and/or one or more other types of therapeutic agents which can be administered orally in the same dosage form, in a separate oral dosage form (e.g., sequentially or non-sequentially) or by injection together or separately (e.g., sequentially or non-sequentially).

Accordingly, in another embodiment the invention provides combinations, comprising:

a) a compound of the invention as described herein; and
b) one or more compounds comprising:
  i) other compounds of the present invention, ii) other medicaments adapted for treatment of a malcondition for which activation of $S1P_1$ is medically indicated, for example multiple sclerosis, transplant rejection, or adult respiratory distress syndrome.

Combinations of the invention include mixtures of compounds from (a) and (b) in a single formulation and compounds from (a) and (b) as separate formulations. Some combinations of the invention can be packaged as separate formulations in a kit. In some embodiments, two or more compounds from (b) are formulated together while a compound of the invention is formulated separately.

The dosages and formulations for the other agents to be employed, where applicable, will be as set out in the latest edition of the *Physicians' Desk Reference*, incorporated herein by reference.

Methods of Treatment

In certain embodiments, the present invention encompasses orally bioavailable compounds that specifically agonize $S1P_1$ without binding ($S1P_2$, $S1P_3$ and $S1P_4$), or having significant specificity over ($S1P_5$), other EDG receptors. A selective $S1P_1$ agonist can be used to treat diseases with an autoimmune, hyperactive immune-response, angiogenesis or inflammatory components, but would not be limited to such conditions. Selective $S1P_1$ agonists have advantages over current therapies by increasing the therapeutic window because of reduced toxicity due to engagement of other EDG receptors.

In certain embodiments, the present invention encompasses compounds that bind with high affinity and specificity to the $S1P_1$ receptor in an agonist manner. Upon ligation of the $S1P_1$ receptor with agonist, signaling proceeds through $G_{\alpha i}$, inhibiting the generation of cAMP by adenylate cyclase.

In certain embodiments, the present invention provides a method for activating or agonizing (i.e., to have an agonic effect, to act as an agonist) a sphingosine-1-phosphate receptor subtype, such as $S1P_1$, with a compound of the invention. The method involves contacting the receptor with a suitable concentration of an inventive compound to bring about activation of the receptor. The contacting can take place in vitro, for example in carrying out an assay to determine the S1P receptor activation activity of an inventive compound undergoing experimentation related to a submission for regulatory approval.

In certain embodiments, the method for activating an S1P receptor, such as $S1P_1$, can also be carried out in vivo, that is, within the living body of a mammal, such as a human patient or a test animal. The inventive compound can be supplied to the living organism via one of the routes as described above, e.g., orally, or can be provided locally within the body tissues, for example by injection of a tumor within the organism. In the presence of the inventive compound, activation of the receptor takes place, and the effect thereof can be studied.

An embodiment of the present invention provides a method of treatment of a malcondition in a patient for which activation of an S1P receptor, such as $S1P_1$, is medically indicated, wherein the patient is administered the inventive compound in a dosage, at a frequency, and for a duration to produce a beneficial effect on the patient. The inventive compound can be administered by any suitable means, examples of which are described above.

Preparation of Certain Embodiments

Scheme 1:

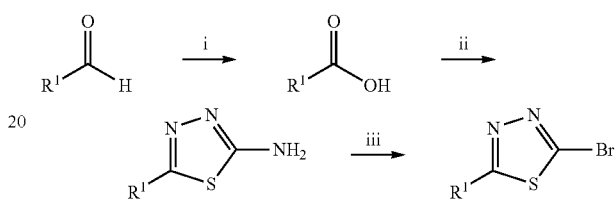

Reagents: (i) $KH_2PO_4$, $H_2O_2$, $NaClO_2$, $CH_3CN$; (ii) $H_2NNHCSNH_2$, $POCl_3$; (iii) $CuBr_2$, isoamylnitrite, $CH_3CN$.

Scheme 2:

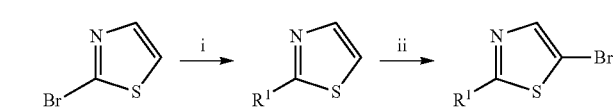

Reagents: (i) $R^1$-boronic acid, $K_2CO_3$, $Pd(PPh_3)_4$, DME, $H_2O$; (ii) NBS, DMF.

Scheme 3:

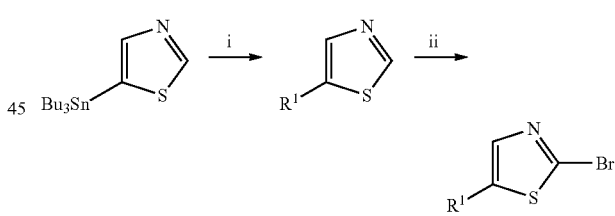

Reagents: (i) $R^1$—I, $Pd(PPh_3)_2Cl_2$, THF; (ii) $Br_2$, AcOK, AcOH.

Scheme 4:

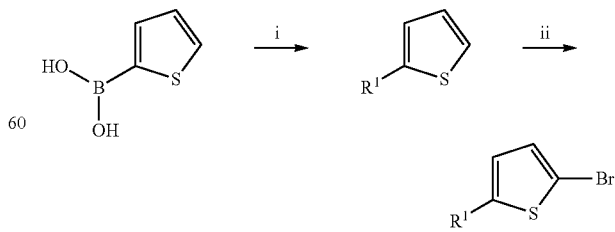

Reagents: (i) $R^1$—Br, $K_2CO_3$, $Pd(PPh_3)_4$, DME, $H_2O$; (ii) NBS, DMF.

Scheme 5:

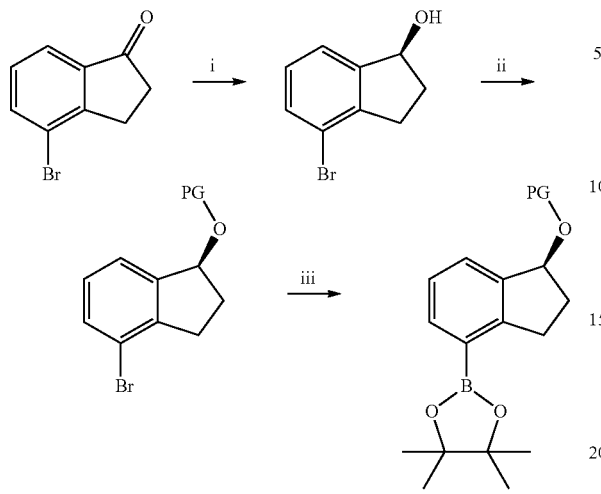

Reagents: (i) (S)-2-methyl-CBS-oxazaborolidine,BH$_3$—Me$_2$S, toluene, DCM; (ii) PG—Cl, (where PG is protecting group), e.g. TBSCl, imidazole, DMF; (iii) bis(pinacolato)diboron, PdCl$_2$(dppf)•CH$_2$Cl$_2$, KOAc, 1,4-dioxane.

The (S)-enantiomer was prepared in same manner as outlined in Scheme 5 by the use of (R)-2-methyl-CBS-oxazaborolidine in Step i. The racemic material can be prepared in an analogous manner using NaBH$_4$ as reducing agent in Step i.

Scheme 6:

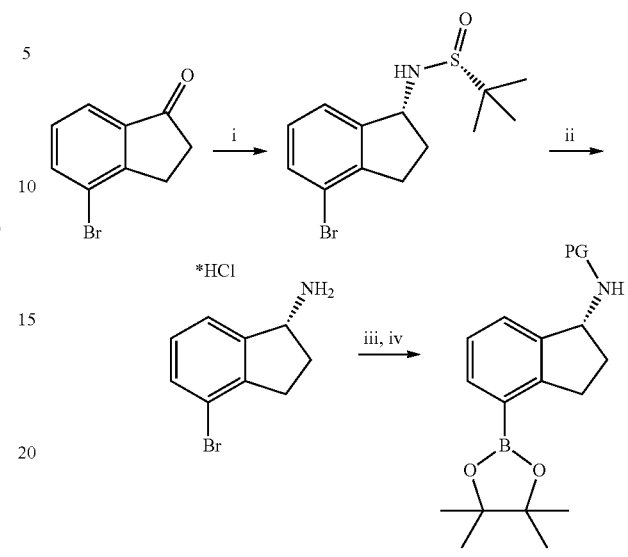

Reagents: (i) (R)-2-methylpropane-2-sulfinamide, NaBH$_4$, THF, toluene; (ii) 4N HCl, 1,4-dioxane; (iii) PG = di-tert-butyldicarbonate, triethylamine, DCM; (iv) bis(pinacolato)diboron, PdCl$_2$(dppf). CH$_2$Cl$_2$, KOAc, 1,4-dioxane.

The (S)-enantiomer was prepared in same manner as outlined in Scheme 6 by the use of (S)-2-methylpropane-2-sulfinamide in Step i.

Scheme 7:

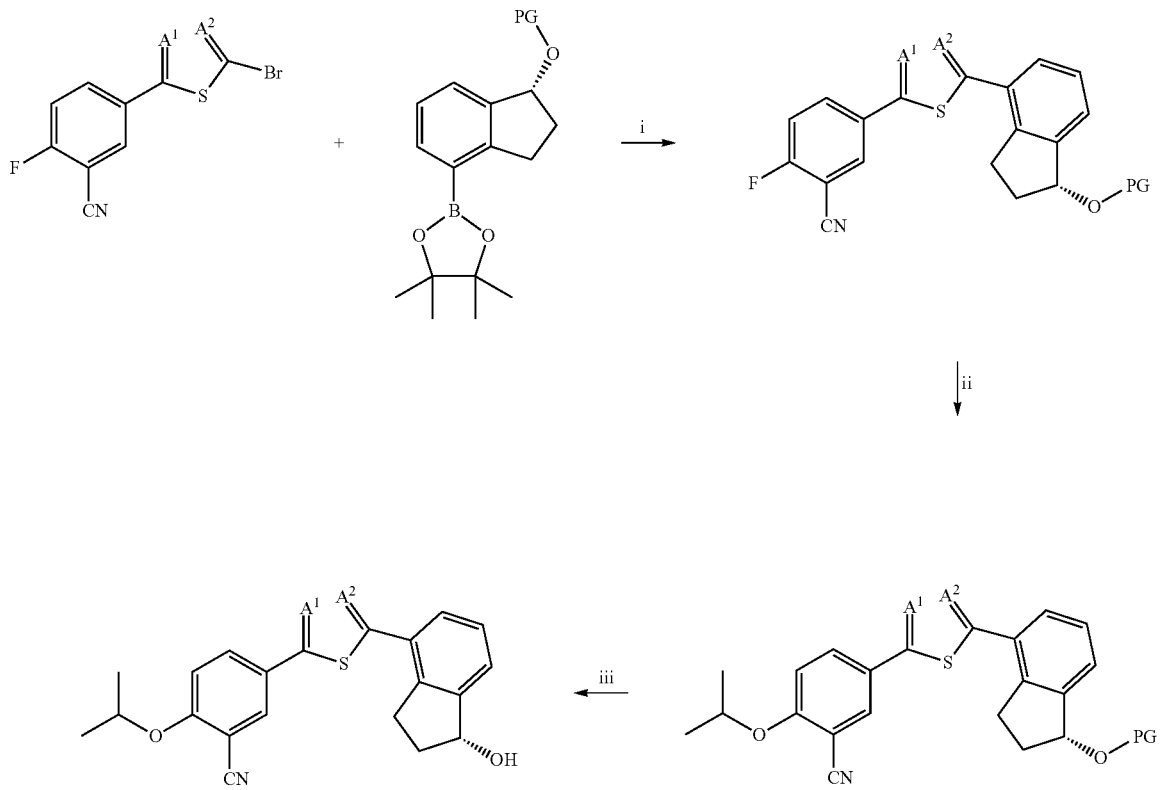

Reagents: (i) K$_2$CO$_3$, Pd(PPh$_3$)$_4$, DME, H$_2$O; (ii) NaOiPr, iPrOH; (iii) deprotection, e.g. TBAF, THF or HCl, 1,4-dioxane.

The (S)-enantiomers were prepared in same manner as outlined in Scheme 7 by the use of (S)-tert-butyldimethyl((4-(4,4,5,5-tetramethyl-1,3,2-dioxaborolan-2-yl)-2,3-dihyro-1H-inden-1-yl)oxy)silane in Step i. Racemic indanol was prepared in same manner using racemic tert-butyldimethyl((4-(4,4,5,5-tetramethyl-1,3,2-dioxaborolan-2-yl)-2,3-dihydro-1H-inden-1-yl)oxy)silane in Step i.

Scheme 8:

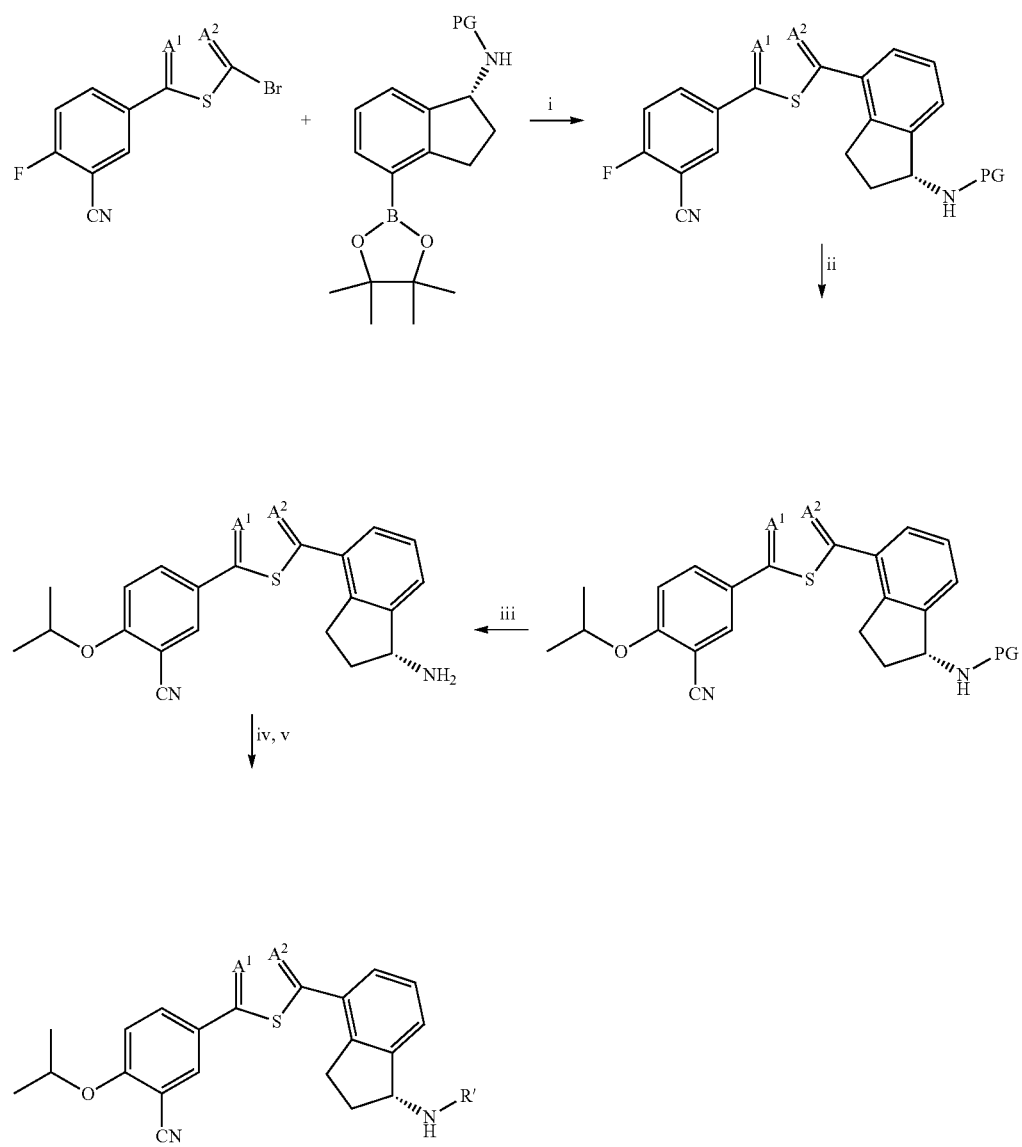

Reagents: (i) K$_2$CO$_3$, Pd(PPh$_3$)$_4$, DME, H$_2$O; (ii) NaOiPr, iPrOH; (iii) 4N HCl, 1,4-dioxane; (iv) (a) R′——LG or R″——LG, where LG represents a leaving group, K$_2$CO$_3$, CH$_3$CN; (b) R$^3$——CO$_2$H or R$^4$——CO$_2$H, HOBt, EDC, DMF or R$^3$——COCl or R$^4$——CO$_2$H, TEA, DCM; (c) R$^3$——SO$_2$Cl or R$^5$——SO$_2$Cl, TEA, DCM (d) R$^4$——CHO, HOAc, NaBH$_4$ or NaCNBH$_3$ or Na(OAc)$_3$BH, MeOH; (e) R$^3$——OCOCl or R$^4$——OCOCl, DIEA, DMF; (f) HN(R$^7$R$^7$), CDI, TEA, DCM; (g) H$_2$NSO$_2$NH$_2$, D, dioxane; (h) dimethyloxirane, D, EtOH; (x) (a) If R′ or R″ = H, then reactions (ix)(a-d) can be performed; (b) If R′ or R″ contains an ester then (i) hydrolysis NaOH, EtOH or (ii) reduction NaBH$_4$, MeOH can be performed; (c) If R′ or R″ contains an acid then couplings HN(R$^7$R$^7$), HOBt, EDC, DMF can be performed; (d) If R′ or R″ contains an appropriate activated alkene then Michael additions HN(R$^7$R$^7$), DMF can be performed.

The (S)-enantiomers were prepared in same manner as outlined in Scheme 8 by the use of (S)-tert-butyl(4-(4,4,5,5-tetramethyl-1,3,2-dioxaborolan-2-yl)-2,3-dihydro-1H-inden-1-yl)carbamate in Step i.

Scheme 9:

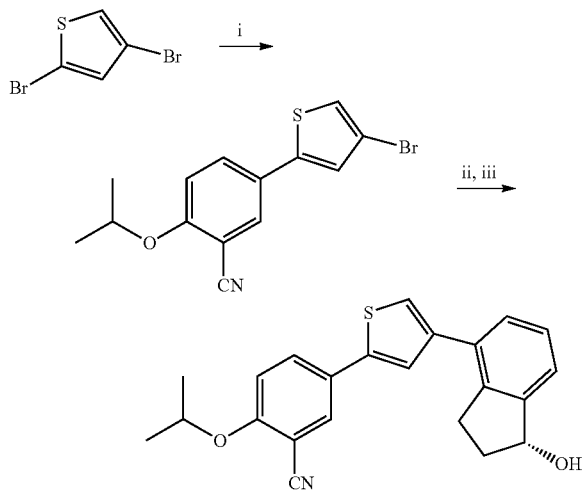

Reagents: (i) (3-cyano-4-isopropoxyphenyl)boronic acid, $K_2CO_3$, $Pd(PPh_3)_4$, DME, $H_2O$; (ii) (R)-, (S)-, or racemic tert-butyldimethyl((4-(4,4,5,5-tetramethyl-1,3,2-dioxaborolan-2-yl)-2,3-dihydro-1H-inden-1-yl)oxy)silane, $K_2CO_3$, $Pd(PPh_3)_4$, DME, $H_2O$; (iii) TBAF, THF.

Scheme 10:

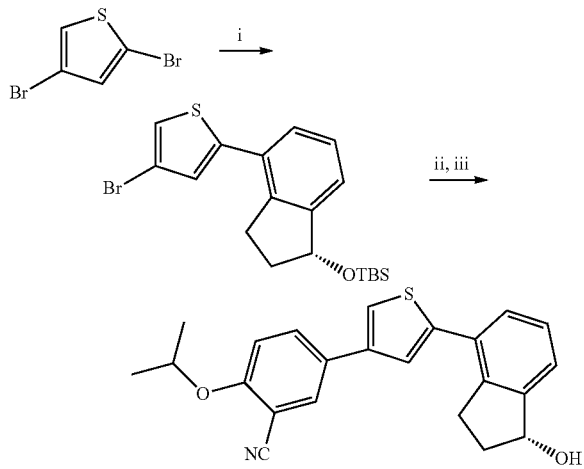

Reagents: (i) (ii) (R)-, (S)-, or racemic tert-butyldimethyl((4-(4,4,5,5-tetramethyl-1,3,2-dioxaborolan-2-yl)-2,3-dihydro-1H-inden-1-yl)oxy)silane, $K_2CO_3$, $Pd(PPh_3)_4$, DME, $H_2O$; (ii) (3-cyano-4-isopropoxyphenyl)boronic acid, $K_2CO_3$, $Pd(PPh_3)_4$, DME, $H_2O$; (iii) TBAF, THF.

EXAMPLES

General Methods $^1$H NMR (400 MHz) and $^{13}$C NMR (100 MHz) were obtained in solution of deuteriochloroform ($CDCl_3$), deuteriomethanol ($CD_3OD$) or dimethyl sulfoxide—$D_6$ (DMSO). NMR spectra were processed using Mestrec 5.3.0 and 6.0.1. $^{13}$C NMR peaks that are bracketed are two rotomers of the same carbon. Mass spectra (LCMS) were obtained using an Agilent 1100/6110 HPLC system equipped with a Thompson ODS-A, 100 A, 5µ (50×4.6 mm) column using water with 0.1% formic acid as the mobile phase A, and acetonitrile with 0.1% formic acid as the mobile phase B. The gradient was 20-100% with mobile phase B over 2.5 min then held at 100% for 2.5 mins. The flow rate was 1 mL/min. Unless otherwise indicated, the LCMS data provided uses this method. For more hydrophobic compounds, the following gradient was used, denoted as Method 1: 40-95% over 0.5 min, hold at 95% for 8.5 min, then return to 40% over 2 min, with a flow rate of 1 mL/min. Final compounds were checked for purity using Method 2: 5% for 1 min, 5-95% over 9 min, then hold at 95% for 5 min, with a flow rate of 1 mL/min. Method 3: 20-100% over 2.5 min then held at 100% for 4.5 min, with the flow rate of 1 mL/min. Enantiomeric excess was determined by integration of peaks that were separated on a Chiralpak AD-H, 250×4.6 mm column at a flow rate of 1 mL/min and an isocratic mobile phase. Unless otherwise indicated, the chiral data provided uses this method. Alternatively, chiral separations were performed under the following conditions, denoted as Chiral Method 1: Chiralpak AY-H, 250×4.6 mm column at a flow rate of 1 mL/min and an isocratic mobile phase. Chiral Method 2: Chiralcel OZ-3, 150×4.6 mm at flow rate of 1 mL/min and an isocratic mobile phase. The pyridine, dichloromethane (DCM), tetrahydrofuran (THF), and toluene used in the procedures were from Aldrich Sure-Seal bottles kept under nitrogen ($N_2$). All reactions were stirred magnetically and temperatures are external reaction temperatures. Chromatographies were carried out using a Combiflash Rf flash purification system (Teledyne Isco) equipped with Redisep (Teledyne Isco) silica gel ($SiO_2$) columns. Preparative HPLC purifications were done on Varian ProStar/PrepStar system using water containing 0.05% trifluoroacetic acid as mobile phase A, and acetonitrile with 0.05% trifluoroacetic acid as mobile phase B. The gradient was 10-80% with mobile phase B over 12 min, hold at 80% for 2 min, and then return to 10% over 2 min with flow rate of 22 mL/min. Other methods similar to this may have been employed. Fractions were collected using a Varian Prostar fraction collector and were evaporated using a Savant SpeedVac Plus vacuum pump. Compounds with salt-able centers were presumed to be the trifluoroacetic acid (TFA) salt. Microwave heating was performed using a Biotage Initiator microwave reactor equipped with Biotage microwave vessels. The following abbreviations are used: ethyl acetate (EA), triethylamine (TEA), diethyl amine (DEA), hydroxybenzotriazole (HOBt), 1-ethyl-3-(3-dimethylaminopropyl) carbodiimide hydrochloride (EDC), isopropanol (IPA), dimethylformamide (DMF), dimethyl acetamide (DMA). Norit is activated charcoal.

Experimental Procedures 3-cyano-4-fluorobenzoic acid

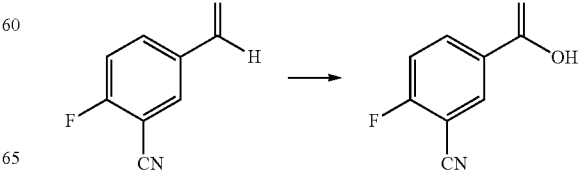

To a solution of 3-cyano-4-fluorobenzaldehyde (45 g, 301 mmol) in CH$_3$CN (450 mL) was added potassium phosphate monobasic (24 g, 176 mmol) in water (225 mL) and 30% hydrogen peroxide in water (30 mL). The reaction mixture was cooled to 0° C. and sodium chlorite (60 g, 663 mmol) in water (450 mL) was added dropwise over 2 h. The resulting yellow suspension was stirred at room temperature until production of oxygen ceased (4 h). Sodium sulfite (30 g, 238 mmol) in water (100 mL) was added and the reaction mixture stirred for 1 h. The reaction was quenched with 2N HCl (500 mL) and the resulting solid was filtered and washed with water. The aqueous phase was extracted with EA (2×500 mL). The combined organic layers were washed with brine (200 mL), dried over MgSO$_4$, concentrated, and combined with the collected solid to produce a total of 48.5 g (97%) of crude 3-cyano-4-fluorobenzoic acid as a white solid. LCMS-ESI (m/z) calculated for C$_8$H$_4$FNO$_2$: 165.0; found 166.1 [M+H]$^+$, t$_R$=2.54 min. $^1$H NMR (400 MHz, DMSO) δ 13.60 (s, 1H), 8.41 (dd, J=6.3, 2.1 Hz, 1H), 8.30 (ddd, J=8.8, 5.3, 2.2 Hz, 1H), 7.66 (t, J=9.0 Hz, 1H).

5-(5-amino-1,3,4-thiadiazol-2-yl)-2-fluorobenzonitrile (TDZ INT-1)

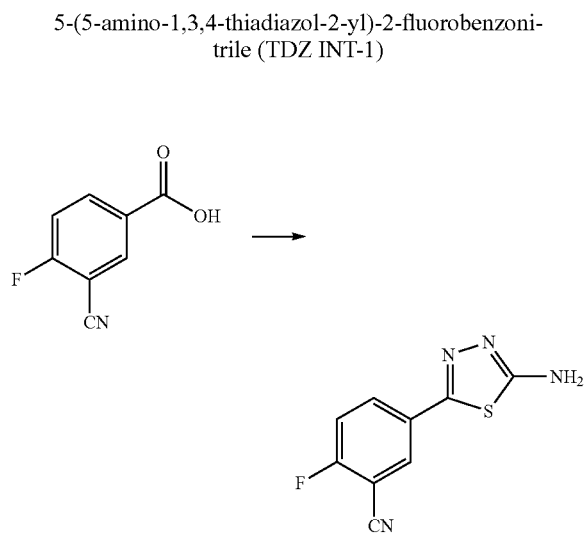

To a stirred mixture of 3-cyano-4-fluorobenzoic acid (37.3 g, 225 mmol) and thiosemicarbazide (22.6 g, 248 mmol) was added POCl$_3$ (148 mL) at 0° C. The reaction mixture was stirred at 0° C. for 1 h and then heated to 85° C. for 6 h. The resulting yellow solution was cooled to room temperature and concentrated to 50% volume. The residue was cooled to 0° C. and water was added (300 mL) drop wise. (Caution: exothermic and violent reaction with gas evolution). The mixture was heated to 90° C. for 1 h then cooled to room temperature. EA was added EA (300 mL) and the reaction mixture stirred for 10 min and before filtration. The collected solid was dispersed into water (270 mL), cooled to 0° C., and neutralized with 50% NaOH aqueous solution to pH8. The resulting solid was filtered, washed thoroughly with water, and dried under high vacuum to afford 26 g (52%) of 5-(5-amino-1,3,4-thiadiazol-2-yl)-2-fluorobenzonitrile TDZ INT-1 as pale yellow solid which was used in next experiment without purification. LCMS-ESI (m/z) calculated for C$_9$H$_5$FN$_4$S: 220.0; found 221.1 [M+H]$^+$, t$_R$=2.44 min. $^1$H NMR (400 MHz, DMSO) δ 8.29 (dd, J=6.1, 2.3 Hz, 1H), 8.19 (ddd, J=8.9, 5.2, 2.4 Hz, 1H), 7.64 (t, J=9.0 Hz, 1H), 7.58 (s, 2H). $^{13}$C NMR (101 MHz, DMSO) δ 169.82, 164.25, 161.68, 133.68, 131.65, 128.96, 117.96, 113.77, 101.59.

5-(3,4-Diethoxyphenyl)-1,3,4-thiadiazol-2-amine TDZ INT-2 was synthesized in a similar manner as 5-(5-amino-1,3,4-thiadiazol-2-yl)-2-fluorobenzonitrile TDZ INT-1 using 3,4-diethoxybenzoic acid. LCMS-ESI (m/z) calculated for C$_{12}$H$_{15}$N$_3$O$_2$S: 265.3; found 266.1. [M+H]$^+$, t$_R$=2.58 min. $^1$H NMR (400 MHz, DMSO) δ 7.45-7.31 (m, 1H), 7.23 (dd, J=8.3, 2.1 Hz, 1H), 7.06 (d, J=8.4 Hz, 1H), 4.31-3.94 (m, 4H), 3.4 (s, 2H), 1.42 (qd, J=6.8, 3.3 Hz, 6H).

5-(5-bromo-1,3,4-thiadiazol-2-yl)-2-fluorobenzonitrile (TDZ INT-3)

To a stirred solution of 5-(5-amino-1,3,4-thiadiazol-2-yl)-2-fluorobenzonitrile TDZ INT-1 (25 g, 113 mmol) and copper bromide (30.4 g, 136 mmol) in CH$_3$CN (400 mL) was added isoamylnitrite (15.9 g, 136 mmol) and the mixture stirred at room temperature for 5 h. The reaction was partitioned between EA (2×250 mL) and 1N HCl (250 mL). The combined organic extracts were washed with brine, dried over MgSO$_4$, and concentrated. The crude product was crystallized from EA to afford 23.5 g (73%) of 5-(5-bromo-1,3,4-thiadiazol-2-yl)-2-fluorobenzonitrile TDZ INT-3 as a pale yellow solid. LCMS-ESI (m/z) calculated for: C$_9$H$_3$BrFN$_3$S: 284.1; found 285.9 [M+H]$^+$, t$_R$=3.27 min. $^1$H NMR (400 MHz, DMSO) δ 8.58 (dd, J=6.0, 2.3 Hz, 1H), 8.40 (ddd, J=8.9, 5.1, 2.4 Hz, 1H), 7.76 (t, J=9.0 Hz, 1H); $^{13}$C NMR (101 MHz, DMSO) δ 168.61, 162.47, 140.32, 134.88, 133.38, 126.13, 117.88, 112.91.

2-Bromo-5-(3,4-diethoxyphenyl)-1,3,4-thiadiazole TDZ INT-4 was synthesized in similar manner as described for the synthesis of 2-bromo-5-(3,4-diethoxyphenyl)-1,3,4-thiadiazole TDZ TNT-3 using 5-(3,4-diethoxyphenyl)-1,3,4-thiadiazol-2-amine. LCMS-ESI (m/z) calculated for: C$_{12}$H$_{13}$BrN$_2$O$_2$S: 328.0; found 329.1 [M+H]$^+$, t$_R$=2.58 min.

$^1$H NMR (400 MHz, CDCl$_3$) δ 7.47 (d, J=2.1 Hz, 1H), 7.25 (d, J=2.1 Hz, 1H), 6.84 (d, J=8.4 Hz, 1H), 4.10 (dq, J=8.9, 7.0 Hz, 4H), 1.42 (t, J=7.0 Hz, 6H).

2-fluoro-5-(thiazol-2-yl)benzonitrile (THZ INT-1)

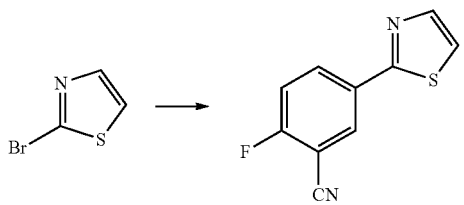 [SMILES: Brc1nccs1 ; N#Cc1cc(-c2nccs2)ccc1F]

A solution of 2-bromothiazole (25 g, 153.4 mmol), (3-cyano-4-fluorophenyl)boronic acid (25.3 g, 153.3 mmol), K$_2$CO$_3$ (63.6 g, 460 mmol) and 3:1 DME/H$_2$O (205 mL) was purged with N$_2$ for 1 h before the addition of Pd(PPh$_3$)$_4$ (9.2 g, 7.9 mmol). The mixture was further degassed with N$_2$ for 5 min and then heated to 85° C. for 7 h under N$_2$. Upon cooling, the reaction mixture was diluted with EA (250 mL), washed with water (200 mL) and brine (200 mL), and dried over MgSO$_4$. The reaction mixture was filtered and concentrated to give beige solid. The crude product was purified by recrystallization from 20% EA/hexanes to afford 22 g (71%) of 2-fluoro-5-(thiazol-2-yl)benzonitrile THZ INT-1 as a pale yellow solid. LCMS-ESI (m/z) calculated for C$_{10}$H$_5$FN$_2$S: 204.2; found 205.0 [M+H]$^+$, $t_R$=3.26 min. $^1$H NMR (400 MHz, CDCl$_3$) δ 8.21-8.16 (m, 1H), 8.15-8.08 (m, 1H), 7.86-7.81 (m, 1H), 7.36-7.32 (m, 1H), 7.27-7.21 (m, 1H). $^{13}$C NMR (101 MHz, CDCl$_3$) δ 164.31, 162.22, 143.73, 132.68, 131.28, 128.34, 119.94, 116.98, 113.10.

5-(5-bromothiazol-2-yl)-2-fluorobenzonitrile (THZ INT-2)

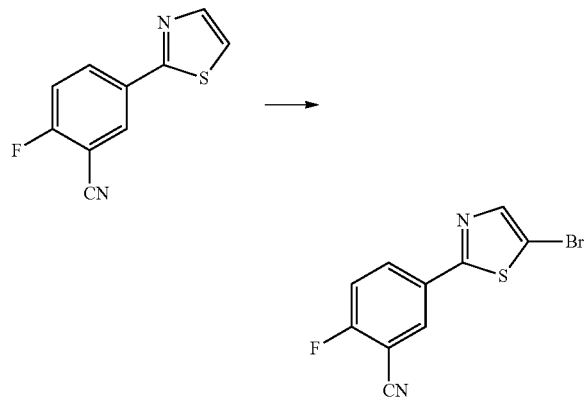

To 2-fluoro-5-(thiazol-2-yl)benzonitrile (21.8 g, 106.7 mmol) in anhydrous DMF (200 mL) was added recrystallized N-bromosuccinimide (22.7 g, 128 mmol). The reaction mixture was stirred at room temperature for 23 h under N$_2$. The reaction mixture was basified with 1N NaOH and washed with EA and brine. The combined organic layers were dried over MgSO$_4$, filtered, and concentrated to yield orange oil. The crude product was purified by silica gel flash chromatography (20% EA/Hexanes) to produce 21 mg (70%) of 5-(5-bromothiazol-2-yl)-2-fluorobenzonitrile THZ INT-2 as half-white solid. LCMS-ESI (m/z) calculated for C$_{10}$H$_4$BrFN$_2$S: 283.1; found 284.9 [M+H]$^+$, $t_R$=3.82 min. $^1$H NMR (400 MHz, CDCl$_3$) δ 8.15 (dd, J=5.9, 2.3 Hz, 1H), 8.08 (ddd, J=8.8, 4.9, 2.3 Hz, 1H), 7.78 (d, J=4.8 Hz, 1H), 7.31 (t, J=8.6 Hz, 1H).

(S)-4-bromo-2,3-dihydro-1H-inden-1-ol (IND INT-1)

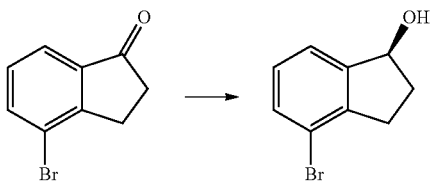 [SMILES: O=C1CCc2c(Br)cccc21 ; O[C@H]1CCc2c(Br)cccc21]

To a 100 mL 3-neck flask equipped with an internal thermometer and an addition funnel was added (R)-(+)-2-methyl-CBS-oxazaborolidine (1.6 ml, 1M solution in toluene) and borane-dimethylsulfide (150 uL) under N$_2$. The reaction was stirred at room temperature for 10 min then diluted with DCM (10 mL). Borane-dimethylsulfide (6.0 mL) was added and the reaction cooled to −20° C. A solution of 4-Bromo-2,3-dihydro-1H-inden-1-one (2.5 g, 11.8 mmol) in DCM (10 mL) was added dropwise over 20 min while maintaining the reaction temperature at −20±5° C. The reaction was stirred for 2 h after the addition was complete, then quenched by the dropwise addition of MeOH (10 mL). The reaction mixture was diluted with MeOH (20 mL) and the solvent distilled at atmospheric pressure. MeOH (30 mL) was added in two portions and the distillation was repeated twice. All the solvent was evaporated to give a solid which was purified by silica gel column chromatography (EA/hexanes) and recrystallization from 5:1 hexane/EA (30 mL) to provide 1.56 g (62%) of (S)-4-bromo-2,3-dihydro-1H-inden-1-ol as a white powder IND INT-1. LCMS-ESI (m/z) calculated for C$_9$H$_9$BrO: 213.1; found 196.9 [M-OH]$^+$, $t_R$=3.06 min. $^1$H NMR (400 MHz, CDCl$_3$) δ 7.40 (d, J=7.9 Hz, 1H), 7.33 (d, J=7.5 Hz, 1H), 7.10 (t, J=7.7 Hz, 1H), 5.29 (dd, J=12.6, 6.9 Hz, 1H), 3.05 (ddd, J=16.6, 8.7, 4.6 Hz, 1H), 2.87-2.71 (m, 1H), 2.50 (dddd, J=13.2, 8.4, 7.0, 4.6 Hz, 1H), 1.94 (dddd, J=13.5, 8.8, 6.6, 5.5 Hz, 1H), 1.80 (d, J=7.1 Hz, 1H). $^{13}$C NMR (101 MHz, CDCl$_3$) δ 146.82, 143.50, 131.24, 128.58, 123.21, 120.25, 76.83, 34.69, 31.19. Chiral HPLC: (S)-4-bromo-2,3-dihydro-1H-inden-1-ol was eluted using 10% IPA in hexanes: >99.9% % ee, $t_R$=6.27 min.

(R)-4-bromo-2,3-dihydro-1H-inden-1-ol IND INT-2 was prepared in an analogous manner using (S)-(−)-2-methyl-CBS-oxazaborolidine: 97.6% ee, $t_R$ for (R)-enantiomer=5.83 min:

(S)-((4-bromo-2,3-dihydro-1H-inden-1-yl)oxy)(tert-butyl)dimethylsilane (IND INT-3)

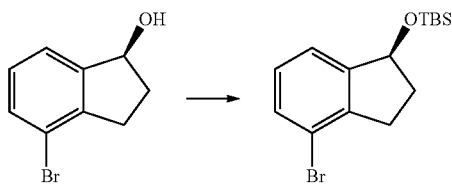 [SMILES: O[C@H]1CCc2c(Br)cccc21 ; CC(C)(C)[Si](C)(C)O[C@H]1CCc2c(Br)cccc21]

To a solution of (S)-4-bromo-2,3-dihydro-1H-inden-1-ol IND INT-1 (1.56 g, 7.3 mm) in DMF (5 mL) was added TBDMSCl (1.3 g, 8.7 mmol) and imidazole (1.24 g, 18.3 mmol) and the reaction mixture was stirred at room temperature overnight. The reaction mixture was diluted with saturated NaHCO$_3$ solution (30 mL) and extracted with EA (2×50 mL). The organic layers were washed with water and brine, and dried over MgSO$_4$. The crude product was purified by chromatography (EA/hexane) to afford 2.1 g (88%) of (S)-((4-bromo-2,3-dihydro-1H-inden-1-yl)oxy)(tert-butyl)dimethylsilane IND INT-3 as white solid. LCMS-ESI (m/z) calculated for C$_{15}$H$_{23}$BrOSi: 327.3; no M$^+$ observed, $t_R$=5.73 min (Method 2). $^1$H NMR (400 MHz, CDCl$_3$) δ 7.35 (d, J=7.8 Hz, 1H), 7.22 (d, J=7.4 Hz, 1H), 7.07 (t, J=7.7 Hz, 1H), 5.28 (t, J=7.1 Hz, 1H), 3.00 (ddd, J=16.4, 9.1, 2.9 Hz, 1H), 2.73 (dt, J=16.5, 8.3 Hz, 1H), 2.42 (dddd, J=12.8, 8.0, 7.1, 3.0 Hz, 1H), 1.91 (dtd, J=12.8, 8.9, 7.1 Hz, 1H), 0.98-0.88 (m, 9H), 0.14 (d, J=7.4 Hz, 6H).

(R)-((4-bromo-2,3-dihydro-1H-inden-1-yl)oxy)(tert-butyl)dimethylsilane IND INT-4 was prepared in an analogous fashion using (R)-4-bromo-2,3-dihydro-1H-inden-1-ol.

(±)-4-bromo-2,3-dihydro-1H-inden-1-ol (IND INT-5)

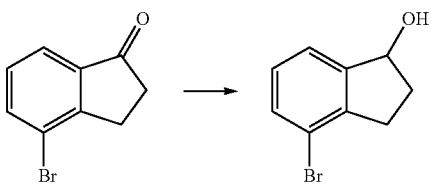 [SMILES: O=C1CCc2c(Br)cccc21 ; OC1CCc2c(Br)cccc21]

To a stirring solution of 4-bromoindanone (3 g, 14.2 mmol) in anhydrous EtOH (30mL) was added sodium borohydride (0.36 g, 9.5 mmol) and silica gel (2 g) at 0° C. The reaction was stirred at 0° C. for 20 min and was allowed to stir at room temperature for 2 h. The reaction mixture was quenched with saturated NaHCO$_3$ solution (10 mL) and concentrated to remove EtOH. The aqueous layer was extracted with EA (3×20 mL) and the organic phase was dried over MgSO$_4$. After concentration, the crude product was purified by chromatography (EA/hexane) to yield (±)-4-bromo-2,3-dihydro-1H-inden-1-ol IND INT-5 (2.56 g, 85%) as a white solid. LCMS-ESI (m/z) calculated for C$_9$H$_9$BrO: 213.07; found 195.0 [M−H$_2$O]$^+$, $t_R$=3.07 min. $^1$H NMR (400 MHz, CDCl$_3$) δ 7.35 (d, J=7.9, 1H), 7.27 (d, J=7.4, 1H), 7.05 (t, J=7.7, 1H), 5.23 (t, J=6.2, 1H), 3.00 (ddd, J=16.6, 8.8, 4.6, 1H), 2.84-2.66 (m, 1H), 2.45 (dddd, J=13.2, 8.4, 7.0, 4.6, 1H), 1.96-1.70 (m, 2H).

(S)-tert-butyldimethyl((4-(4,4,5,5-tetramethyl-1,3,2-dioxaborolan-2-yl)-2,3-dihydro-1H-inden-1-yl)oxy)silane (IND INT-6)

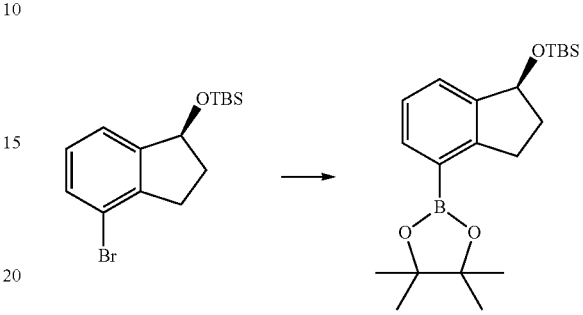

A solution of (S)-((4-bromo-2,3-dihydro-1H-inden-1-yl)oxy)(tert-butyl)dimethylsilane IND INT-3 (0.2 mg, 0.61 mmol), 4,4,4',4',5,5,5',5'-octamethyl-2,2'-bi(1,3,2-dioxaborolane) (0.17 g, 0.67 mmol), and potassium acetate (1.8 g, 0.45 mmol) in anhydrous 1,4-dioxane (4 mL) was degassed by passing N$_2$ through the solution for 10 min. PdCl$_2$(dppf).CH$_2$Cl$_2$ (99 mg, 0.12 mmol) was added and the reaction mixture heated at 85° C. overnight. The solvent was removed under vacuum. The residue was dissolved in EA (10 mL), and filtered through celite. The filtrate was washed with water and brine, dried over MgSO$_4$ and filtered. The crude product was purified by chromatography (EA/hexanes) to afford 26 mg (45%) (S)-tert-butyldimethyl((4-(4,4,5,5-tetramethyl-1,3,2-dioxaborolan-2-yl)-2,3-dihydro-1H-inden-1-yl)oxy)silane IND INT-6 as a white solid. LCMS-ESI (m/z) calculated for C$_{21}$H$_{35}$BO$_3$Si: 374.4; found 245.0 [M−OTBS]$^+$, $t_R$=6.57 min (Method 1). $^1$H NMR (400 MHz, CDCl$_3$) δ 7.66 (d, J=7.2 Hz, 1H), 7.36 (dd, J=8.7, 4.3 Hz, 1H), 7.19 (dd, J=9.4, 5.4 Hz, 1H), 5.21 (t, J=7.0 Hz, 1H), 3.26 (ddd, J=16.9, 8.9, 3.0 Hz, 1H), 2.86 (dt, J=16.8, 8.3 Hz, 1H), 2.48-2.23 (m, 1H), 1.86 (dtd, J=12.6, 8.8, 7.0 Hz, 1H), 1.38-1.23 (m, 12H), 1.00-0.81 (m, 9H), 0.22-0.07 (m, 6H). $^{13}$C NMR (101 MHz, CDCl$_3$) δ 149.59, 145.08, 134.83, 134.75, 126.92, 125.78, 83.39, 76.52, 36.29, 30.78, 25.96, 24.96, 18.28, −4.29, −4.55.

(R)-tert-butyldimethyl((4-(4,4,5,5-tetramethyl-1,3,2-dioxaborolan-2-yl)-2,3-dihydro-1H-inden-1-yl)oxy)silane IND INT-7 was prepared in an analogous fashion using (R)-((4-bromo-2,3-dihydro-1H-inden-1-yl)oxy)(tert-butyl)dimethylsilane IND INT-4. Racemic (±)-tert-butyldimethyl((4-(4,4,5,5-tetramethyl-1,3,2-dioxaborolan-2-yl)-2,3-dihydro-1H-inden-1-yl)oxy)silane IND INT-8 was prepared in an analogous fashion from IND INT-5.

General Procedure 1: Coupling of Heterocyclic Bromide to Indanol Boronate

A 20 mL microwave vial was charged sequentially with heterocyclic bromide (1 eq), (R)-(S)- or racemic indanol dioxaborolane (IND INT-6, 7 or 8, 1 eq), DME:H$_2$O (3:1, 0.05 M) and potassium carbonate (3 eq). The mixture was degassed by bubbling N$_2$ gas through the stirring solution for 10 min. Pd(PPh$_3$)$_4$ (0.07 eq) was added and the mixture degassed for additional 2 min. The vial as was capped and subjected to microwave irradiation at 100° C. until reaction completed (40-60 min). Additional bromide was added if needed. The vial was cooled to room temperature, diluted with EA (10× volume), washed with water and brine, dried over MgSO$_4$, and concentrated. The crude product was purified by silica gel column chromatography (EA/hexanes).

(S)-5-(5-(1-(((tert-butyldimethylsilyl)oxy)-2,3-dihydro-1H-inden-4-yl)-1,3,4-thiadiazol-2-yl)-2-fluorobenzonitrile

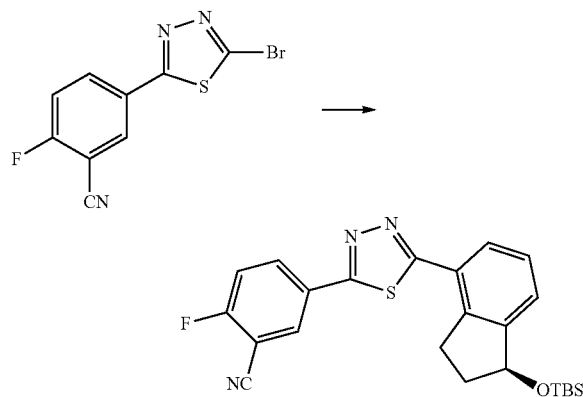

Prepared using General Procedure 1: A 20 mL microwave vial was charged with 5-(5-bromo-1,3,4-thiadiazol-2-yl)-2-fluorobenzonitrile TDZ INT-3 (30 mg, 0.1 mmol), (S)-tert-butyldimethyl((4-(4,4,5,5-tetramethyl-1,3,2-dioxaborolan-2-yl)-2,3-dihydro-1H-inden-1-yl)oxy)silane IND INT-6 (43.6 mg, 0.11 mmol), potassium carbonate (44 mg, 0.32 mmol) and a 3:1 mixture of DME/H$_2$O (2 mL). The reaction mixture was degassed by bubbling N$_2$ gas through the stirring solution for 10 min. Pd(PPh$_3$)$_4$ was added and mixture degassed for additional 2 min. The vial was subjected to microwave irradiation at 100° C. for 40 min. The reaction mixture was cooled to room temperature, diluted with EA (10 mL), and washed with water and brine. The organic layer dried over MgSO$_4$, concentrated, and purified by silica gel chromatography (EA/hexanes) to provide 25 mg (44%) of (S)-5-(5-(1-(((tert-butyldimethylsilyl)oxy)-2,3-dihydro-1H-inden-4-yl)-1,3,4-thiadiazol-2-yl)-2-fluorobenzonitrile as a light yellow solid. LCMS-ESI (m/z) calculated for C$_{24}$H$_{26}$FN$_3$OSSi: 451.15; found 452.1 [M+H]$^+$, t$_R$=4.53 min (Method 1). $^1$H NMR (400 MHz, CDCl$_3$) δ 8.34-8.25 (m, 2H), 7.85 (d, J=7.6 Hz, 1H), 7.49 (d, J=7.5 Hz, 1H), 7.44-7.34 (m, 2H), 5.34 (t, J=7.1 Hz, 1H), 3.46 (ddd, J=16.8, 9.0, 2.8 Hz, 1H), 3.13 (dt, J=16.8, 8.3 Hz, 1H), 2.61-2.50 (m, 1H), 2.08-1.96 (m, 1H), 0.98-0.95 (m, 9H), 0.22-0.17 (m, 6H).

(R)-5-(5-(1-(((tert-butyldimethylsilyl)oxy)-2,3-dihydro-1H-inden-4-yl)-1,3,4-thiadiazol-2-yl)-2-fluorobenzonitrile was prepared in an analogous fashion using (R)-tert-butyldimethyl((4-(4,4,5,5-tetramethyl-1,3,2-dioxaborolan-2-yl)-2,3-dihydro-1H-inden-1-yl)oxy)silane IND INT-7.

(S)-5-(5-(1-(((tert-butyldimethylsilyl)oxy)-2,3-dihydro-1H-inden-4-yl)thiazol-2-yl)-2-fluorobenzonitrile

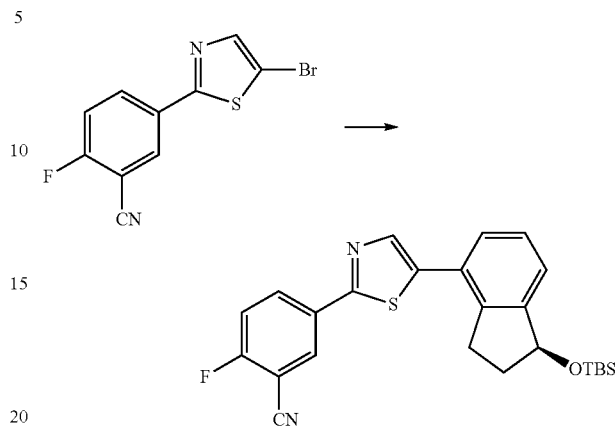

Prepared using General Procedure 1. A solution of 5-(5-bromothiazol-2-yl)-2-fluorobenzonitrile THZ INT-2 (0.12 g, 0.42 mmol), (S)-tert-butyldimethyl((4-(4,4,5,5-tetramethyl-1,3,2-dioxaborolan-2-yl)-2,3-dihydro-1H-inden-1-yl)oxy)silane IND INT-6 (0.16 g, 0.42 mmol), potassium carbonate (0.176 g, 1.2 mmol) and 3:1 mixture of DME/H$_2$O (2 mL) was degassed with N$_2$ for 10 min before the addition of Pd(PPh$_3$)$_4$ (0.034 g, 0.03 mmol). The mixture reaction was degassed with N$_2$ for additional 2 min and then heated under microwave at 90° C. for 1.5 h. Upon cooling, the reaction mixture was diluted with EA (20 mL) and washed with brine (20 mL). The combined organic layers were dried over MgSO$_4$, filtered, and concentrated. The crude product was purified by silica gel flash chromatography (30% EA/hexanes) to produce 0.116 g (60%) of (S)-5-(5-(1-(((tert-butyldimethylsilyl)oxy)-2,3-dihydro-1H-inden-4-yl)thiazol-2-yl)-2-fluorobenzonitrile as a white solid. LCMS-ESI (m/z) calculated for C$_{25}$H$_{27}$FN$_2$OSSi: 450.6; found 451.1 [M+H]$^+$, t$_R$=4.86 min (Method 1). $^1$H NMR (400 MHz, CDCL$_3$) δ 8.30-8.14 (m, 2H), 7.95 (s, 1H), 7.45 (dd, J=7.0, 0.9, 1H), 7.32 (ddd, J=23.9, 14.6, 11.0, 3H), 5.32 (t, J=7.0, 1H), 3.19 (ddd, J=15.9, 8.8, 2.7, 1H), 2.95 (dt, J=16.1, 8.1, 1H), 2.59-2.40 (m, 1H), 2.08-1.89 (m, 1H), 0.94 (s, 9H), 0.17 (dd, J=13.7, 7.8, 6H).

(R)-5-(5-(1-(((tert-butyldimethylsilyl)oxy)-2,3-dihydro-1H-inden-4-yl)thiazol-2-yl)-2-fluorobenzonitrile was prepared in an analogous fashion using (R)-tert-butyldimethyl((4-(4,4,5,5-tetramethyl-1,3,2-dioxaborolan-2-yl)-2,3-dihydro-1H-inden-1-yl)oxy)silane.

General Procedure 2: Displacement of Fluorine with Isopropoxide

To a stirred solution of the (R)- or (S)-fluorobenzene derivative (1 eq) in IPA (0.02 M) was added sodium isopropoxide (1.3 eq). The reaction was stirred at 60° C. under N$_2$ for 2 h or until reaction is complete. Upon cooling the solvent was evaporated to dryness and the product was purified by silica gel column chromatography (EA/hexanes).

(S)-5-(5-(1-((tert-butyldimethylsilyl)oxy)-2,3-dihydro-1H-inden-4-yl)-1,3,4-thiadiazol-2-yl)-2-isopropoxybenzonitrile

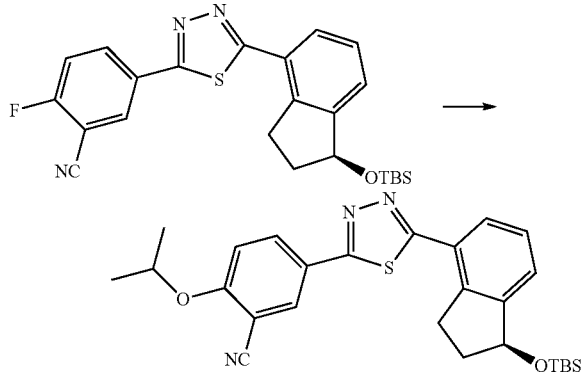

Prepared using General Procedure 2: To a solution of (S)-5-(5-(1-((tert-butyldimethylsilyl)oxy)-2,3-dihydro-1H-inden-4-yl)-1,3,4-thiadiazol-2-yl)-2-fluorobenzonitrile (21 mg, 0.04 mmol) in IPA (2 mL) was added sodium isopropoxide (5 mg, 0.06 mmol). The reaction mixture was heated at 60° C. for 2 h. Upon cooling, the solvent was evaporated and the product was purified by a silica gel column chromatography (EA/hexanes) to afford (S)-5-(5-(1-((tert-butyldimethylsilyl)oxy)-2,3-dihydro-1H-inden-4-yl)-1,3,4-thiadiazol-2-yl)-2-isopropoxybenzonitrile (15 mg, 68%). LCMS-ESI (m/z) calculated for $C_{28}H_{34}N_2O_2SSi$: 491.7, found 492.2 $[M+H]^+$, $t_R$=5.17 min (Method 1).

(R)-5-(5-(1-((tert-butyldimethylsilyl)oxy)-2,3-dihydro-1H-inden-4-yl)-1,3,4-thiadiazol-2-yl)-2-isopropoxybenzonitrile was prepared in an analogous fashion using (R)-5-(5-(1-((tert-butyldimethylsilyl)oxy)-2,3-dihydro-1H-inden-4-yl)-1,3,4-thiadiazol-2-yl)-2-fluorobenzonitrile.

(S)-5-(5-(1-(tert-butyldimethylsilyloxy)-2,3-dihydro-1H-inden-4-yl)thiazol-2-yl)-2-isopropoxybenzonitrile

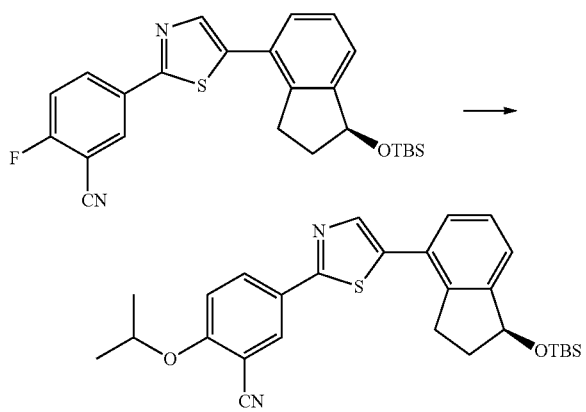

Prepared using General Procedure 2. To a solution of (S)-5-(5-(1-((tert-butyldimethylsilyl)oxy)-2,3-dihydro-1H-inden-4-yl)thiazol-2-yl)-2-fluorobenzonitrile (116 mg, 0.25 mmol) in IPA (2 mL) was added sodium isopropoxide (21.1 mg, 0.25 mmol). The reaction mixture was heated at 60° C. for 2 h. Upon cooling, the solvent was evaporated and the product was purified by a silica gel column chromatography (EA/hexanes) to afford 151 mg (88%) of (S)-5-(5-(1-(tert-butyldimethylsilyloxy)-2,3-dihydro-1H-inden-4-yl)thiazol-2-yl)-2-isopropoxy-benzonitrile LCMS-ESI (m/z) calculated for $C_{28}H_{34}N_2O_2SSi$: 490.7, found 491.1 $[M+H]^+$, $t_R$=6.81 min (Method 1).

(R)-5-(5-(1-(tert-butyldimethylsilyloxy)-2,3-dihydro-1H-inden-4-yl)thiazol-2-yl)-2-isopropoxybenzonitrile was prepared in an analogous fashion using (R)-5-(5-(1-((tert-butyldimethylsilyl)oxy)-2,3-dihydro-1H-inden-4-yl)thiazol-2-yl)-2-fluorobenzonitrile.

General Procedure 3: Deprotection of Silyl Protected Indanols

To a stirred solution of the (R)- or (S)-silyl protected indanol (1 eq) in anhydrous THF (0.06 M) was added 1 M tetrabutyl ammonium fluoride (5 eq) in THF and the mixture was stirred at room temperature under $N_2$. Upon completion, the reaction mixture was diluted with EA (10× volume), and washed thoroughly with $NaHCO_3$, water and brine, dried over $MgSO_4$, and concentrated. The crude product was purified by silica gel column chromatography (EA/hexanes).

Compounds 1-3, and 69-70 were prepared using a sequence of General Procedures 1-3.

(S)-5-(5-(1-hydroxy-2,3-dihydro-1H-inden-4-yl)-1,3,4-thiadiazol-2-yl)-2-isopropoxybenzonitrile (Compound 1)

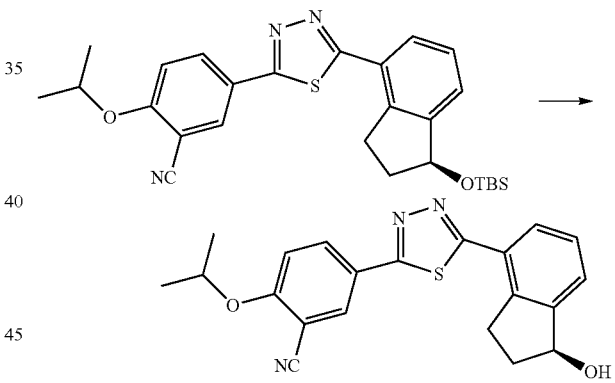

To a stirred solution of (S)-5-(5-(1-((tert-butyldimethylsilyl)oxy)-2,3-dihydro-1H-inden-4-yl)-1,3,4-thiadiazol-2-yl)-2-isopropoxybenzonitrile (21 mg, 0.06 mmol) in anhydrous THF (1 mL) was added 1M tetrabutyl ammonium fluoride (0.3 mL, 0.3 mmol) and the reaction mixture stirred at room temperature overnight. The reaction mixture was diluted with EA (10 mL), washed with saturated $NaHCO_3$ and brine, and dried over $MgSO_4$. The product was purified by chromatography (EA/hexanes) to afford 8 mg (81%) of (S)-5-(5-(1-hydroxy-2,3-dihydro-1H-inden-4-yl)-1,3,4-thiadiazol-2-yl)-2-isopropoxybenzonitrile 1 as a white solid. LCMS-ESI (m/z) calculated for $C_{21}H_{19}N_3O_2S$: 377.1; found 378.1 $[M+H]^+$, $t_R$=3.67 min. $^1$H NMR (400 MHz, $CDCl_3$) δ 8.28-8.07 (m, 2H), 7.86 (d, J=7.5 Hz, 1H), 7.57 (d, J=7.5 Hz, 1H), 7.40 (t, J=7.6 Hz, 1H), 7.08 (d, J=9.0 Hz, 1H), 5.41-5.18 (m, 1H), 4.74 (dd, J=12.2, 6.0 Hz, 1H), 3.48 (ddd, J=17.1, 8.7, 4.6 Hz, 1H), 3.30-3.06 (m, 1H), 2.72-2.40 (m, 1H), 2.04 (ddd, J=13.6, 8.7, 6.5 Hz, 1H), 1.64 (s, 2H), 1.44 (d, J=6.1 Hz, 5H). $^{13}$C NMR (101 MHz, $CDCl_3$) δ 167.61, 166.22, 162.23, 147.58, 142.93, 134.04, 133.83, 129.81, 128.30, 127.45, 127.09, 123.37, 116.14, 114.45, 104.34, 77.23, 76.71, 73.09, 36.24, 31.69, 22.32.

(R)-5-(5-(1-hydroxy-2,3-dihydro-1H-inden-4-yl)-1,3,4-thiadiazol-2-yl)-2-isopropoxybenzonitrile 2 was prepared in an analogous fashion using (R)-5-(5-(1-((tert-butyldimethylsilyl)oxy)-2,3-dihydro-1H-inden-4-yl)-1,3,4-thiadiazol-2-yl)-2-isopropoxybenzonitrile.

(S)-5-(5-(1-hydroxy-2,3-dihydro-1H-inden-4-yl)thiazol-2-yl)-2-isopropoxybenzonitrile (Compound 70)

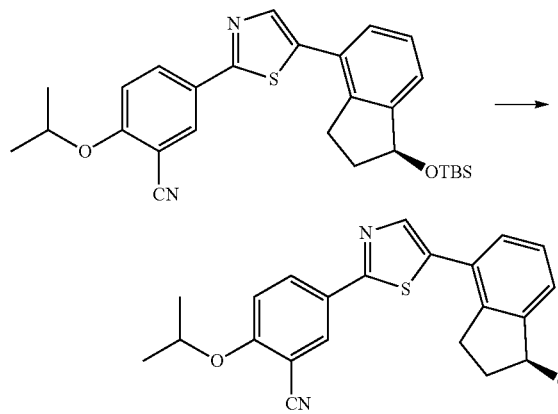

Prepared using General Procedure 3. To a solution of crude (S)-5-(5-(1-(tert-butyldimethylsilyloxy)-2,3-dihydro-1H-inden-4-yl)thiazol-2-yl)-2-isopropoxybenzonitrile (0.11 g, 0.22 mmol) in anhydrous THF (3 mL) was added 1.0 M solution of TBAF (1.0 mL) in THF. The reaction mixture was stirred at room temperature for 2 h. The solvent was concentrated under vacuum and the reside purified by a silica gel chromatography to afford 35 mg (41%) of (S)-5-(5-(1-hydroxy-2,3-dihydro-1H-inden-4-yl)thiazol-2-yl)-2-isopropoxybenzonitrile 70 as white solid. LCMS-ESI (m/z): calcd for: $C_{22}H_{20}N_2O_2S$: 376.4; found 377.1 [M+H]$^+$, $t_R$=3.66 min. $^1$H NMR (400 MHz, CDCl$_3$) δ 8.14-7.89 (m, 2H), 7.82-7.62 (m, 1H), 7.35 (dd, J=7.5, 2.6 Hz, 2H), 7.22 (dd, J=15.0, 7.5 Hz, 1H), 7.02-6.77 (m, 1H), 5.36-5.08 (m, 1H), 4.65 (hept, J=6.0 Hz, 1H), 3.10 (ddd, J=16.1, 8.5, 4.6 Hz, 1H), 2.93-2.80 (m, 1H), 2.68-2.54 (m, 1H), 2.44 (dddd, J=11.7, 8.3, 7.0, 4.7 Hz, 1H), 2.01-1.77 (m, 1H), 1.41-1.29 (m, 6H). $^{13}$C NMR (101 MHz, CDCl$_3$) δ 164.98, 161.11, 146.82, 141.23, 140.87, 137.98, 132.11, 131.99, 128.40, 128.03, 127.91, 126.67, 124.62, 116.13, 113.98, 103.76, 76.43, 72.55, 35.89, 30.78, 22.01. Chiral HPLC: (S)-5-(5-(1-hydroxy-2,3-dihydro-1H-inden-4-yl)thiazol-2-yl)-2-isopropoxybenzonitrile was eluted using 15% IPA in hexanes: 100% ee; $t_R$=24.19 min.

(R)-5-(5-(1-hydroxy-2,3-dihydro-1H-inden-4-yl)thiazol-2-yl)-2-isopropoxy benzonitrile 69 was prepared in an analogous fashion using (R)-5-(5-(1-(tert-butyldimethylsilyloxy)-2,3-dihydro-1H-inden-4-yl)thiazol-2-yl)-2-isopropoxybenzonitrile: 97% ee, $t_R$ for (R)-enantiomer=47.32 min.

(S,E)-N-(4-bromo-2,3-dihydro-1H-inden-1-ylidene)-2-methylpropane-2-sulfinamide (IND INT-9)

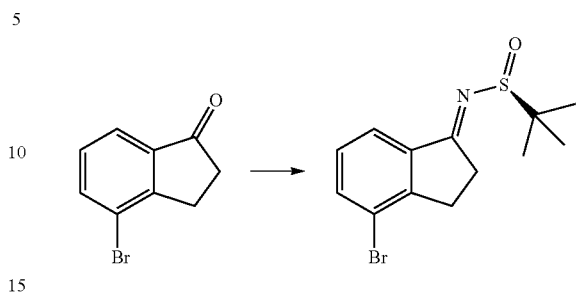

An oven dried 2 L RB flask was charged with (S)-2-methylpropane-2-sulfinamide (31.5 g, 260 mmol), titanium tetraethoxide (81 g, 355 mmol) and anhydrous toluene (250 mL). The reaction mixture was heated at 90° C. and a solution of 4-bromo-2,3-dihydro-1H-inden-1-one (50.0 g, 236 mmol) in anhydrous toluene was added dropwise over 90 min. The reaction mixture was then stirred at 90° C. for 4 h and then overnight at 70° C. The crude (S,E)-N-(4-bromo-2,3-dihydro-1H-inden-1-ylidene)-2-methylpropane-2-sulfinamide IND INT-9 was used in the next experiment without purification. LCMS-ESI (m/z) calculated $C_{13}H_{18}BrNOS$: 315.0; found 316.0 [M+H]$^+$, $t_R$=3.65 min.

(R,E)-N-(4-bromo-2,3-dihydro-1H-inden-1-ylidene)-2-methylpropane-2-sulfinamide IND INT-10 was prepared in an analogous fashion using (R)-2-methylpropane-2-sulfinamide.

(S)-N-((S)-4-bromo-2,3-dihydro-1H-inden-1-yl)-2-methylpropane-2-sulfinamide (IND INT-11)

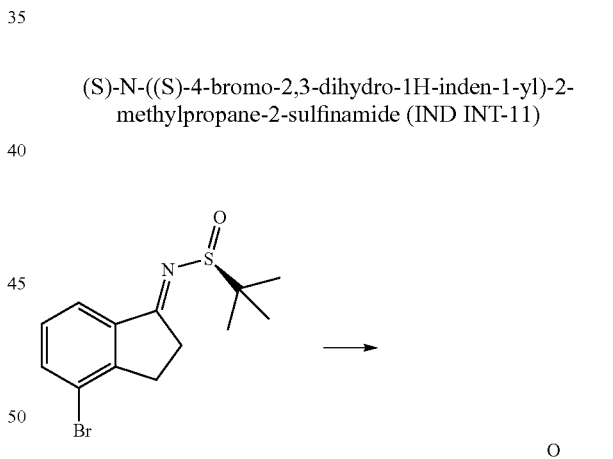

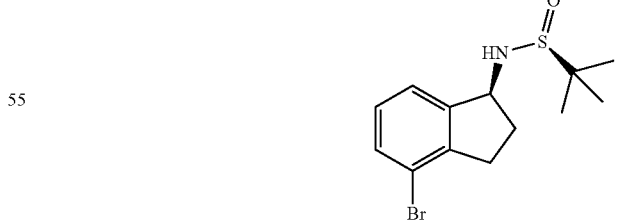

To a stirred suspension of crude (S,E)-N-(4-bromo-2,3-dihydro-1H-inden-1-ylidene)-2-methylpropane-2-sulfinamide IND INT-9 in toluene (250 mL) under N$_2$ was added anhydrous THF (250 mL) and the reaction mixture was cooled to −78° C. Sodium borohydride (26.8 g, 710 mmol) was added in four portions over 30 min (internal temperature maintained below −65° C.). The reaction mixture was stirred at −78° C. for 30 min before it was warmed to room temperature over 1 h and continued to stir for additional 1 h. The reaction mixture was filtered through Celite pad to remove Ti salts. The filtrate was treated with EA (500 mL), saturated sodium potassium tartrate (200 mL), and brine (50 mL) and the mixture stirred at room temperature overnight. The mixture was filtered through a celite pad and the filtrate dried over MgSO$_4$. The crude product was obtained by concentration to dryness gave 46 g (61%) of (S)-N-((S)-4-bromo-2,3-dihydro-1H-inden-1-yl)-2-methylpropane-2-sulfinamide IND INT-11 as an off-white solid which was used in the next experiment without purification. LCMS-ESI (m/z) calculated C$_{13}$H$_{16}$BrNOS: 313.0; found 314.0 [M+H]$^+$, t$_R$=3.84 min.

(R)-N-((R)-4-bromo-2,3-dihydro-1H-inden-1-yl)-2-methylpropane-2-sulfinamide IND INT-12 was prepared in an analogous fashion using (R,E)-N-(4-bromo-2,3-dihydro-1H-inden-1-ylidene)-2-methylpropane-2-sulfinamide IND INT-10.

(S)-4-bromo-2,3-dihydro-1H-inden-1-amine hydrochloride (IND INT-13)

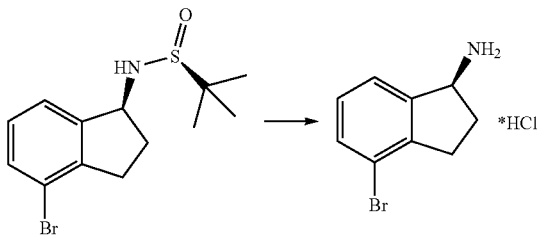

To a stirred suspension of crude (S)-N-((S)-4-bromo-2,3-dihydro-1H-inden-1-yl)-2-methylpropane-2-sulfinamide IND INT-11 (46 g, 145 mol) in MeOH (100 mL) was added 4N HCl in dioxane (109 mL) and the yellow suspension was stirred at room temperature for 3 h. The crude reaction was diluted with MeOH (100 mL) and filtered. The filtrate was concentrated and the solid obtained was dispersed into acetonitrile (600 mL) and refluxed for 90 min. The suspension was cooled to 0° C. and the solid filtered to produce 25 g of (69%) (S)-4-bromo-2,3-dihydro-1H-inden-1-amine hydrochloride IND INT-13 which was used in the next step without purification. LCMS-ESI (m/z) calculated for C$_9$H$_{10}$BrN: 211.09; found 197.0 [M-NH$_2$]$^+$, t$_R$=1.76 min. $^1$H NMR (400 MHz, DMSO) δ 8.76 (s, 2H), 7.71 (d, J=7.5 Hz, 1H), 7.57 (d, J=7.9 Hz, 1H), 7.26 (t, J=7.7 Hz, 1H), 4.80 (s, 1H), 3.06 (ddd, J=16.9, 8.9, 5.2 Hz, 1H), 2.93-2.76 (m, 1H), 2.57-2.39 (m, 1H), 2.11-1.92 (m, 1H); $^{13}$C NMR (101 MHz, DMSO) δ 144.12, 141.60, 131.71, 129.02, 124.54, 119.29, 55.30, 31.52, 29.10.

(R)-4-bromo-2,3-dihydro-1H-inden-1-amine hydrochloride IND INT-14 was prepared in an analogous fashion using (R)-N-((S)-4-bromo-2,3-dihydro-1H-inden-1-yl)-2-methylpropane-2-sulfinamide IND INT-12.

(S)-tert-butyl 4-bromo-2,3-dihydro-1H-inden-1-ylcarbamate (IND INT-15)

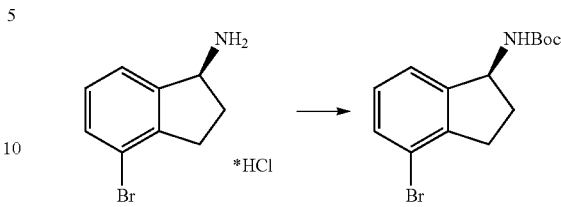

To crude (S)-4-bromo-2,3-dihydro-1H-inden-1-amine hydrochloride IND INT-13 (16.6 g, 66 mmol) in DCM (140 mL) at 0° C. was added triethylamine (14.8 g, 146 mmol) and di-tert-butyl dicarbonate (16.0 g, 73 mmol). The reaction was stirred at room temperature overnight. The reaction was diluted with DCM (50 mL) and washed with water and brine. The organic layers were dried over MgSO$_4$ and the product purified by crystallization from 10% EA/hexanes to afford 14 g of (70%) (S)-tert-butyl 4-bromo-2,3-dihydro-1H-inden-1-ylcarbamate IND INT-15 as an off-white solid. LCMS-ESI (m/z) calculated for C$_{14}$H$_{18}$BrNO$_2$: 312.2; found 197.0 [M-NH$_2$Boc]$^+$, t$_R$=3.94 min. $^1$H NMR (400 MHz, CDCl$_3$) δ 7.38 (d, J=7.9 Hz, 1H), 7.25 (d, J=7.8 Hz, 1H), 7.08 (t, J=7.7 Hz, 1H), 5.25 (dd, J=15.9, 7.9 Hz, 1H), 4.78 (d, J=7.6 Hz, 1H), 2.99 (ddd, J=16.5, 9.0, 3.4 Hz, 1H), 2.81 (dt, J=16.5, 8.2 Hz, 1H), 2.70-2.36 (m, 1H), 1.94-1.71 (m, 1H), 1.47 (d, J=5.2 Hz, 9H). $^{13}$C NMR (101 MHz, CDCl$_3$) δ 155.99, 146.13, 143.83, 131.35, 129.02, 123.41, 120.64, 80.10, 57.21, 33.71, 31.82, 28.86; Chiral HPLC: (S)-tert-butyl 4-bromo-2,3-dihydro-1H-inden-1-ylcarbamate was eluted using 2% IPA in hexanes: >99.9% ee, t$_R$=11.08 min.

(R)-tert-butyl 4-bromo-2,3-dihydro-1H-inden-1-ylcarbamate IND INT-16 was prepared in an analogous fashion from (R)-4-bromo-2,3-dihydro-1H-inden-1-amine hydrochloride IND INT-14: >99.9% ee t$_R$ for (R)-enantiomer=9.98 min.

(S)-tert-butyl 4-(4,4,5,5-tetramethyl-1,3,2-dioxaborolan-2-yl)-2,3-dihydro-1H-inden-1-ylcarbamate (IND INT-17)

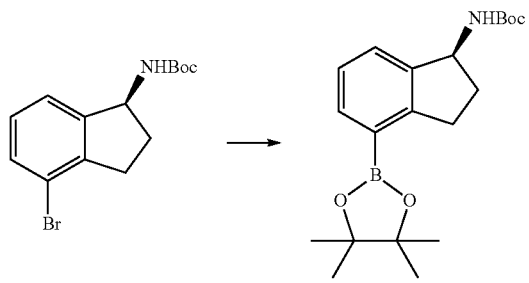 [SMILES: CC(C)(C)OC(=O)N[C@H]1CCc2c(Br)cccc21 ; CC(C)(C)OC(=O)N[C@H]1CCc2c(B3OC(C)(C)C(C)(C)O3)cccc21]

A solution of (S)-tert-butyl 4-bromo-2,3-dihydro-1H-inden-1-ylcarbamate IND INT-15 (13.1 g, 42 mmol), 4,4,4',4',5,5,5',5'-octamethyl-2,2'-bi(1,3,2-dioxaborolane) (11.7 g, 46 mmol), and potassium acetate (12.3 mg, 125 mmol) in anhydrous 1,4-dioxane (100 mL) was degassed by passing N$_2$ through the solution for 30 min before the addition of PdCl$_2$(dppt).CH$_2$Cl$_2$ (6.8 g, 8.3 mmol). The reaction mixture was heated at 85° C. for 8 h. The solvent was removed under vacuum and the residue was dissolved in EA (500 mL) and filtered through celite. The filtrate was washed with water and brine, dried over MgSO₄, and purified by chromatography (EA/hexanes) to afford 13 g (87%) of (S)-tert-butyl 4-(4,4,5,5-tetramethyl-1,3,2-dioxaborolan-2-yl)-2,3-dihydro-1H-inden-1-ylcarbamate IND INT-17 as white solid. LCMS-ESI (m/z) calculated for $C_{20}H_{30}BNO_4$: 359.2; found 382.2 [M+Na]⁺, $t_R$=4.26 min. ¹H NMR (400 MHz, CDCl₃) δ 7.66 (d, J=7.3 Hz, 1H), 7.39 (d, J=7.5 Hz, 1H), 7.19 (t, J=7.4 Hz, 1H), 5.14 (dd, J=15.8, 7.8 Hz, 1H), 4.69 (d, J=8.7 Hz, 1H), 3.23 (ddd, J=17.0, 8.8, 3.5 Hz, 1H), 2.94 (dt, J=16.6, 8.2 Hz, 1H), 2.53 (ddd, J=11.4, 8.0, 3.9 Hz, 1H), 1.73 (ddd, J=16.4, 12.8, 8.6 Hz, 1H), 1.46 (s, 9H), 1.36-1.25 (m, 12H). ¹³C NMR (101 MHz, CDCl₃) δ 156.21, 150.64, 143.43, 135.37, 127.25, 126.43, 83.95, 79.78, 56.19, 34.60, 31.57, 28.88, 25.37, 25.34.

(R)-tert-butyl 4-(4,4,5,5-tetramethyl-1,3,2-dioxaborolan-2-yl)-2,3-dihydro-1H-inden-1-ylcarbamate IND INT-18 was prepared in an analogous fashion using (R)-tert-butyl 4-bromo-2,3-dihydro-1H-inden-1-ylcarbamate IND INT-16.

General Procedure 4: Coupling of Heterocyclic Bromides to Indane Amine

A reaction pressure flask was charged sequentially with the heterocyclic bromide (1 eq), (R)- or (S)-Boc-protected indane amine (1 eq), DME:H₂O (3:1, 0.07 M) and potassium carbonate (3 eq). The mixture was degassed by bubbling N₂ gas through the stirring solution for 20 min. Then Pd(PPh₃)₄ (0.07 eq) was added and the mixture was degassed for additional 5 min. The reaction flask was capped tightly and the mixture was heated at 85° C. for 12-24 h. The reaction was cooled to room temperature, diluted with water (2× volume), and stirred for 30 min. The resulting solid was filtered, washed with hexanes, and dried under high vacuum. The crude product was purified by silica gel column chromatography (EA/hexanes) or used in the next experiment without purification.

(S)-tert-butyl(4-(5-(3-cyano-4-fluorophenyl)-1,3,4-thiadiazol-2-yl)-2,3-dihydro-1H-inden-1-yl)carbamate

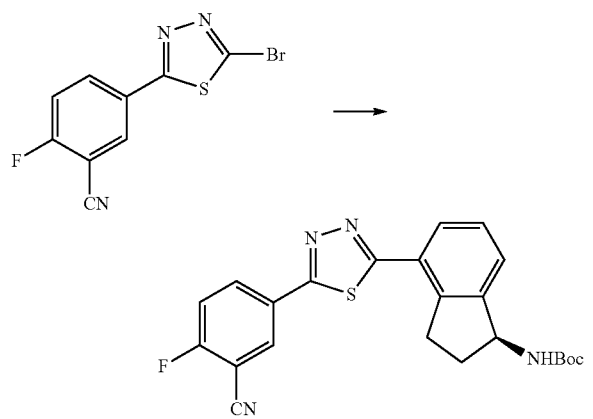

Prepared using General Procedure 4. A suspension of 5-(5-bromo-1,3,4-thiadiazol-2-yl)-2-fluorobenzonitrile TDZ INT-3 (1.5 g, 5.3 mmol), (S)-tert-butyl(4-(4,4,5,5-tetramethyl-1,3,2-dioxaborolan-2-yl)-2,3-dihydro-1H-inden-1-yl)carbamate IND INT-17 (1.9 g, 5.3 mmol) and potassium carbonate (2.2 g, 16 mmol) in DME:H₂O (3:1, 70 mL) was degassed with N₂ for 20 min before the addition of Pd(PPh₃)₄ (0.43 g, 0.3 mmol). The mixture was degassed with N₂ for an additional 5 min and the suspension was heated under N₂ at 85° C. for 12 h. Upon cooling, the reaction mixture was diluted with water (150 mL) and the mixture stirred for 30 min. The resulting solid was filtered, washed with water, and dried under high vacuum to afford 2.3 g (100%) of crude (S)-tert-butyl(4-(5-(3-cyano-4-fluorophenyl)-1,3,4-thiadiazol-2-yl)-2,3-dihydro-1H-inden-1-yl)carbamate as light brown solid which was used in the next experiment without purification. LCMS-ESI (m/z) calculated for $C_{23}H_{21}FN_4O_2S$: 436.1; found 459.1 [M+Na]⁺, $t_R$=4.19 min.

(R)-tert-butyl(4-(5-(3-cyano-4-fluorophenyl)-1,3,4-thiadiazol-2-yl)-2,3-dihydro-1-inden-1-yl)carbamate was prepared in an analogous fashion using (R)-tert-butyl(4-(4,4,5,5-tetramethyl-1,3,2-dioxaborolan-2-yl)-2,3-dihydro-1H-inden-1-yl)carbamate IND INT-18.

(S)-tert-butyl(4-(2-(3-cyano-4-fluorophenyl)thiazol-5-yl)-2,3-dihydro-1H-inden-1-yl)carbamate

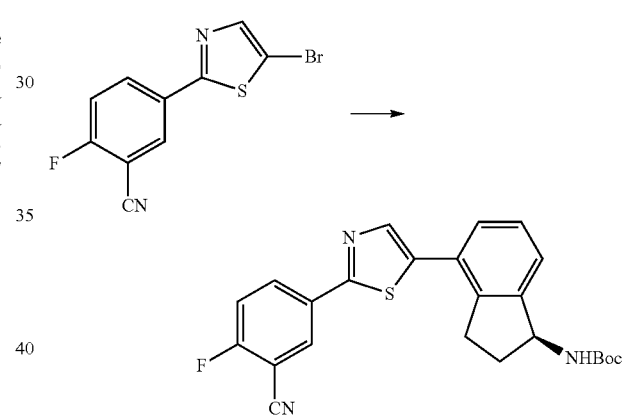

Prepared using General Procedure 4. A solution of 5-(5-bromothiazol-2-yl)-2-fluorobenzonitrile THZ INT-2 (2.0 g, 7.0 mmol), (S)-tert-butyl(4-(4,4,5,5-tetramethyl-1,3,2-dioxaborolan-2-yl)-2,3-dihydro-1H-inden-1-yl)carbamate IND INT-17 (2.5 g, 7.0 mmol), potassium carbonate (2.9 g, 21 mmol) and a 3:1 mixture of DME/H₂O (30 mL) was degassed with N₂ for 10 min before the addition of Pd(PPh₃)₄ (0.57 g, 0.005 mmol). The mixture was degassed with N₂ for an additional 2 min and the suspension was heated under nitrogen at 80° C. for 12 h. Upon cooling, the reaction mixture was diluted with EA (20 mL) and washed with brine (20 mL). The combined organic layers were dried over MgSO₄, filtered, and concentrated. The crude product was purified by silica gel flash chromatography (30% EA/hexanes) to produce 3.0 g (83%) of (S)-tert-butyl(4-(2-(3-cyano-4-fluorophenyl)thiazol-5-yl)-2,3-dihydro-1H-inden-1-yl)carbamate as a white solid. LCMS-ESI (m/z) calculated for $C_{24}H_{22}FN_3O_2S$: 435.5; found 436.1 [M+H]⁺, $t_R$=4.14 min. ¹H NMR (400 MHz, CDCl₃) δ 8.20 (m, 2H), 7.93 (s, 1H), 7.44 (d, J=7.5 Hz, 1H), 7.32 (m, 3H), 5.26 (m, 1H), 4.76 (d, J=8.4 Hz, 1H), 3.09 (m, 2H), 2.65 (ddd, J=12.5, 8.3, 4.6 Hz, 1H), 1.84 (dq, J=12.9, 8.5 Hz, 1H), 1.48 (s, 9H).

(S)-tert-butyl(4-(5-(3-cyano-4-isopropoxyphenyl)-1,3,4-thiadiazol-2-yl)-2,3-dihydro-1H-inden-1-yl)carbamate

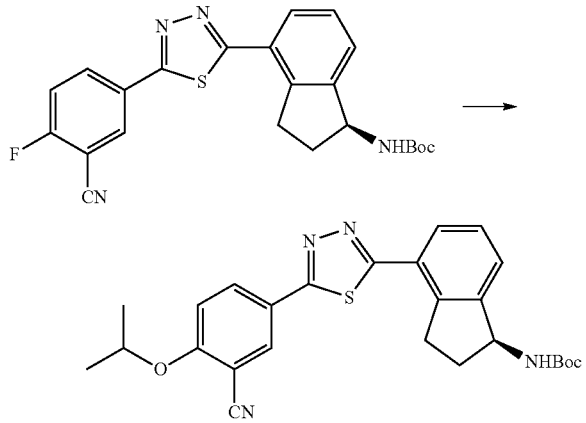

Prepared using General Procedure 2. To a solution of (S)-tert-butyl(4-(5-(3-cyano-4-fluorophenyl)-1,3,4-thiadiazol-2-yl)-2,3-dihydro-1H-inden-1-yl)carbamate (2.5 g 5.7 mmol) in IPA (30 mL) was added sodium isopropoxide (0.61 g, 7.4 mmol). The reaction mixture was heated at 60° C. for 4 h. Upon cooling, the mixture was concentrated to 50% volume and the suspension was cooled to 0° C. The resulting solid was filtered and dried under high vacuum to afford 1.14 g (42%) of (S)-tert-butyl(4-(5-(3-cyano-4-isopropoxyphenyl)-1,3,4-thiadiazol-2-yl)-2,3-dihydro-1H-inden-1-yl)carbamate as off-white solid. LCMS-ESI (m/z) calculated for $C_{26}H_{28}N_4O_3S$: 476.2; found 477.2 (M+H). $t_R$=4.12 min. $^1$H NMR (400 MHz, CDCl$_3$) δ 8.26-8.04 (m, 2H), 7.82 (d, J=7.7 Hz, 1H), 7.49 (d, J=7.5 Hz, 1H), 7.38 (d, J=7.6 Hz, 1H), 7.09 (d, J=9.0 Hz, 1H), 5.38-5.08 (m, 1H), 4.94-4.62 (m, 1H), 3.54-3.32 (m, 1H), 3.21 (s, 1H), 2.80-2.59 (m, 1H), 1.97-1.74 (m, 1H), 1.52-1.35 (m, 15H). $^{13}$C NMR (101 MHz, CDCl$_3$) δ 166.93, 165.54, 161.59, 155.65, 145.84, 142.05, 133.28, 128.71, 127.59, 126.64, 126.33, 122.72, 115.54, 113.86, 103.69, 79.59, 72.50, 60.35, 55.73, 33.78, 31.27, 28.39, 21.74.

(R)-tert-butyl(4-(5-(3-cyano-4-isopropoxyphenyl)-1,3,4-thiadiazol-2-yl)-2,3-dihydro-1H-inden-1-yl)carbamate was prepared in an analogous fashion using (R)-tert-butyl(4-(5-(3-cyano-4-fluorophenyl)-1,3,4-thiadiazol-2-yl)-2,3-dihydro-1H-inden-1-yl)carbamate.

(S)-tert-butyl(4-(5-(3-cyano-4-isopropoxyphenyl) thiazol-2-yl)-2,3-dihydro-1H-inden-1-yl)carbamate

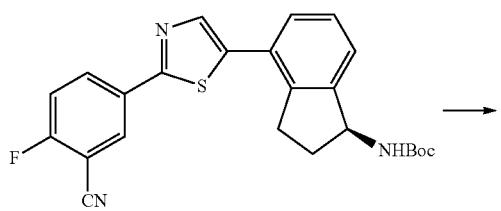

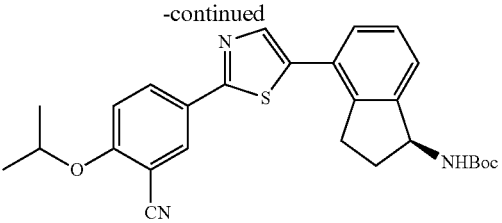

Prepared using General Procedure 2. To a solution of (S)-tert-butyl(4-(2-(3-cyano-4-fluorophenyl)thiazol-5-yl)-2,3-dihydro-1H-inden-1-yl)carbamate (2.5 g, 5.7 mmol) in IPA (50 mL) was added sodium isopropoxide (0.61 g, 7.4 mmol). The reaction mixture was heated at 60° C. for 4 h. Upon cooling, the mixture was concentrated to 50% volume and the suspension was cooled to 0° C. The resulting solid was filtered and dried under high vacuum to afford 2.66 g (98%) of (S)-tert-butyl(4-(5-(3-cyano-4-isopropoxyphenyl) thiazol-2-yl)-2,3-dihydro-1H-inden-1-yl)carbamate. LCMS-ESI (m/z) calculated for $C_{27}H_{29}N_3O_3S$: 475.1; found 476.2 (M+H). $t_R$=4.30 min. $^1$H NMR (400 MHz, CDCl$_3$) δ 8.19-8.05 (m, 2H), 7.89 (s, 1H), 7.43 (s, 1H), 7.39-7.28 (m, 2H), 7.04 (d, J=8.9 Hz, 1H), 5.39-5.15 (m, 1H), 4.73 (s, 2H), 3.20-2.94 (m, 2H), 2.69-2.57 (m, 1H), 1.94-1.77 (m, 1H), 1.49 (s, 9H), 1.44 (d, J=6.1 Hz, 6H).

General Procedure 5: Preparation of Heterocyclic Indane Amines

To a stirred suspension of the (R)- or (S)-Boc protected indane amine (1 eq) in 1,4-dioxane (0.2 M) was added 4N HCl in 1,4-dioxane (10 eq) and the mixture was heated at 55° C. until completion of the reaction (3-5 h). The reaction was cooled to room temperature and diluted with diethyl ether. The resulting solid was filtered and dried under vacuum to obtain the pure product as the hydrochloride salt.

Compounds 4-6 and 71-72 were prepared by the sequential use of General Procedures 4, 2, and 5.

(S)-5-(5-(1-amino-2,3-dihydro-1H-inden-4-yl)-1,3,4-thiadiazol-2-yl)-2-isopropoxybenzonitrile hydrochloride (Compound 4)

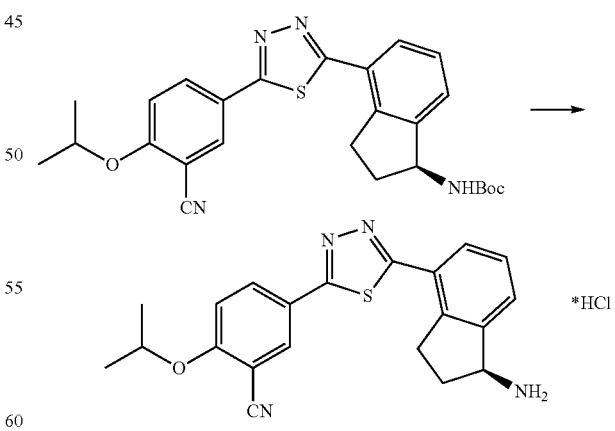

Prepared using General Procedure 5. To a stirred solution of (S)-tert-butyl(4-(5-(3-cyano-4-isopropoxyphenyl)-1,3,4-thiadiazol-2-yl)-2,3-dihydro-1H-inden-1-yl)carbamate (1.1 g, 2.3 mmol) in 1,4-dioxane (10 mL) was added 4N HCl solution of in 1,4-dioxane (10 mL). The reaction mixture was stirred at 55° C. for 2.5 h. Upon cooling to 0° C., the reaction mixture was diluted with diethyl ether (100 mL) and the resulting solid was filtered and dried to afford 980 mg (96%) of (S)-5-(5-(1-amino-2,3-dihydro-1H-inden-4-yl)-1,3,4-thiadiazol-2-yl)-2-isopropoxybenzonitrile hydrochloride 4 as off-white solid. LCMS-ESI (m/z) calculated for $C_{21}H_{20}N_4OS$, 376.1; found 377.1 (M+H). $t_R$=2.35 min. $^1$H NMR (400 MHz, DMSO) δ 8.64-8.51 (m, 3H), 8.41 (d, J=2.3 Hz, 1H), 8.32 (dd, J=8.9, 2.4 Hz, 1H), 7.99 (d, J=7.4 Hz, 1H), 7.84 (d, J=7.6 Hz, 1H), 7.59-7.49 (m, 2H), 4.95 (dt, J=12.2, 6.1 Hz, 1H), 4.84 (s, 1H), 3.54-3.32 (m, 1H), 3.30-3.15 (m, 1H), 2.65-2.53 (m, 1H), 2.12 (ddd, J=13.9, 5.6, 3.0 Hz, 1H), 1.37 (dd, J=10.4, 6.1 Hz, 6H). $^{13}$C NMR (101 MHz, CDCl$_3$) δ 166.61, 166.11, 161.5, 143.05, 141.73, 134.16, 133.45, 129.74, 128.26, 127.84, 126.47, 122.33, 115.79, 115.2, 102.53, 72.43, 54.75, 31.48, 30.12, 21.74. Chiral HPLC: (S)-5-(5-(1-amino-2,3-dihydro-1H-inden-4-yl)-1,3,4-thiadiazol-2-yl)-2-isopropoxybenzonitrile hydrochloride 4 was eluted using 30% EtOH in hexanes plus 0.1% DEA: 99.0% ee, $t_R$=34.2 min.

(R)-5-(5-(1-amino-2,3-dihydro-1H-inden-4-yl)-1,3,4-thiadiazol-2-yl) -2 isopropoxybenzonitrile hydrochloride 5 was prepared in an analogous fashion using (R)-tert-butyl(4-(5-(3-cyano-4-isopropoxyphenyl)-1,3,4-thiadiazol-2-yl)-2,3-dihydro-1H-inden-1-yl)carbamate: >99.9% ee, $t_R$=28.8 min.

(S)-5-(2-(1-amino-2,3-dihydro-1H-inden-4-yl)thiazol-5-yl)-2-isopropoxybenzonitrile hydrochloride (Compound 71)

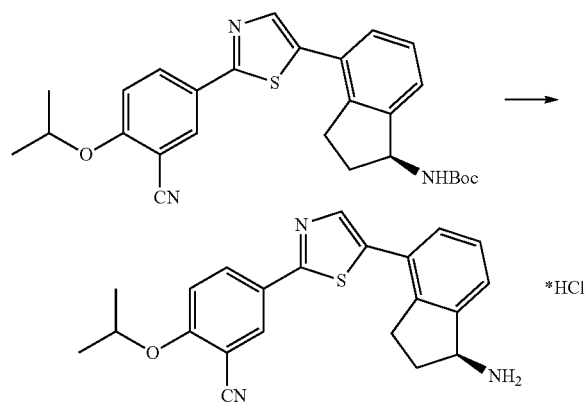

Prepared using General Procedure 5. To a stirred solution of (S)-tert-butyl(4-(5-(3-cyano-4-isopropoxyphenyl)thiazol-2-yl)-2,3-dihydro-1H-inden-1-yl)carbamate (1.0 g, 2.1 mmol) in 1,4-dioxane (5 mL) was added 4N HCl solution in 1,4-dioxane (5 mL). The reaction mixture was stirred at 55° C. for 2.5 h. Upon cooling to 0° C., the reaction mixture was diluted with diethyl ether (50 mL) and the resulting solid was filtered, washed with ether (20 mL), and dried to afford 0.86 g (100%) of (S)-5-(2-(1-amino-2,3-dihydro-1H-inden-4-yl)thiazol-5-yl)-2-isopropoxybenzonitrile hydrochloride 71. LCMS-ESI (m/z) calculated for $C_{22}H_{21}N_3OS$: 375.1; found 376.2 (M+H). $t_R$=2.45 min. $^1$H NMR (400 MHz, DMSO) δ 8.64 (d, J=3.6 Hz, 2H), 8.30 (d, J=2.3 Hz, 1H), 8.23 (dd, J=8.9, 2.4 Hz, 1H), 8.21 (s, 1H), 7.70 (dd, J=7.6, 2.6 Hz, 2H), 7.45 (dd, J=8.4, 5.4 Hz, 2H), 4.91 (dt, J=12.2, 6.1 Hz, 1H), 4.85-4.58 (m, 1H), 3.36-3.21 (m, 1H), 3.21-3.04 (m, 1H), 2.63-2.51 (m, 1H), 2.09 (td, J=8.3, 2.8 Hz, 1H), 1.43-1.28 (m, 6H). $^{13}$C NMR (101 MHz, DMSO) δ 166.61, 166.11, 161.50, 143.05, 141.73, 134.16, 133.45, 129.74, 128.26, 127.84, 126.47, 122.33, 115.79, 115.20, 102.53, 72.43, 54.75, 31.48, 30.12, 21.74. Chiral HPLC: (S)-5-(2-(1-amino-2,3-dihydro-1H-inden-4-yl)thiazol-5-yl)-2-isopropoxybenzonitrile hydrochloride was eluted in 8% EtOH/hexanes: >99.9% ee, $t_R$=67.15 min (Chiral Method 1).

(R)-5-(2-(1-amino-2,3-dihydro-1H-inden-4-yl)thiazol-5-yl)-2-isopropoxybenzonitrile hydrochloride 72 was prepared in an analogous fashion using (R)-tert-butyl(4-(5-(3-cyano-4-isopropoxyphenyl)thiazol-2-yl)-2,3-dihydro-1H-inden-1-yl)carbamate: 99.0% ee, $t_R$ for (R)-enantiomer=62.18 min.

General Procedure 6. Preparation of Indane Amides via Acid Coupling

To the appropriate acid (1 eq) in DMF (0.05 M) was added HOBt (1.3 eq), and EDC (1.3 eq). The reaction was stirred at room temperature for 0.5 h or until the acid was fully activated. The (R)- or (S)-indane amine (1 eq) was added in one portion and the reaction was stirred at room temperature for 12 h. The crude reaction mixture was subjected to preparative HPLC purification. Products that contain Boc protected amine side chains were further treated with 4N HCl in 1,4-dioxane and heated 55° C. for 2 h. The reaction mixture was diluted with diethyl ether and filtered to afford the desired products as the hydrochloride salts.

Compounds 7-13, 49, 73, 74, 77-86 were prepared using General Procedure 6.

(S)-N-(4-(5-(3-cyano-4-isopropoxyphenyl)-1,3,4-thiadiazol-2-yl)-2,3-dihydro-1H-inden-1-yl)-2-hydroxyacetamide (Compound 7)

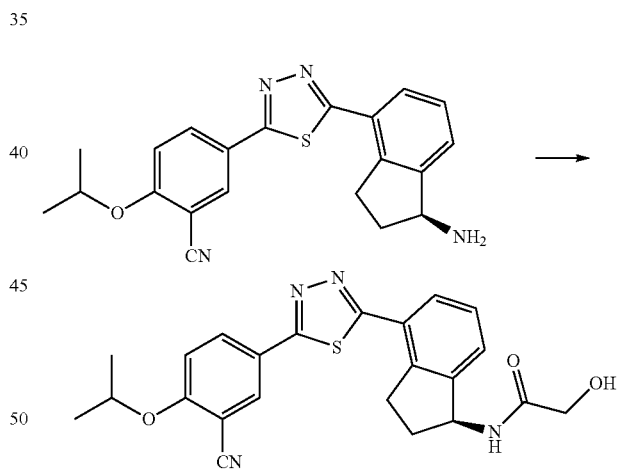

Prepared using General Procedure 6. A solution of 2-hydroxyacetic acid (4 mg, 0.05 mmol), HOBt (8.8 mg, 0.06 mmol), EDC (12.5 mg, 0.06 mmol) and DIEA (15 mg, 0.11 mmol) in DMF (1 mL) was stirred for 30 min before the addition of (S)-5-(5-(1-amino-2,3-dihydro-1H-inden-4-yl)-1,3,4-thiadiazol-2-yl)-2-isopropoxybenzonitrile hydrochloride 4 in DMF (0.5 mL). The reaction mixture was stirred at room temperature overnight. The crude reaction mixture was preparative HPLC to produce 10 mg (50%) of (S)-N-(4-(5-(3-cyano-4-isopropoxyphenyl)-1,3,4-thiadiazol-2-yl)-2,3-dihydro-1H-inden-1-yl)-2-hydroxyacetamide 7 as white solid. LCMS-ESI (m/z) calculated for: $C_{23}H_{22}N_4O_3S$: 434.1; found 435.1 [M+H]$^+$, $t_R$=3.11 min. $^1$H NMR (400 MHz, CDCl$_3$) δ 8.19 (dd, J=8.9, 2.3 Hz, 1H), 8.12 (d, J=2.2 Hz, 1H), 7.79 (d, J=7.6 Hz, 1H), 7.42 (d, J=7.5 Hz, 1H), 7.34 (t, J=7.6 Hz, 1H), 7.09 (d, J=9.0 Hz, 1H), 6.85 (d, J=8.5 Hz, 1H), 5.71-5.46 (m, 1H), 4.76 (dt, J=12.2, 6.1 Hz, 1H), 4.21 (s, 2H), 3.46 (ddd, J=17.0, 8.7, 3.6 Hz, 1H), 3.30-3.09 (m, 1H), 2.69 (ddd, J=16.6, 8.3, 4.0 Hz, 1H), 2.08-1.80 (m, 2H), 1.46 (d, J=6.1 Hz, 6H). $^{13}$C NMR (101 MHz, CDCl$_3$) δ 167.44, 166.23, 162.20, 145.53, 142.82, 133.89, 133.79, 129.53, 128.28, 127.20, 126.93, 123.12, 116.03, 114.38, 104.22, 73.06, 62.72, 54.46, 33.91, 31.98, 22.24.

(R)-N-(4-(5-(3-cyano-4-isopropoxyphenyl)-1,3,4-thiadiazol-2-yl)-2,3-dihydro-1H-inden-1-yl)-2-hydroxyacetamide 8 was prepared in an analogous fashion using (R)-5-(5-(1-amino-2,3-dihydro-1H-inden-4-yl)-1,3,4-thiadiazol-2-yl)-2-isopropoxybenzonitrile hydro-chloride 5.

(S)-N-(4-(2-(3-cyano-4-isopropoxyphenyl)thiazol-5-yl)-2,3-dihydro-1H-inden-1-yl)-2-hydroxyacetamide (Compound 73)

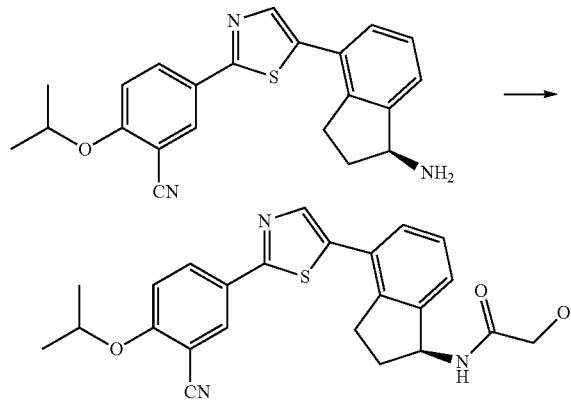

Prepared using General Procedure 6. A solution of 2-hydroxyacetic acid (2 mg, 0.02 mmol), HOBt (4.8 mg, 0.06 mmol), EDC (7.0 mg, 0.06 mmol) and DIEA (7.7 mg, 0.06 mmol) in DMF (1 mL) was stirred for 30 min before the addition of (S)-5-(2-(1-amino-2,3-dihydro-1H-inden-4-yl)thiazol-5-yl)-2-isopropoxybenzonitrile hydrochloride 71 in DMF (0.5 mL). The reaction mixture was stirred at room temperature overnight. The crude reaction mixture was subjected to preparative HPLC to produce 5 mg (58%) of ((S)-N-(4-(2-(3-cyano-4-isopropoxyphenyl)thiazol-5-yl)-2,3-dihydro-1H-inden-1-yl)-2-hydroxyacetamide 73 as white solid. LCMS-ESI (m/z) calculated for: C$_{24}$H$_{23}$N$_3$O$_3$S: 433.2; found 434.1 [M+H]$^+$, t$_R$=3.11 min.

General Procedure 7. Preparation of Indane Amides Via Acid Chlorides

To a stirred solution of (R)- or (S)-indane amine hydrochloride (1 eq) in anhydrous DCM (0.03 M) was added triethylamine (3 eq) followed by the appropriate acid chloride (1.5 eq). The reaction mixture was stirred overnight at room temperature. The solvent was evaporated and the product was purified by preparative HPLC.

Compounds 14, 15, 75, 76, 87, and 88 were prepared using General Procedure 7.

(S)-N-(4-(5-(3-cyano-4-isopropoxyphenyl)-1,3,4-thiadiazol-2-yl)-2,3-dihydro-1H-inden-1-yl)acetamide (Compound 14)

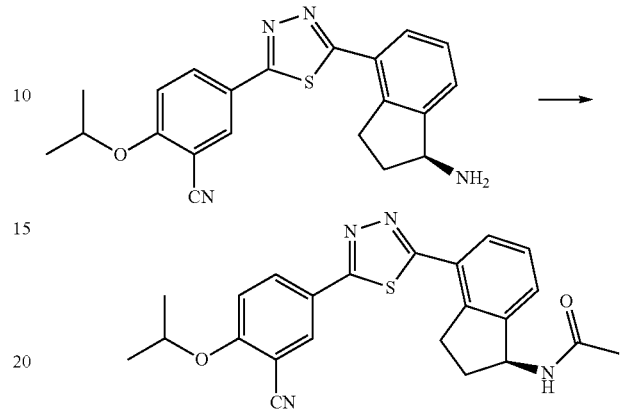

Prepared using General Procedure 7: To a stirred solution of (S)-5-(5-(1-amino-2,3-dihydro-1H-inden-4-yl)-1,3,4-thiadiazol-2-yl)-2-isopropoxybenzonitrile hydrochloride 4 (15 mg, 0.03 mmol) in anhydrous DCM (1 mL) was added triethylamine (11 mg, 0.1 mmol) followed by acetyl chloride (4.2 mg, 0.05 mmol) and the reaction mixture was stirred at room temperature overnight. The solvent was evaporated and the crude mixture purified by preparative HPLC to afford (S)-N-(4-(5-(3-cyano-4-isopropoxyphenyl)-1,3,4-thiadiazol-2-yl)-2,3-dihydro-1H-inden-1-yl)acetamide 14. LCMS-ESI (m/z) calculated for: C$_{23}$H$_{22}$N$_4$O$_2$S: 418.2; found 419.3 [M+H]$^+$, t$_R$=3.34 min. $^1$H NMR (400 MHz, CDCl$_3$) δ 8.20 (dd, J=8.9, 2.3 Hz, 1H), 8.13 (d, J=2.2 Hz, 1H), 7.81 (d, J=7.6 Hz, 1H), 7.45 (d, J=7.5 Hz, 1H), 7.36 (t, J=7.6 Hz, 1H), 7.08 (d, J=9.0 Hz, 1H), 5.83 (d, J=8.4 Hz, 1H), 5.57 (q, J=7.9 Hz, 1H), 4.76 (dt, J=12.2, 6.1 Hz, 1H), 3.46 (ddd, J=17.1, 8.8, 3.8 Hz, 1H), 3.28-3.15 (m, 1H), 2.75-2.62 (m, 1H), 2.07 (s, 3H), 1.98-1.80 (m, 1H), 1.46 (d, J=6.1 Hz, 6H). $^{13}$C NMR (101 MHz, CDCl$_3$) δ 170.36, 167.43, 166.14, 162.16, 145.92, 142.83, 133.89, 133.77, 129.44, 128.23, 127.18, 126.95, 123.21, 116.05, 114.36, 104.23, 73.03, 55.00, 34.03, 31.95, 23.92, 22.24.

(R)-N-(4-(5-(3-cyano-4-isopropoxyphenyl)-1,3,4-thiadiazol-2-yl)-2,3-dihydro-1H-inden-1-yl)acetamide 15 was prepared in an analogous fashion using (R)-5-(5-(1-amino-2,3-dihydro-1H-inden-4-yl)-1,3,4-thiadiazol-2-yl)-2-isopropoxybenzonitrile hydrochloride 5.

(S)-N-(4-(2-(3-cyano-4-isopropoxyphenyl)thiazol-5-yl)-2,3-dihydro-1H-inden-1-yl)-2-methoxyacetamide (Compound 76)

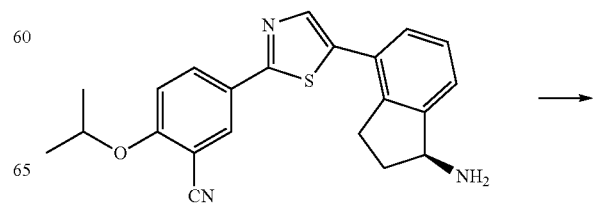

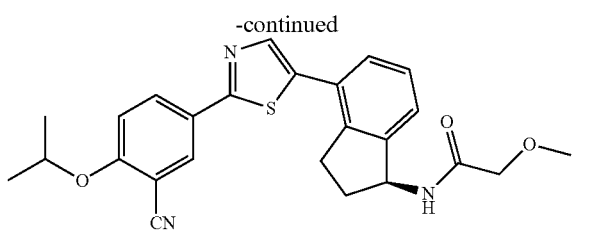

Prepared using General Procedure 7: To a stirred solution of (S)-5-(2-(1-amino-2,3-dihydro-1H-inden-4-yl)thiazol-5-yl)-2-isopropoxybenzonitrile hydrochloride 71 (15 mg, 0.03 mmol) in anhydrous DCM (1 mL) was added triethylamine (11 mg, 0.1 mmol) followed by 2-methoxyacetyl chloride (11.8 mg, 0.1, mmol) and the reaction mixture was stirred at room temperature overnight. The solvent was evaporated and the crude mixture was purified by preparative HPLC to afford (S)-N-(4-(2-(3-cyano-4-isopropoxyphenyl)thiazol-5-yl)-2,3-dihydro-1H-inden-1-yl)-2-methoxyacetamide 76. LCMS-ESI (m/z) calculated for: $C_{25}H_{25}N_3O_3S$: 447.2; found 448.1 $[M+H]^+$, $t_R$=3.70 min.

General Procedure 8. Preparation of Indane Carbamates

To a stirred solution of (R)- or (S)-indane amine (1 eq) in DCM (0.03M) was added TEA (3 eq) and the appropriate carbonochloridate (1.5 eq) at room temperature. The reaction was stirred at room temperature for 4 h. The solvent was evaporated and the pure product isolated by precipitation with water or preparative HPLC.

Compounds 16, 68, 89, and 90 were prepared using General Procedure 8.

(S)-methyl(4-(5-(3-cyano-4-isopropoxyphenyl)-1,3,4-thiadiazol-2-yl)-2,3-dihydro-1H-inden-1-yl)carbamate (Compound 16)

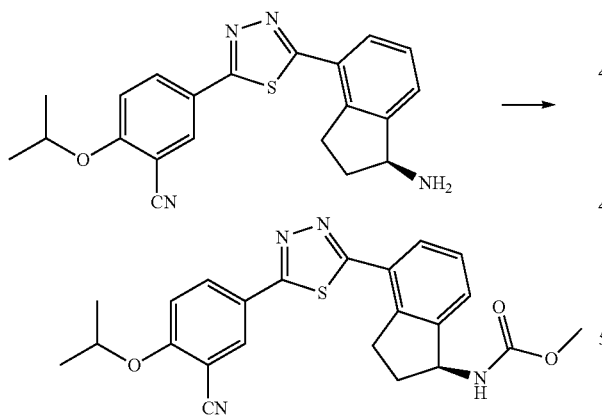

Prepared using General Procedure 8. To a stirred solution of (S)-5-(5-(1-amino-2,3-dihydro-1H-inden-4-yl)-1,3,4-thiadiazol-2-yl)-2-isopropoxybenzonitrile hydrochloride 4 (15 mg, 0.03 mmol) and TEA (11 mg, 0.1 mmol) in DCM (1 mL) was added methyl chloroformate (10 mg, 0.1). The reaction mixture was stirred at room temperature for 16 h. The solvent was evaporated and water (2 mL) was added. The resulting solid was filtered, washed with water, and dried under high vacuum to afford 12 mg (92%) of (S)-methyl(4-(5-(3-cyano-4-isopropoxyphenyl)-1,3,4-thiadiazol-2-yl)-2,3-dihydro-1H-inden-1-yl)carbamate 16 as white solid. LCMS-ESI (m/z) calculated for $C_{23}H_{22}N_4O_3S$: 434.1; found 435.3 $[M+H]^+$, $t_R$=3.69 min.

(S)-methyl(4-(2-(3-cyano-4-isopropoxyphenyl)thiazol-5-yl)-2,3-dihydro-1H-inden-1-yl)carbamate (Compound 90)

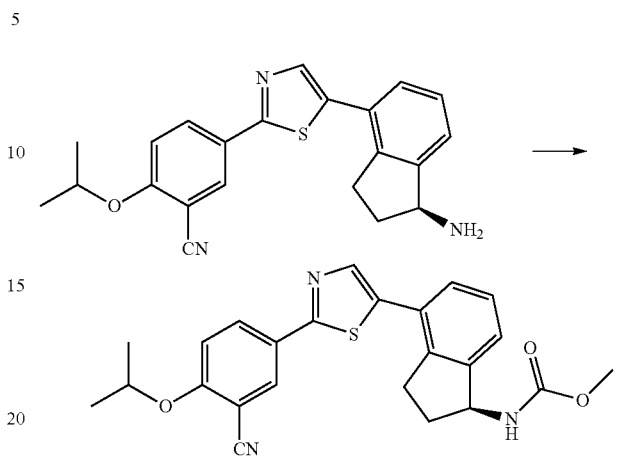

Prepared using General Procedure 8. To a stirred solution of (S)-5-(2-(1-amino-2,3-dihydro-1H-inden-4-yl)thiazol-5-yl)-2-isopropoxybenzonitrile hydrochloride 71 (15 mg, 0.03 mmol) and TEA (11 mg, 0.1 mmol) in DCM (1 mL) was added methyl chloroformate (10 mg, 0.1). The reaction mixture was stirred at room temperature for 16 h. The solvent was evaporated and water (2 mL) was added. The resulting solid was filtered, washed with water, and dried under high vacuum to afford 6 mg (51%) of (S)-methyl(4-(2-(3-cyano-4-isopropoxyphenyl)thiazol-5-yl)-2,3-dihydro-1H-inden-1-yl)carbamate 90 as white solid. LCMS-ESI (m/z) calculated for $C_{24}H_{23}N_3O_3S$: 433.2; found 434.1 $[M+H]^+$, $t_R$=3.86 min.

General Procedure 9. Alkylation of Indane Amines

To a solution of the (R)- or (S)-indane amine in $CH_3CN$ (0.2 M) was added $K_2CO_3$ (3 eq) and the appropriate alkyl halide (1.2 eq). In some cases TEA (3 eq) and DMF (0.1 M) was used. The mixture was heated at 80-95° C. until the starting material was consumed or di-alkylation of the amine becomes prevalent. If necessary, additional alkyl halide is added to drive the reaction. The reaction mixture was filtered to remove inorganic solids and concentrated, re-suspended in EA and washed with water. The organic layer is dried and concentrated, then purified by chromatography (MeOH/DCM) or preparative HPLC to provide the desired product. TBS-protected alcohols were deprotected using 4N HCl.

Compounds 17-20 and 91-95 were prepared using General Procedure 9.

(R)-5-(5-(1-((2-((tert-butyldimethylsilyl)oxy)ethyl)amino)-2,3-dihydro-1H-inden-4-yl)-1,3,4-thiadiazol-2-yl)-2-isopropoxybenzonitrile

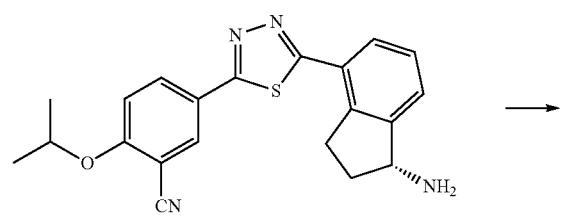

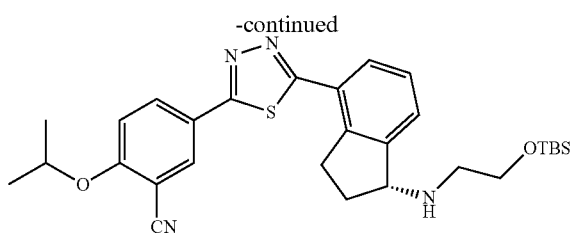

Prepared using General Procedure 9. To a suspension of (R)-5-(5-(1-amino-2,3-dihydro-1H-inden-4-yl)-1,3,4-thiadiazol-2-yl)-2-isopropoxybenzonitrile hydrochloride 5 (50 mg, 0.12 mmol) in anhydrous DMF (5 mL) was added TEA (36.7 mg, 0.36 mmol) and (2-bromoethoxy)(tert-butyl)dimethylsilane (34.6 mg, 0.14 mmol). The solution was stirred at 95° C. After 16 h more (2-bromoethoxy)(tert-butyl)dimethylsilane (34.6 mg, 0.14 mmol) was added and heating continued for 12 h. Water (5 mL) was added and the reaction mixture was extracted with EA (2×5 mL). The organic layers were washed with brine, dried, and purified by column chromatography (EA/hexanes) to afford 10 mg (15%) of (R)-5-(5-(1-((2-((tert-butyldimethylsilyl)oxy)ethyl)amino)-2,3-dihydro-1H-inden-4-yl)-1,3,4-thiadiazol-2-yl)-2-isopropoxybenzonitrile. LCMS-ESI (m/z) calculated for: $C_{29}H_{38}N_4O_2SSi$: 534.3; found 535.3 [M+H]$^+$, $t_R$=3.08 min.

(S)-5-(5-(1-((2-((tert-butyldimethylsilyl)oxy)ethyl)amino)-2,3-dihydro-1H-inden-4-yl)-1,3,4-thiadiazol-2-yl)-2-isopropoxybenzonitrile was prepared in an analogous fashion using (S)-5-(5-(1-amino-2,3-dihydro-1H-inden-4-yl)-1,3,4-thiadiazol-2-yl)-2-isopropoxybenzonitrile hydrochloride 4.

(R)-5-(5-(1-((2-hydroxyethyl)amino)-2,3-dihydro-1H-inden-4-yl)-1,3,4-thiadiazol-2-yl)-2-isopropoxy-benzonitrile (Compound 17)

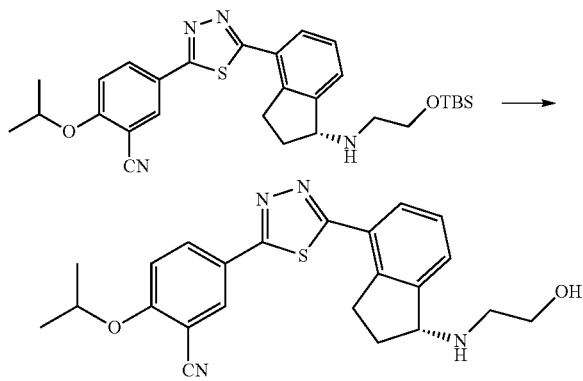

To (R)-5-(5-(1-((2-((tert-butyldimethylsilyl)oxy)ethyl)amino)-2,3-dihydro-1H-inden-4-yl)-1,3,4-thiadiazol-2-yl)-2-isopropoxybenzonitrile (10 mg, 0.018 mmol), in 1,4-dioxane (1.5 mL) was added 4N HCl in dioxanes (0.5 mL). The mixture was stirred at room temperature for 3 h and solvent was evaporated. The crude material was purified by a preparative HPLC to afford 7 mg (90%) of (R)-5-(5-(1-((2-hydroxyethylamino)-2,3-dihydro-1H-inden-4-yl)-1,3,4-thiadiazol-2-yl)-2-isopropoxybenzonitrile 17. LCMS-ESI (m/z) calculated for: $C_{23}H_{24}N_4O_2S$: 420.2; found 421.2 [M+H]$^+$, $t_R$=2.38 min. 1H NMR (400 MHz, CDCl$_3$) δ 8.19 (dd, J=8.9, 2.3 Hz, 1H), 8.15 (d, J=2.2 Hz, 1H), 7.97 (d, J=7.6 Hz, 1H), 7.88 (d, J=7.7 Hz, 1H), 7.48 (t, J=7.7 Hz, 1H), 7.10 (d, J=9.0 Hz, 1H), 4.94 (d, J=4.2 Hz, 1H), 4.76 (dt, J=12.2, 6.1 Hz, 1H), 3.89 (d, J=16.3 Hz, 2H), 3.68-3.20 (m, 2H), 3.20-2.89 (m, 2H), 2.72-2.53 (m, 2H), 2.65-2.53 (m, 1H), 2.49-2.27 (m, 1H), 1.44 (d, J=6.1 Hz, 6H).

(S)-5-(5-(1-((2-hydroxyethyl)amino)-2,3 dihydro-1H-inden-4-yl)-1,3,4-thiadiazol-2-yl)-2-isopropoxy-benzonitrile 18 was prepared in an analogous fashion using (S)-5-(5-(1-((2-((tert-butyldimethylsilyl)oxy)ethyl)amino)-2,3-dihydro-1H-inden-4-yl)-1,3,4-thiadiazol-2-yl) -2-isopropoxybenzonitrile.

(S)-5-(5-(1((2-((tert-butyldimethylsilyl)oxy)ethyl)amino)-2,3-dihydro-1H-inden-4-yl)thiazol-2-yl)-2-isopropoxybenzonitrile

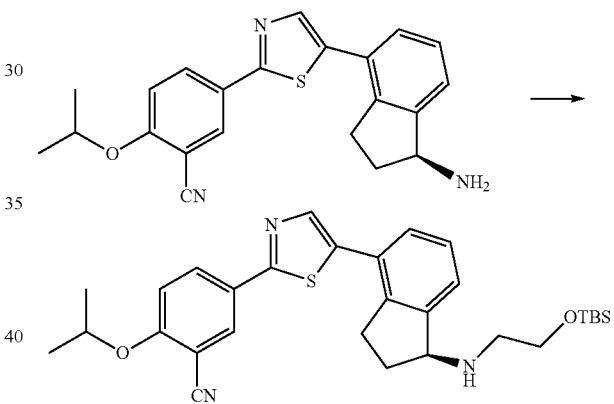

Prepared using General Procedure 9. To a suspension of (S)-5-(2-(1-amino-2,3-dihydro-1H-inden-4-yl)thiazol-5-yl)-2-isopropoxybenzonitrile hydrochloride 71 (25 mg, 0.06 mmol) in anhydrous DMF (2 mL) was added TEA (7.3 mg, 0.36 mmol) and (2-bromoethoxy)(tert-butyl)dimethylsilane (6.9 mg, 0.14 mmol). The solution was stirred at 100° C. for 48 hours. The reaction was diluted with EA (10 mL), washed with water and brine and dried. Concentration and purification by column chromatography (EA/hexanes) gave 29 mg (90%) of (S)-5-(5-(1-((2-((tert-butyldimethylsilyl)oxy)ethyl)amino)-2,3-dihydro-1H-inden-4-yl)thiazol-2-yl)-2-isopropoxybenzonitrile as a dark gray solid. LCMS-ESI (m/z) calculated for: $C_{30}H_{39}N_3O_2SSi$: 533.3; found 534.3 [M+H]$^+$, $t_R$=3.22 min.

(R)-5-(5-(1-((2-((tert-butyldimethylsilyl)oxy)ethyl)amino)-2,3-dihydro-1H-inden-4-yl)-thiazol-2-yl)-2-isopropoxybenzonitrile was prepared in an analogous fashion using (R)-5-(2-(1-amino-2,3-dihydro-1H-inden-4-yl)thiazol-5-yl)-2-isopropoxybenzonitrile hydrochloride 72.

(S)-5-(5-(1-((2-hydroxyethyl)amino)-2,3-dihydro-1H-inden-4-yl)thiazol-2-yl)-2-isopropoxybenzonitrile (Compound 92)

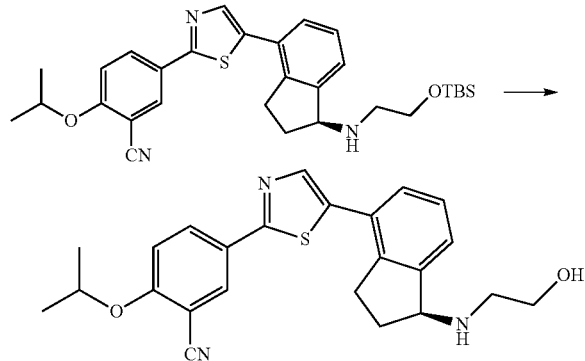

To a solution of (S)-5-(5-(1-((2-((tert-butyldimethylsilyl)oxy)ethyl)amino)-2,3-dihydro-1H-inden-4-yl)thiazol-2-yl)-2-isopropoxybenzonitrile (10 mg, 0.018 mmol) in ether (1 mL) was added 2N HCl in ether (0.1 mL). The mixture was stirred at room temperature for 12 h and solvent was evaporated. The crude material was purified by a preparative HPLC to afford 6 mg (80%) of (S)-5-(5-(1-((2-hydroxyethyl)amino)-2,3-dihydro-1H-inden-4-yl)thiazol-2-yl)-2-isopropoxybenzonitrile 92. LCMS-ESI (m/z) calculated for: $C_{24}H_{25}N_3O_2S$: 419.2; found 420.2 $[M+H]^+$, $t_R$=2.43 min.

(R)-5-(5-(1-((2-hydroxyethyl)amino)-2,3-dihydro-1H-inden-4-yl)thiazol-2-yl)-2-isopropoxybenzonitrile 91 was prepared in an analogous fashion using (R)-5-(5-(1-((2-((tert-butyldimethylsilyl)oxy)ethyl)amino)-2,3-dihydro-1H-inden-4-yl)thiazol-2-yl)-2-isopropoxybenzonitrile.

(S)-methyl 2-((4-(5-(3-cyano-4-isopropoxyphenyl)-1,3,4-thiadiazol-2-yl)-2,3-dihydro-1H-inden-1-yl)amino)acetate

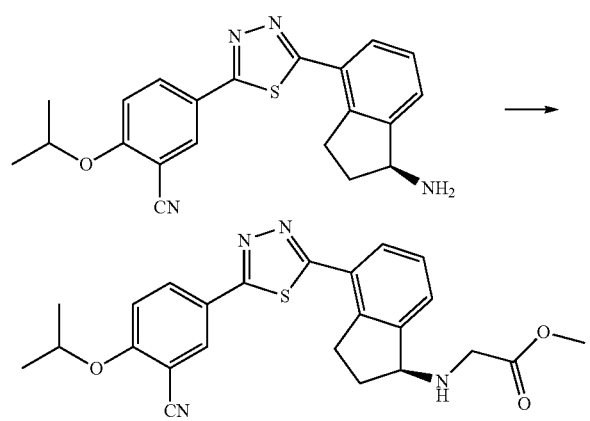

Prepared using General Procedure 9. To a suspension of (S)-5-(5-(1-amino-2,3-dihydro-1H-inden-4-yl)-1,3,4-thiadiazol-2-yl)-2-isopropoxybenzonitrile hydrochloride 4 (150 mg, 0.36 mmol) in $CH_3CN$ (5 mL) was added $K_2CO_3$ (150.9 mg, 1.09 mmol) and methyl 2-bromoacetate (67 mg, 0.43 mmol). The suspension was stirred at 80° C. After 6 h more methyl 2-bromoacetate (6.7 mg, 0.043 mmol) was added and heating continued for 12 h. The reaction mixture was filtered and concentrated. The residue was re-suspended in EA (15 mL), washed with water and brine, dried and concentrated. The product was purified by a silica gel column chromatography (MeOH/DCM) to afford 146 mg (90%) of (S)-methyl 2-((4-(5-(3-cyano-4-isopropoxyphenyl)-1,3,4-thiadiazol-2-yl)-2,3-dihydro-1H-inden-1-yl)amino)acetate as white solid. LCMS-ESI (m/z) calculated for $C_{24}H_{24}N_4O_3S$: 448.2; found 449.1 $[M+H]^+$, $t_R$=2.48 min.

(R)-methyl 2-((4-(5-(3-cyano-4-isopropoxyphenyl)-1,3,4-thiadiazol-2-yl)-2,3-dihydro-1H-inden-1-yl)amino)acetate was prepared in an analogous fashion using (R)-5-(5-(1-amino-2,3-dihydro-1H-inden-4-yl)-1,3,4-thiadiazol-2-yl)-2-isopropoxybenzonitrile hydrochloride 5.

(S)-methyl 2-((tert-butoxycarbonyl)(4-(5-(3-cyano-4-isopropoxyphenyl)-1,3,4-thiadiazol-2-yl)-2,3-dihydro-1H-inden-1-yl)amino)acetate

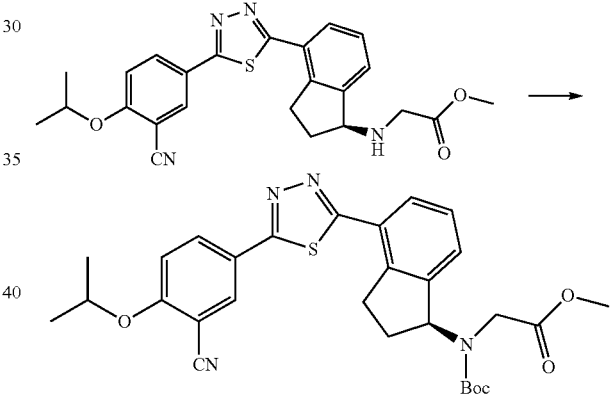

To a solution of (S)-methyl 2-((4-(5-(3-cyano-4-isopropoxyphenyl)-1,3,4-thiadiazol-2-yl)-2,3-dihydro-1H-inden-1-yl)amino)acetate (146 mg, 0.35 mmol) in DCM (2 mL) was added di-tert-butyl dicarbonate (85.3 mg, 0.39 mmol) and reaction was stirred at room temperature for 16 h. Reaction was diluted with DCM (10 mL) and washed with $NaHCO_3$, water, and brine. The product was purified by a silica gel column chromatography (EA/hexanes) to afford 118 mg (66%) of (S)-methyl 2-((tert-butoxycarbonyl)(4-(5-(3-cyano-4-isopropoxyphenyl)-1,3,4-thiadiazol-2-yl)-2,3-dihydro-1H-inden-1-yl)amino)acetate as white solid. LCMS-ESI (m/z) calculated for $C_{29}H_{32}N_4O_5S$: 548.2; found no $M^+$, $t_R$=4.19 min.

(R)-methyl 2-((tert-butoxycarbonyl)(4-(5-(3-cyano-4-isopropoxyphenyl)-1,3,4-thiadiazol-2-yl)-2,3-dihydro-1H-inden-1-yl)amino)acetate was prepared in an analogous fashion using (R)-methyl 2-((4-(5-(3-cyano-4-isopropoxyphenyl)-1,3,4-thiadiazol-2-yl)-2,3-dihydro-1H-inden-1-yl)amino)acetate.

105

(S)-2-((tert-butoxycarbonyl)(4-(5-(3-cyano-4-isopropoxyphenyl)-1,3,4-thiadiazol-2-yl)-2,3-dihydro-1H-inden-1-yl)amino)acetic acid

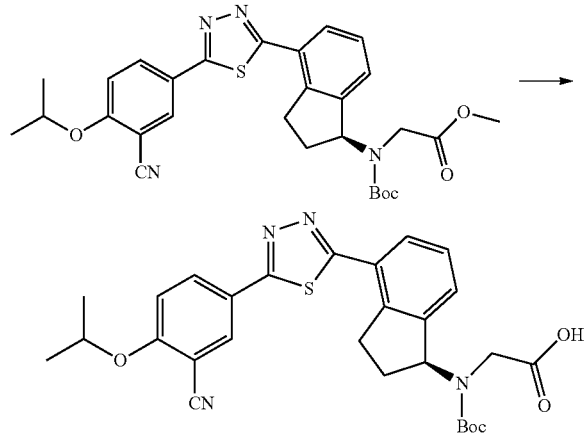

To a stirred solution of (S)-methyl 2-((tert-butoxycarbonyl)(4-(5-(3-cyano-4-isopropoxyphenyl)-1,3,4-thiadiazol-2-yl)-2,3-dihydro-1H-inden-1-yl)amino)acetate (120 mg, 0.21 mmol) in MeOH (2 mL) was added 6N solution of sodium hydroxide (180 µL) and the mixture was stirred at room temperature for overnight. The solvent was evaporated and the residue was dissolved in water (5 mL) and acidified with 1N HCl. The mixture was extracted with EA (3×5 mL) and the organic layers washed with brine, dried over MgSO$_4$, and concentrated to afford 108 mg (92%) of (S)-2-((tert-butoxycarbonyl)(4-(5-(3-cyano-4-isopropoxyphenyl)-1,3,4-thiadiazol-2-yl)-2,3-dihydro-1H-inden-1yl)amino)acetic acid as white solid which was used in the next experiments without purification. LCMS-ESI (m/z) calculated for C$_{28}$H$_{30}$N$_4$O$_5$S: 534.2; found no M$^+$, t$_R$=3.81 min.

(R)-2-((tert-butoxycarbonyl)(4-(5-(3-cyano-4-isopropoxyphenyl)-1,3,4-thiadiazol-2-yl)-2,3-dihydro-1H-inden-1yl)amino)acetic acid was prepared in an analogous fashion using (R)-methyl 2-((tert-butoxycarbonyl)(4-(5-(3-cyano-4-isopropoxyphenyl)-1,3,4-thiadiazol-2-yl)-2,3-dihydro-1H-inden-1-yl)amino)acetate.

(S)-methyl 2-((4-(2-(3-cyano-4-isopropoxyphenyl)thiazol-5-yl)-2,3-dihydro-1H-inden-1-yl)amino)acetate (Compound 99)

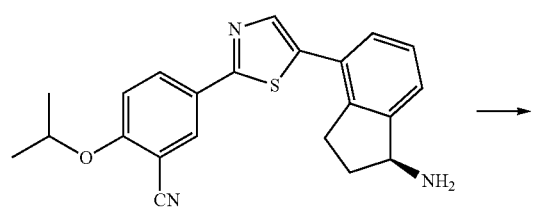

106

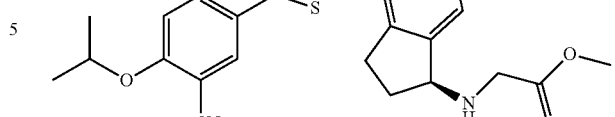

Prepared using General Procedure 9. To a suspension of (S)-5-(2-(1-amino-2,3-dihydro-1H-inden-4-yl)thiazol-5-yl)-2-isopropoxybenzonitrile hydrochloride 71 (150 mg, 0.36 mmol) in CH$_3$CN (5 mL) was added K$_2$CO$_3$ (150.9 mg, 1.09 mmol) and methyl 2-bromoacetate (66 mg, 0.43 mmol). The suspension was stirred at 80° C. for 16 h. The reaction mixture was filtered and concentrated. The residue was re-suspended in EA (15 mL), washed with water and brine, dried and concentrated. The product was purified by a silica gel column chromatography (EA/hexanes) to afford 76 mg (47%) of (S)-methyl 2-((4-(2-(3-cyano-4-isopropoxyphenyl)thiazol-5-yl)-2,3-dihydro-1H-inden-1-yl)amino)acetate as white solid. LCMS-ESI (m/z) calculated for C$_{25}$H$_{25}$N$_3$O$_3$S: 447.2; found 448.2 [M+H]$^+$, t$_R$=2.57 min. $^1$H NMR (400 MHz, CDCl$_3$) δ 8.23-8.01 (m, 2H), 7.90 (s, 1H), 7.41 (dd, J=21.0, 7.4 Hz, 1H), 7.29 (dd, J=9.8, 5.2 Hz, 1H), 7.04 (d, J=8.9 Hz, 1H), 7.04 (d, J=8.9 Hz, 1H), 4.74 (dt, J=12.1, 6.1 Hz, 1H), 4.33 (t, J=6.1 Hz, 1H), 3.76 (d, J=4.8 Hz, 3H), 3.55 (s, 2H), 3.24 (ddd, J=15.8, 8.2, 5.6 Hz, 1H), 3.05-2.86 (m, 1H), 2.47-2.25 (m, 2H), 2.02-1.84 (m, 1H), 1.53-1.36 (m, 6H). $^{13}$C NMR (101 MHz, CDCl$_3$) δ 173.14, 164.87, 161.08, 146.06, 141.45, 141.28, 138.20, 132.13, 131.96, 128.08, 127.98, 127.56, 126.77, 124.66, 116.17, 114.01, 103.76, 72.55, 62.94, 52.19, 48.53, 32.99, 31.34, 22.04.

(R)-methyl 2-((4-(2-(3-cyano-4-isopropoxyphenyl)thiazol-5-yl)-2,3-dihydro-1H-inden-1-yl)amino)acetate was prepared in an analogous fashion using (R)-5-(2-(1-amino-2,3-dihydro-1H-inden-4-yl)thiazol-5-yl)-2-isopropoxybenzonitrile hydrochloride 72.

(S)-methyl 2-((tert-butoxycarbonyl)(4-(2-(3-cyano-4-isopropoxyphenyl)thiazol-5-yl)-2,3-dihydro-1H-inden-1-yl)amino)acetate

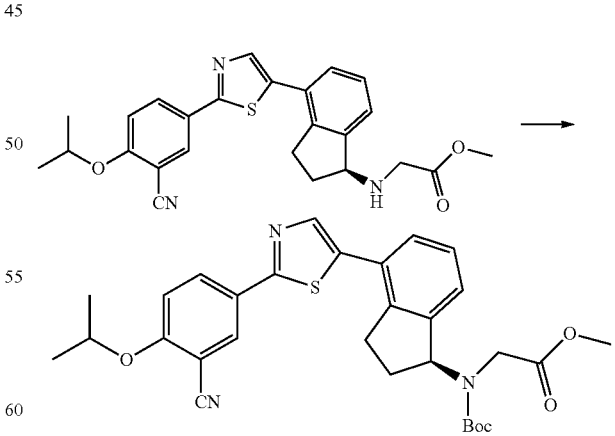

To a solution of (S)-methyl 2-((4-(2-(3-cyano-4-isopropoxyphenyl)thiazol-5-yl)-2,3-dihydro-1H-inden-1-yl)amino)acetate (76 mg, 0.17 mmol) in DCM (1 mL) was added di-tert-butyl dicarbonate (44.5 mg, 0.20 mmol) and reaction was stirred at room temperature for 16 h. Reaction was diluted with DCM (10 mL) and washed with NaHCO$_3$, water, brine and then dried. Concentration of the filtrate gave 90 mg (96%) of (S)-methyl 2-((tert-butoxycarbonyl)(4-(2-(3-cyano-4-isopropoxyphenyl)thiazol-5-yl)-2,3-dihydro-1H-inden-1-yl)amino)acetate as white solid. LCMS-ESI (m/z) calculated for C$_{30}$H$_{33}$N$_3$O$_5$S: 547.21; found no M$^+$, t$_R$=4.42 min.

(R)-methyl 2-((tert-butoxycarbonyl)(4-(2-(3-cyano-4-isopropoxyphenyl)thiazol-5-yl)-2,3-dihydro-1H-inden-1-yl)amino)acetate was prepared in an analogous fashion using (R)-methyl 2-((4-(5-(3-cyano-4-isopropoxyphenyl)-1,3,4-thiadiazol-2-yl)-2,3-dihydro-1H-inden-1-yl)amino)acetate.

EDC (1.35 eq) and the reaction was stirred at room temperature for 60 min. The appropriate amine (1.1 eq) was added and the reaction was stirred at room temperature for 2 h. The Boc-protected amino amide was precipitated out of water or extracted with EA and dried over MgSO$_4$. The product was purified by recrystallization or preparative HPLC. The resulting solid was heated in 4M HCl/dioxane at 50° C. until the reaction was complete. The product was precipitated as the hydrochloride salt by the addition of diethyl ether.

Compounds 21-25, 39, and 98, 100-108 were prepared using General Procedure 10.

(S)-2-((tert-butoxycarbonyl)(4-(2-(3-cyano-4-isopropoxyphenyl)thiazol-5-yl)-2,3-dihydro-1H-inden-1-yl)amino)acetic acid (S)-2-((4-(5-(3-cyano-4-isopropoxyphenyl)-1,3,4-thiadiazol-2-yl)-2,3-dihydro-1H-inden-1-yl)amino)-N,N-dimethylacetamide hydrochloride (Compound 21)

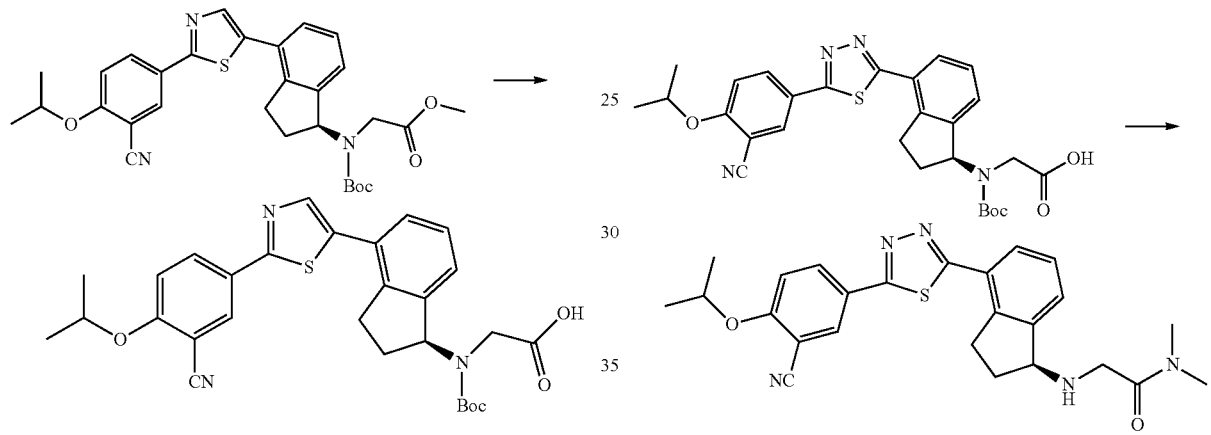

To a stirred solution of (S)-methyl 2-((tert-butoxycarbonyl)(4-(2-(3-cyano-4-isopropoxyphenyl)thiazol-5-yl)-2,3-dihydro-1H-inden-1-yl)amino)acetate (120 mg, 0.22 mmol) in MeOH (2 mL) was added 6N sodium hydroxide (180 µL) and the mixture was stirred at room temperature for overnight. The solvent was evaporated and the residue was dissolved in water (5 mL) and acidified with 1N HCl. The mixture was extracted with EA (3×5 mL) and the organic layers washed with brine, dried over MgSO$_4$, and concentrated to afford 110 mg (94%) of (S)-2-((tert-butoxycarbonyl)(4-(2-(3-cyano-4-isopropoxyphenyl)thiazol-5-yl)-2,3-dihydro-1H-inden-1-yl)amino)acetic acid as white solid which was used in the next experiments without purification. LCMS-ESI (m/z) calculated for C$_{29}$H$_{31}$N$_3$O$_5$S: 533.2; found 534.2 [M+H]$^+$, t$_R$=3.92 min.

(R)-2-((tert-butoxycarbonyl)(4-(2-(3-cyano-4-isopropoxyphenyl)thiazol-5-yl)-2,3-dihydro-1H-inden-1-yl)amino)acetic acid was prepared in an analogous fashion using (R)-methyl 2-((tert-butoxycarbonyl)(4-(2-(3-cyano-4-isopropoxyphenyl)thiazol-5-yl)-2,3-dihydro-1H-inden-1-yl)amino)acetate.

General Procedure 10. Preparation of Indane Amino Amides

To the Boc-protected (R)- or (S)-indane aminoacid (1 equivalent) in DMF (2 M) was added HOBt (1.35 eq) and Prepared using General Procedure 10. To (S)-2-((tert-butoxycarbonyl)(4-(5-(3-cyano-4-isopropoxyphenyl)-1,3,4-thiadiazol-2-yl)-2,3-dihydro-1H-inden-1yl)amino)acetic (25 mg, 0.04 mmol) was added HOBt (9.4 mg, 0.07 mmol) and EDC (13.3 mg, 0.07 mmol) in anhydrous DMF (1 mL) and the reaction mixture stirred at room temperature for 60 min. Dimethyl amine (2.3 mg, 0.05 mmol) was added and the mixture was stirred at room temperature for 12 h. The crude reaction was purified by preparative HPLC purification to provide the Boc-product amido amide as white solid. This material was treated with 4N HCl in dioxane at 50° C. for 2 h. The reaction mixture was diluted with diethyl ether (5 mL), and the resulting solid collected to afford 10 mg (46% over two steps) of (S)-2-((4-(5-(3-cyano-4-isopropoxyphenyl)-1,3,4-thiadiazol-2-yl)-2,3-dihydro-1H-inden-1-yl)amino)-N,N-dimethylacetamide hydrochloride 21. LCMS-ESI (m/z) calculated for C$_{25}$H$_{27}$N5O$_2$S: 461.2; found 462.1 [M+H]$^+$, t$_R$=3.90 min.

(R)-2-((4-(5-(3-cyano-4-isopropoxyphenyl)-1,3,4-thiadiazol-2-yl)-2,3-dihydro-1H-inden-1-yl)amino)-N,N-dimethylacetamide hydrochloride 22 was prepared in an analogous fashion using (R)-2-((tert-butoxycarbonyl)(4-(5-(3-cyano-4-isopropoxyphenyl)-1,3,4-thiadiazol-2-yl)-2,3-dihydro-1H-inden-1yl)amino)acetic.

5-(5-((S)-1-((2-((S)-3-hydroxypyrrolidin-1-yl)-2-oxoethyl)amino)-2,3-dihydro-1H-inden-4-yl)thiazol-2-yl)-2-isopropoxybenzonitrile (Compound 104)

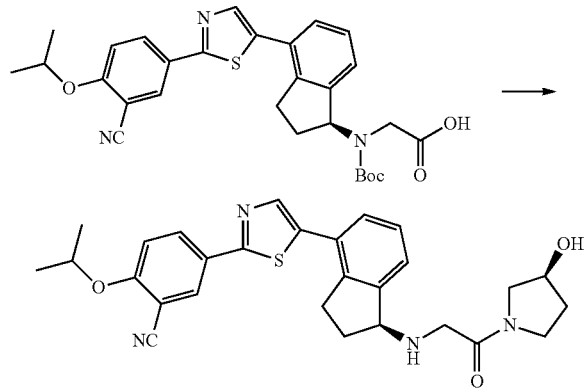

Prepared using General Procedure 10. To (5)-2-((tert-butoxycarbonyl)(4-(2-(3-cyano-4-isopropoxyphenyl)thiazol-5-yl)-2,3-dihydro-1H-inden-1-yl)amino)acetic acid (12 mg, 0.02 mmol) and HOBt (4.5 mg, 0.03 mmol) was added EDC (6.4 mg, 0.03 mmol) in anhydrous DMF (1 mL) and the reaction mixture stirred at room temperature for 60 min. (S)-pyrrolidin-3-ol (2.3 mg, 0.02 mmol) was added and the mixture was stirred at room temperature for 12 h. The crude reaction was purified by preparative HPLC purification to provide the Boc-product amido amide as white solid. This material was treated with 4N HCl in dioxane at 50° C. for 2 h. The reaction mixture was diluted with diethyl ether (5 mL), and the resulting solid collected to afford 5 mg (50% over two steps) of 5-(5-((S)-1-((2-((S)-3-hydroxypyrrolidin-1-yl)-2-oxoethyl)amino)-2,3-dihydro-1H-inden-4-yl)thiazol-2-yl)-2-isopropoxybenzonitrile hydrochloride 104. LCMS-ESI (m/z) calculated for $C_{28}H_{30}N_4O_3S$: 502.2; found 503.2 $[M+H]^+$, $t_R$=3.77 min.

5-(5-((R)-1-((2-((S)-3-hydroxypyrrolidin-1-yl)-2-oxoethyl)amino)-2,3-dihydro-1H-inden-4-yl) thiazol-2-yl)-2-isopropoxybenzonitrile hydrochloride 102 was prepared in an analogous fashion using (R)-2-((tert-butoxycarbonyl)(4-(2-(3-cyano-4-isopropoxyphenyl)thiazol-5-yl)-2,3-dihydro-1H-inden-1-yl)amino)acetic acid.

(R)-2-((4-(5-(3-cyano-4-isopropoxyphenyl)-1,3,4-thiadiazol-2-yl)-2,3-dihydro-1H-inden-1-yl)amino)acetic acid (Compound 27)

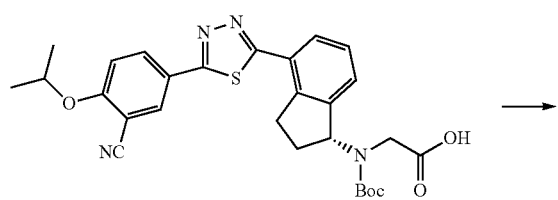

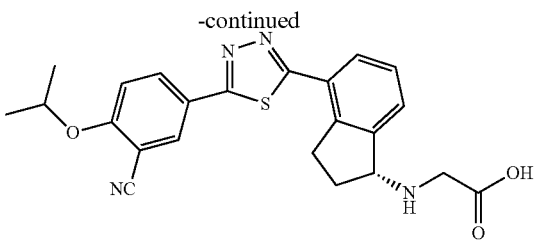

To a stirred solution of (R)-2-((tert-butoxycarbonyl)(4-(5-(3-cyano-4-isopropoxyphenyl)-1,3,4-thiadiazol-2-yl)-2,3-dihydro-1H-inden-1-yl)amino)acetic acid (20 mg, 0.03) mmol in 1,4-dioxane (0.5 mL) was added 4N HCl in 1,4-dioxane (0.2 mL). The mixture was stirred at 50° C. for 2 h before it was concentrated and triturated with ether to afford 13 mg of (R)-2-((4-(5-(3-cyano-4-isopropoxyphenyl)-1,3,4-thiadiazol-2-yl)-2,3-dihydro-1H-inden-1-yl)amino)acetic acid as yellow-green solid. LCMS-ESI (m/z) calculated for $C_{23}H_{22}N_4O_3S$: 434.14, found 435.2 $[M+H]^+$, $t_R$=2.51 min.

(S)-2-((4-(5-(3-cyano-4-isopropoxyphenyl)-1,3,4-thiadiazol-2-yl)-2,3-dihydro-1H-inden-1-yl)amino)acetic acid 26 was in prepared in similar fashion using (S)-2-((tert-butoxycarbonyl)(4-(5-(3-cyano-4-isopropoxyphenyl)-1,3,4-thiadiazol-2-yl)-2,3-dihydro-1H-inden-1-yl)amino)acetic acid.

(R)-2-((4-(2-(3-cyano-4-isopropoxyphenyl)thiazol-5-yl)-2,3-dihydro-1H-inden-1-yl)amino)acetic acid (Compound 96)

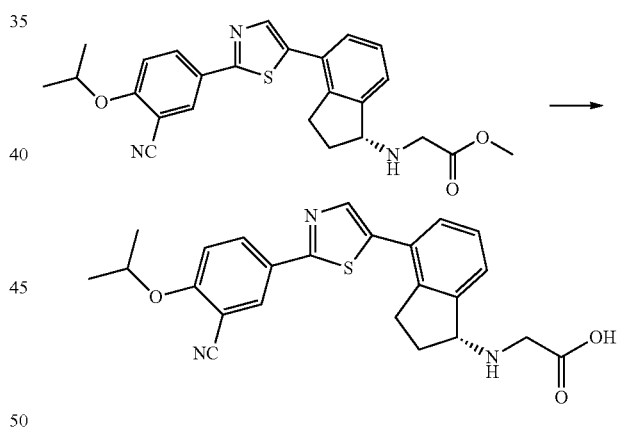

To (R)-methyl 2-((4-(2-(3-cyano-4-isopropoxyphenyl)thiazol-5-yl)-2,3-dihydro-1H-inden-1-yl)amino)acetate (100 mg, 0.22 mmol) in ethanol was added 2N NaOH (1.1 mL) and the mixture stirred at room temperature for 12 h. The solvent was evaporated and the residue dissolved in water and acidified with 1N HCl. The resulting solid was filtered and dried to give 60 mg (63%) of (R)-2-((4-(2-(3-cyano-4-isopropoxyphenyl)thiazol-5-yl)-2,3-dihydro-1H-inden-1-yl) amino)acetic acid 96 as yellow-green solid. LCMS-ESI (m/z) calculated for $C_{24}H_{23}N_3O_3S$: 433.1; found 434.2 $[M+H]^+$, $t_R$=2.61 min.

(S)-2-((4-(2-(3-cyano-4-isopropoxyphenyl)thiazol-5-yl)-2,3-dihydro-1H-inden-1-yl)amino)acetic acid 97 was prepared in an analogous fashion using (S)-methyl 2-((4-(2-(3-cyano-4-isopropoxyphenyl)thiazol-5-yl)-2,3-dihydro-1H-inden-1-yl)amino)acetate.

General Procedure 11. Reductive Aminations of Indane Amines.

To a solution of the primary or optionally substituted secondary (R)- or (S)-indane amine (1 eq) in MeOH (0.01 M) was added acetic acid (0.01 eq) and the appropriate aldehyde (1.1 eq). The reaction was stirred at 25-50° C. until imine formation was complete (2-18 h). Sodium borohydride or sodium triacetoxyborohydride (10 eq) was added and the reaction was stirred at room temperature until reduction was complete (2-8 h). The solvent was evaporated and the residue partitioned between NaHCO$_3$ and EA. The organic layer was collected, dried and purified by preparative HPLC.

Compounds 28-30, 109 and 110 were prepared using General Procedure 11.

(S)-5-(5-(1-(((1H-imidazol-2-yl)methyl)amino)-2,3-dihydro-1H-inden-4-yl)-1,3,4-thiadiazol-2-yl)-2-isopropoxybenzonitrile (Compound 28)

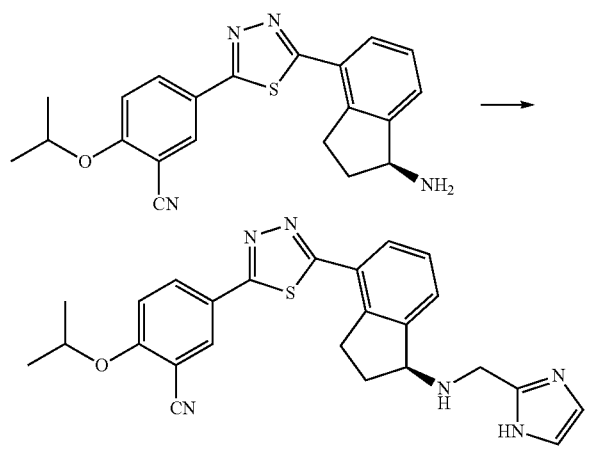

Prepared using General Procedure 11. To (S)-5-(5-(1-amino-2,3-dihydro-1H-inden-4-yl)-1,3,4-thiadiazol-2-yl)-2-isopropoxybenzonitrile hydrochloride 4 (25 mg, 0.06 mmol) and 1H-imidazole-2-carbaldehyde (6.4 mg, 0.06 mmol) in anhydrous MeOH (1 mL) was added acetic acid (1 drop). The solution was stirred at 55° C. for 3 h before cooling to room temperature and the addition of NaBH$_4$ (4.6 mg, 0.12 mmol). The mixture was stirred at room temperature for 12 h. The reaction mixture was quenched with water (0.5 mL) and partitioned between EA (5 mL) and water (5 mL). The organic layers washed with water and brine, and the product purified by preparative HPLC to afford 22 mg (81%) of (S)-5-(5-(1-(((1H-imidazol-2-yl)methyl)amino)-2,3-dihydro-1H-inden-4-yl)-1,3,4-thiadiazol-2-yl)-2-isopropoxybenzonitrile 28 as half-white solid. LCMS-ESI (m/z) calculated for C$_{25}$H$_{24}$N$_6$OS: 456.2; found 457.2 [M+H]$^+$, t$_R$=2.38 min.

(R)-5-(5-(1-(((1H-imidazol-2-yl)methyl)amino)-2,3-dihydro-1H-inden-4-yl)-1,3,4-thiadiazol-2-yl) -2-isopropoxybenzonitrile 29 was prepared in an analogous fashion using (R)-5-(5-(1-amino-2,3-dihydro-1H-inden-4-yl)-1,3,4-thiadiazol-2-yl)-2-isopropoxybenzonitrile hydrochloride 5.

(R)-5-(5-(1-(((1H-imidazol-2-yl)methyl)amino)-2,3-dihydro-1H-inden-4-yl)thiazol-2-yl)-2-isopropoxybenzonitrile (Compound 109)

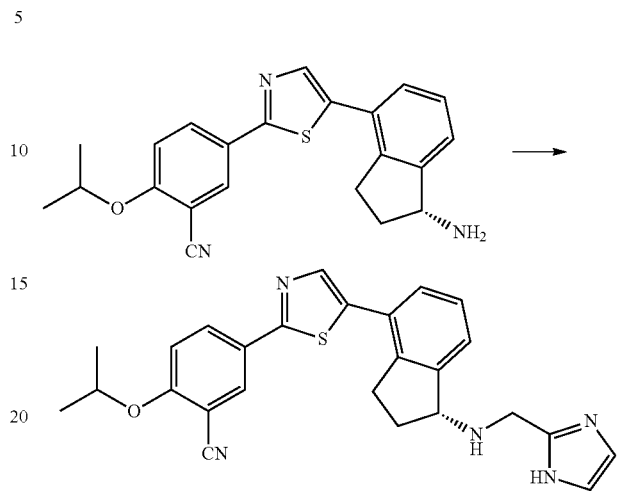

Prepared using General Procedure 11. To (R)-5-(5-(1-amino-2,3-dihydro-1H-inden-4-yl)thiazol-2-yl)-2-isopropoxybenzonitrile hydrochloride 72 (20 mg, 0.05 mmol) and 1H-imidazole-2-carbaldehyde (7 mg, 0.07 mmol) in anhydrous MeOH (0.5 mL) was added acetic acid (1 drop). The solution was stirred at 55° C. for 3 h before cooling to room temperature and the addition of NaBH$_4$ (37.8 mg, 0.1 mmol). The mixture was stirred at room temperature for 12 h. The reaction mixture was quenched with water (0.5 mL) and partitioned between EA (5 mL) and water (5 mL). The organic layers washed with water and brine, and the product purified by preparative HPLC to afford 17 mg (77%) of (R)-5-(5-(1-(((1H-imidazol-2-yl)methyl)amino)-2,3-dihydro-1H-inden-4-yl)thiazol-2-yl)-2-isopropoxybenzonitrile 109. LCMS-ESI (m/z) calculated for C$_{26}$H$_{25}$N$_5$OS: 455.2; found 456.2 [M+H]$^+$, t$_R$=2.53 min.

(S)-5-(5-(1-(((1H-imidazol-2-yl)methyl)amino)-2,3-dihydro-1H-inden-4-yl)thiazol-2-yl)-2-isopropoxybenzonitrile 110 was prepared in an analogous fashion using (S)-5-(5-(1-amino-2,3-dihydro-1H-inden-4-yl)thiazol-2-yl)-2-isopropoxybenzonitrile hydrochloride 71.

(S)-2-isopropoxy-5-(5-(1-((2-(methylsulfonyl)ethyl)amino)-2,3-dihydro4H-inden-4-yl)-1,3,4-thiadiazol-2-yl)benzonitrile (Compound 31)

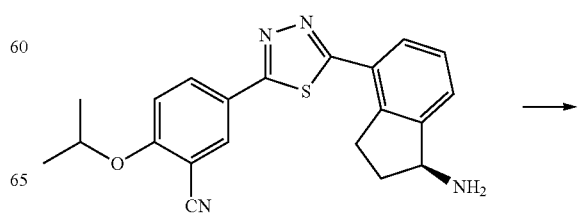

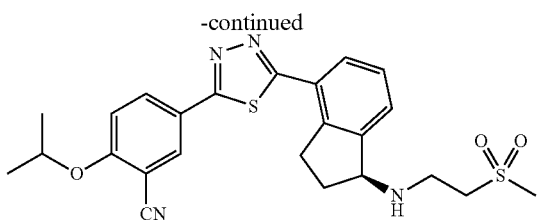

To a stirred solution of (S)-5-(5-(1-amino-2,3-dihydro-1H-inden-4-yl)-1,3,4-thiadiazol-2-yl)-2-isopropoxybenzonitrile hydrochloride 4 (25 mg, 0.06 mmol) and DIEA (32 mg, 0.24 mmol) in DMA (1 mL) was added (methylsulfonyl)ethene (20 mg, 0.18 mmol). The reaction mixture was heated at 90° C. for 24 h. The solvent was evaporated and the product purified by preparative HPLC to afford 9 mg (31%) of (S)-2-isopropoxy-5-(5-(1-((2-(methylsulfonyl)ethyl)amino)-2,3-dihydro-1H-inden-4-yl)-1,3,4-thiadiazol-2-yl)benzonitrile 31 as half-white solid. LCMS-ESI (m/z) calculated for. $C_{24}H_{26}N_4O_3S_2$: 482.1; found 483.1 [M+H]$^+$, $t_R$=2.49 min.

(R)-2-isopropoxy-5-(5-(1-((2-(methylsulfonyl)ethyl)amino)-2,3-dihydro-1H-inden-4-yl)-1,3,4-thiadiazol-2-yl)benzonitrile 32 was prepared in an analogous fashion using (R)-5-(5-(1-amino-2,3-dihydro-1H-inden-4-yl)-1,3,4-thiadiazol-2-yl)-2-isopropoxybenzonitrile hydrochloride 5.

(S)-2-isopropoxy-5-(5-(1-((2-(methylsulfonyl)ethyl)amino)-2,3-dihydro-1H-inden-4-yl)thiazol-2-yl)benzonitrile (Compound 221)

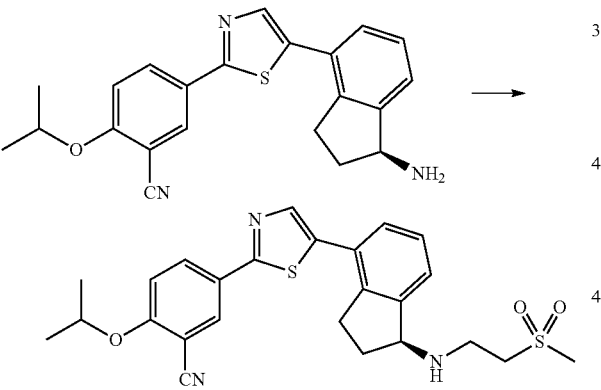

To a stirred solution of (S)-5-(5-(1-amino-2,3-dihydro-1H-inden-4-yl)thiazol-2-yl)-2-isopropoxybenzonitrile hydrochloride 71 (60 mg, 0.15 mmol) and DIEA (32 mg, 0.24 mmol) in 1,4-dioxane (0.5 mL) was added (methylsulfonyl)ethene (92 mg, 0.88 mmol). The reaction mixture was heated at 90° C. for 24 h. The reaction was diluted with DCM (5 mL) and washed with saturated aqueous ammonium chloride (2×5 mL) and saturated aqueous sodium bicarbonate (2×5 mL) and then dried. The crude reaction was purified by a silica gel column (MeOH/DCM) to yield 44 mg (61%) of (S)-2-isopropoxy-5-(5-(1-((2-(methylsulfonyl)ethyl)amino)-2,3-dihydro-1H-inden-4-yl)thiazol-2-yl)benzonitrile 221 as brown liquid. LCMS-ESI (m/z) calculated for $C_{25}H_{27}N_3O_3S_2$: 481.1; found 482.1 [M+H]$^+$, $t_R$=2.49 min. $^1$H NMR (400 MHz, CDCl$_3$) δ 8.19-8.08 (m, 2H), 7.92 (s, 1H), 7.46 (dd, J=7.4, 0.9 Hz, 1H), 7.33 (dt, J=14.9, 7.3 Hz, 2H), 7.06 (d, J=8.9 Hz, 1H), 5.31 (s, 1H), 4.75 (dt, J=12.2, 6.1 Hz, 1H), 4.35 (t, J=6.6 Hz, 1H), 3.41-3.15 (m, 5H), 3.10-2.96 (m, 4H), 2.57-2.45 (m, 1H), 1.93 (ddd, J=12.8, 6.2, 1.7 Hz, 1H), 1.46 (d, J=6.1 Hz, 6H).

(R)-2-isopropoxy-5-(5-(1-((2-(methylsulfonyl)ethyl)amino)-2,3-dihydro-1H-inden-4-yl)thiazol-2-yl)benzonitrile 220 was prepared in an analogous fashion using (R)-5-(5-(1-amino-2,3-dihydro-1H-inden-4-yl)thiazol-2-yl)-2-isopropoxybenzonitrile hydrochloride 72.

General Procedure 12. Preparation of Indane Sulfonamides Via Sulfonyl Chlorides

To a stirred solution of (R)- or (S)-indane amine (1 eq) in DCM (0.08M) was added TEA (3 eq) and the appropriate sulfonyl chloride (1.5 eq.) at room temperature. The reaction was stirred at room temperature for 18 h. The solvent was evaporated and the pure product isolated after preparative HPLC purification.

Compounds 33-36 and 111-120 were prepared using General Procedure 12.

(S)-N-(4-(5-(3-cyano-4-isopropoxyphenyl)-1,3,4-thiadiazol-2-yl)-2,3-dihydro-1H-inden-1-yl)methanesulfonamide (Compound 33)

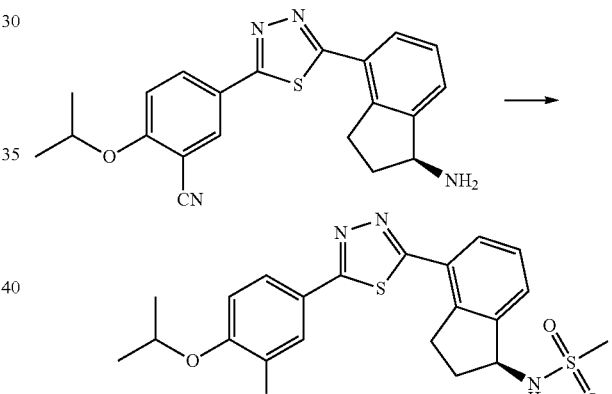

Prepared using General Procedure 12. To a stirred solution of (S)-5-(5-(1-amino-2,3-dihydro-1H-inden-4-yl)-1,3,4-thiadiazol-2-yl)-2-isopropoxybenzonitrile hydrochloride 4 (20 mg, 0.04 mmol) and TEA (14.7 mg, 0.14 mmol) in DCM (2 mL) was added methane sulfonylchloride (8.3 mg, 0.07 mmol) and the mixture was stirred at room temperature for 16 h. The solvent was evaporated and the residue purified by preparative HPLC to afford 12 mg (55%) of (S)-N-(4-(5-(3-cyano-4-isopropoxyphenyl)-1,3,4-thiadiazol-2-yl)-2,3-dihydro-1H-inden-1-yl)methanesulfonamide 33 as white solid. LCMS-ESI (m/z) calculated for $C_{22}H_{22}N_4O_3S_2$: 454.1; found 455.1 [M+H]$^+$, $t_R$=3.48 min.

(R)-N-(4-(5-(3-cyano-4-isopropoxyphenyl)-1,3,4-thiadiazol-2-yl)-2,3-dihydro-1H-inden-1-yl)methanesulfonamide 34 was prepared in an analogous fashion using (R)-5-(5-(1-amino-2,3-dihydro-1H-inden-4-yl)-1,3,4-thiadiazol-2-yl)-2-isopropoxybenzonitrile hydrochloride 5.

(R)-N-(4-(2-(3-cyano-4-isopropoxyphenyl)thiazol-5-yl)-2,3-dihydro-1H-inden-1-yl)methanesulfonamide (Compound 111H)

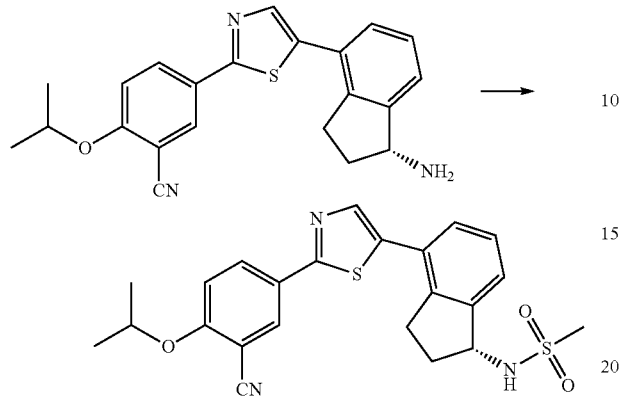

Prepared using General Procedure 12. (R)-5-(5-(1-amino-2,3-dihydro-1H-inden-4-yl)thiazol-2-yl)-2-isopropoxybenzonitrile hydrochloride 72 (60 mg, 0.15 mmol) and TEA (0.06 mL, 0.4 mmol) in DCM (0.5 mL) was added methane sulfonylchloride (8.3 mg, 0.07 mmol) at 0° C. and the reaction mixture was stirred at room temperature for 16 h. The mixture was diluted with DCM (5 mL) and washed with aqueous ammonium chloride, and brine. The crude material was purified by silica gel column chromatography (MeOH/DCM) to afford 39 mg (58%) of (R)-N-(4-(2-(3-cyano-4-isopropoxyphenyl)thiazol-5-yl) -2,3-dihydro-1H-inden-1-yl)methane sulfonamide 111 as white solid. LCMS-ESI (m/z) calculated for $C_{23}H_{23}N_3O_3S_2$: 453.1; found 454.1 $[M+H]^+$, $t_R$=3.64 min.

(S)-N-(4-(2-(3-cyano-4-isopropoxyphenyl)thiazol-5-yl)-2,3-dihydro-1H-inden-1-yl)methanesulfonamide 112 was prepared in an analogous fashion using (S)-5-(5-(1-amino-2,3-dihydro-1H-inden-4-yl)thiazol-2-yl)-2-isopropoxybenzonitrile hydrochloride 71.

(S)-N-(4-(5-(3-cyano-4-isopropoxyphenyl)-1,3,4-thiadiazol-2-yl)-2,3-dihydro-1H-inden-1-yl)ethenesulfonamide

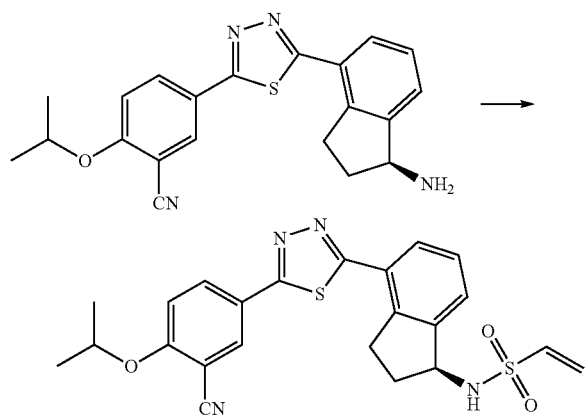

To a stirred solution of (S)-5-(5-(1-amino-2,3-dihydro-1H-inden-4-yl)-1,3,4-thiadiazol-2-yl)-2-isopropoxybenzonitrile hydrochloride 4 (40 mg, 0.5 mmol) and TEA (49 mg, 0.48 mmol) in DCM (2 mL) was added 2-chloroethanesulfonyl chloride (79 mg, 0.48 mmol) at 0° C. The reaction was warmed to room temperature and stirred for 2 h. The reaction was quenched by the addition of $NaHCO_3$. The product was purified by chromatography (EA/hexane) to provide 30 mg (66%) of (S)-N-(4-(5-(3-cyano-4-isopropoxyphenyl)-1,3,4-thiadiazol-2-yl)-2,3-dihydro-1H-inden-1-yl)ethenesulfonamide as yellow solid. LCMS-ESI (m/z) calculated for $C_{23}H_{22}N_4O_3S_2$: 466.1; found 467.1 $[M+H]^+$, $t_R$=3.63 min.

(R)-N-(4-(5-(3-cyano-4-isopropoxyphenyl)-1,3,4-thiadiazol-2-yl)-2,3-dihydro-1H-inden-1-yl)ethenesulfonamide was prepared in an analogous fashion using (R)-5-(5-(1-amino-2,3-dihydro-1H-inden-4-yl)-1,3,4-thiadiazol-2-yl)-2-isopropoxybenzonitrile hydrochloride 5.

(R)-N-(4-(2-(3-cyano-4-isopropoxyphenyl)thiazol-5-yl)-2,3-dihydro-1H-inden-1-yl)ethenesulfonamide

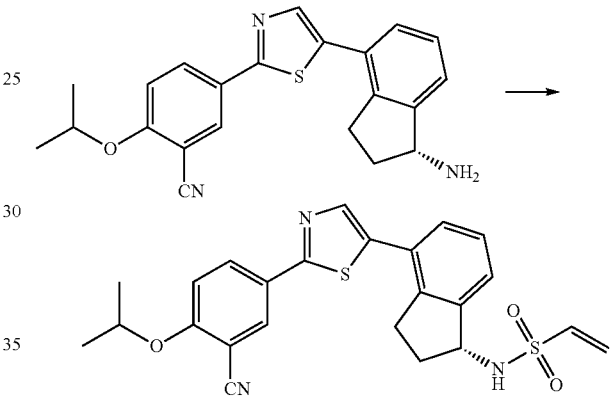

To (R)-5-(5-(1-amino-2,3-dihydro-1H-inden-4-yl)thiazol-2-yl)-2-isopropoxybenzonitrile hydrochloride 72 (0.5 g, 1.3 mmol) in DCM (10 mL) was added TEA (0.88 mL, 6.3 mmol) followed by 2-chloroethanesulfonyl chloride (0.4 mL, 163 mmol) at 0° C. and the reaction was stirred at room temperature overnight. During this time additional reagents TEA (0.2 mL) and 2-chloroethanesulfonyl chloride (0.15 mL) were added to drive the reaction to completion. The reaction mixture was concentrated and the crude residue was purified by a silica gel column (EA/hexanes) to afford 378 mg of (R)-N-(4-(2-(3-cyano-4-isopropoxyphenyl)thiazol-5-yl)-2,3-dihydro-1H-inden-1-yl)ethenesulfonamide as fine yellow powder. LCMS-ESI (m/z) calculated for $C_{24}H_{23}N_3O_3S_2$: 465.12; found 466.1 $[M+H]^+$, $t_R$=3.82 min. $^1$H NMR (400 MHz, $CDCl_3$) δ 8.10 (s, 2H), 7.85 (s, 1H), 7.48-7.26 (m, 3H), 7.01 (d, J=7.3 Hz, 1H), 6.64 (dd, J=16.5, 9.8 Hz, 1H), 6.33 (d, J=16.5 Hz, 1H), 5.97 (d, J=9.8 Hz, 1H), 4.90 (d, J=7.3 Hz, 1H), 4.77- 4.46 (m, 2H), 3.32-2.83 (m, 2H), 2.64 (s, 1H), 2.02-1.84 (m, 1H), 1.40 (t, J=5.8 Hz, 6H).

(S)-N-(4-(2-(3-cyano-4-isopropoxyphenyl)thiazol-5-yl)-2,3-dihydro-1H-inden-1-yl)ethane sulfonamide was prepared in an analogous fashion using (S)-5-(5-(1-amino-2,3-dihydro-1H-inden-4-yl)thiazol-2-yl)-2-isopropoxybenzonitrile hydrochloride 71.

General Procedure 13. Preparation of Indane Sulfonamides Via Michael Addition

To a stirred solution of the (R)- or (S)-indane vinyl sulfonamide (1 eq) in DMF (0.1M) was added the appropriate amine (10 eq) The reaction was stirred at 80° C. for 18 h. The product was purified by preparative HPLC.

Compounds 37-38 and 121-153 were prepared using General Procedure 13.

N-((S)-4-(5-(3-cyano-4-isopropoxyphenyl)-1,3,4-thiadiazol-2-yl)-2,3-dihydro-1H-inden-1-yl)-2-((R)-3-hydroxypyrrolidin-1-yl)ethanesulfonamide (Compound 37)

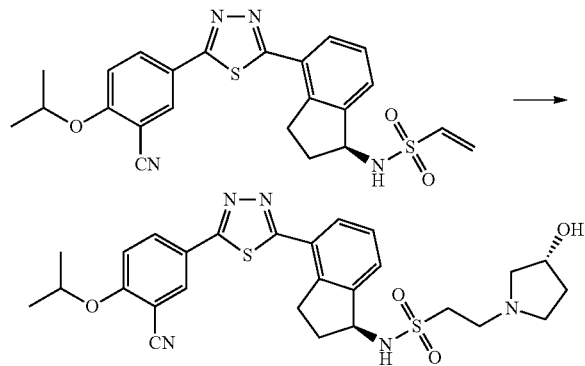

Prepared using General Procedure 13. To a solution of (S)-N-(4-(5-(3-cyano-4-isopropoxyphenyl)-1,3,4-thiadiazol-2-yl)-2,3-dihydro-1H-inden-1-yl)ethenesulfonamide (40 mg, 0.5 mmol) in DMF (0.5 mL) was added (R)-pyrrolidin-3-ol (18.7 mg, 0.21 mmol) and the reaction was heated to 80° C. for 18 h. The product was purified by preparative HPLC to give 30 mg (56%) of N-((S)-4-(5-(3-cyano-4-isopropoxyphenyl)-1,3,4-thiadiazol-2-yl)-2,3-dihydro-1H-inden-1-yl)-2-((R)-3-hydroxypyrrolidin-1-yl)ethanesulfonamide 37 as an off-white solid. LCMS-ESI (m/z) calculated for $C_{27}H_{31}N_5O_4S_2$: 553.2; found 554.2 [M+H]$^+$, $t_R$=2.52 min.

N-((R)-4-(5-(3-cyano-4-isopropoxyphenyl)-1,3,4-thiadiazol-2-yl)-2,3-dihydro-1H-inden-1-yl)-2-((R)-3-hydroxypyrrolidin-1-yl)ethanesulfonamide 38 was prepared in an analogous fashion using (R)-N-(4-(5-(3-cyano-4-isopropoxyphenyl)-1,3,4-thiadiazol-2-yl)-2,3-dihydro-1H-inden-1-yl)ethenesulfonamide.

N-((R)-4-(2-(3-cyano-4-isopropoxyphenyl)thiazol-5-yl)-2,3-dihydro-1H-inden-1-yl)-2-((R)-3-hydroxypiperidin-1-yl)ethanesulfonamide (Compound 143)

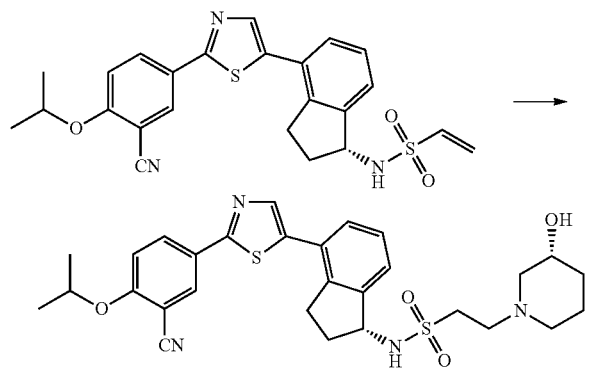

Prepared using General Procedure 13. To a solution of (R)-N-(4-(2-(3-cyano-4-isopropoxyphenyl)thiazol-5-yl)-2,3-dihydro-1H-inden-1-yl)ethenesulfonamide (10 mg, 0.02 mmol) in DMF (0.5 mL) was added (R)-piperidin-3-ol hydrochloride (20.6 mg, 0.15 mmol) and the reaction was heated to 80° C. for 18 h. The product was purified by preparative HPLC to give 10 mg (80%) of N-((R)-4-(2-(3-cyano-4-isopropoxyphenyl)thiazol-5-yl)-2,3-dihydro-1H-inden-1-yl)-2-((R)-3-hydroxypiperidin-1-yl)ethanesulfonamide 143. LCMS-ESI (m/z) calculated for $C_{29}H_{34}N_4O_4S_2$: 566.2; found 567.2 [M+H]$^+$, $t_R$=2.62 min.

N-((S)-4-(2-(3-cyano-4-isopropoxyphenyl)thiazol-5-yl)-2,3-dihydro-1H-inden-1-yl)-2-((R)-3-hydroxypiperidin-1-yl)ethanesulfonamide 141 was prepared in an analogous fashion using (S)-N-(4-(2-(3-cyano-4-isopropoxyphenyl)thiazol-5-yl)-2,3-dihydro-1H-inden-1-yl)ethenesulfonamide.

General Procedure 14. Preparation of Indane Sulfonamide Esters

To a stirred solution of (R)- or (S)-indane amine (1 eq) in DCM (0.2 M) was added the sulfonyl chloride (1.5 eq) at room temperature. For less reactive or hindered sulfonyl chloride esters DIEA (2-3 eq) was added. The reaction was stirred at room temperature for 18 h. The crude reaction was partitioned between DCM and NaHCO$_3$. The organic layer was dried over MgSO$_4$, concentrated, and purified by column chromatography.

Compounds 154-157 were prepared using General Procedure 14.

(S)-ethyl 2-(N-(4-(5-(3-cyano-4-isopropoxyphenyl)-1,3,4-thiadiazol-2-yl)-2,3-dihydro-1H-inden-1-yl)sulfamoyl)acetate

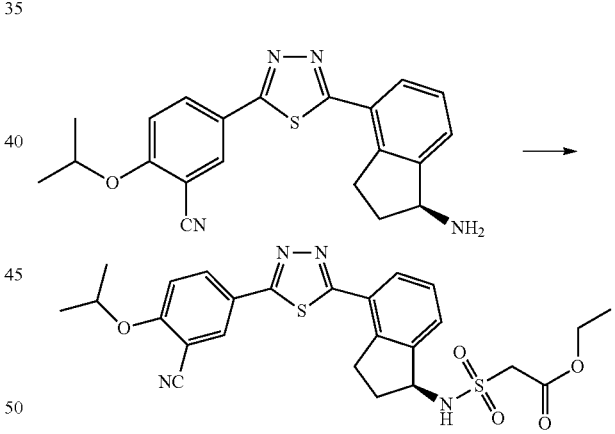

Prepared using General Procedure 14: To a stirred solution of (S)-5-(5-(1-amino-2,3-dihydro-1H-inden-4-yl)-1,3,4-thiadiazol-2-yl)-2-isopropoxybenzonitrile 4 (177 g, 0.47 mmol) and DIEA (182 mg, 1.4 mmol) in DCM (8 mL) was added freshly prepared ethyl-2-(chlorosulfonyl)acetate (131 mg, 0.7 mmol). After 45 min, the crude reaction was partitioned between DCM and NaHCO$_3$. The organic layer was dried over MgSO$_4$, concentrated, and purified by column chromatography (EA/hexanes) to provide 75 mg (30%) of (S)-ethyl 2-(N-(4-(5-(3-cyano-4-isopropoxyphenyl)-1,3,4-thiadiazol-2-yl)-2,3-dihydro-1H-inden-1-yl)sulfamoyl)acetate as light yellow solid. LCMS-ESI (m/z) calculated for $C_{25}H_{26}N_4O_5S_2$: 526.1; found 527.1 [M+H]$^+$, $t_R$=3.71 min. $^1$H NMR (400 MHz, CDCl$_3$) δ 8.16 (dd, J=8.9, 2.3 Hz, 1H), 8.09 (d, J=2.2 Hz, 1H), 7.76 (d, J=7.7 Hz, 1H), 7.57 (d, J=7.6

Hz, 1H), 7.35 (t, J=7.6 Hz, 1H), 7.03 (d, J=9.0 Hz, 1H), 5.46 (t, J=7.9 Hz, 1H), 4.70 (dt, J=12.2, 6.1 Hz, 1H), 4.26-4.17 (m, 2H), 4.00 (d, J=8.2 Hz, 2H), 3.49 (ddd, J=17.4, 9.5, 3.9 Hz, 1H), 3.26-3.05 (m, 1H), 2.56 (ddd, J=12.9, 9.0, 4.4 Hz, 1H), 2.23-2.08 (m, 1H), 1.41-1.37 (m, 6H), 1.28 (dd, J=11.7, 4.6 Hz, 3H).

(R)-ethyl 2-(N-(4-(5-(3-cyano-4-isopropoxyphenyl)-1,3,4-thiadiazol-2-yl)-2,3-dihydro-1H-inden-1-yl)sulfamoyl)acetate was prepared in an analogous fashion using (R)-5-(5-(1-amino-2,3-dihydro-1H-inden-4-yl)-1,3,4-thiadiazol-2-yl)-2-isopropoxybenzonitrile 5.

(S)-methyl 2-(N-(4-(2-(3-cyano-4-isopropoxyphenyl)thiazol-5-yl)-2,3-dihydro-1H-inden-1-yl)sulfamoyl)acetate (Compound 155)

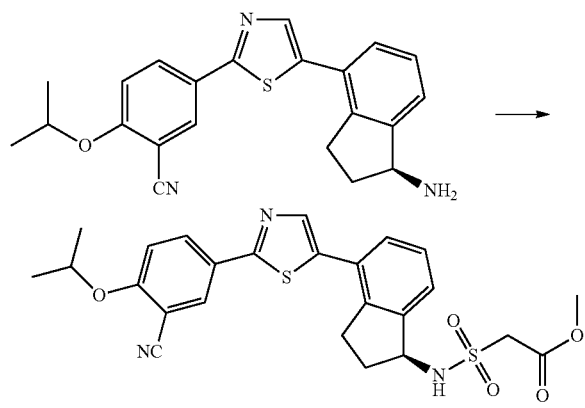

Prepared using General Procedure 14: To a solution of (S)-5-(5-(1-amino-2,3-dihydro-1H-inden-4-yl)thiazol-2-yl)-2-isopropoxybenzonitrile 71 (20 mg, 0.04 mmol) in DCM (1 mL) was added methyl-2-(chlorosulfonyl)acetate (10 mg, 0.04 mmol). The reaction mixture was stirred at room temperature overnight and then diluted with DCM (5 mL), washed with saturated aq. NaHCO₃, and brine. The organic layers were dried over MgSO₄, and the crude product purified by silica gel column chromatography to afford 11.2 mg (41%) of (S)-methyl 2-(N-(4-(2-(3-cyano-4-isopropoxyphenyl)thiazol-5-yl)-2,3-dihydro-1H-inden-1-yl)sulfamoyl)acetate 155 as orange-brown oil. LCMS-ESI (m/z) calculated for $C_{25}H_{25}N_3O_5S_2$: 511.1; found 512.2 [M+H]$^+$, $t_R$=3.71 min.

(R)-methyl 2-(N-(4-(2-(3-cyano-4-isopropoxyphenyl)thiazol-5-yl)-2,3-dihydro-1H-inden-1-yl)sulfamoyl)acetate 154 was prepared in an analogous fashion using (R)-5-(5-(1-amino-2,3-dihydro-1H-inden-4-yl)thiazol-2-yl)-2-isopropoxybenzonitrile 72.

General Procedure 15. Preparation of Indane Sulfonamide Acids

To a solution of (R)- or (S)-indane sulfonamide ester (1 eq) in 2:1 EtOH/THF (0.2 M) was added 6N NaOH (5 eq) at room temperature. The reaction was stirred at room temperature for 24 h. The crude reaction was concentrated then partitioned between DCM/IPA and 1N HCl. The organic layer was dried over MgSO₄, concentrated, and isolated after preparative HPLC purification.

Compounds 40-41 and 158-161 were prepared using General Procedure 15.

(S)-2-(N-(4-(5-(3-cyano-4-isopropoxyphenyl)-1,3,4-thiadiazol-2-yl)-2,3-dihydro-1H-inden-1-yl)sulfamoyl)acetic acid (Compound 40)

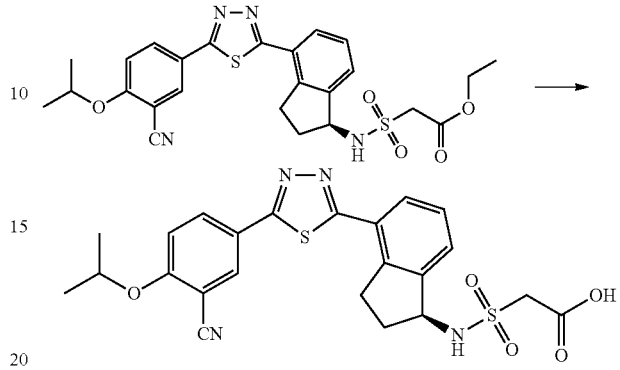

Prepared using General Procedure 15: To a stirred solution of (S)-ethyl 2-(N-(4-(5-(3-cyano-4-isopropoxyphenyl)-1,3,4-thiadiazol-2-yl)-2,3-dihydro-1H-inden-1-yl)sulfamoyl)acetate (75 mg, 0.8 mmol) in MeOH (4 mL) was added 6N NaOH (0.12 mL). After 3 h, the crude reaction was concentrated then partitioned between DCM/IPA and 1N HCl. The organic layer was dried over MgSO₄ and concentrated to give 43 mg (60%) of (S)-2-(N-(4-(5-(3-cyano-4-isopropoxyphenyl)-1,3,4-thiadiazol-2-yl)-2,3-dihydro-1H-inden-1-yl)sulfamoyl)acetic acid 40 as light yellow solid. LCMS-ESI (m/z) calculated for $C_{23}H_{22}N_4O_5S_2$: 498.1; found 499.1 [M+H]$^+$, $t_R$=3.34 min.

(R)-2-(N-(4-(5-(3-cyano-4-isopropoxyphenyl)-1,3,4-thiadiazol-2-yl)-2,3-dihydro-1H-inden-1-yl)sulfamoyl)acetic acid 41 was prepared in an analogous fashion using (R)-ethyl 2-(N-(4-(5-(3-cyano-4-isopropoxyphenyl)-1,3,4-thiadiazol-2-yl)-2,3-dihydro-1H-inden-1-yl) sulfamoyl)acetate.

(S)-2-(N-(4-(2-(3-cyano-4-isopropoxyphenyl)thiazol-5-yl)-2,3-dihydro-1H-inden-1-yl)sulfamoyl)acetic acid (Compound 159)

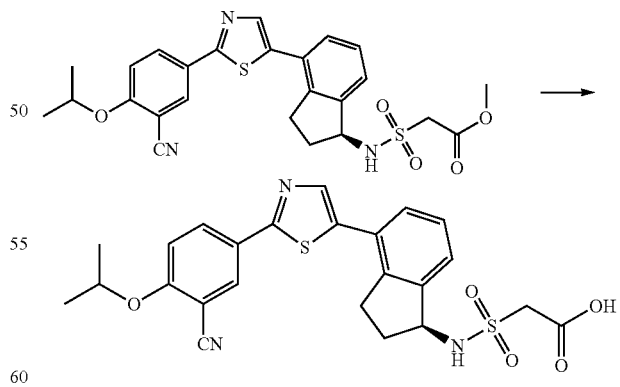

Prepared using General Procedure 15: To a stirred solution containing (S)-methyl 2-(N-(4-(2-(3-cyano-4-isopropoxyphenyl)thiazol-5-yl)-2,3-dihydro-1H-inden-1-yl)sulfamoyl)acetate (11.2 mg, 0.02 mmol) in MeOH (1 mL) was added 6N NaOH (100 uL). After 1 h, the crude reaction was concentrated and the product purified by preparative HPLC to give 5 mg (45%) of (S)-2-(N-(4-(2-(3-cyano-4-isopropoxyphenyl)thiazol-5-yl)-2,3-dihydro-1H-inden-1-yl)sulfamoyl)acetic acid 159 as light yellow solid. LCMS-ESI (m/z) calculated for $C_{24}H_{23}N_3O_5S_2$: 497.1; found 498.1 [M+H]$^+$, $t_R$=3.44 min.

(R)-2-(N-(4-(2-(3-cyano-4-isopropoxyphenyl)thiazol-5-yl)-2,3-dihydro-1H-inden-1-yl)sulfamoyl)acetic acid 158 was prepared in an analogous fashion using (R)-methyl 2-(N-(4-(2-(3-cyano-4-isopropoxyphenyl)thiazol-5-yl)-2,3-dihydro-1H-inden-1-yl)sulfamoyl)acetate.

General Procedure 16. Preparation of Indane Sulfonamide Amides

To a stirred solution of (R)- or (S)-indane sulfonamide acid (1 eq) in DCM (0.25 M) was added HATU (3 eq) and DIEA (2 eq). After 30 min, the amine was added and the reaction mixture stirred 18 h at room temperature. The reaction was quenched with water and purified by preparative HPLC.

Compounds 42-44, 162, and 163 were prepared using General Procedure 16.

3.50 (ddd, J=17.0, 8.8, 3.4 Hz, 1H), 3.20 (dt, J=9.7, 7.1 Hz, 1H), 3.15 (s, 3H), 3.02 (s, 3H), 2.72 (dtd, J=11.4, 8.0, 3.5 Hz, 1H), 2.20 (dq, J=13.1, 8.4 Hz, 1H), 1.46 (d, J=6.1 Hz, 6H). $^{13}$C NMR (101 MHz, CDCl$_3$) δ 166.99, 165.73, 163.22, 161.71, 144.17, 141.92, 133.44, 133.34, 129.31, 127.92, 127.33, 126.37, 122.70, 115.57, 113.91, 103.71, 72.56, 59.23, 54.92, 38.30, 35.99, 31.36, 21.74. Chiral HPLC: (R)-2-(N-(4-(5-(3-cyano-4-isopropoxyphenyl)-1,3,4-thiadiazol-2-yl)-2,3-dihydro-1H-inden-1-yl)sulfamoyl)-N,N-dimethylacetamide was eluted in 40% IPA in hexanes, 100% ee, $t_R$=22.87 min.

(S)-2-(N-(4-(5-(3-cyano-4-isopropoxyphenyl)-1,3,4-thiadiazol-2-yl)-2,3-dihydro-1H-inden-1-yl)sulfamoyl)-N,N-dimethylacetamide 42 was prepared in an analogous fashion using (S)-2-(N-(4-(5-(3-cyano-4-isopropoxyphenyl)-1,3,4-thiadiazol-2-yl)-2,3-dihydro-1H-inden-1-yl)sulfamoyl)acetic acid. Chiral HPLC: 97.8% ee, $t_R$ for S-enantiomer=29.06 min.

(R)-2-(N-(4-(5-(3-cyano-4-isopropoxyphenyl)-1,3,4-thiadiazol-2-yl)-2,3-dihydro-1H-inden-1-yl)sulfamoyl)-N,N-dimethylacetamide (Compound 43)

R)-N-(4-(2-(3-cyano-4-isopropoxyphenyl)thiazol-5-yl)-2,3-dihydro-1H-inden1-yl)-2-morpholino-2-oxoethanesulfonamide (Compound 162)

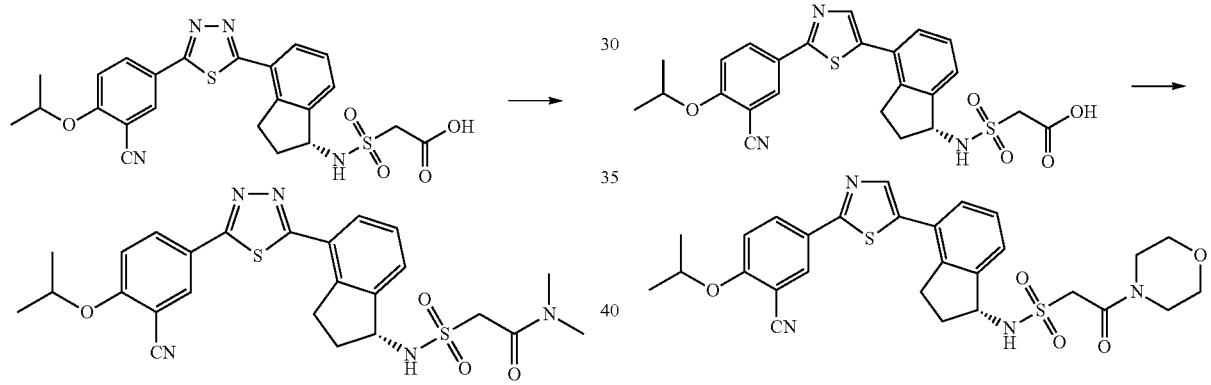

Prepared using General Procedure 16: To (R)-2-(N-(4-(5-(3-cyano-4-isopropoxyphenyl)-1,3,4-thiadiazol-2-yl)-2,3-dihydro-1H-inden-1-yl)sulfamoyl)acetic acid (20 mg, 0.04 mmol) in DCM (0.4 mL) was added HATU (45 mg, 0.12 mmol) and DIEA (10.3 mg, 0.08 mmol). After 30 min, dimethylamine (2M solution in THF, 200 μL, 0.4 mmol) was added and the reaction stirred for 18 h at room temperature. The reaction was quenched with water (100 μL) and the solvent evaporated. The crude material was purified by preparative HPLC to afford 14 mg (66%) of (R)-2-(N-(4-(5-(3-cyano-4-isopropoxyphenyl)-1,3,4-thiadiazol-2-yl)-2,3-dihydro-1H-inden-1-yl)sulfamoyl)-N,N-dimethylacetamide 43 as white solid. LCMS-ESI (m/z) calculated for $C_{25}H_{27}N_5O_4S_2$: 525.2; found 526.2 [M+H]$^+$, $t_R$=3.42 min. $^1$H NMR (400 MHz, CDCl$_3$) δ 8.20 (dd, J=8.9, 2.3 Hz, 1H), 8.14 (d, J=2.3 Hz, 1H), 7.82 (d, J=7.7 Hz, 1H), 7.73 (d, J=7.6 Hz, 1H), 7.40 (t, J=7.7 Hz, 1H), 7.09 (d, J=9.0 Hz, 1H), 5.50 (d, J=8.2 Hz, 1H), 5.07 (q, J=7.7 Hz, 1H), 4.76 (hept, J=6.1 Hz, 1H), 4.28 (d, J=14.6 Hz, 1H), 4.09 (d, J=14.6 Hz, 1H), Prepared using General Procedure 16: To (R)-2-(N-(4-(2-(3-cyano-4-isopropoxyphenyl)thiazol-5-yl)-2,3-dihydro-1H-inden-1-yl)sulfamoyl)acetic acid 158 (15 mg, 0.03 mmol) in DCM (0.4 mL) was added HATU (26 mg, 0.07 mmol) and DIEA (7.8 mg, 0.06 mmol). After 30 min, morpholine (52 mg, 0.6 mmol) was added and the reaction stirred for 18 h at room temperature. The reaction was quenched with water (100 μL) and the solvent evaporated. The crude material was purified by preparative HPLC to afford 8 mg (47%) of (R)—N-(4-(2-(3-cyano-4-isopropoxyphenyl)thiazol-5-yl)-2,3-dihydro-1H-inden-1-yl)-2-morpholino-2-oxoethanesulfonamide 162. LCMS-ESI (m/z) calculated for $C_{28}H_{30}N_4O_5S_2$: 566.1; found 567.2 [M+H]$^+$, $t_R$=3.77 min.

General Procedure 17. Preparation of Indane Sulfonamide Alcohols

To a stirred solution of (R)- or (S)-indane sulfonamide ester (1 eq) in THF (0.06 M) was added sodium borohydride (4 eq) at room temperature. The reaction was heated to 75° C. and methanol (10 eq) was added dropwise. After 1 h, the reaction was cooled and concentrated. The pure product was obtained by preparative HPLC purification.

Compounds 45, 46, 164, and 165 were prepared using General Procedure 17.

123

(R)-N-(4-(5-(3-cyano-4-isopropoxyphenyl)-1,3,4-thiadiazol-2-yl)-2,3-dihydro-1H-inden-1-yl)-2-hydroxyethanesulfonamide (Compound 46)

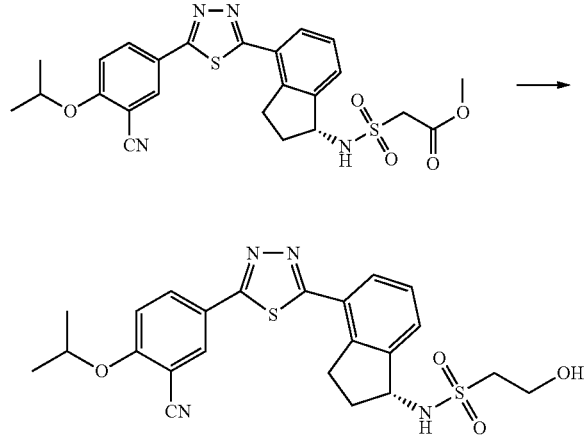

Prepared using General Procedure 17: To a stirred solution of (R)-methyl 2-(N-(4-(5-(3-cyano-4-isopropoxyphenyl)-1,3,4-thiadiazol-2-yl)-2,3-dihydro-1H-inden-1-yl)sulfamoyl)acetate (13 mg, 0.02 mmol) in THF (0.5 mL) was added sodium borohydride (2.3 mg, 0.06 mmol) at room temperature. The reaction was heated to 75° C. and methanol (0.03 mL, 0.7 mmol) was added dropwise. After 1 h, the reaction was cooled and concentrated. Purification of the crude material by preparative HPLC gave 6 mg (60%) of (R)-N-(4-(5-(3-cyano-4-isopropoxyphenyl)-1,3,4-thiadiazol-2-yl)-2,3-dihydro-1H-inden-1-yl)-2-hydroxyethanesulfonamide 46. LCMS-ESI (m/z) calculated for $C_{23}H_{24}N_4O_4S_2$: 484.1; found 485.1 [M+H]$^+$, $t_R$=3.26 min. $^1$H NMR (400 MHz, CDCl$_3$) δ 8.23 (dd, J=8.9, 2.3 Hz, 1H), 8.16 (d, J=2.3 Hz, 1H), 7.83 (d, J=7.7 Hz, 1H), 7.64 (d, J=7.6 Hz, 1H), 7.43 (t, J=7.6 Hz, 1H), 7.11 (d, J=9.0 Hz, 1H), 5.19-4.96 (m, 1H), 4.87-4.63 (m, 3H), 4.17 (dd, J=8.2, 4.4 Hz, 2H), 3.53 (ddd, J=17.2, 8.8, 3.5 Hz, 1H), 3.46-3.34 (m, 2H), 3.32-3.11 (m, 1H), 2.86-2.59 (m, 1H), 2.19-1.97 (m, 1H), 1.48 (d, J=6.1 Hz, 6H). $^{13}$C NMR (101 MHz, CDCl$_3$) δ 166.83, 165.72, 161.71, 144.11, 141.85, 133.47, 133.26, 129.53, 127.99, 126.92, 126.58, 122.64, 115.51, 113.87, 103.79, 72.54, 58.86, 57.43, 55.67, 34.69, 31.27, 21.73. Chiral HPLC: (R)-N-(4-(5-(3-cyano-4-isopropoxyphenyl)-1,3,4-thiadiazol-2-yl)-2,3-dihydro-1H-inden-1-yl)-2-hydroxyethanesulfonamide was eluted in MeOH, 96.2% ee, $t_R$=12.58 min (Chiral Method 2).

(S)-N-(4-(5-(3-cyano-4-isopropoxyphenyl)-1,3,4-thiadiazol-2-yl)-2,3-dihydro-1H-inden-1-yl)-2-hydroxyethanesulfonamide 45 was prepared in an analogous fashion using (S)-methyl 2-(N-(4-(5-(3-cyano-4-isopropoxyphenyl)-1,3,4-thiadiazol-2-yl)-2,3-dihydro-1H-inden-1-yl)sulfamoyl)acetate. Chiral HPLC: 97.6% ee, $t_R$ for S-enantiomer=10.99 min (Chiral Method 2).

124

(S)-N-(4-(2-(3-cyano-4-isopropoxyphenyl)thiazol-5-yl)-2,3-dihydro-1H-inden-1-yl)-2-hydroxyethanesulfonamide (Compound 165)

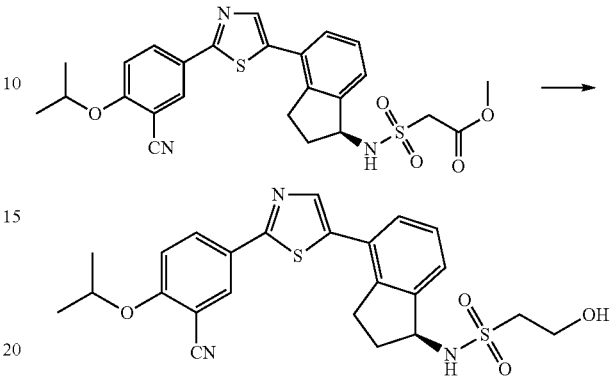

Prepared using General Procedure 17: To a stirred solution of (S)-methyl 2-(N-(4-(2-(3-cyano-4-isopropoxyphenyl)thiazol-5-yl)-2,3-dihydro-1H-inden-1-yl)sulfamoyl)acetate (20 mg, 0.04 mmol) in THF (0.5 mL) was added sodium borohydride (3.6 mg, 0.09 mmol) at room temperature. The reaction was heated to 75° C. and methanol (0.06 mL, 1.4 mmol) was added dropwise. After 1 h, the reaction was cooled and concentrated. Purification of the crude material by preparative HPLC gave 12.2 mg (64%) of (S)-N-(4-(2-(3-cyano-4-isopropoxyphenyl)thiazol-5-yl)-2,3-dihydro-1H-inden-1-yl)-2-hydroxyethanesulfonamide 165. LCMS-ESI (m/z) calculated for $C_{24}H_{25}N_3O_4S_2$: 483.1; found 484.2 [M+H]$^+$, $t_R$=3.45 min.

(R)-N-(4-(2-(3-cyano-4-isopropoxyphenyl)thiazol-5-yl)-2,3-dihydro-1H-inden-1-yl)-2-hydroxyethanesulfonamide 164 was prepared in an analogous fashion using (R)-methyl 2-(N-(4-(2-(3-cyano-4-isopropoxyphenyl)thiazol-5-yl)-2,3-dihydro-1H-inden-1-yl)sulfamoyl)acetate.

General Procedure 18. Preparation of Indane Sulfamides

To a stirred solution of (R)- or (S)-indane amine (1 eq) in 1,4-dioxane (0.06M) was added sulfamide (5 eq) and the reaction was stirred at 90° C. for 16 h. The solvent was evaporated and the reaction mixture was purified by preparative HPLC.

Compounds 47, 48, 166, and 167 were prepared using General Procedure 18.

(S)-N-(4-(5-(3-cyano-4-isopropoxyphenyl)-1,3,4-thiadiazol-2-yl)-2,3-dihydro-1H-inden-1-yl)sulfamide (Compound 47)

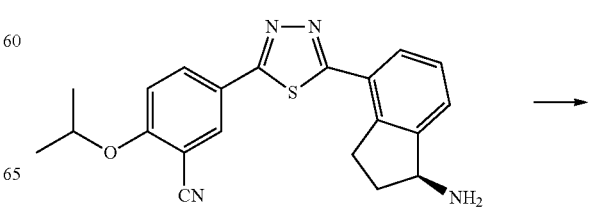

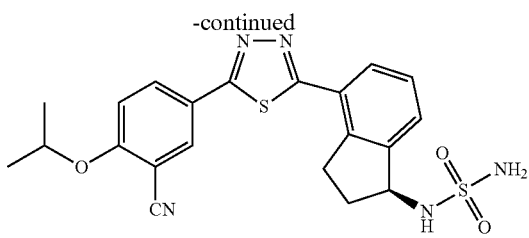

Prepared using General Procedure 18: To (S)-5-(5-(1-amino-2,3-dihydro-1H-inden-4-yl)-1,3,4-thiadiazol-2-yl)-2-isopropoxybenzonitrile hydrochloride 4 (25 mg, 0.06 mmol) in dioxane (1 mL) was added sulfamide (30 mg, 0.3 mmol) and the mixture was heated to 90° C. After 16 h, the solvent was evaporated and the residue was purified by column chromatography. Additional purification by recrystallization from MeOH provided 15.9 mg (26%) of (S)-N-(4-(5-(3-cyano-4-isopropoxyphenyl)-1,3,4-thiadiazol-2-yl)-2,3-dihydro-1H-inden-1-yl)sulfamide 47. LCMS-ESI (m/z) calculated for $C_{21}H_{21}N_5O_3S_2$: 455.1; found 456.1 [M+H]$^+$, $t_R$=3.33 min. $^1$H NMR (400 MHz, DMSO) δ 8.40 (d, J=2.3 Hz, 1H), 8.32 (dd, J=8.9, 2.4 Hz, 1H), 7.88 (d, J=7.7 Hz, 1H), 7.66 (d, J=7.6 Hz, 1H), 7.56-7.38 (m, 2H), 7.23 (d, J=9.0 Hz, 1H), 6.75 (s, 2H), 4.95 (dt, J=12.2, 6.1 Hz, 1H), 4.87 (dd, J=16.6, 8.2 Hz, 1H), 3.42-3.26 (m, 1H), 3.07 (dt, J=16.4, 8.3 Hz, 1H), 2.61 (dtd, J=11.0, 7.9, 3.0 Hz, 1H), 2.00 (dq, J=12.7, 8.8 Hz, 1H), 1.38 (d, J=6.0 Hz, 6H). $^{13}$C NMR (101 MHz, DMSO) δ 166.64, 165.62, 161.19, 146.08, 141.36, 133.89, 133.15, 127.97, 127.51, 127.27, 125.78, 122.22, 115.57, 114.95, 102.29, 72.17, 57.67, 33.41, 30.73, 21.52. Chiral HPLC: (S)-N-(4-(5-(3-cyano-4-isopropoxyphenyl)-1,3,4-thiadiazol-2-yl)-2,3-dihydro-1H-inden-1-yl)sulfamide was eluted in MeOH: 98.6% ee, $t_R$=7.63 min (Chiral Method 2).

(R)-N-(4-(5-(3-cyano-4-isopropoxyphenyl)-1,3,4-thiadiazol-2-yl)-2,3-dihydro-1H-inden-1-yl)sulfamide 48 was prepared in an analogous fashion using (R)-5-(5-(1-amino-2,3-dihydro-1H-inden-4-yl)-1,3,4-thiadiazol-2-yl)-2-isopropoxybenzonitrile hydrochloride. Chiral HPLC: 98% ee, $t_R$ for R-enantiomer=9.10 min (Chiral Method 2).

(R)-N-(4-(2-(3-cyano-4-isopropoxyphenyl)thiazol-5-yl)-2,3-dihydro-1H-inden-1-yl)sulfamide (Compound 166)

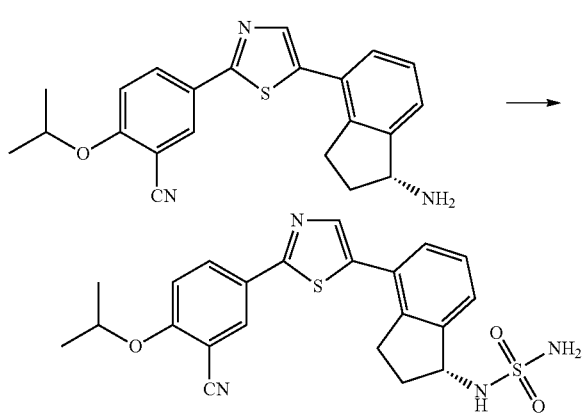

Prepared using General Procedure 18: To (R)-5-(5-(1-amino-2,3-dihydro-1H-inden-4-yl)thiazol-2-yl)-2-isopropoxybenzonitrile hydrochloride 72 (100 mg, 0.02 mmol) in dioxane (1 mL) was added DIEA (58 mg, 0.32 mmol) and sulfamide (115 mg, 1.2 mmol) and the reaction was heated to 90° C. for 4 h. The solvent was evaporated and the residue was diluted with EA (10 mL) and washed with successively with NH$_4$Cl and brine. The product was purified by column chromatography (MeOH/DCM) to yield 80 mg (73%) of (R)-N-(4-(2-(3-cyano-4-isopropoxyphenyl)thiazol-5-yl)-2,3-dihydro-1H-inden-1-yl)sulfamide 166. LCMS-ESI (m/z) calculated for $C_{22}H_{22}N_4O_3S_2$: 454.1; found 455.4 [M+H]$^+$, $t_R$=3.46 min. $^1$H NMR (400 MHz, DMSO) δ 8.29 (d, J=2.3 Hz, 1H), 8.23 (dd, J=8.9, 2.4 Hz, 1H), 8.16 (s, 1H), 7.55 (d, J=7.6 Hz, 1H), 7.47 (dd, J=18.4, 8.3 Hz, 2H), 7.36 (t, J=7.6 Hz, 1H), 7.17 (d, J=9.0 Hz, 1H), 6.73 (s, 2H), 4.98-4.75 (m, 2H), 3.19-3.05 (m, 1H), 3.00 (dd, J=16.3, 8.0 Hz, 1H), 2.61-2.54 (m, 1H), 2.04-1.89 (m, 1H), 1.38 (t, J=5.5 Hz, 6H). $^{13}$C NMR (101 MHz, CDCl$_3$) δ 165.43, 161.42, 144.43, 141.31, 140.70, 138.02, 132.43, 132.20, 128.52, 128.18, 128.08, 126.65, 124.98, 116.30, 114.25, 103.78, 72.82, 59.25, 34.62, 31.13, 22.14. Chiral HPLC: (R)-N-(4-(2-(3-cyano-4-isopropoxyphenyl)thiazol-5-yl)-2,3-dihydro-1H-inden-1-yl)sulfamide was eluted in 50% ethanol in hexanes, 99.0% ee, $t_R$=40.47 min.

(S)-N-(4-(2-(3-cyano-4-isopropoxyphenyl)thiazol-5-yl)-2,3-dihydro-1H-inden-1-yl)sulfamide 167 was prepared in an analogous fashion using (S)-5-(5-(1-amino-2,3-dihydro-1H-inden-4-yl)thiazol-2-yl)-2-isopropoxybenzonitrile 71. Chiral HPLC: 99.1% ee, $t_R$ for S-enantiomer=27.67 min.

General Procedure 19. Preparation of Indane Ureas

To a stirred solution of CDI (1.7 eq) in DCM (0.16M) was added the stirred suspension of (R)- or (S)-indane amine (1 eq) and Et$_3$N (3 eq) in DCM (0.16M) and the mixture was stirred for 2 h or until all the indane amine consumed. If necessary, additional CDI was added. This solution was added to the appropriate amine and the reaction mixture stirred at room temperature for 16 h. The solvent was evaporated and the pure product isolated after preparative HPLC.

Compounds 50-67 and 168-205 were prepared using General Procedure 19.

(R)-N-((R)-4-(5-(3-cyano-4-isopropoxyphenyl)-1,3,4-thiadiazol-2-yl)-2,3-dihydro-1H-inden-1-yl)-3-(dimethylamino)pyrrolidine-1-carboxamide (Compound 56)

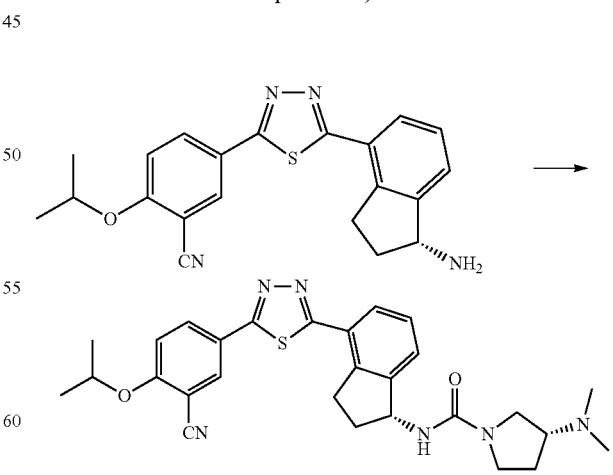

Prepared using General Procedure 19: To a CDI ((13.4 mg, 0.08 mmol) in DCM (0.5 mL) was added a suspension of (R)-5-(5-(1-amino-2,3-dihydro-1H-inden-4-yl))-1,3,4-thiadiazol-2-yl)-2-isopropoxybenzonitrile hydrochloride 5 (20.0 mg, 0.04 mmol) and Et$_3$N (14.7 mg, 0.14 mmol) in DCM (0.5 mL) and the mixture stirred for 2 h at room temperature. The resulting solution was added to the preparative solution of azetidin-3-ol hydrochloride (15.9 mg, 0.14 mmol)) at room temperature. The reaction was stirred at room temperature for 16 h. The solvent was evaporated and the crude material was purified by preparative HPLC to afford 15 mg of (62%) of (R)-N-((R)-4-(5-(3-cyano-4-isopropoxyphenyl)-1,3,4-thiadiazol-2-yl)-2,3-dihydro-1H-inden-1-yl)-3-(dimethylamino)pyrrolidine-1-carboxamide 56. LCMS-ESI (m/z) calculated for C$_{28}$H$_{32}$N$_6$O$_2$S: 516.2; found 517.2 [M+H]$^+$, t$_R$=2.43 min. $^1$H NMR (400 MHz, DMSO) δ 8.40 (d, J=2.4 Hz, 1H), 8.32 (dd, J=9.0, 2.4 Hz, 1H), 7.99-7.76 (m, 1H), 7.51 (d, J=9.2 Hz, 1H), 7.49-7.34 (m, 2H), 6.73 (d, J=8.4 Hz, 1H), 5.32 (d, J=8.2 Hz, 1H), 5.09-4.80 (m, 1H), 3.86 (dd, J=14.3, 7.0 Hz, 1H), 3.75 (dd, J=11.0, 7.5 Hz, 1H), 3.63-3.48 (m, 1H), 3.45-3.22 (m, 3H), 3.10 (dt, J=16.5, 8.3 Hz, 1H), 2.82 (t, J=5.1 Hz, 6H), 2.56-2.40 (m, 1H), 2.32 (dd, J=9.8, 2.5 Hz, 1H), 2.15-2.02 (m, 1H), 2.00-1.81 (m, 1H), 1.38 (d, J=6.0 Hz, 6H). $^{13}$C NMR (101 MHz, CDCl$_3$) δ 167.10, 165.84, 161.80, 145.94, 142.30, 133.54, 133.36, 128.86, 127.82, 126.94, 126.41, 122.72, 115.78, 114.01, 103.72, 72.71, 64.71, 55.95, 46.76, 44.20, 42.04, 34.06, 31.45, 27.30, 21.90, 21.89.

(S)-N-((R)-4-(5-(3-cyano-4-isopropoxyphenyl)-1,3,4-thiadiazol-2-yl)-2,3-dihydro-1H-inden-1-yl)-3-(dimethylamino)pyrrolidine-1-carboxamide 57 was prepared in an analogous fashion using (S)-5-(5-(1-amino-2,3-dihydro-1H-inden-4-yl)-1,3,4-thiadiazol-2-yl)-2-isopropoxybenzonitrile hydrochloride.

(R)-N-(4-(5-(3-cyano-4-isopropoxyphenyl)-1,3,4-thiadiazol-2-yl)-2,3-dihydro-1H-inden-1-yl)morpholine-4-carboxamide (compound 58)

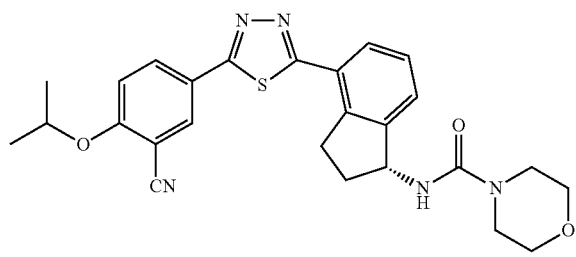 [SMILES: CC(C)Oc1ccc(-c2nnc(-c3cccc4c3CC[C@H]4NC(=O)N3CCOCC3)s2)cc1C#N]

Prepared using General Procedure 19. LCMS-ESI (m/z) calculated for C$_{26}$H$_{27}$N$_5$O$_3$S: 489.2; found 490.2 [M+H]$^+$, t$_R$=3.54 min. $^1$H NMR (400 MHz, CDCl$_3$) δ 8.20 (dd, J=8.9, 2.3 Hz, 1H), 8.13 (d, J=2.2 Hz, 1H), 7.82 (d, J=7.7 Hz, 1H), 7.49 (d, J=7.5 Hz, 1H), 7.36 (t, J=7.6 Hz, 1H), 7.08 (d, J=9.0 Hz, 1H), 5.51 (d, J=7.6 Hz, 1H), 4.83-4.56 (m, 2H), 3.71 (dd, J=10.0, 5.0 Hz, 4H), 3.54-3.33 (m, 5H), 3.29-3.05 (m, 1H), 2.81-2.56 (m, 1H), 1.91 (ddd, J=16.4, 13.1, 7.9 Hz, 1H), 1.46 (d, J=6.1 Hz, 6H). $^{13}$C NMR (101 MHz, CDCl$_3$) δ 167.45, 166.17, 162.16, 157.98, 146.58, 142.87, 133.90, 133.77, 129.34, 128.20, 127.29, 126.95, 123.21, 116.06, 114.36, 104.22, 73.03, 66.92, 56.41, 44.54, 34.72, 31.85, 22.25.

(R)-N-(4-(2-(3-cyano-4-isopropoxyphenyl)thiazol-5-yl)-2,3-dihydro-1H-inden-1-yl)pyrrolidine-1-carboxamide (Compound 172)

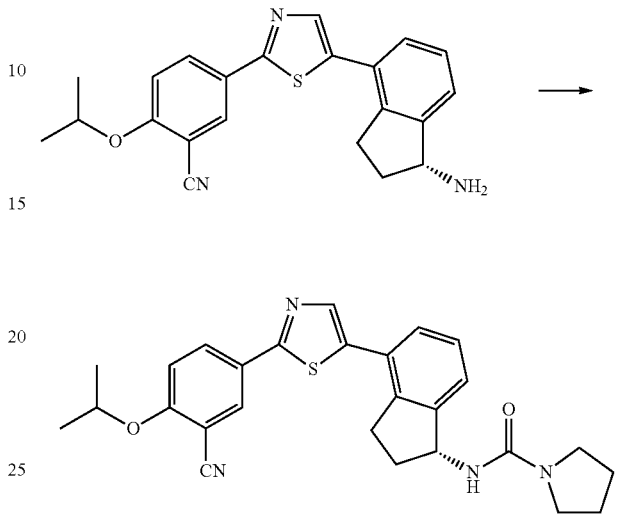

Prepared using General Procedure 19: To CDI (117 mg, 0.72 mmol) in DCM (1 mL) was added a suspension of (R)-5-(5-(1-amino-2,3-dihydro-1H-inden-4-yl)thiazol-2-yl)-2-isopropoxybenzonitrile hydrochloride 72 (150 mg, 0.36 mmol), Et$_3$N (145 mg, 1.44 mmol) and DCM (1 mL) and the mixture stirred for 2 h at room temperature. The resulting solution was added to the preparative solution of pyrrolidine (77 mg, 1.08 mmol)) at room temperature. The reaction was stirred at room temperature for 16 h. The solvent was evaporated and the crude material was purified by preparative HPLC to afford 110 mg of (78%) of (R)-N-(4-(2-(3-cyano-4-isopropoxyphenyl)thiazol-5-yl)-2,3-dihydro-1H-inden-1-yl)pyrrolidine-1-carboxamide 172. LCMS-ESI (m/z) calculated for C$_{27}$H$_{28}$N$_4$O$_2$S: 472.1; found 473.2 [M+H]$^+$, t$_R$=3.79 min. $^1$H NMR (400 MHz, DMSO) δ 8.28 (d, J=2.3 Hz, 1H), 8.22 (dd, J=8.9, 2.4 Hz, 1H), 8.15 (s, 1H), 7.53 (d, J=7.3 Hz, 1H), 7.44 (d, J=9.1 Hz, 1H), 7.36-7.24 (m, 2H), 6.42 (d, J=8.6 Hz, 1H), 5.29 (q, J=8.4 Hz, 1H), 4.91 (hept, J=5.9 Hz, 1H), 3.31-3.20 (m, 4H), 3.17-2.95 (m, 2H), 2.43 (ddd, J=10.7, 6.2, 2.8 Hz, 1H), 2.00-1.87 (m, 1H), 1.87-1.72 (m, 4H), 1.37 (d, J=6.0 Hz, 6H); $^{13}$C NMR (101 MHz, CDCl$_3$) δ 164.79, 160.90, 156.46, 146.16, 141.10, 140.75, 137.75, 131.89, 131.80, 127.75, 127.71, 127.63, 126.53, 124.27, 115.92, 113.78, 103.60, 72.34, 55.78, 45.61, 34.87, 30.80, 25.57, 21.81.

(S)-N-(4-(2-(3-cyano-4-isopropoxyphenyl)thiazol-5-yl)-2,3-dihydro-1H-inden-1-yl)pyrrolidine-1-carboxamide 173 was prepared in an analogous fashion using (S)-5-(5-(1-amino-2,3-dihydro-1H-inden-4-yl)thiazol-2-yl)-2-isopropoxybenzonitrile hydrochloride 71.

(R)-N-(4-(2-(3-cyano-4-isopropoxyphenyl)thiazol-5-yl)-2,3-dihydro-1H-inden-1-yl)morpholine-4-carboxamide (Compound 186)

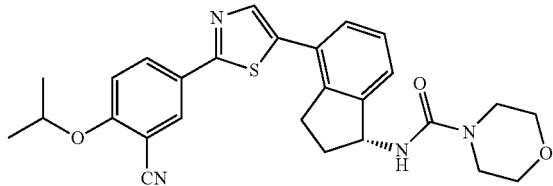 [SMILES: CC(C)Oc1ccc(-c2ncc(-c3cccc4c3CC[C@H]4NC(=O)N3CCOCC3)s2)cc1C#N]

Prepared using General Procedure 19. LCMS-ESI (m/z) calculated for $C_{27}H_{28}N_4O_3S$: 488.2; found 489.2 $[M+H]^+$, $t_R$=3.54 min. $^1$H NMR (400 MHz, DMSO) δ 8.28 (d, J=2.3 Hz, 1H), 8.22 (dd, J=8.9, 2.4 Hz, 1H), 8.16 (s, 1H), 7.54 (d, J=7.5 Hz, 1H), 7.44 (d, J=9.1 Hz, 1H), 7.36-7.24 (m, 2H), 6.89 (d, J=8.3 Hz, 1H), 5.30 (d, J=8.2 Hz, 1H), 4.99-4.83 (m, 1H), 3.61-3.50 (m, 4H), 3.42-3.24 (m, 4H), 3.23-2.91 (m, 2H), 2.48-2.40 (m, 1H), 2.00-1.82 (m, 1H), 1.37 (d, J=6.0 Hz, 6H). $^{13}$C NMR (101 MHz, CDCl$_3$) δ 165.23, 161.35, 157.93, 146.06, 141.53, 141.16, 138.11, 132.35, 132.20, 128.26, 128.14, 126.90, 124.68, 116.38, 114.20, 103.97, 72.80, 66.91, 56.53, 44.50, 34.89, 31.31, 22.26.

General Procedure 20. Preparation of Indane Amines from Indanols

To a flask containing the indanol (1 eq) in DCM (0.14M) at 0° C. was added SOCl$_2$ (2 eq). After stirring for 30 min, the reaction mixture was concentrated in vacuo and placed under high vacuum for 2 h. The resulting crude chloride was dissolved in DMA (0.02M). The amine (3 eq), DIEA (3 eq), and in some cases NaBr (3 eq) were added and the resulting reactions were stirred at 55-60° C. overnight and purified either by preparative HPLC or column chromatography.

Compounds 206-219 and were prepared using General Procedure 20.

5-(5-(1-(3-hydroxyazetidin-1-yl)-2,3-dihydro-1H-inden-4-yl)thiazol-2-yl)-2-isopropoxybenzonitrile (Compound 207)

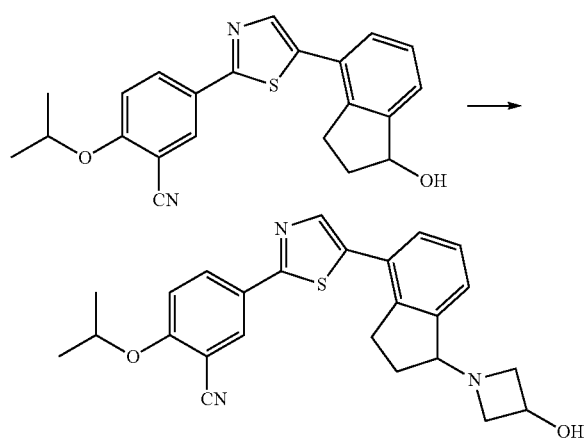

Prepared using General Procedure 20: To a stirred solution of 5-(5-(1-hydroxy-2,3-dihydro-1H-inden-4-yl)thiazol-2-yl)-2-isopropoxybenzonitrile (20 mg, 0.05 mmol) in DCM (1 mL) was added thionyl chloride (12.6 mg, 0.106 mmol) at 0° C. The reaction was stirred at room temperature for 3 h. The solvent was evaporated and the crude chloride re-dissolved in dimethyl acetamide (1 mL). Diisopropyl ethylamine (20.5 mg, 0.16 mmol) and ethanolamine (9.7 mg, 0.16 mmol) were added and the reaction mixture was stirred at 70° C. overnight. The reaction mixture was quenched with water (200 uL) and purified by preparative HPLC to afford 11 mg (46%) of 5-(5-(1-(3-hydroxyazetidin-1-yl)-2,3-dihydro-1H-inden-4-yl)thiazol-2-yl)-2-isopropoxybenzonitrile 208. LCMS-ESI (m/z) calculated for $C_{25}H_{25}N_3O_2S$: 431.1; found 432.1 $[M+H]^+$, $t_R$=6.48 min (Method 2).

2-fluoro-5-(thiazol-5-yl)benzonitrile (THZ INT-3)

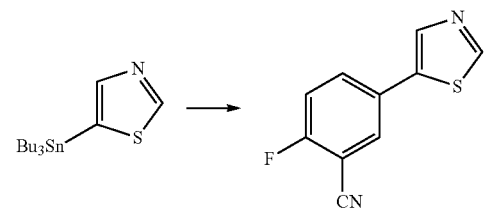

To 5-(tributylstannyl)thiazole (1.00 g, 2.7 mmol) in THF (10 mL) was added 2-fluoro-5-iodobenzonitrile (0.791 g, 3.2 mmol). The solution was degassed with N$_2$ and bis(triphenylphosphine)palladium(II) chloride Pd(Ph)$_2$Cl$_2$ (0.187 g, 0.27 mmol) was added. The solution was further degassed for five minutes before heating to 85° C. for 2 h. Upon cooling, the reaction mixture was diluted with saturated NaHCO$_3$ and washed with EA (3×50 mL). The combined organic layers were dried over MgSO$_4$, filtered, and concentrated. The crude product was purified by chromatography (10% EA/Hexanes) to afford 0.450 g (82%) of 2-fluoro-5-(thiazol-5-yl)benzonitrile THZ INT-3 as a tan solid. LCMS-ESI (m/z) calculated for $C_{10}H_5FN_2S$: 204.2; found 205.0 $[M+H]^+$, $t_R$=3.00 min.

5-(2-bromothiazol-5-yl)-2-fluorobenzonitrile (THZ INT-4)

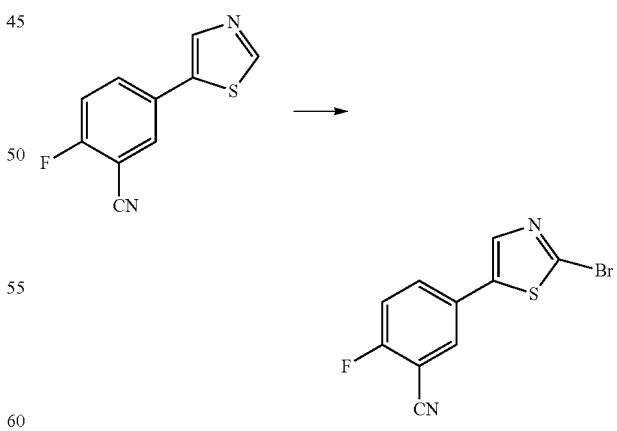

To a stirring solution of 2-fluoro-5-(thiazol-5-yl)benzonitrile THZ INT-3 (0.429 g, 2.1 mmol) in acetic acid (10.5 mL) was added potassium acetate (0.412 g, 4.2 mmol). Bromine (0.647 mL, 12.6 mmol) was added dropwise over 10 minutes and the reaction mixture stirred at room temperature for 48 h. The reaction mixture was basified with 1N NaOH and washed with EA and brine. The combined organic layers were dried over MgSO₄, filtered, and concentrated. The crude product was purified by chromatography (20% EA/Hexanes) to produce 0.10 g (30%) of 5-(2-bromothiazol-5-yl)-2-fluorobenzonitrile THZ INT-4. LCMS-ESI (m/z) calculated for $C_{10}H_4BrFN_2S$: 283.1; found 284.9 [M+H]⁺, $t_R$=3.33 min.

5-(2-(1-(tert-butyldimethylsilyloxy)-2,3-dihydro-1H-inden-4-yl)thiazol-5-yl)-2-fluorobenzonitrile

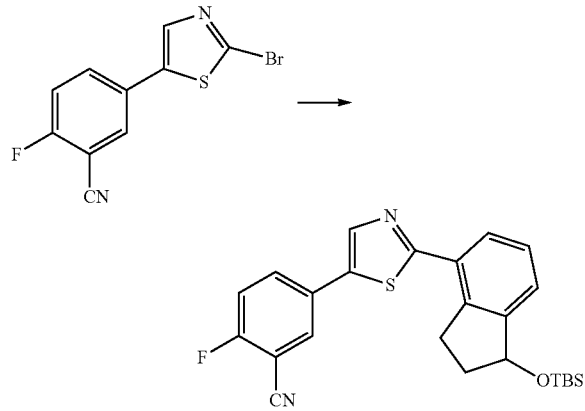

Prepared using General Procedure 1. To 5-(2-bromothiazol-5-yl)-2-fluorobenzonitrile THZ INT-4 (0.100 g, 0.35 mmol), tert-butyldimethyl(4-(4,4,5,5-tetramethyl-1,3,2-dioxaborolan-2-yl)-2,3-dihydro-1H-inden-1-yloxy) silane IND INT-8 (0.143 g, 0.38 mmol) and sodium carbonate (0.112 g, 1.1 mmol) in dioxane (1.8 mL) and H₂O (0.2 mL) was added tetrakis(triphenylphosphine)palladium (0.041 g, 0.035 mmol). The solution was degassed with N₂ and the reaction mixture heated at 85° C. for 6 h. Upon cooling, the reaction mixture was diluted with brine and washed with DCM (3×100 mL). The combined organic layers were dried over MgSO₄, filtered, and concentrated. The crude product was purified by chromatography (30% EA/Hexanes) to produce 0.05 g (32%) of 5-(2-(1-(tert-butyldimethylsilyloxy)-2,3-dihydro-1H-inden-4-yl)thiazol-5-yl)-2-fluorobenzo-nitrile as a white solid. LCMS-ESI (m/z) calculated for $C_{25}H_{27}FN_2OSSi$: 450.6; found 451.1 [M+H] ⁺, $t_R$=4.84 min (Method 3).

5-(2-(1-(tert-butyldimethylsilyloxy)-2,3-dihydro-1H-inden-4-yl)thiazol-5-yl)-2-isopropoxy-benzonitrile

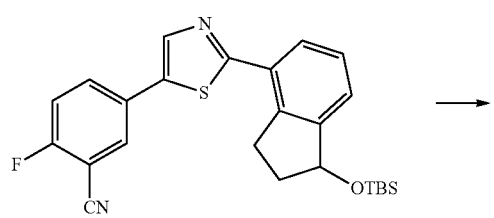

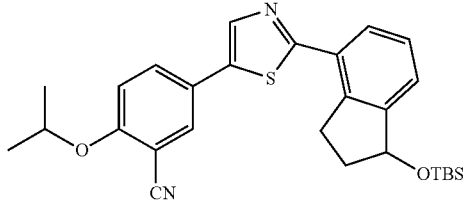

Prepared using General Procedure 2. To a solution of 5-(2-(1-(tert-butyldimethylsilyloxy)-2,3-dihydro-1H-inden-4-yl)thiazol-5-yl)-2-fluorobenzonitrile (0.043 g, 0.095 mmol) in isopropanol (2 mL) was added sodium isopropoxide (0.07 g, 0.090 mmol). The reaction mixture was heated at 60° C. for 12 h. Upon cooling, the solvent was removed under a stream of N₂ and the crude reaction mixture was carried onto the next step without further purification. LCMS-ESI (m/z) calculated for $C_{28}H_{34}N_2O_2SSi$: 490.7, $t_R$=5.06 min (Method 3).

5-(2-(1-hydroxy-2,3-dihydro-1H-inden-4-yl)thiazol-5-yl)-2-isopropoxy-benzonitrile (Compound 222)

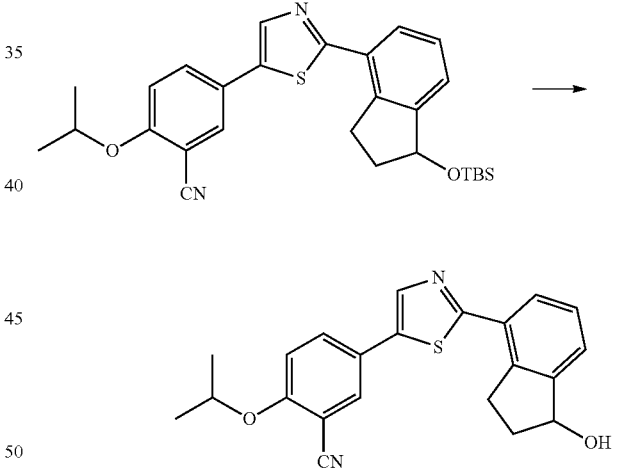

Prepared using General Procedure 3. To crude 5-(2-(1-(tert-butyldimethylsilyloxy)-2,3-dihydro-1H-inden-4-yl)thiazol-5-yl)-2-isopropoxybenzonitrile (0.043 g, 0.095 mmol) was added 4N HCl in dioxane (1.0 mL). The reaction mixture was stirred at room temperature for 2 h. The solvent was concentrated under a stream of N₂ and the mixture dissolved in MeOH (1.0 mL). The crude product was purified by preparative HPLC to yield 0.02 g (43%) of 5-(2-(1-hydroxy-2,3-dihydro-1H-inden-4-yl)thiazol-5-yl)-2-isopropoxybenzonitrile 222. LCMS-ESI (m/z): calcd for: $C_{22}H_{20}N_2O_2S$: 376.5; found 377.1 [M+H] ⁺, $t_R$=3.31 min.

2-isopropoxy-5-(thiophen-2-yl)benzonitrile (THIO INT-1)

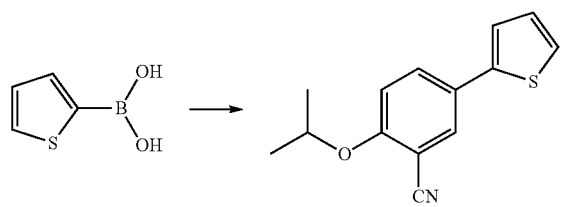 [SMILES: OB(O)c1cccs1 ; CC(C)Oc1ccc(-c2cccs2)cc1C#N]

A microwave vial was charged with 5-bromo-2-isopropoxybenzonitrile (200 mg, 0.83 mmol), thiophen-2-ylboronic acid (106.5 mg, 0.83 mmol), potassium carbonate (345.3 mg, 2.49 mmol) and 3:1 mixture of dimethylethylene glycol/H$_2$O (2 mL). The reaction mixture was degassed by bubbling N$_2$ gas through the stirred solution for 10 min. Pd(PPh$_3$)$_4$ (20.4 mg, 0.02 mmol) was added and the solution degassed for additional 2 min. The vial was subjected to microwave irradiation at 100° C. for 30 min. The solvent was removed and the residue dissolved in EA (10 mL), washed with brine, and dried over MgSO$_4$. The product was purified chromatography (EA/hexanes) to afford 165 mg (82%) of 2-isopropoxy-5-(thiophen-2-yl)benzonitrile TRIO INT-1 as colorless oil. LCMS-ESI (m/z) calculated for C$_{14}$H$_{13}$NOS: 243.1; found 266.0 [M+Na]$^+$, t$_R$=3.90 min. $^1$H NMR (400 MHz, CDCl$_3$) δ 7.74 (d, J=2.3 Hz, 1H), 7.69 (dd, J=8.8, 2.4 Hz, 1H), 7.28-7.23 (m, 1H), 7.19 (dd, J=3.6, 1.1 Hz, 1H), 7.05 (dd, J=5.1, 3.6 Hz, 1H), 6.95 (d, J=8.8 Hz, 1H), 4.65 (dt, J=12.2, 6.1 Hz, 1H), 1.43-1.37 (m, 6H).

5-(5-bromothiophen-2-yl)-2-isopropoxybenzonitrile (THIO INT-2)

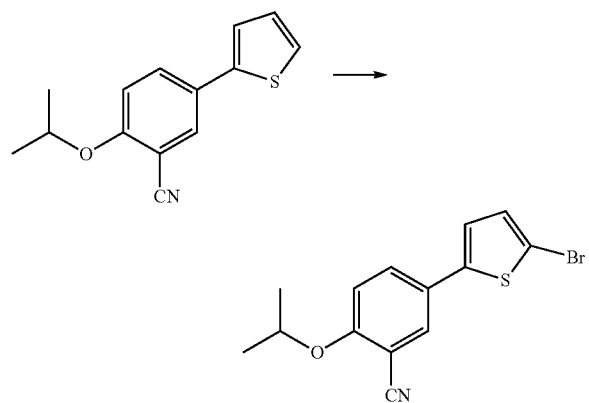

To a solution of 2-isopropoxy-5-(thiophen-2-yl)benzonitrile THIO INT-1 (160 mg, 0.66 mmol) in anhydrous DMF (5 mL) was added freshly crystallized N-bromosuccinimide (118 mg, 0.66 mmol) at 0° C. The reaction mixture was stirred at room temperature for 3 h (longer reaction times and use of excess NBS caused dibromination). The reaction mixture was diluted with EA (10 mL), washed with water (2×10 mL) and brine, and dried over MgSO$_4$. The crude product was purified by silica gel column (EA/hexanes) to provide 126 mg (60%) of 5-(5-bromothiophen-2-yl)-2-isopropoxybenzonitrile THIO INT-2 as white solid. LCMS-ESI (m/z) calculated for C$_{14}$H$_{12}$BrNOS: 320.9; no M+, t$_R$=4.26 min. $^1$H NMR (400 MHz, CDCl$_3$) δ 7.60 (d, J=2.3 Hz, 1H), 7.53 (dd, J=8.8, 2.4 Hz, 1H), 6.95 (d, J=3.9 Hz, 1H), 6.89 (t, J=6.2 Hz, 2H), 4.60 (dt, J=12.1, 6.1 Hz, 1H), 1.35 (d, J=6.1 Hz, 6H).

5-(5-(1-(tert-butyldimethylsilyloxy)-2,3-dihydro-1H-inden-4-yl)thiophen-2-yl)-2-isopropoxybenzonitrile

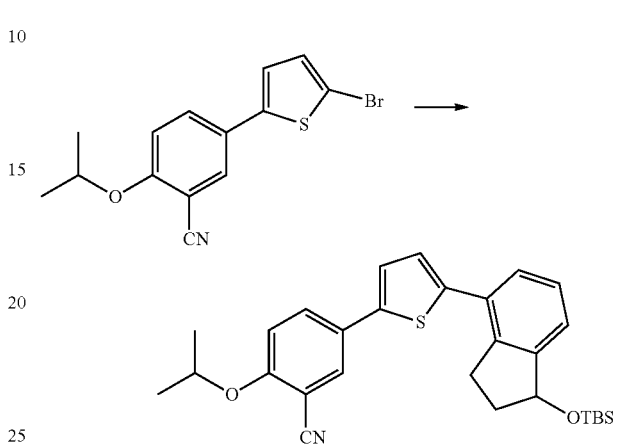

Prepared from 5-(5-bromothiophen-2-yl)-2-isopropoxybenzonitrile THIO INT-2 and (±)-((4-bromo-2,3-dihydro-1H-inden-1-yl)oxy)(tert-butyl)dimethylsilane IND INT 8 using General Procedure 1. LCMS-ESI (m/z) calculated for C$_{29}$H$_{35}$NO$_2$SSi: 489.2; no M+ found, t$_R$=8.10 min (Method 1). $^1$H NMR (400 MHz, CDCl$_3$) δ 7.77 (d, J=2.3 Hz, 1H), 7.71 (dd, J=8.8, 2.4 Hz, 1H), 7.44 (t, J=4.4 Hz, 1H), 7.27 (d, J=4.5 Hz, 2H), 7.17 (dd, J=12.5, 3.8 Hz, 2H), 6.96 (d, J=8.9 Hz, 1H), 5.29 (t, J=7.1 Hz, 1H), 4.78-4.55 (m, 1H), 3.21 (ddd, J=15.9, 8.8, 2.8 Hz, 1H), 2.95 (dt, J=16.2, 8.1 Hz, 1H), 2.56-2.36 (m, 1H), 1.94 (dd, J=12.6, 7.3 Hz, 1H), 1.41 (d, J=6.1 Hz, 6H), 1.01-0.86 (m, 9H), 0.17 (d, J=9.3 Hz, 6H).

5-(5-(1-hydroxy-2,3-dihydro-1H-inden-4-yl)thiophen-2-yl)-2-isopropoxybenzonitrile (Compound 223)

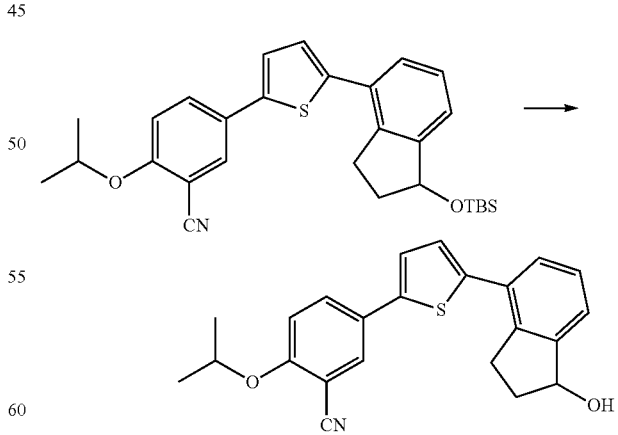

To a stirred solution of 5-(5-(1-(tert-butyldimethylsilyloxy)-2,3-dihydro-1H-inden-4-yl)thiophen-2-yl)-2-isopropoxybenzonitrile (80 mg, 0.16 mmol) in 1,4-dioxane (1 mL) was added 4N HCl solution in 1,4-dioxane (1 mL). The reaction mixture was stirred at room temperature for 2 h. Solvent was evaporated and the crude product was purified by chromatography (EA/hexanes) to afford 26 mg (40%) of 5-(5-(1-hydroxy-2,3-dihydro-1H-inden-4-yl)thiophen-2-yl)-2-isopropoxybenzonitrile 223 as a white solid. LCMS-ESI (m/z) calculated for $C_{23}H_{21}NO_2S$: 375.1; found 398.1 [M+Na]$^+$, $t_R$=3.96 min. $^1$H NMR (400 MHz, CDCl$_3$) δ 7.77 (d, J=2.3 Hz, 1H), 7.71 (dd, J=8.8, 2.4 Hz, 1H), 7.53-7.45 (m, 1H), 7.38 (d, J=7.4 Hz, 1H), 7.30 (t, J=7.5 Hz, 1H), 7.19 (q, J=3.8 Hz, 2H), 6.97 (d, J=8.9 Hz, 1H), 5.28 (t, J=6.1 Hz, 1H), 4.66 (dt, J=12.2, 6.1 Hz, 1H), 3.28 (ddd, J=16.2, 8.5, 4.7 Hz, 1H), 3.11-2.91 (m, 1H), 2.53 (dddd, J=13.1, 8.2, 6.9, 4.7 Hz, 1H), 2.08-1.92 (m, 1H), 1.57 (s, 1H), 1.41 (d, J=6.1 Hz, 6H). $^{13}$C NMR (101 MHz, CDCl$_3$) δ 159.37, 146.65, 142.74, 141.52, 140.36, 131.55, 131.08, 130.96, 130.79, 127.79, 127.54, 126.67, 123.82, 116.57, 114.40, 103.82, 76.59, 72.43, 36.07, 30.88, 22.08.

5-(5-(1-(2-hydroxyethylamino)-2,3-dihydro-1H-inden-4-yl)thiophen-2-yl)-2-isopropoxybenzonitrile (Compound 224)

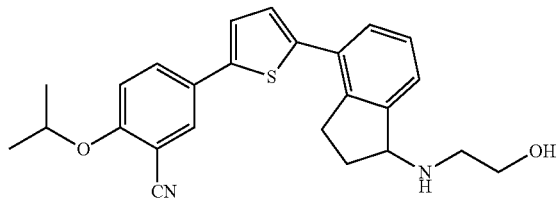 [SMILES: CC(C)Oc1ccc(-c2ccc(-c3cccc4c3CCC4NCCO)s2)cc1C#N]

Prepared using General Procedure 20 from 5-(5-(1-hydroxy-2,3-dihydro-1H-inden-4-yl)thiophen-2-yl)-2-isopropoxybenzonitrile and ethanolamine. LCMS-ESI (m/z) calculated for $C_{25}H_{26}N_2O_2S$: 418.2; found 419.1 [M+H]$^+$, $t_R$=2.73 min.

(R)-tert-butyl 4-(5-(3-cyano-4-isopropoxyphenyl)thiophen-2-yl)-2,3-dihydro-1H-inden-1-ylcarbamate

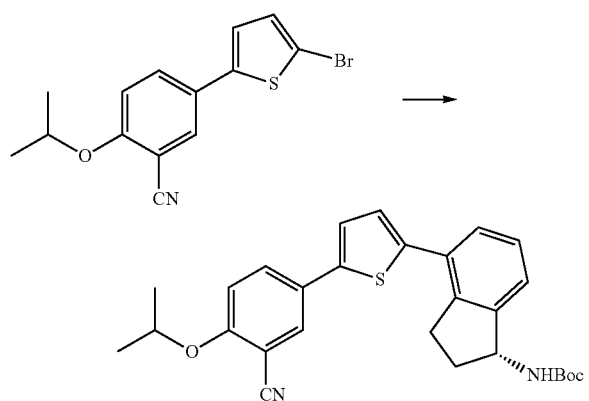

A 20 mL microwave vial was charged with (R)-tert-butyl 4-(4,4,5,5-tetramethyl-1,3,2-dioxaborolan-2-yl)-2,3-dihydro-1H-inden-1-ylcarbamate IND INT-18 (44 mg, 0.12 mmol), 5-(5-bromothiophen-2-yl)-2-isopropoxybenzonitrile THIO INT-2 (40 mg, 0.12 mmol), potassium carbonate (51 mg, 0.37 mmol) and a 3:1 mixture of dimethylethylene glycol/H$_2$O (2 mL). The reaction mixture was degassed by bubbling N$_2$ gas through the stirred solution for 10 min. Pd(PPh$_3$)$_4$ (10.1 mg, 0.008 mmol) was added and the solution degassed for an additional 2 min. The vial was subjected to microwave irradiation at 100° C. for 30 min. The solvent was removed and the residue dissolved in EA (10 mL), washed with brine, and dried over MgSO$_4$. The product was purified by chromatography (EA/hexanes) to afford 15 mg (51%) of (R)-tert-butyl 4-(5-(3-cyano-4-isopropoxyphenyl)thiophen-2-yl)-2,3-dihydro-1H-inden-1-ylcarbamate as an off-white solid. LCMS-ESI (m/z) calculated for $C_{28}H_{30}N_2O_3S$: 474.2; no M+ found, $t_R$=4.43 min. $^1$H NMR (400 MHz, CDCl$_3$) δ 7.76 (d, J=2.3 Hz, 1H), 7.70 (dd, J=8.8, 2.4 Hz, 1H), 7.45 (dd, J=6.3, 2.2 Hz, 1H), 7.27 (d, J=6.6 Hz, 2H), 7.17 (dd, J=11.9, 3.8 Hz, 2H), 6.97 (d, J=8.9 Hz, 1H), 5.30-5.11 (m, 1H), 4.78 (d, J=8.6 Hz, 1H), 4.66 (dt, J=12.2, 6.1 Hz, 1H), 3.18 (ddd, J=16.1, 8.7, 3.4 Hz, 1H), 3.02 (dt, J=16.1, 8.1 Hz, 1H), 2.68-2.51 (m, 1H), 1.90-1.73 (m, 1H), 1.47 (d, J=8.2 Hz, 9H), 1.41 (d, J=6.1 Hz, 6H).

(R)-5-(5-(1-amino-2,3-dihydro-1H-inden-4-yl)thiophen-2-yl)-2-isopropoxybenzonitrile (Compound 225)

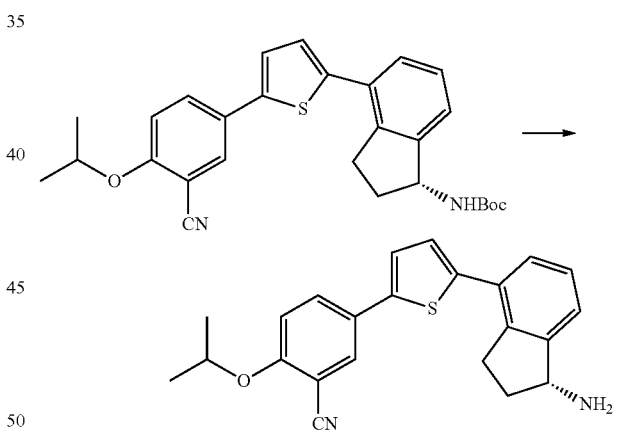

Prepared using General Procedure 5. To a stirred solution of (R)-tert-butyl 4-(5-(3-cyano-4-isopropoxyphenyl)thiophen-2-yl)-2,3-dihydro-1H-inden-1-ylcarbamate (15 mg, 0.03 mmol) in 1,4-dioxane (1 mL) was added 4N HCl solution in 1,4-dioxane (0.5 mL). The reaction mixture was stirred at room temperature for 16 h. Solvent was evaporated the resulting solid was dissolved 1:1 DMSO:MeOH (1 mL) and purified by preparative HPLC to afford 10 mg (90%) of (R)-5-(5-(1-amino-2,3-dihydro-1H-inden-4-yl)thiophen-2-yl)-2-isopropoxybenzonitrile 225 as a white solid. LCMS-ESI (m/z) calculated for $C_{23}H_{22}N_2OS$: 374.2; found 358.1. [M-NH$_2$]$^+$, $t_R$=2.69 min.

5-(4-bromothiophen-2-yl)-2-isopropoxybenzonitrile (THIO INT-3)

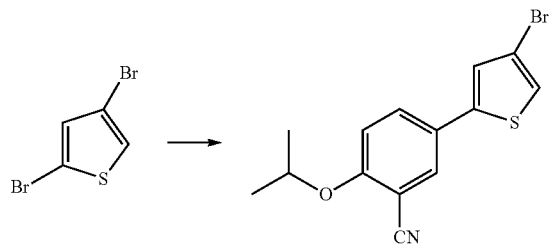 [SMILES: Brc1csc(Br)c1 ; CC(C)Oc1ccc(-c2cc(Br)cs2)cc1C#N]

A 2 mL microwave vial was charged with 2,4-dibromothiophene (20 mg, 0.08 mmol), (3-cyano-4-isopropoxyphenyl)boronic acid (17 mg, 0.08 mmol), potassium carbonate (35 mg, 0.25 mmol) and 3:1 mixture of DME/H$_2$O (4 mL). The reaction mixture was degassed by bubbling N$_2$ through the stirred solution for 10 min. Pd(PPh$_3$)$_4$ (7 mg, 0.006 mmol) was added and the solution degassed for an additional 2 min. The vial was subjected to microwave irradiation at 70° C. for 30 min or until starting material consumed. 5-(4-bromothiophen-2-yl)-2-isopropoxybenzonitrile THIO INT-3 was used in the next experiment without purification. LCMS-ESI (m/z) calculated for C$_{14}$H$_{12}$BrNOS: 320.9; no M+ observed, t$_R$=4.15 min.

5-(4-(1-((tert-butyldimethylsilyl)oxy)-2,3-dihydro-1H-inden-4-yl)thiophen-2-yl)-2-isopropoxybenzonitrile

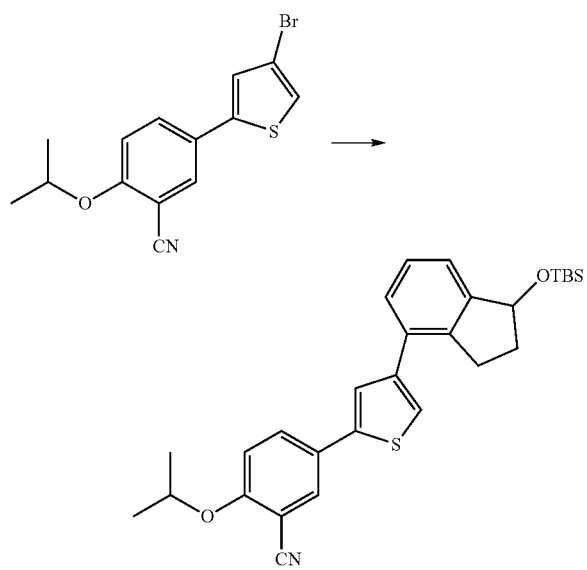

Prepared from 5-(4-bromothiophen-2-yl)-2-isopropoxybenzonitrile THIO INT-3 (0.08 mmol) and tert-butyldimethyl((4-(4,4,5,5-tetramethyl-1,3,2-dioxaborolan-2-yl)-2,3-dihydro-1H-inden-1-yl)oxy)silane IND INT-8 (31 mg, 0.08 mmol) using General Procedure 1, to afford 12 mg (30%, for two steps) of 5-(4-(1-((tert-butyldimethylsilyl)oxy)-2,3-dihydro-1H-inden-4-yl)thiophen-2-yl)-2-isopropoxybenzonitrile. LCMS-ESI (m/z) calculated for C$_{29}$H$_{35}$NO$_2$SSi: 489.2; no M+ found, t$_R$=6.66 min (Method 1). $^1$H NMR (400 MHz, CDCl$_3$) δ 7.76 (d, J=2.3 Hz, 1H), 7.70 (dd, J=8.8, 2.4 Hz, 1H), 7.36-7.31 (m, 2H), 7.29-7.25 (m, 2H), 7.25-7.19 (m, 1H), 6.96 (d, J=8.9 Hz, 1H), 5.28 (t, J=6.9 Hz, 1H), 4.73-4.50 (m, 1H), 3.09 (ddd, J=15.8, 8.7, 2.9 Hz, 1H), 2.88 (dt, J=16.0, 8.1 Hz, 1H), 2.47-2.30 (m, 1H), 1.96-1.81 (m, 1H), 1.40 (d, J=6.1 Hz, 6H), 0.94 (s, 9H), 0.16 (d, J=9.9 Hz, 6H).

5-(4-(1-hydroxy-2,3-dihydro-1H-inden-4-yl)thiophen-2-yl)-2-isopropoxybenzonitrile (Compound 226)

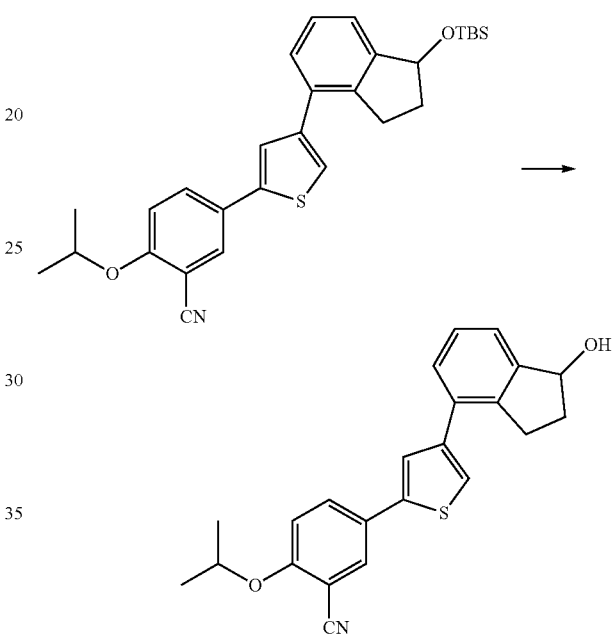

Prepared using General Procedure 3. To a solution of 5-(4-(1-((tert-butyldimethylsilyl)oxy)-2,3-dihydro-1H-inden-4-yl)thiophen-2-yl)-2-isopropoxybenzonitrile (17 mg, 0.03 mmol) in THF (1 mL) was added 1M solution of TBAF in tetrahydrofuran (0.3 mL, 0.3 mmol) and the reaction mixture was stirred at room temperature overnight. The reaction mixture was concentrated and purified by preparative HPLC to yield 8 mg (46%) of 5-(4-(1-hydroxy-2,3-dihydro-1H-inden-4-yl)thiophen-2-yl)-2-isopropoxybenzonitrile 226 as white solid. LCMS-ESI (m/z) calculated for C$_{23}$H$_{21}$NO$_2$S: 375.1; found 398.1 [M+Na]$^+$. t$_R$=3.84 min; $^1$H NMR (400 MHz, CDCl$_3$) δ 7.78 (d, J=2.3 Hz, 1H), 7.72 (dd, J=8.8, 2.4 Hz, 1H), 7.43-7.36 (m, 2H), 7.35-7.28 (m, 1H), 7.26 (d, J=1.4 Hz, 1H), 7.24 (s, 1H), 7.06-6.89 (m, 1H), 5.29 (t, J=6.1 Hz, 1H), 4.77-4.49 (m, 1H), 3.20 (ddd, J=16.0, 8.4, 4.7 Hz, 1H), 3.01-2.86 (m, 1H), 2.50 (dddd, J=13.0, 8.1, 6.8, 4.7 Hz, 1H), 2.11-1.88 (m, 1H), 1.58 (s, 1H), 1.41 (d, J=6.1 Hz, 6H); $^{13}$C NMR (101 MHz, CDCl$_3$) δ 159.51, 146.35, 142.55, 142.00, 140.88, 133.16, 131.79, 131.24, 128.14, 127.69, 127.56, 124.16, 123.54, 122.06, 116.54, 114.39, 103.84, 76.68, 72.45, 36.28, 30.50, 22.08.

((4-(4-bromothiophen-2-yl)-2,3-dihydro-1H-inden-1-yl)oxy)(tert-butyl)dimethylsilane (THIO INT-4)

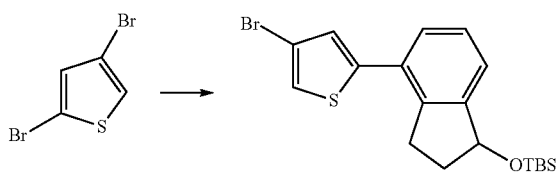 [SMILES: Brc1csc(Br)c1 ; CC(C)(C)[Si](C)(C)OC1CCc2c(-c3cc(Br)cs3)cccc21]

Prepared using General Procedure 1. A 2 mL microwave vial was charged with 2,4-dibromothiophene (15 mg, 0.06 mmol), tert-butyldimethyl((4-(4,4,5,5-tetramethyl-1,3,2-dioxaborolan-2-yl)-2,3-dihydro-1H-inden-1-yl)oxy)silane IND INT-8 (23 mg, 0.06 mmol), potassium carbonate (26 mg, 0.18 mmol) and 3:1 mixture of DME/$H_2O$ (2 mL). The reaction mixture was degassed by bubbling $N_2$ through the stirred solution for 10 min. Pd(PPh$_3$)$_4$ (5 mg, 0.004 mmol) was added and the solution degassed for an additional 2 min. The vial was subjected to microwave irradiation at 70° C. for 30 min or until starting material consumed. The resulting ((4-(4-bromothiophen-2-yl)-2,3-dihydro-1H-inden-1-yl)oxy)(tert-butyl)dimethylsilane THIO INT-4 was carried onto the next experiment without workup and purification. LCMS-ESI (m/z) calculated for $C_{19}H_{25}BrOSSi$: 408.1; no M+ found, $t_R$=6.50 min (Method 1).

2-isopropoxy-5-(4,4,5,5-tetramethyl-1,3,2-dioxaborolan-2-yl)benzonitrile

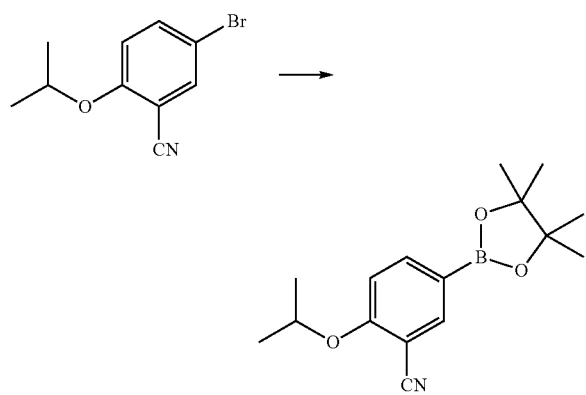

A suspension of 5-bromo-2-isopropoxybenzonitrile (200 mg, 0.83 mmol), 4,4,4',4',5,5,5',5'-octamethyl-2,2'-bi(1,3,2-dioxaborolane) (233.7 mg, 920 mmol), and potassium acetate (246 mg, 2.5 mmol) in anhydrous 1,4-dioxane (100 mL) was degassed by passing $N_2$ through the solution for 30 min. PdCl$_2$(dppf).CH$_2$Cl$_2$ (136 mg, 0.16 mmol) was added and the reaction mixture was heated at 85° C. for 6 h. The solvent was removed under vacuum and the residue was dissolved in EA (100 mL) and filtered through celite. The filtrate was washed with water and brine, dried over MgSO$_4$, and purified by chromatography (EA/hexanes) to afford 40 mg (13%) of 2-isopropoxy-5-(4,4,5,5-tetramethyl-1,3,2-dioxaborolan-2-yl)benzonitrile as white solid. LCMS-ESI (m/z) calculated for $C_{16}H_{22}BNO_3$: 287.2; found 288.2 [M+H]$^+$, $t_R$=4.07 min. $^1$H NMR (400 MHz, CDCl$_3$) δ 7.97 (d, J=1.5 Hz, 1H), 7.88 (dd, J=8.5, 1.7 Hz, 1H), 6.91 (d, J=8.5 Hz, 1H), 4.67 (dt, J=12.2, 6.1 Hz, 1H), 1.38 (d, J=6.1 Hz, 6H), 1.30 (s, 12H).

5-(5-(1-((tert-butyldimethylsilyl)oxy)-2,3-dihydro-1H-inden-4-yl)thiophen-3-yl)-2-isopropoxybenzonitrile (THIO INT-5)

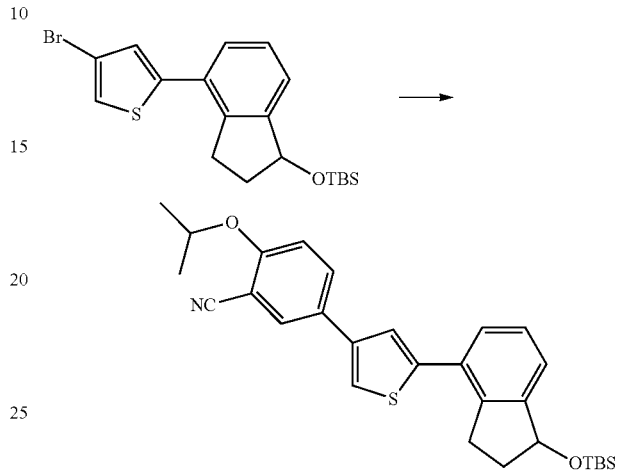

To the crude reaction mixture containing ((4-(4-bromothiophen-2-yl)-2,3-dihydro-1H-inden-1-yl)oxy)(tert-butyl)dimethylsilane THIO INT-4 (0.12 mmol) in 3:1 mixture of DME/$H_2O$ (4 mL) was added 2-isopropoxy-5-(4,4,5,5-tetramethyl-1,3,2-dioxaborolan-2-yl)benzonitrile (17.9 mg, 0.06 mmol) and the solution was degassed for 2 min. Pd(PPh$_3$)$_4$ (7 mg, 0.006 mmol) was added and the reaction mixture degassed for an additional 2 min. The reaction mixture was heated under microwave condition at 100° C. for 30 min. The reaction mixture was diluted with EA (10 mL), washed with water and brine, and dried over MgSO$_4$. The crude product was purified by silica gel column chromatography (EA/Hexanes) to afford 12 mg (40%, for two steps) of 5-(4-(1-((tert-butyldimethylsilyl)oxy)-2,3-dihydro-1H-inden-4-yl)thiophen-2-yl)-2-isopropoxybenzonitrile THIO LCMS-ESI (m/z) calculated for $C_{29}H_{35}NO_2SSi$: 489.2; no M+ found, $t_R$=6.66 min (Method 1).

5-(5-(1-hydroxy-2,3-dihydro-1H-inden-4-yl)thiophen-3-yl)-2-isopropoxybenzonitrile (Compound 227)

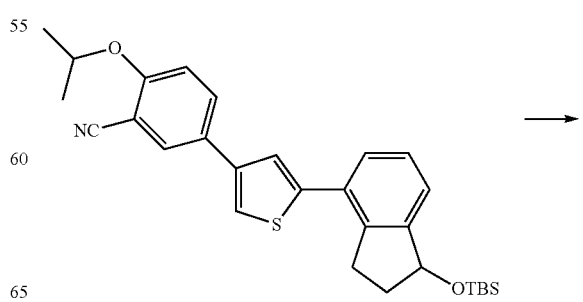

-continued

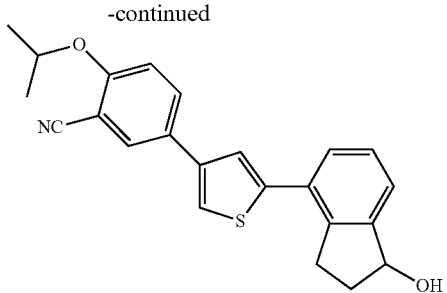

Prepared using General Procedure 3. To a solution of 5-(4-(1-(((tert-butyldimethylsilyl)oxy)-2,3-dihydro-1H-inden-4-yl)thiophen-2-yl)-2-isopropoxybenzonitrile THIO INT-5 (12 mg, 0.02 mmol) in THF (1 mL) was added 1M solution of TBAF in tetrahydrofuran (0.2 mL, 0.2 mmol) and the reaction mixture was stirred at room temperature overnight. The reaction mixture was concentrated and purified by preparative HPLC to yield 3 mg (22%) of 5-(5-(1-hydroxy-2,3-dihydro-1H-inden-4-yl)thiophen-3-yl)-2-isopropoxybenzonitrile 227 as white solid. LCMS-ESI (m/z) calculated for $C_{23}H_{21}NO_2S$: 375.1; found 398.1 [M+Na]$^+$. $t_R$=3.85 min; $^1$H NMR (400 MHz, CDCl$_3$) δ 7.77 (dd, J=6.9, 2.2 Hz, 1H), 7.74-7.68 (m, 1H), 7.51 (d, J=8.0 Hz, 1H), 7.45-7.36 (m, 1H), 7.36-7.28 (m, 1H), 7.27-7.22 (m, 2H), 7.10-6.74 (m, 1H), 5.37-5.15 (m, 1H), 4.67 (dt, J=12.2, 6.1 Hz, 1H), 3.90 (ddd, J=16.2, 8.5, 4.7 Hz, 1H), 3.14-2.98 (m, 1H), 2.66-2.40 (m, 1H), 2.09-1.87 (m, 1H), 1.57 (s, 1H), 1.41 (d, J=6.1 Hz, 6H).

Selected compounds and their corresponding analytical data is shown in Table 1, where the LCMS data was collected using Method 2 (see General Methods). The enantiomeric purity was determined for key intermediates and selected final compounds and is presumed from the synthesis for the remaining compounds.

TABLE 1

| STRUCTURE | COMPOUND NUMBER | LCMS RETENTION TIME (min) |
|---|---|---|
| 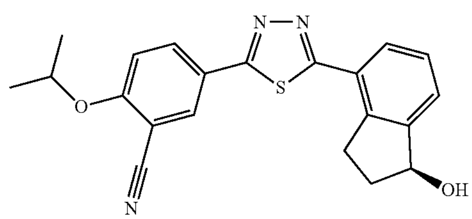 [SMILES: CC(C)Oc1ccc(-c2nnc(-c3cccc4c3CC[C@@H]4O)s2)cc1C#N] | 1 | 8.53 |
| 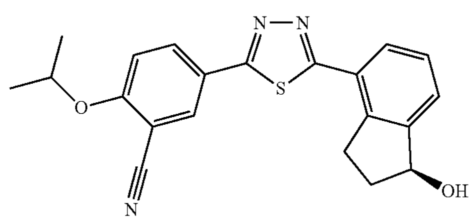 [SMILES: CC(C)Oc1ccc(-c2nnc(-c3cccc4c3CC[C@@H]4O)s2)cc1C#N] | 2 | 8.54 |
| 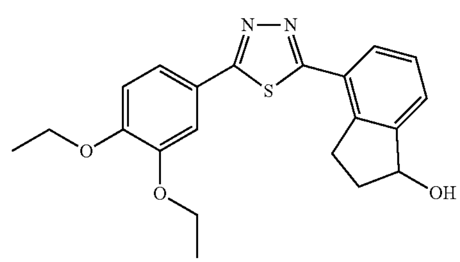 [SMILES: CCOc1ccc(-c2nnc(-c3cccc4c3CCC4O)s2)cc1OCC] | 3 | 8.52 |
| 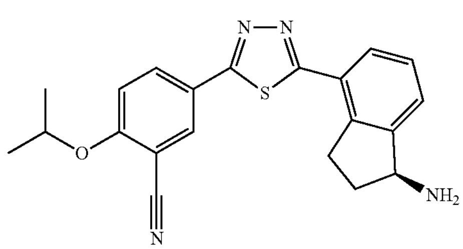 [SMILES: CC(C)Oc1ccc(-c2nnc(-c3cccc4c3CC[C@@H]4N)s2)cc1C#N] | 4 | 6.08 |

TABLE 1-continued

| STRUCTURE | COMPOUND NUMBER | LCMS RETENTION TIME (min) |
|---|---|---|
| 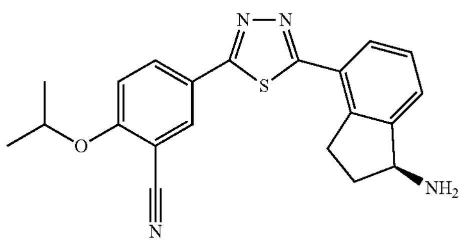 [SMILES: CC(C)Oc1ccc(-c2nnc(-c3cccc4c3CC[C@@H]4N)s2)cc1C#N] | 5 | 6.08 |
| 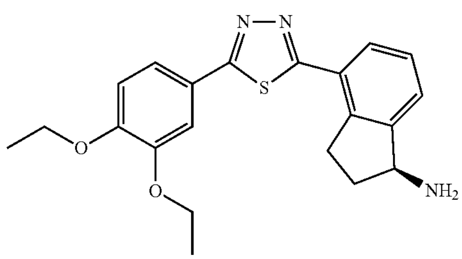 [SMILES: CCOc1ccc(-c2nnc(-c3cccc4c3CC[C@@H]4N)s2)cc1OCC] | 6 | 5.98 |
| 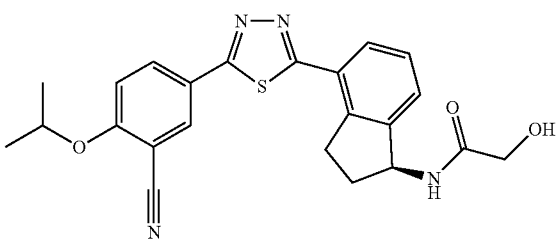 [SMILES: CC(C)Oc1ccc(-c2nnc(-c3cccc4c3CC[C@@H]4NC(=O)CO)s2)cc1C#N] | 7 | 7.82 |
| 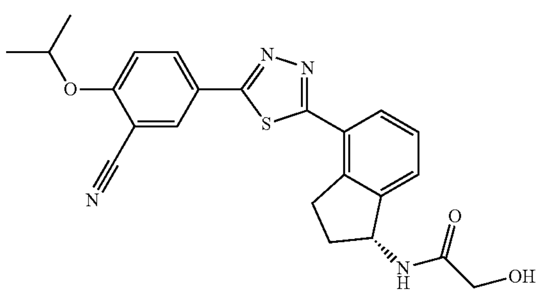 [SMILES: CC(C)Oc1ccc(-c2nnc(-c3cccc4c3CC[C@H]4NC(=O)CO)s2)cc1C#N] | 8 | 7.78 |
| 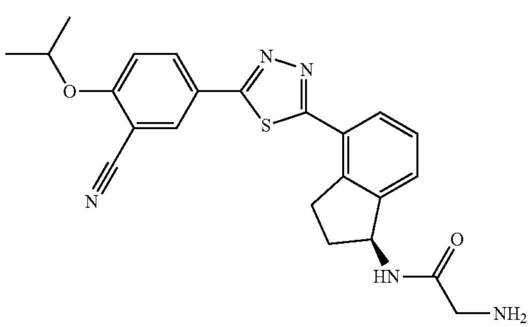 [SMILES: CC(C)Oc1ccc(-c2nnc(-c3cccc4c3CC[C@@H]4NC(=O)CN)s2)cc1C#N] | 9 | 6.18 |

TABLE 1-continued
| STRUCTURE | COMPOUND NUMBER | LCMS RETENTION TIME (min) |
|---|---|---|
| 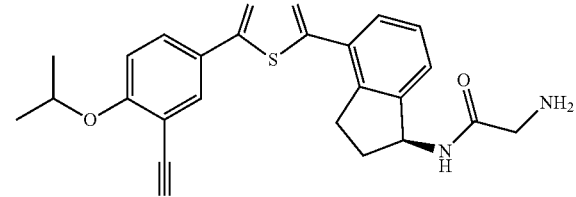 | 10 | 6.18 |
| 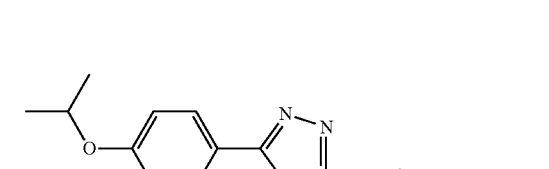 | 11 | 8.68 |
| 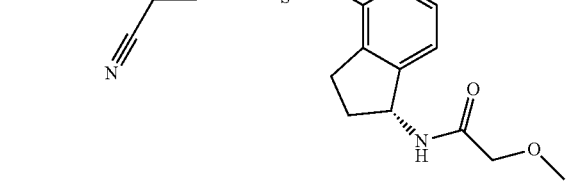 | 12 | 8.70 |
| 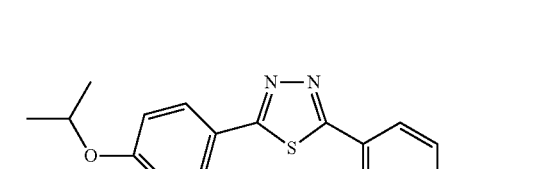 | 13 | 6.43 |
| 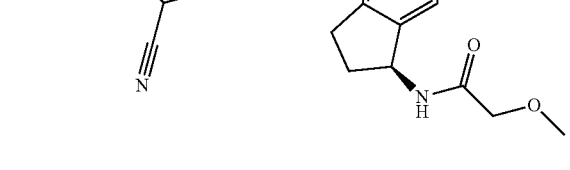 | 14 | 8.26 |

TABLE 1-continued

| STRUCTURE | COMPOUND NUMBER | LCMS RETENTION TIME (min) |
|---|---|---|
| (structure) | 15 | 8.26 |
| (structure) | 16 | 9.26 |
| (structure) | 17 | 6.19 |
| (structure) | 18 | 6.09 |
| (structure) | 19 | 6.42 |

TABLE 1-continued
| STRUCTURE | COMPOUND NUMBER | LCMS RETENTION TIME (min) |
|---|---|---|
| 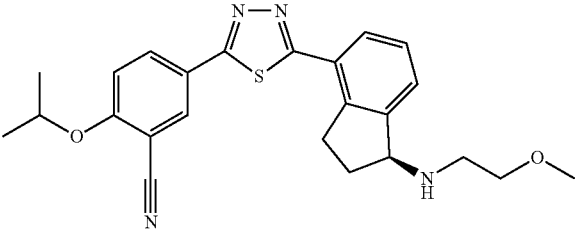 [SMILES: COCCN[C@H]1CCc2c(-c3nnc(-c4ccc(OC(C)C)c(C#N)c4)s3)cccc21] | 20 | 6.48 |
| 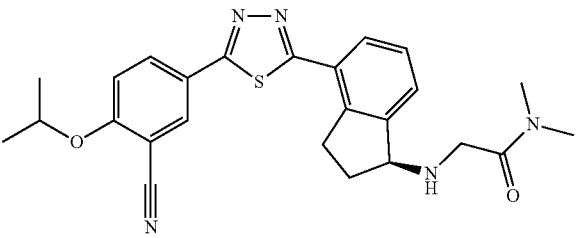 | 21 | 6.34 |
| 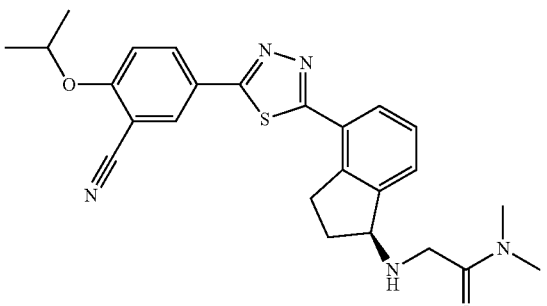 | 22 | 6.30 |
| 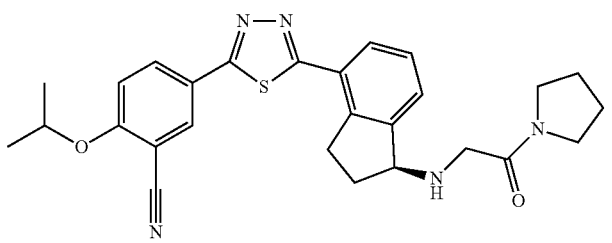 [SMILES: CC(C)Oc1ccc(-c2nnc(-c3cccc4c3CC[C@@H]4NCC(=O)N3CCCC3)s2)cc1C#N] | 23 | 6.50 |
| 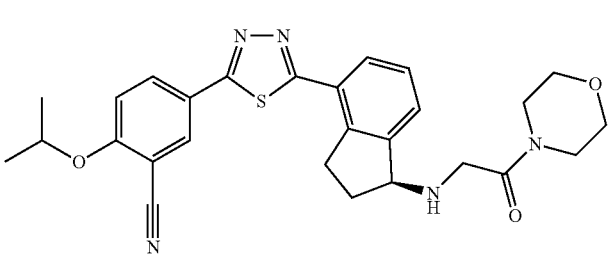 [SMILES: CC(C)Oc1ccc(-c2nnc(-c3cccc4c3CC[C@@H]4NCC(=O)N3CCOCC3)s2)cc1C#N] | 24 | 6.35 |

TABLE 1-continued

| STRUCTURE | COMPOUND NUMBER | LCMS RETENTION TIME (min) |
|---|---|---|
| 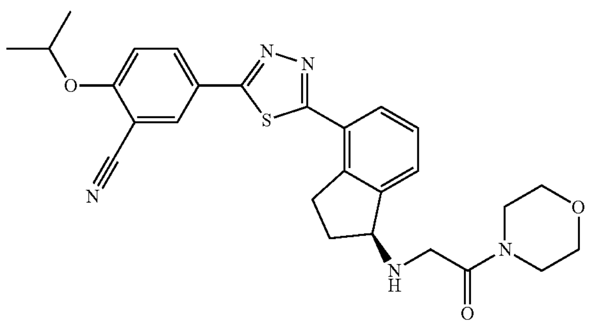 [SMILES: CC(C)Oc1ccc(-c2nnc(-c3cccc4c3CC[C@@H]4NCC(=O)N3CCOCC3)s2)cc1C#N] | 25 | 6.31 |
| 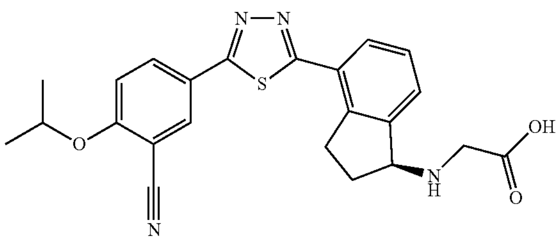 [SMILES: CC(C)Oc1ccc(-c2nnc(-c3cccc4c3CC[C@@H]4NCC(=O)O)s2)cc1C#N] | 26 | 6.44 |
| 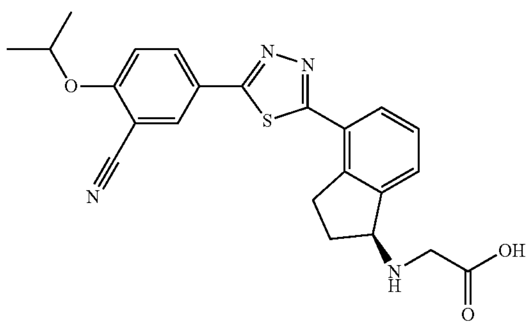 [SMILES: CC(C)Oc1ccc(-c2nnc(-c3cccc4c3CC[C@@H]4NCC(=O)O)s2)cc1C#N] | 27 | 6.41 |
| 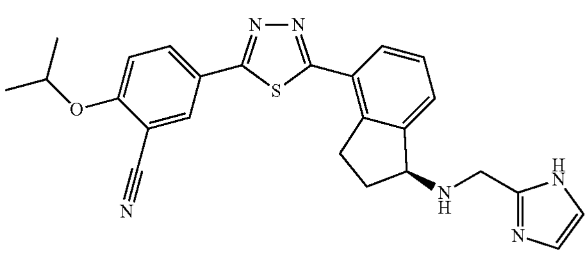 [SMILES: CC(C)Oc1ccc(-c2nnc(-c3cccc4c3CC[C@@H]4NCc3ncc[nH]3)s2)cc1C#N] | 28 | 6.21 |
| 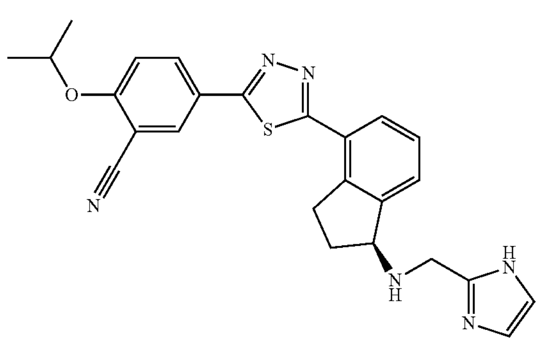 [SMILES: CC(C)Oc1ccc(-c2nnc(-c3cccc4c3CC[C@@H]4NCc3ncc[nH]3)s2)cc1C#N] | 29 | 6.10 |

TABLE 1-continued

| STRUCTURE | COMPOUND NUMBER | LCMS RETENTION TIME (min) |
| --- | --- | --- |
| 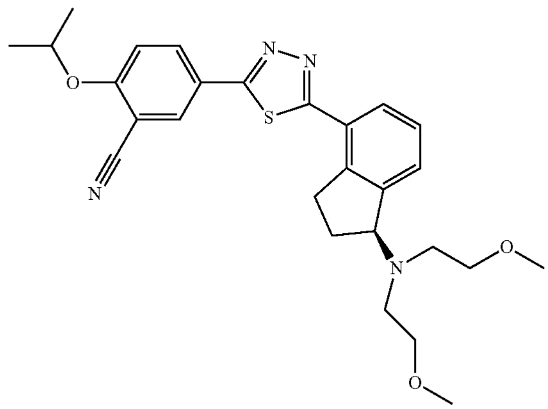 [SMILES: COCCN(CCOC)[C@H]1CCc2c(-c3nnc(-c4ccc(OC(C)C)c(C#N)c4)s3)cccc21] | 30 | 6.81 |
| 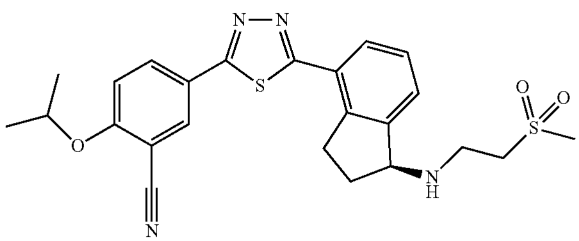 [SMILES: CC(C)Oc1ccc(-c2nnc(-c3cccc4c3CC[C@@H]4NCCS(C)(=O)=O)s2)cc1C#N] | 31 | 6.38 |
| 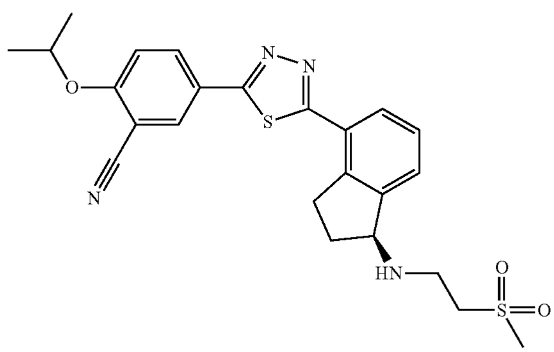 [SMILES: CC(C)Oc1ccc(-c2nnc(-c3cccc4c3CC[C@@H]4NCCS(C)(=O)=O)s2)cc1C#N] | 32 | 6.32 |
| 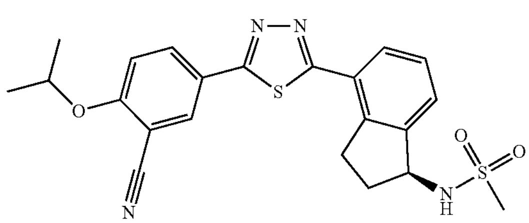 [SMILES: CC(C)Oc1ccc(-c2nnc(-c3cccc4c3CC[C@@H]4NS(C)(=O)=O)s2)cc1C#N] | 33 | 8.84 |
| 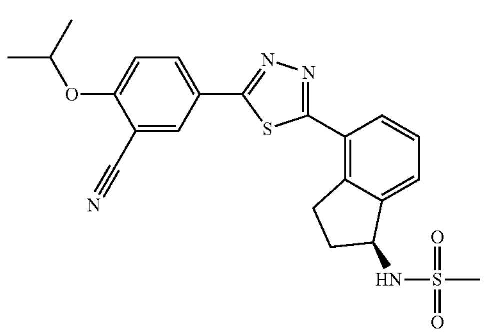 [SMILES: CC(C)Oc1ccc(-c2nnc(-c3cccc4c3CC[C@@H]4NS(C)(=O)=O)s2)cc1C#N] | 34 | 8.80 |

TABLE 1-continued

| STRUCTURE | COMPOUND NUMBER | LCMS RETENTION TIME (min) |
|---|---|---|
| 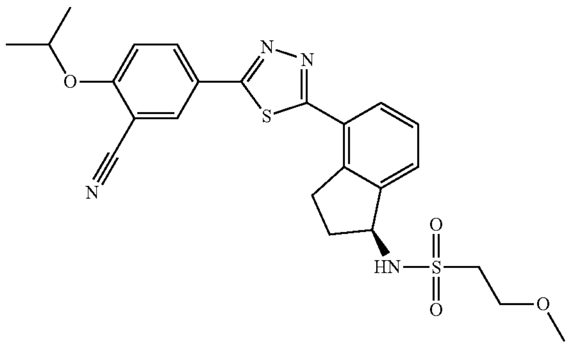 [SMILES: COCCS(=O)(=O)N[C@H]1CCc2c(-c3nnc(-c4ccc(OC(C)C)c(C#N)c4)s3)cccc21] | 35 | 9.10 |
| 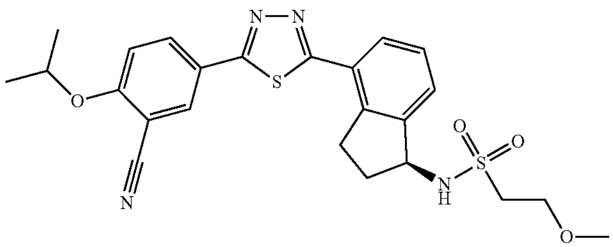 [SMILES: COCCS(=O)(=O)N[C@H]1CCc2c(-c3nnc(-c4ccc(OC(C)C)c(C#N)c4)s3)cccc21] | 36 | 9.13 |
| 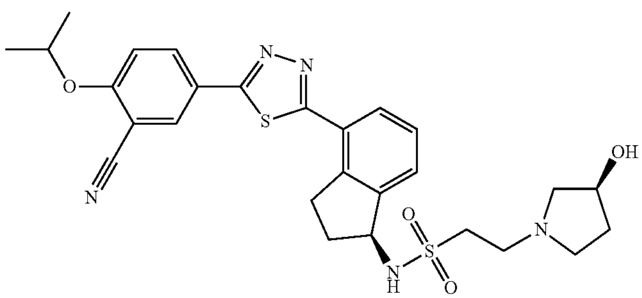 [SMILES: CC(C)Oc1ccc(-c2nnc(-c3cccc4c3CC[C@@H]4NS(=O)(=O)CCN3CC[C@H](O)C3)s2)cc1C#N] | 37 | 6.52 |
| 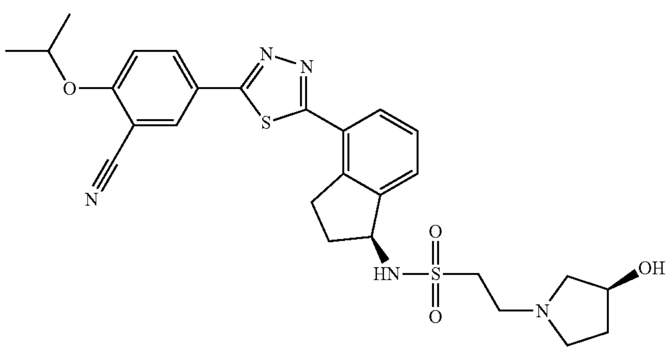 [SMILES: CC(C)Oc1ccc(-c2nnc(-c3cccc4c3CC[C@@H]4NS(=O)(=O)CCN3CC[C@H](O)C3)s2)cc1C#N] | 38 | 6.54 |
| 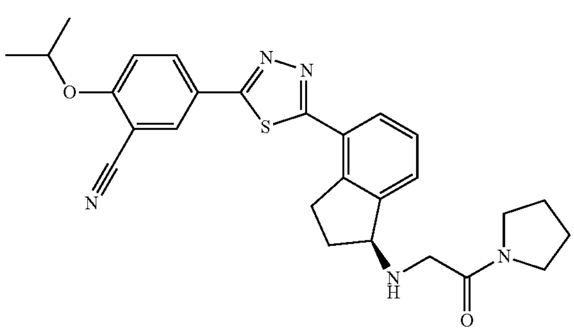 [SMILES: CC(C)Oc1ccc(-c2nnc(-c3cccc4c3CC[C@@H]4NCC(=O)N3CCCC3)s2)cc1C#N] | 39 | 6.46 |

TABLE 1-continued
| STRUCTURE | COMPOUND NUMBER | LCMS RETENTION TIME (min) |
|---|---|---|
| 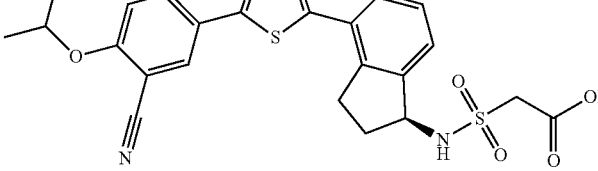 | 40 | 8.37 |
| 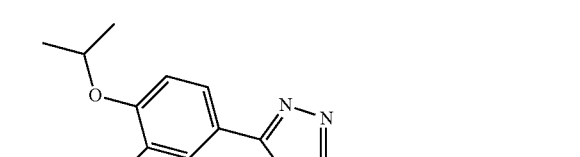 | 41 | 8.33 |
| 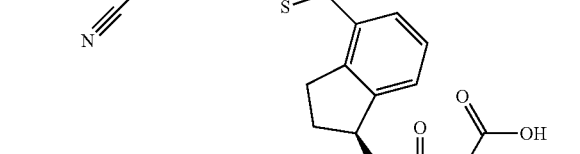 | 42 | 8.58 |
| 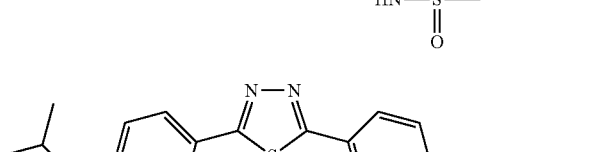 | 43 | 8.55 |
| 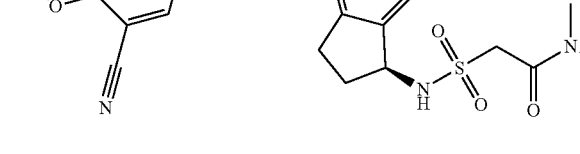 | 44 | 7.95 |

TABLE 1-continued
| STRUCTURE | COMPOUND NUMBER | LCMS RETENTION TIME (min) |
|---|---|---|
| 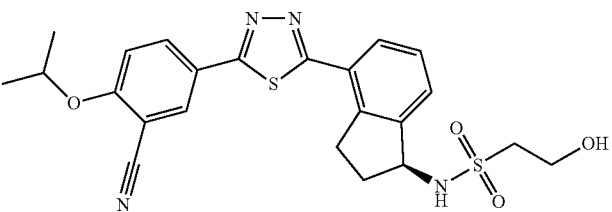 [SMILES: CC(C)Oc1ccc(-c2nnc(-c3cccc4c3CC[C@@H]4NS(=O)(=O)CCO)s2)cc1C#N] | 45 | 8.21 |
| 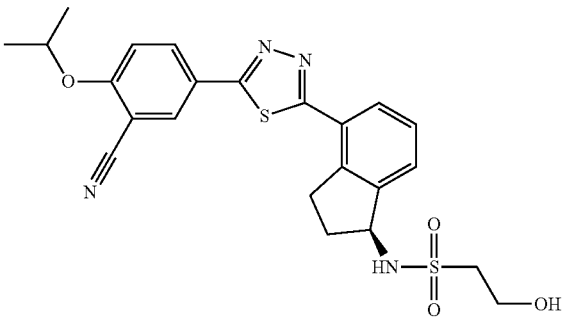 [SMILES: CC(C)Oc1ccc(-c2nnc(-c3cccc4c3CC[C@@H]4NS(=O)(=O)CCO)s2)cc1C#N] | 46 | 8.18 |
| 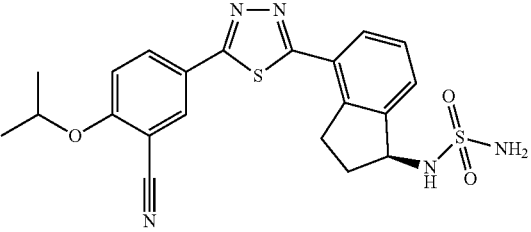 [SMILES: CC(C)Oc1ccc(-c2nnc(-c3cccc4c3CC[C@@H]4NS(N)(=O)=O)s2)cc1C#N] | 47 | 8.29 |
| 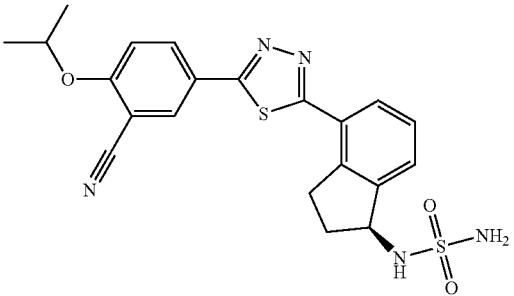 [SMILES: CC(C)Oc1ccc(-c2nnc(-c3cccc4c3CC[C@@H]4NS(N)(=O)=O)s2)cc1C#N] | 48 | 8.26 |
| 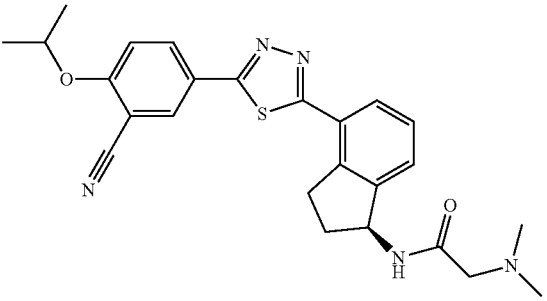 [SMILES: CC(C)Oc1ccc(-c2nnc(-c3cccc4c3CC[C@@H]4NC(=O)CN(C)C)s2)cc1C#N] | 49 | 6.23 |

TABLE 1-continued

| STRUCTURE | COMPOUND NUMBER | LCMS RETENTION TIME (min) |
|---|---|---|
| 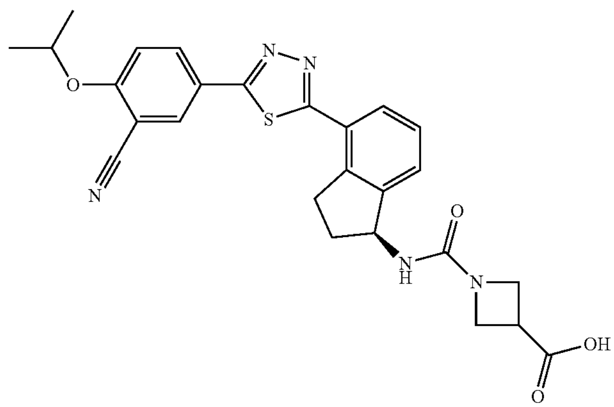 [SMILES: CC(C)Oc1ccc(-c2nnc(-c3cccc4c3CC[C@@H]4NC(=O)N3CC(C(=O)O)C3)s2)cc1C#N] | 50 | 7.75 |
| 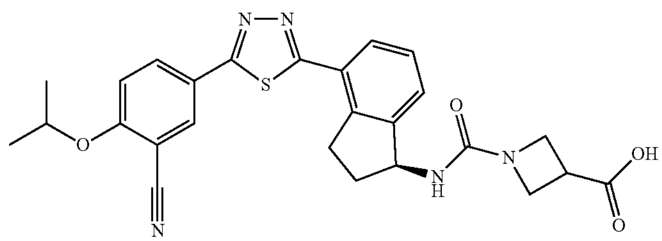 [SMILES: CC(C)Oc1ccc(-c2nnc(-c3cccc4c3CC[C@@H]4NC(=O)N3CC(C(=O)O)C3)s2)cc1C#N] | 51 | 7.81 |
| 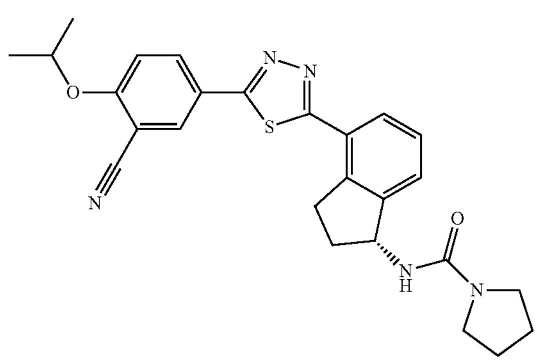 [SMILES: CC(C)Oc1ccc(-c2nnc(-c3cccc4c3CC[C@H]4NC(=O)N3CCCC3)s2)cc1C#N] | 52 | 8.88 |
| 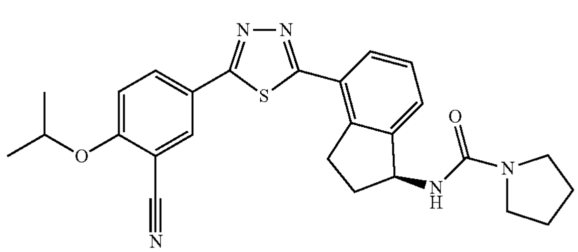 [SMILES: CC(C)Oc1ccc(-c2nnc(-c3cccc4c3CC[C@@H]4NC(=O)N3CCCC3)s2)cc1C#N] | 53 | 8.92 |

TABLE 1-continued

| STRUCTURE | COMPOUND NUMBER | LCMS RETENTION TIME (min) |
|---|---|---|
| 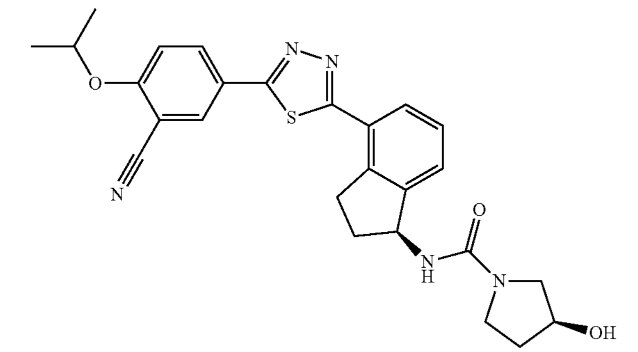 [SMILES: CC(C)Oc1ccc(-c2nnc(-c3cccc4c3CC[C@@H]4NC(=O)N3CC[C@H](O)C3)s2)cc1C#N] | 54 | 7.61 |
| 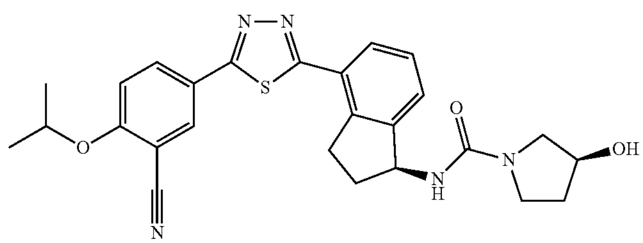 [SMILES: CC(C)Oc1ccc(-c2nnc(-c3cccc4c3CC[C@@H]4NC(=O)N3CC[C@H](O)C3)s2)cc1C#N] | 55 | 7.65 |
| 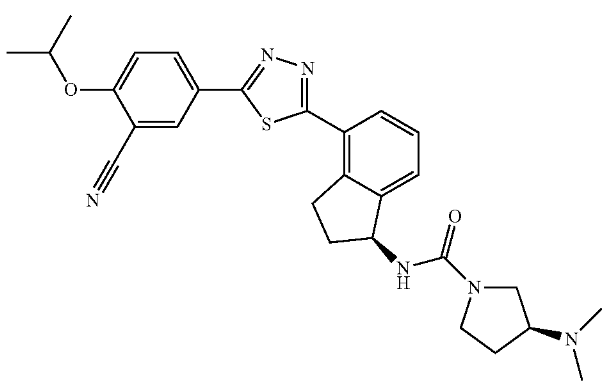 [SMILES: CC(C)Oc1ccc(-c2nnc(-c3cccc4c3CC[C@@H]4NC(=O)N3CC[C@H](N(C)C)C3)s2)cc1C#N] | 56 | 6.26 |
| 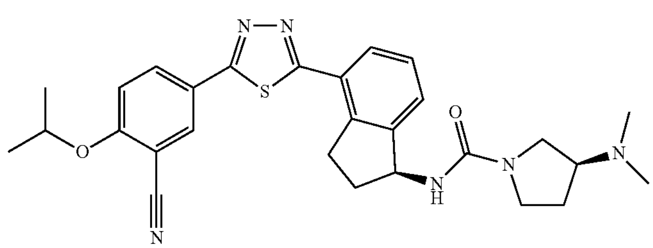 [SMILES: CC(C)Oc1ccc(-c2nnc(-c3cccc4c3CC[C@@H]4NC(=O)N3CC[C@H](N(C)C)C3)s2)cc1C#N] | 57 | 6.30 |
| 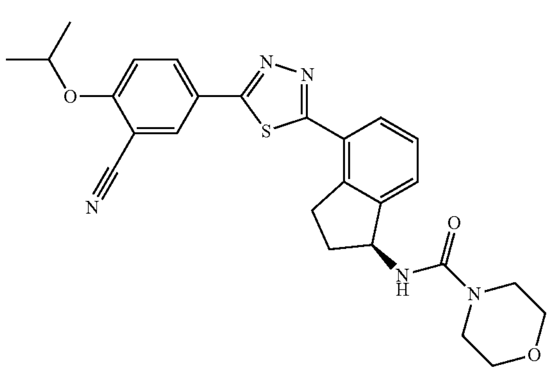 [SMILES: CC(C)Oc1ccc(-c2nnc(-c3cccc4c3CC[C@@H]4NC(=O)N3CCOCC3)s2)cc1C#N] | 58 | 8.39 |

TABLE 1-continued

| STRUCTURE | COMPOUND NUMBER | LCMS RETENTION TIME (min) |
|---|---|---|
| 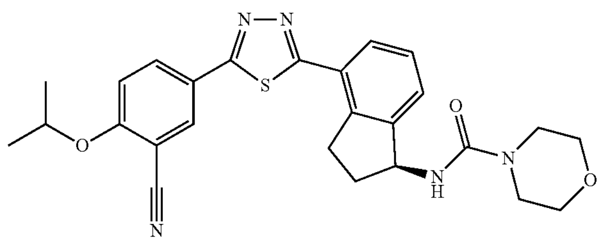 [SMILES: CC(C)Oc1ccc(-c2nnc(-c3cccc4c3CC[C@@H]4NC(=O)N3CCOCC3)s2)cc1C#N] | 59 | 8.43 |
| 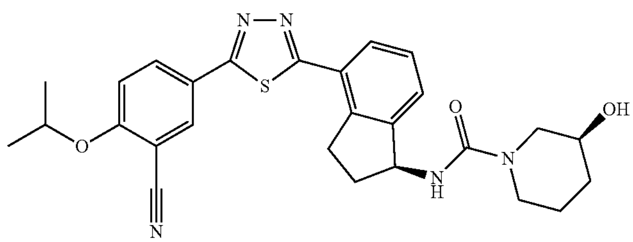 [SMILES: CC(C)Oc1ccc(-c2nnc(-c3cccc4c3CC[C@@H]4NC(=O)N3CCC[C@H](O)C3)s2)cc1C#N] | 60 | 8.02 |
| 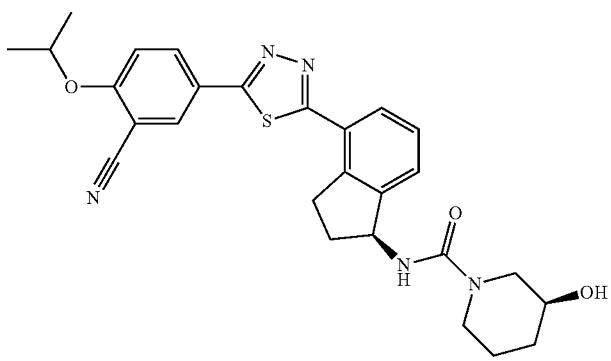 [SMILES: CC(C)Oc1ccc(-c2nnc(-c3cccc4c3CC[C@@H]4NC(=O)N3CCC[C@H](O)C3)s2)cc1C#N] | 61 | 7.98 |
| 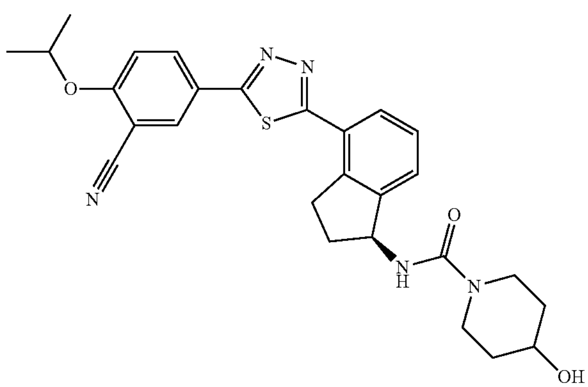 [SMILES: CC(C)Oc1ccc(-c2nnc(-c3cccc4c3CC[C@@H]4NC(=O)N3CCC(O)CC3)s2)cc1C#N] | 62 | 7.75 |
| 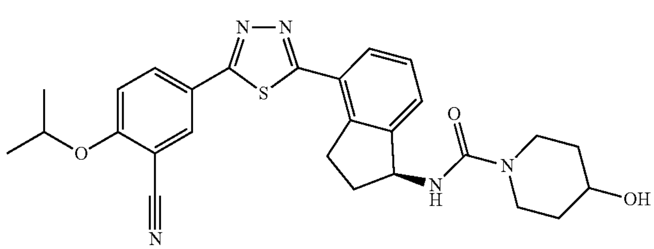 [SMILES: CC(C)Oc1ccc(-c2nnc(-c3cccc4c3CC[C@@H]4NC(=O)N3CCC(O)CC3)s2)cc1C#N] | 63 | 7.79 |

TABLE 1-continued

| STRUCTURE | COMPOUND NUMBER | LCMS RETENTION TIME (min) |
|---|---|---|
| 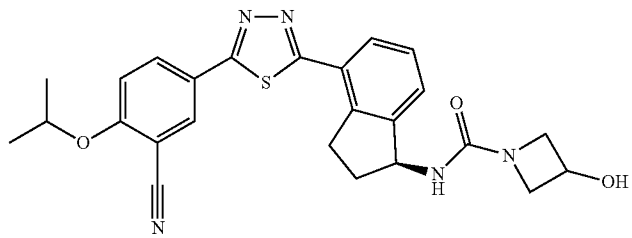 [SMILES: CC(C)Oc1ccc(-c2nnc(-c3cccc4c3CC[C@@H]4NC(=O)N3CC(O)C3)s2)cc1C#N] | 64 | 7.60 |
| 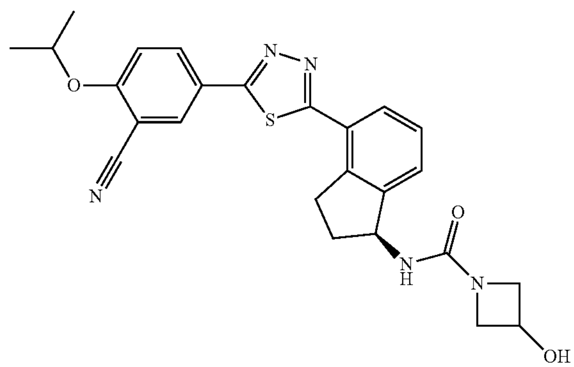 [SMILES: CC(C)Oc1ccc(-c2nnc(-c3cccc4c3CC[C@@H]4NC(=O)N3CC(O)C3)s2)cc1C#N] | 65 | 7.55 |
| 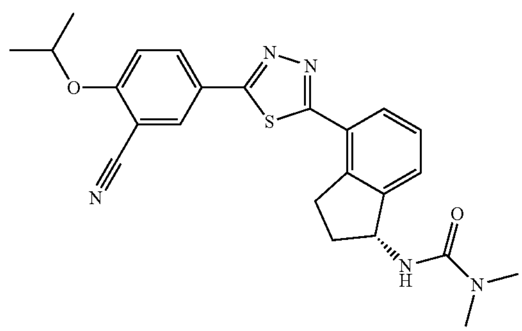 [SMILES: CC(C)Oc1ccc(-c2nnc(-c3cccc4c3CC[C@H]4NC(=O)N(C)C)s2)cc1C#N] | 66 | 8.55 |
| 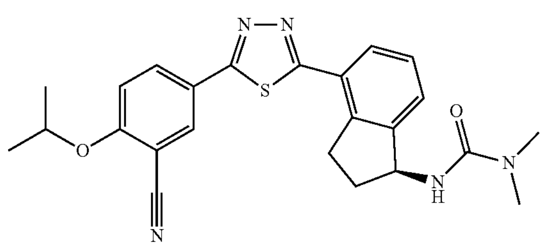 [SMILES: CC(C)Oc1ccc(-c2nnc(-c3cccc4c3CC[C@@H]4NC(=O)N(C)C)s2)cc1C#N] | 67 | 8.58 |
| 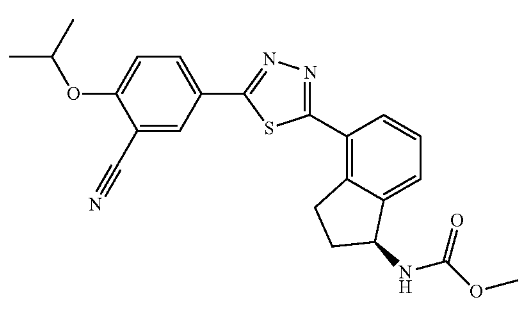 [SMILES: COC(=O)N[C@H]1CCc2c(-c3nnc(-c4ccc(OC(C)C)c(C#N)c4)s3)cccc21] | 68 | 9.25 |

TABLE 1-continued

| STRUCTURE | COMPOUND NUMBER | LCMS RETENTION TIME (min) |
|---|---|---|
| 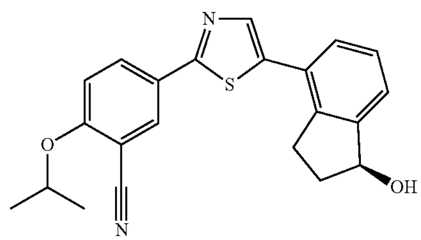 [SMILES: CC(C)Oc1ccc(-c2ncc(-c3cccc4c3CC[C@@H]4O)s2)cc1C#N] | 69 | 9.11 |
| 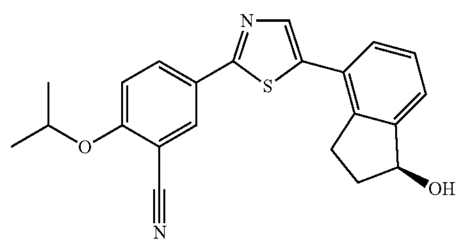 [SMILES: CC(C)Oc1ccc(-c2ncc(-c3cccc4c3CC[C@@H]4O)s2)cc1C#N] | 70 | 9.12 |
| 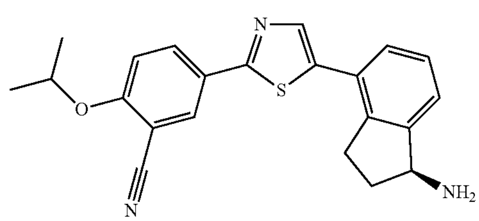 [SMILES: CC(C)Oc1ccc(-c2ncc(-c3cccc4c3CC[C@@H]4N)s2)cc1C#N] | 71 | 6.20 |
| 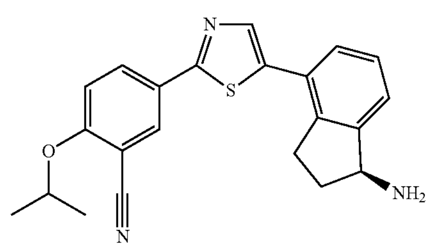 [SMILES: CC(C)Oc1ccc(-c2ncc(-c3cccc4c3CC[C@@H]4N)s2)cc1C#N] | 72 | 6.29 |
| 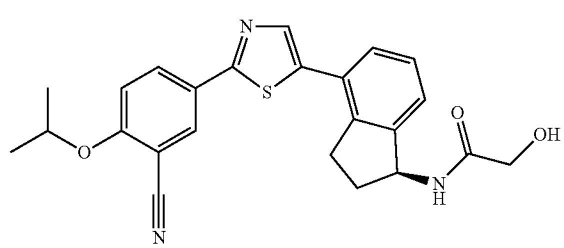 | 73 | 8.22 |
| 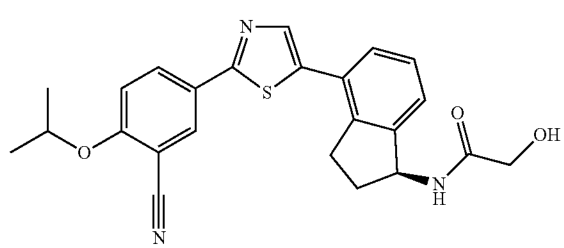 | 74 | 8.22 |

TABLE 1-continued

| STRUCTURE | COMPOUND NUMBER | LCMS RETENTION TIME (min) |
|---|---|---|
| (structure) | 75 | 9.23 |
| (structure) | 76 | 9.22 |
| (structure) | 77 | 6.47 |
| (structure) | 78 | 6.45 |
| (structure) | 79 | 6.42 |
| (structure) | 80 | 6.44 |

TABLE 1-continued
| STRUCTURE | COMPOUND NUMBER | LCMS RETENTION TIME (min) |
|---|---|---|
| 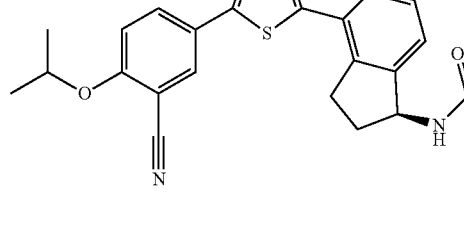 | 81 | 6.62 |
| 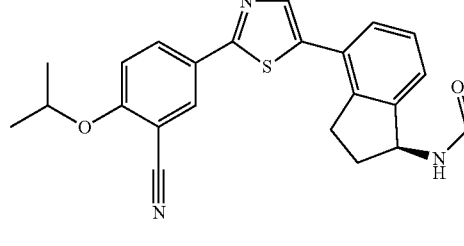 | 82 | 6.63 |
| 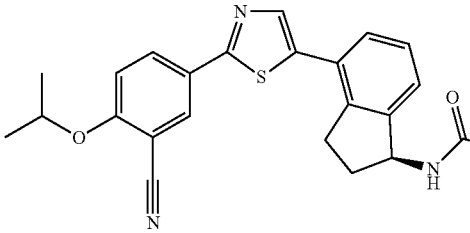 | 83 | 9.99 |
| 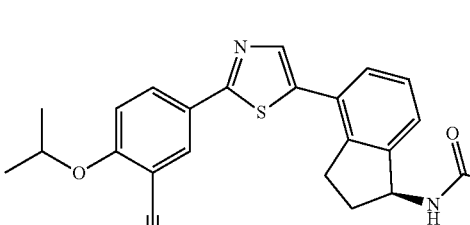 | 84 | 9.98 |
| 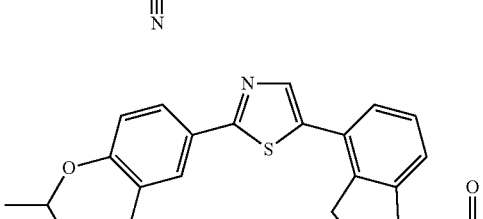 | 85 | 6.93 |
| 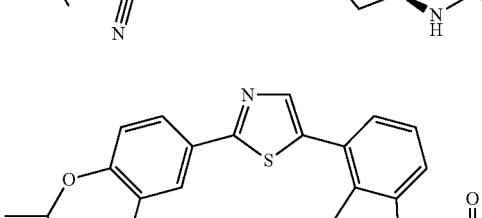 | 86 | 6.92 |

TABLE 1-continued

| STRUCTURE | COMPOUND NUMBER | LCMS RETENTION TIME (min) |
|---|---|---|
| 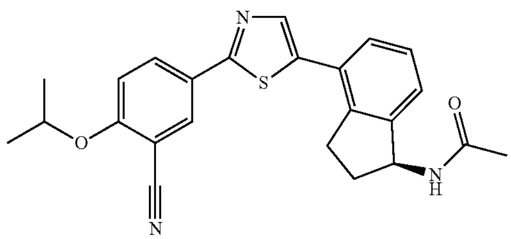 [SMILES: CC(=O)N[C@H]1CCc2c(-c3cnc(-c4ccc(OC(C)C)c(C#N)c4)s3)cccc21] | 87 | 8.74 |
| 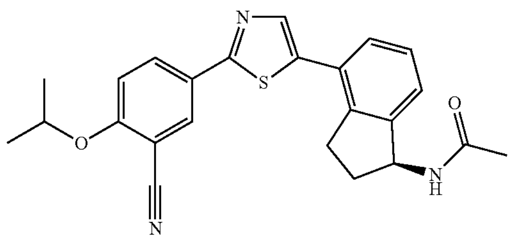 [SMILES: CC(=O)N[C@H]1CCc2c(-c3cnc(-c4ccc(OC(C)C)c(C#N)c4)s3)cccc21] | 88 | 8.75 |
| 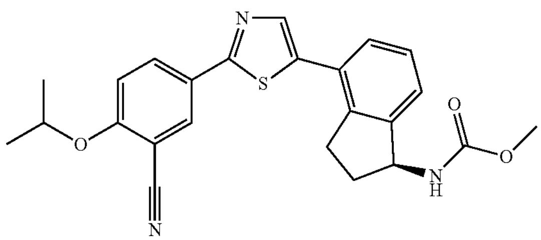 [SMILES: COC(=O)N[C@H]1CCc2c(-c3cnc(-c4ccc(OC(C)C)c(C#N)c4)s3)cccc21] | 89 | 9.77 |
| 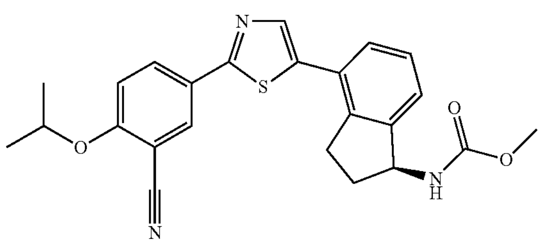 [SMILES: COC(=O)N[C@H]1CCc2c(-c3cnc(-c4ccc(OC(C)C)c(C#N)c4)s3)cccc21] | 90 | 9.76 |
| 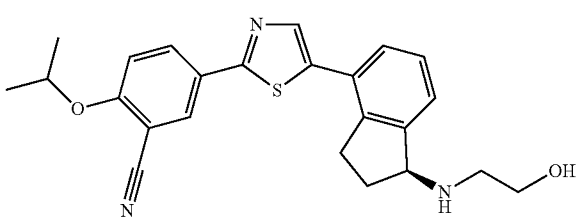 [SMILES: CC(C)Oc1ccc(-c2ncc(-c3cccc4c3CC[C@@H]4NCCO)s2)cc1C#N] | 91 | 6.39 |
| 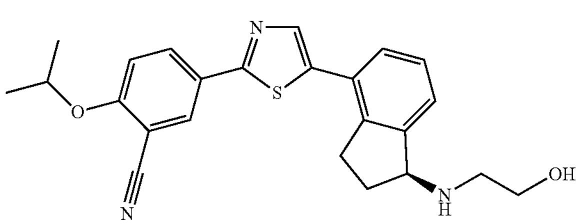 [SMILES: CC(C)Oc1ccc(-c2ncc(-c3cccc4c3CC[C@@H]4NCCO)s2)cc1C#N] | 92 | 6.34 |

TABLE 1-continued
| STRUCTURE | COMPOUND NUMBER | LCMS RETENTION TIME (min) |
|---|---|---|
| 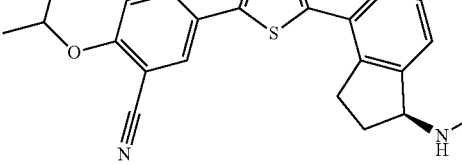 | 93 | 6.80 |
| 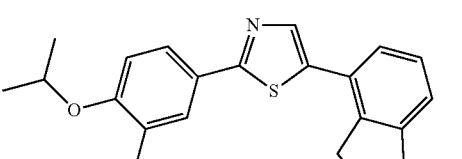 | 94 | 6.62 |
| 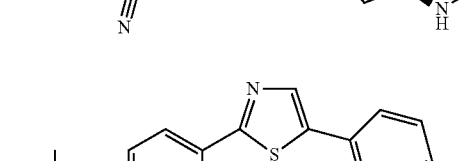 | 95 | 6.47 |
| 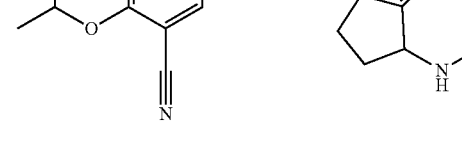 | 96 | 6.65 |
| 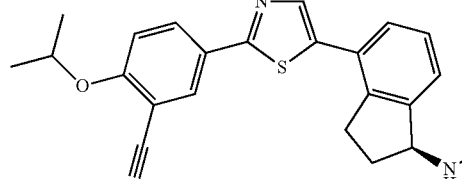 | 97 | 6.63 |
| 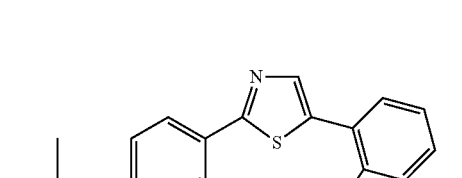 | 98 | 6.54 |

TABLE 1-continued
| STRUCTURE | COMPOUND NUMBER | LCMS RETENTION TIME (min) |
|---|---|---|
| 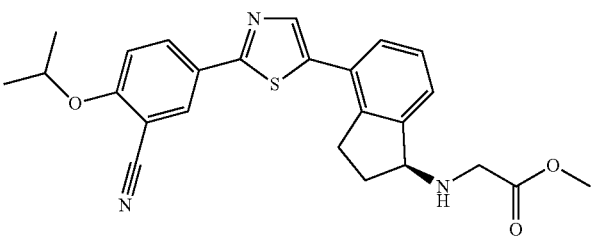 [SMILES: COC(=O)CN[C@H]1CCc2c(-c3cnc(-c4ccc(OC(C)C)c(C#N)c4)s3)cccc21] | 99 | 6.57 |
| 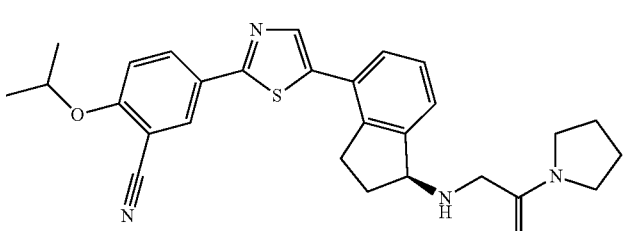 | 100 | 6.83 |
| 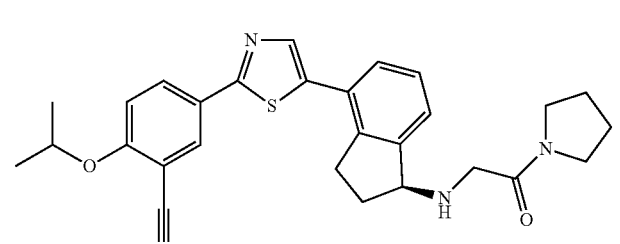 | 101 | 6.66 |
| 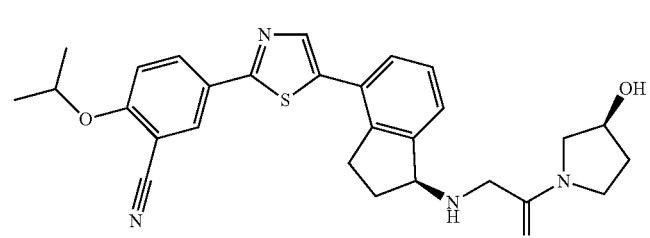 | 102 | 6.34 |
| 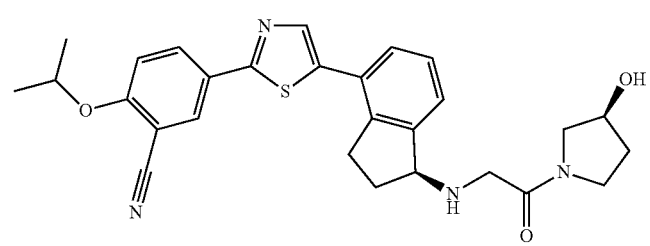 [SMILES: CC(C)Oc1ccc(-c2ncc(-c3cccc4c3CC[C@@H]4NCC(=O)N3CC[C@H](O)C3)s2)cc1C#N] | 103 | 6.36 |
| 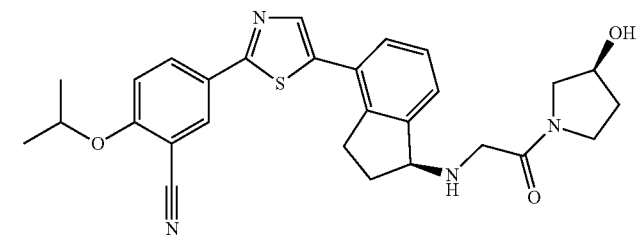 [SMILES: CC(C)Oc1ccc(-c2ncc(-c3cccc4c3CC[C@@H]4NCC(=O)N3CC[C@H](O)C3)s2)cc1C#N] | 104 | 6.28 |

TABLE 1-continued
| STRUCTURE | COMPOUND NUMBER | LCMS RETENTION TIME (min) |
|---|---|---|
| 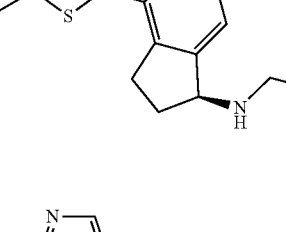 | 105 | 6.31 |
| 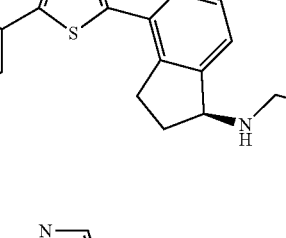 | 106 | 6.43 |
| 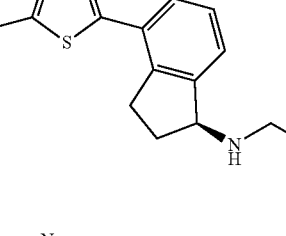 | 107 | 6.78 |
| 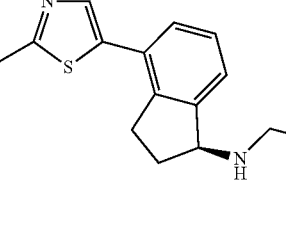 | 108 | 5.40 |
| 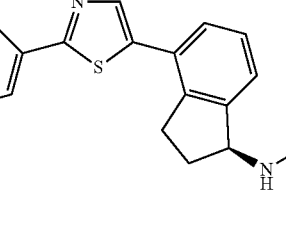 | 109 | 6.43 |
| 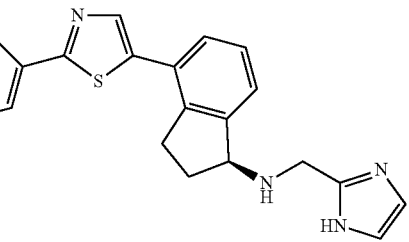 | 110 | 6.51 |

TABLE 1-continued
| STRUCTURE | COMPOUND NUMBER | LCMS RETENTION TIME (min) |
|---|---|---|
| 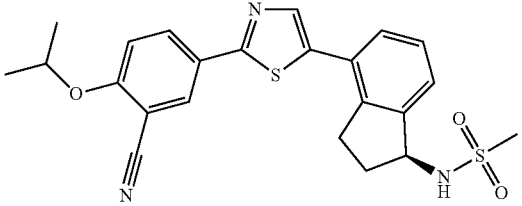 [SMILES: CC(C)Oc1ccc(-c2ncc(-c3cccc4c3CC[C@@H]4NS(C)(=O)=O)s2)cc1C#N] | 111 | 9.24 |
| 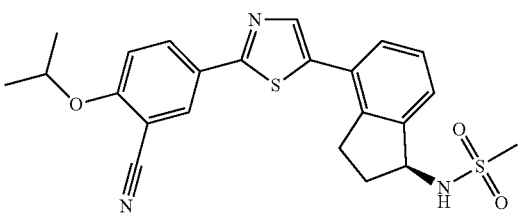 [SMILES: CC(C)Oc1ccc(-c2ncc(-c3cccc4c3CC[C@@H]4NS(C)(=O)=O)s2)cc1C#N] | 112 | 9.25 |
| 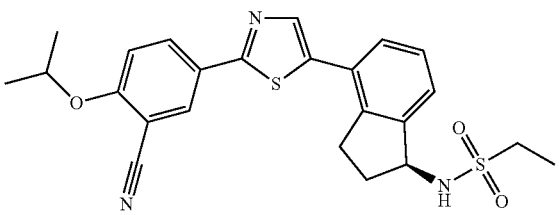 [SMILES: CCS(=O)(=O)N[C@H]1CCc2c(-c3cnc(-c4ccc(OC(C)C)c(C#N)c4)s3)cccc21] | 113 | 9.54 |
| 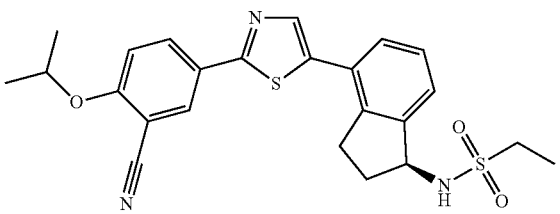 [SMILES: CCS(=O)(=O)N[C@H]1CCc2c(-c3cnc(-c4ccc(OC(C)C)c(C#N)c4)s3)cccc21] | 114 | 9.56 |
| 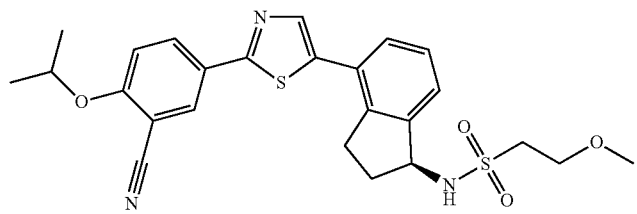 [SMILES: COCCS(=O)(=O)N[C@H]1CCc2c(-c3cnc(-c4ccc(OC(C)C)c(C#N)c4)s3)cccc21] | 115 | 9.44 |
| 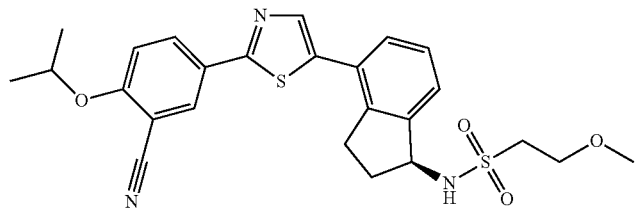 [SMILES: COCCS(=O)(=O)N[C@H]1CCc2c(-c3cnc(-c4ccc(OC(C)C)c(C#N)c4)s3)cccc21] | 116 | 9.55 |
| 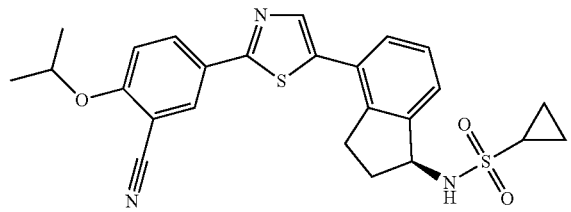 [SMILES: CC(C)Oc1ccc(-c2ncc(-c3cccc4c3CC[C@@H]4NS(=O)(=O)C3CC3)s2)cc1C#N] | 117 | 9.72 |

TABLE 1-continued

| STRUCTURE | COMPOUND NUMBER | LCMS RETENTION TIME (min) |
|---|---|---|
| 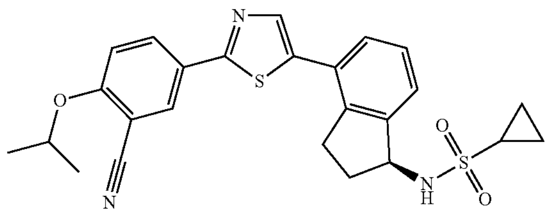 [SMILES: CC(C)Oc1ccc(-c2ncc(-c3cccc4c3CC[C@@H]4NS(=O)(=O)C3CC3)s2)cc1C#N] | 118 | 9.70 |
| 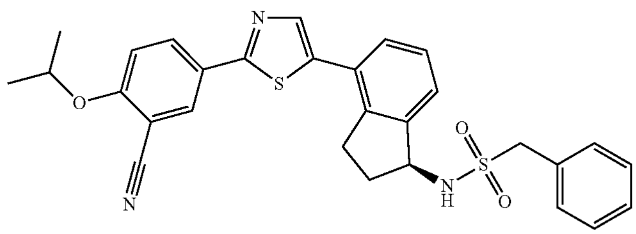 [SMILES: CC(C)Oc1ccc(-c2ncc(-c3cccc4c3CC[C@@H]4NS(=O)(=O)Cc3ccccc3)s2)cc1C#N] | 119 | 10.32 |
| 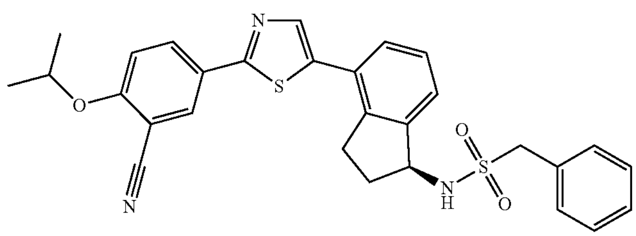 [SMILES: CC(C)Oc1ccc(-c2ncc(-c3cccc4c3CC[C@@H]4NS(=O)(=O)Cc3ccccc3)s2)cc1C#N] | 120 | 10.33 |
| 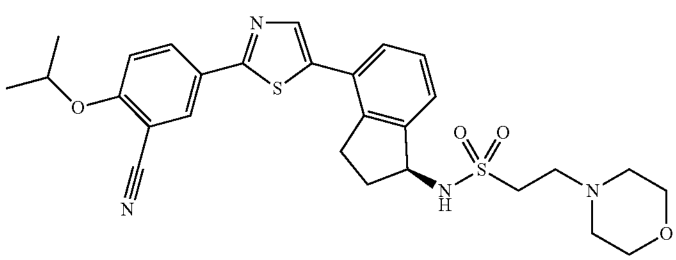 [SMILES: CC(C)Oc1ccc(-c2ncc(-c3cccc4c3CC[C@@H]4NS(=O)(=O)CCN3CCOCC3)s2)cc1C#N] | 121 | 7.15 |
| 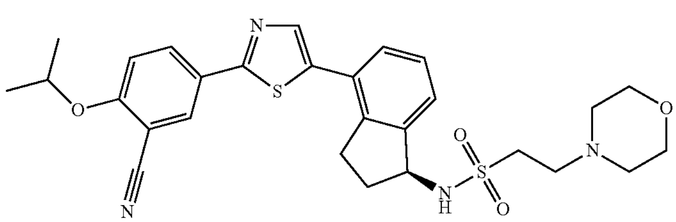 [SMILES: CC(C)Oc1ccc(-c2ncc(-c3cccc4c3CC[C@@H]4NS(=O)(=O)CCN3CCOCC3)s2)cc1C#N] | 122 | 6.99 |
| 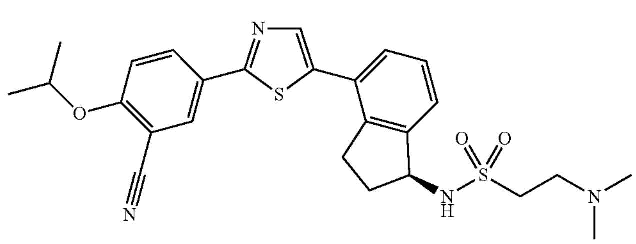 [SMILES: CC(C)Oc1ccc(-c2ncc(-c3cccc4c3CC[C@@H]4NS(=O)(=O)CCN(C)C)s2)cc1C#N] | 123 | 6.99 |

TABLE 1-continued

| STRUCTURE | COMPOUND NUMBER | LCMS RETENTION TIME (min) |
|---|---|---|
| 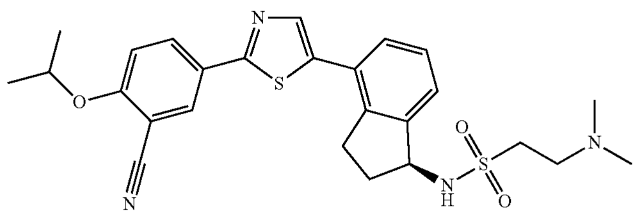 [SMILES: CC(C)Oc1ccc(-c2ncc(-c3cccc4c3CC[C@@H]4NS(=O)(=O)CCN(C)C)s2)cc1C#N] | 124 | 6.81 |
| 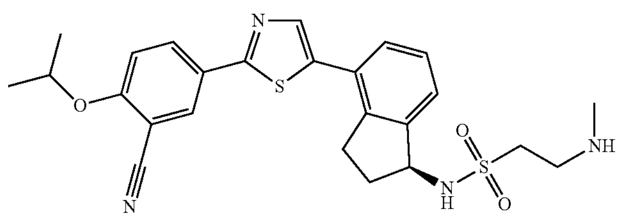 [SMILES: CNCCS(=O)(=O)N[C@H]1CCc2c(-c3cnc(-c4ccc(OC(C)C)c(C#N)c4)s3)cccc21] | 125 | 6.72 |
| 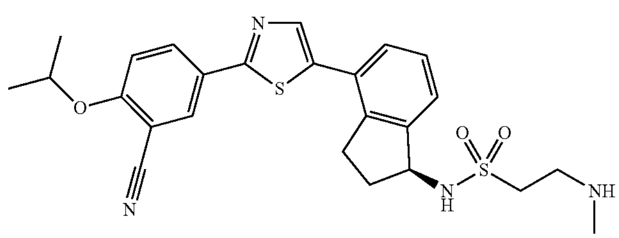 [SMILES: CNCCS(=O)(=O)N[C@H]1CCc2c(-c3cnc(-c4ccc(OC(C)C)c(C#N)c4)s3)cccc21] | 126 | 6.89 |
| 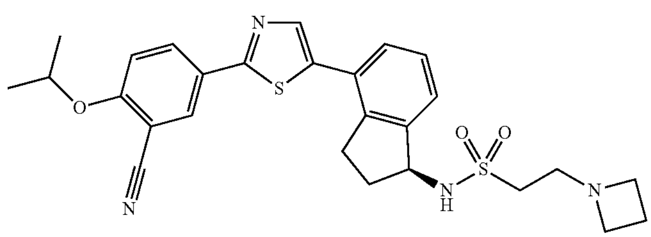 [SMILES: CC(C)Oc1ccc(-c2ncc(-c3cccc4c3CC[C@@H]4NS(=O)(=O)CCN3CCC3)s2)cc1C#N] | 127 | 7.04 |
| 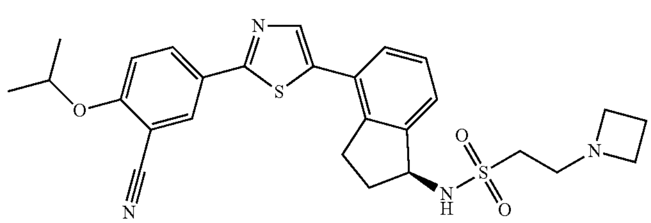 [SMILES: CC(C)Oc1ccc(-c2ncc(-c3cccc4c3CC[C@@H]4NS(=O)(=O)CCN3CCC3)s2)cc1C#N] | 128 | 6.90 |
| 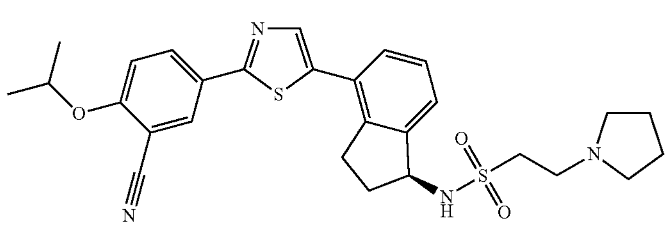 [SMILES: CC(C)Oc1ccc(-c2ncc(-c3cccc4c3CC[C@@H]4NS(=O)(=O)CCN3CCCC3)s2)cc1C#N] | 129 | 6.95 |

TABLE 1-continued

| STRUCTURE | COMPOUND NUMBER | LCMS RETENTION TIME (min) |
|---|---|---|
| 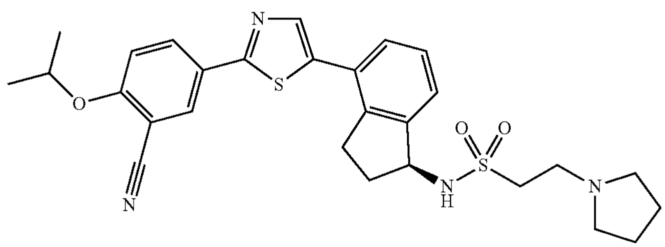 [SMILES: CC(C)Oc1ccc(-c2ncc(-c3cccc4c3CC[C@@H]4NS(=O)(=O)CCN3CCCC3)s2)cc1C#N] | 130 | 7.15 |
| 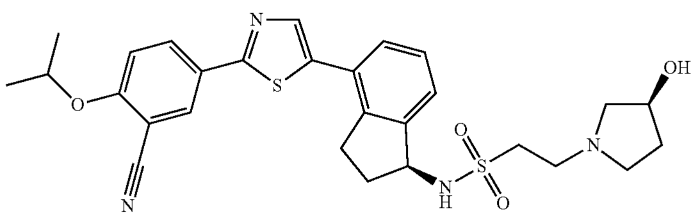 [SMILES: CC(C)Oc1ccc(-c2ncc(-c3cccc4c3CC[C@@H]4NS(=O)(=O)CCN3CC[C@H](O)C3)s2)cc1C#N] | 131 | 6.73 |
| 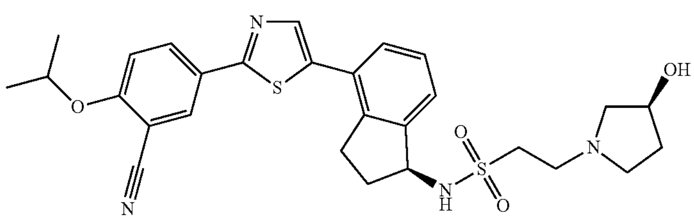 [SMILES: CC(C)Oc1ccc(-c2ncc(-c3cccc4c3CC[C@@H]4NS(=O)(=O)CCN3CC[C@H](O)C3)s2)cc1C#N] | 132 | 6.72 |
| 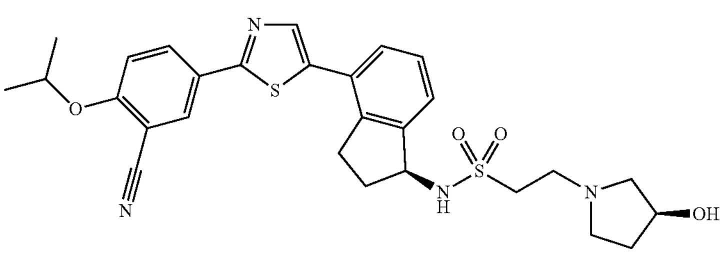 [SMILES: CC(C)Oc1ccc(-c2ncc(-c3cccc4c3CC[C@@H]4NS(=O)(=O)CCN3CC[C@H](O)C3)s2)cc1C#N] | 133 | 6.90 |
| 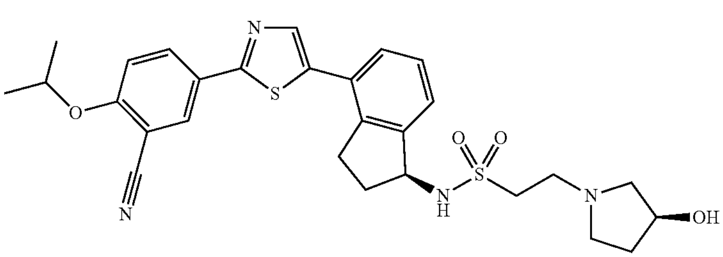 [SMILES: CC(C)Oc1ccc(-c2ncc(-c3cccc4c3CC[C@@H]4NS(=O)(=O)CCN3CC[C@H](O)C3)s2)cc1C#N] | 134 | 6.88 |
| 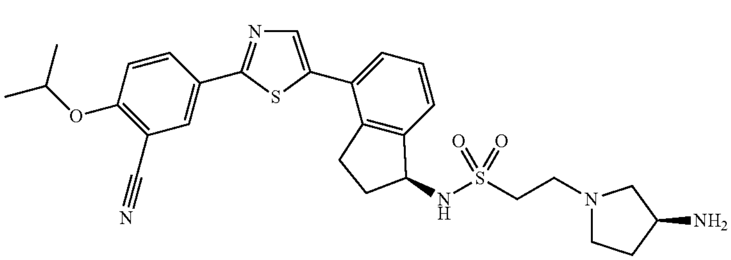 [SMILES: CC(C)Oc1ccc(-c2ncc(-c3cccc4c3CC[C@@H]4NS(=O)(=O)CCN3CC[C@H](N)C3)s2)cc1C#N] | 135 | 6.27 |

TABLE 1-continued
| STRUCTURE | COMPOUND NUMBER | LCMS RETENTION TIME (min) |
|---|---|---|
| 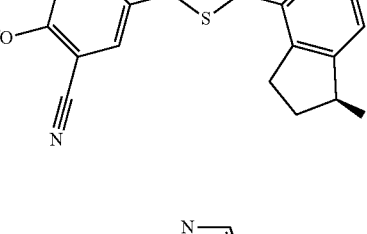 | 136 | 6.24 |
| 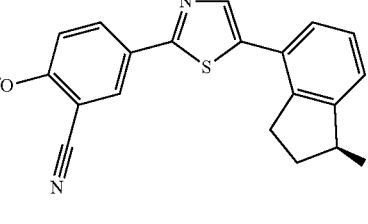 | 137 | 6.78 |
| 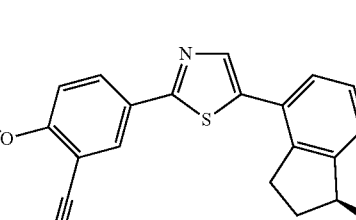 | 138 | 6.78 |
| 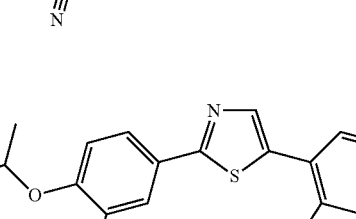 | 139 | 7.09 |
| 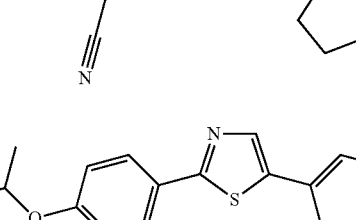 | 140 | 7.25 |
| 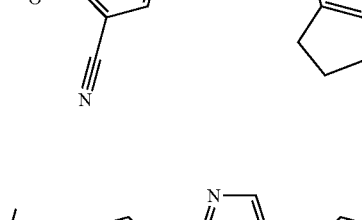 | 141 | 6.81 |

TABLE 1-continued

| STRUCTURE | COMPOUND NUMBER | LCMS RETENTION TIME (min) |
|---|---|---|
| 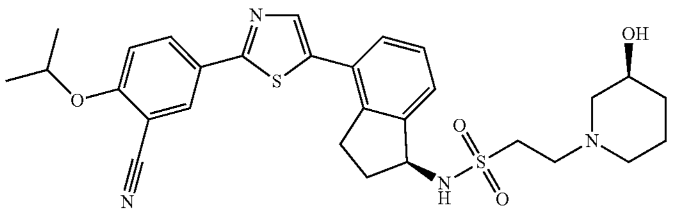 [SMILES: CC(C)Oc1ccc(-c2ncc(-c3cccc4c3CC[C@@H]4NS(=O)(=O)CCN3CCC[C@H](O)C3)s2)cc1C#N] | 142 | 6.84 |
| 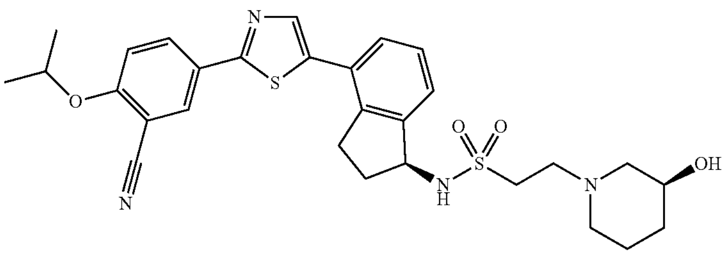 [SMILES: CC(C)Oc1ccc(-c2ncc(-c3cccc4c3CC[C@@H]4NS(=O)(=O)CCN3CCC[C@H](O)C3)s2)cc1C#N] | 143 | 6.93 |
| 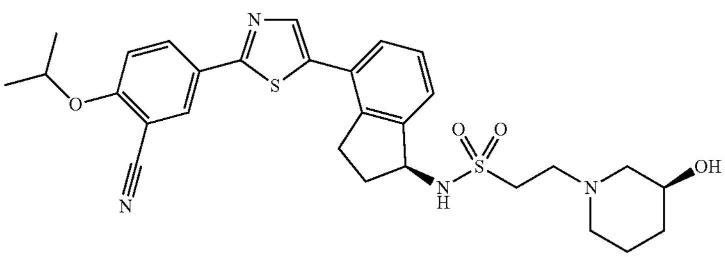 [SMILES: CC(C)Oc1ccc(-c2ncc(-c3cccc4c3CC[C@@H]4NS(=O)(=O)CCN3CCC[C@H](O)C3)s2)cc1C#N] | 144 | 6.95 |
| 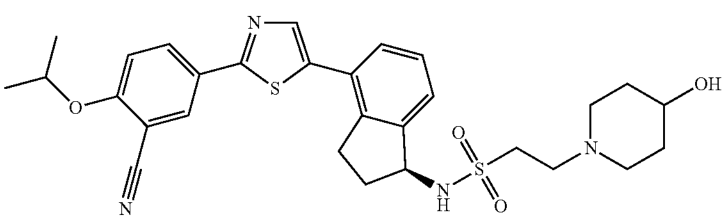 [SMILES: CC(C)Oc1ccc(-c2ncc(-c3cccc4c3CC[C@@H]4NS(=O)(=O)CCN3CCC(O)CC3)s2)cc1C#N] | 145 | 6.72 |
| 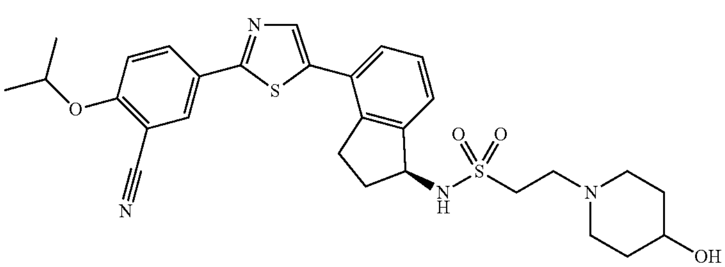 [SMILES: CC(C)Oc1ccc(-c2ncc(-c3cccc4c3CC[C@@H]4NS(=O)(=O)CCN3CCC(O)CC3)s2)cc1C#N] | 146 | 6.84 |
| 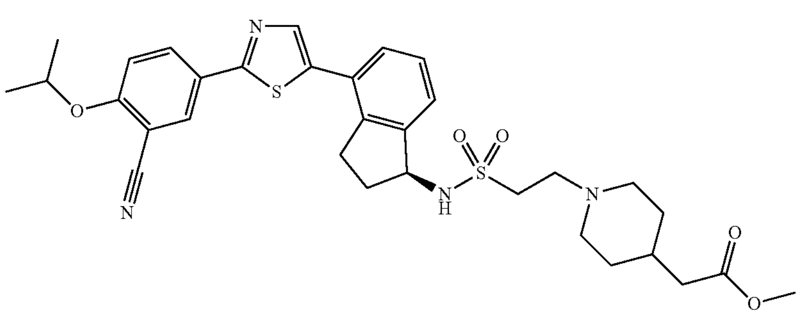 [SMILES: COC(=O)CC1CCN(CCS(=O)(=O)N[C@H]2CCc3c(-c4cnc(-c5ccc(OC(C)C)c(C#N)c5)s4)cccc32)CC1] | 147 | 7.38 |

TABLE 1-continued

| STRUCTURE | COMPOUND NUMBER | LCMS RETENTION TIME (min) |
|---|---|---|
| 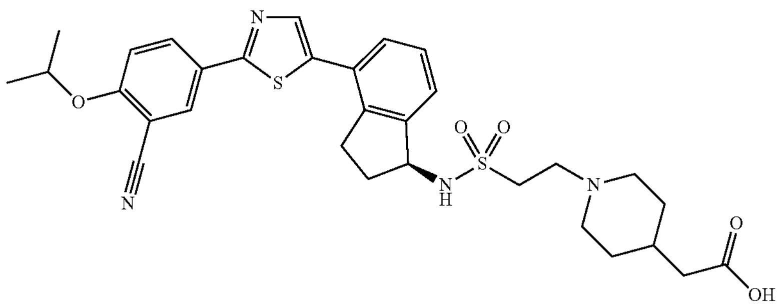 [SMILES: CC(C)Oc1ccc(-c2ncc(-c3cccc4c3CC[C@@H]4NS(=O)(=O)CCN3CCC(CC(=O)O)CC3)s2)cc1C#N] | 148 | 7.02 |
| 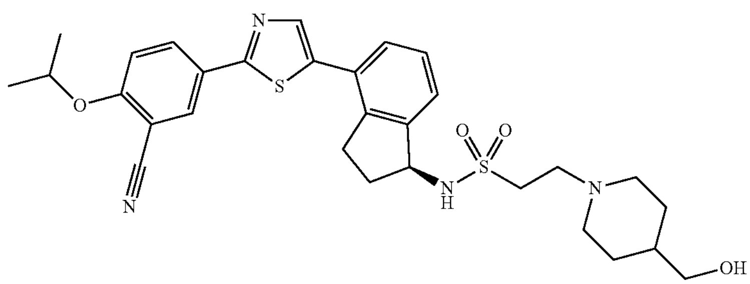 [SMILES: CC(C)Oc1ccc(-c2ncc(-c3cccc4c3CC[C@@H]4NS(=O)(=O)CCN3CCC(CO)CC3)s2)cc1C#N] | 149 | 6.90 |
| 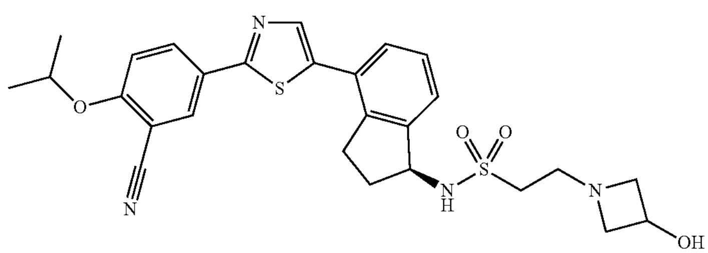 [SMILES: CC(C)Oc1ccc(-c2ncc(-c3cccc4c3CC[C@@H]4NS(=O)(=O)CCN3CC(O)C3)s2)cc1C#N] | 150 | 6.88 |
| 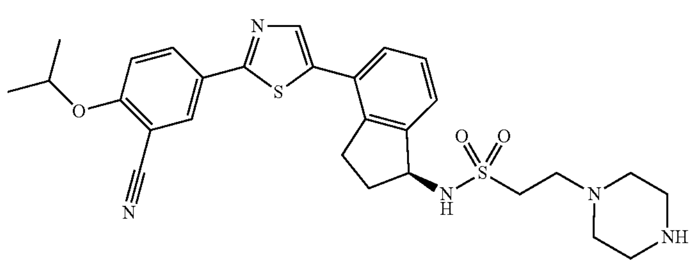 [SMILES: CC(C)Oc1ccc(-c2ncc(-c3cccc4c3CC[C@@H]4NS(=O)(=O)CCN3CCNCC3)s2)cc1C#N] | 151 | 6.83 |
| 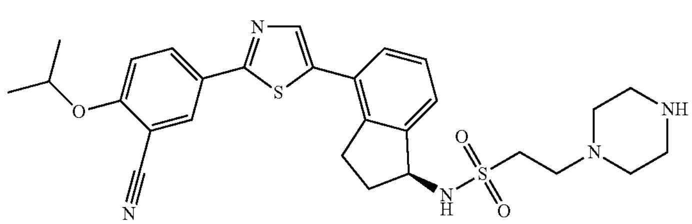 [SMILES: CC(C)Oc1ccc(-c2ncc(-c3cccc4c3CC[C@@H]4NS(=O)(=O)CCN3CCNCC3)s2)cc1C#N] | 152 | 6.75 |

TABLE 1-continued

| STRUCTURE | COMPOUND NUMBER | LCMS RETENTION TIME (min) |
|---|---|---|
| 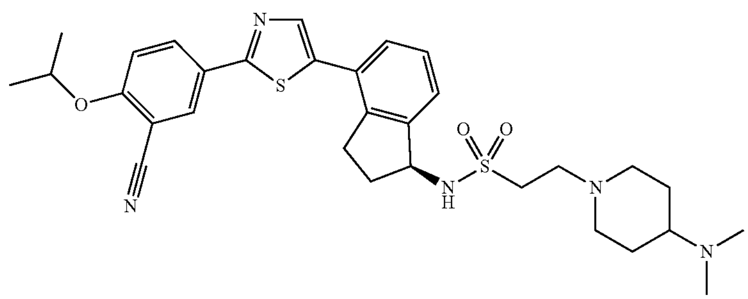 [SMILES: CC(C)Oc1ccc(-c2ncc(-c3cccc4c3CC[C@@H]4NS(=O)(=O)CCN3CCC(N(C)C)CC3)s2)cc1C#N] | 153 | 6.52 |
| 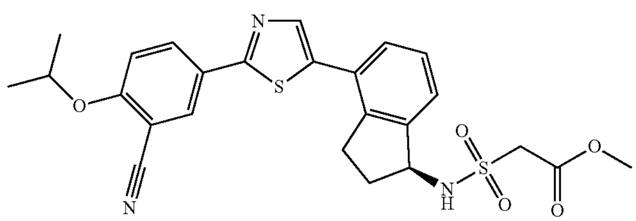 [SMILES: COC(=O)CS(=O)(=O)N[C@H]1CCc2c(-c3cnc(-c4ccc(OC(C)C)c(C#N)c4)s3)cccc21] | 154 | 9.50 |
| 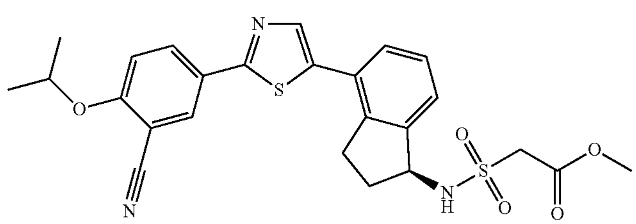 | 155 | 9.48 |
| 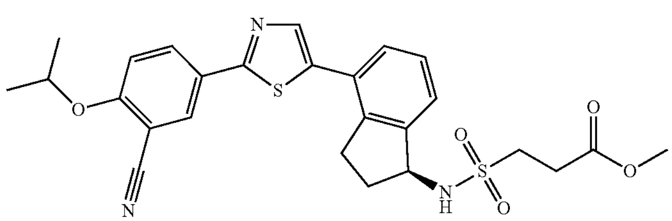 [SMILES: COC(=O)CCS(=O)(=O)N[C@H]1CCc2c(-c3cnc(-c4ccc(OC(C)C)c(C#N)c4)s3)cccc21] | 156 | 9.54 |
| 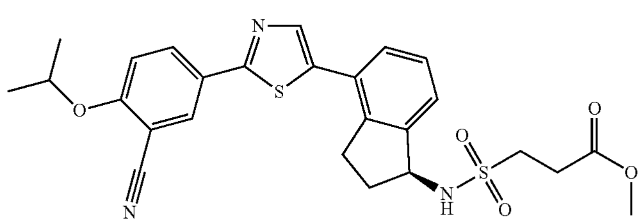 [SMILES: COC(=O)CCS(=O)(=O)N[C@H]1CCc2c(-c3cnc(-c4ccc(OC(C)C)c(C#N)c4)s3)cccc21] | 157 | 9.50 |
| 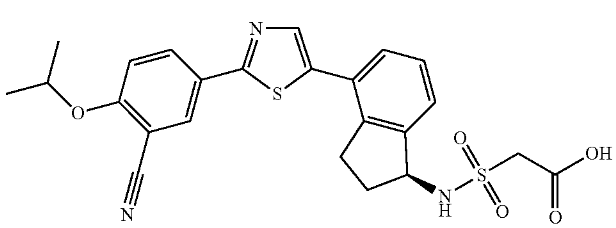 [SMILES: CC(C)Oc1ccc(-c2ncc(-c3cccc4c3CC[C@@H]4NS(=O)(=O)CC(=O)O)s2)cc1C#N] | 158 | 8.73 |

TABLE 1-continued

| STRUCTURE | COMPOUND NUMBER | LCMS RETENTION TIME (min) |
|---|---|---|
| 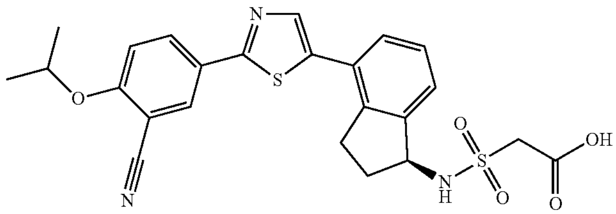 | 159 | 8.69 |
| 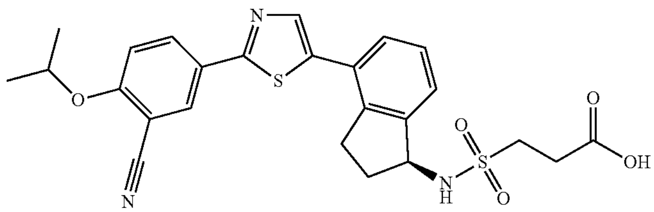 [SMILES: CC(C)Oc1ccc(-c2ncc(-c3cccc4c3CC[C@@H]4NS(=O)(=O)CCC(=O)O)s2)cc1C#N] | 160 | 8.71 |
| 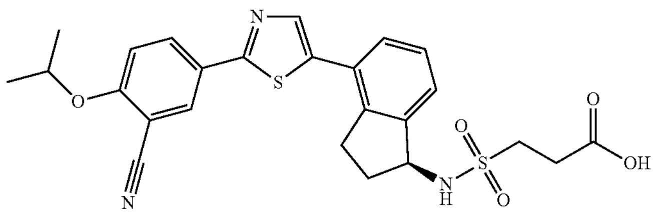 [SMILES: CC(C)Oc1ccc(-c2ncc(-c3cccc4c3CC[C@@H]4NS(=O)(=O)CCC(=O)O)s2)cc1C#N] | 161 | 8.74 |
| 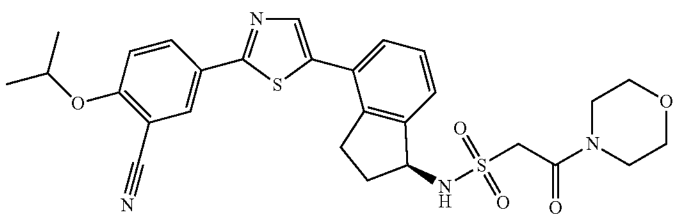 [SMILES: CC(C)Oc1ccc(-c2ncc(-c3cccc4c3CC[C@@H]4NS(=O)(=O)CC(=O)N3CCOCC3)s2)cc1C#N] | 162 | 8.89 |
| 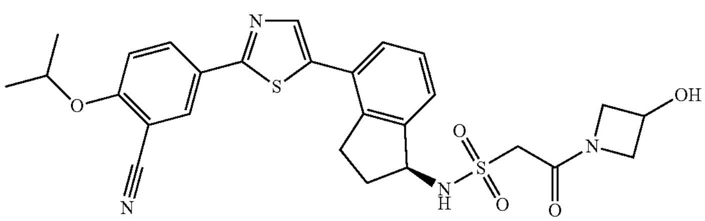 [SMILES: CC(C)Oc1ccc(-c2ncc(-c3cccc4c3CC[C@@H]4NS(=O)(=O)CC(=O)N3CC(O)C3)s2)cc1C#N] | 163 | 8.39 |
| 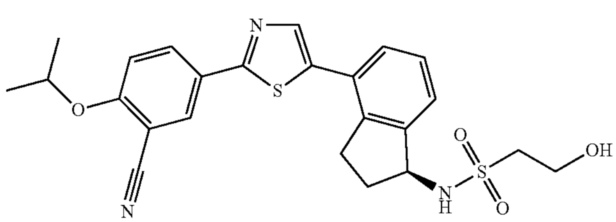 [SMILES: CC(C)Oc1ccc(-c2ncc(-c3cccc4c3CC[C@@H]4NS(=O)(=O)CCO)s2)cc1C#N] | 164 | 8.66 |
| 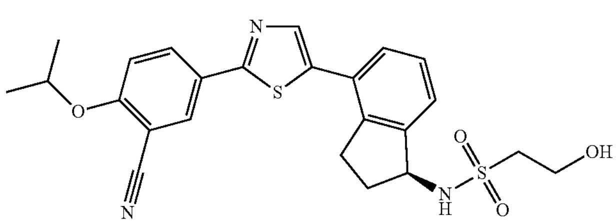 [SMILES: CC(C)Oc1ccc(-c2ncc(-c3cccc4c3CC[C@@H]4NS(=O)(=O)CCO)s2)cc1C#N] | 165 | 8.66 |

TABLE 1-continued

| STRUCTURE | COMPOUND NUMBER | LCMS RETENTION TIME (min) |
|---|---|---|
| 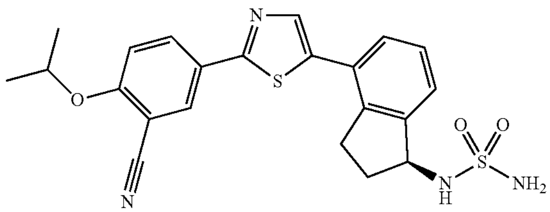 [SMILES: CC(C)Oc1ccc(-c2ncc(-c3cccc4c3CC[C@@H]4NS(N)(=O)=O)s2)cc1C#N] | 166 | 8.66 |
| 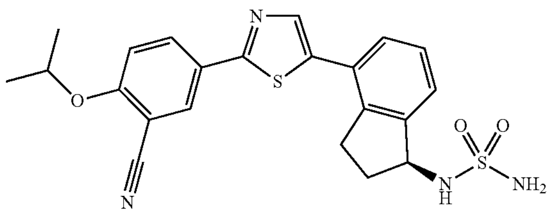 [SMILES: CC(C)Oc1ccc(-c2ncc(-c3cccc4c3CC[C@@H]4NS(N)(=O)=O)s2)cc1C#N] | 167 | 8.65 |
| 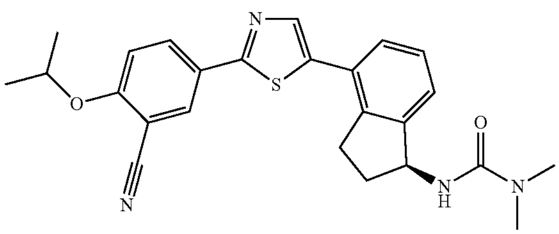 [SMILES: CC(C)Oc1ccc(-c2ncc(-c3cccc4c3CC[C@@H]4NC(=O)N(C)C)s2)cc1C#N] | 168 | 9.05 |
| 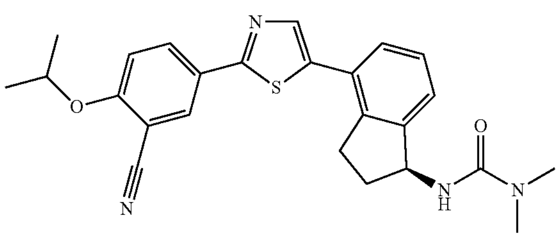 [SMILES: CC(C)Oc1ccc(-c2ncc(-c3cccc4c3CC[C@@H]4NC(=O)N(C)C)s2)cc1C#N] | 169 | 9.06 |
| 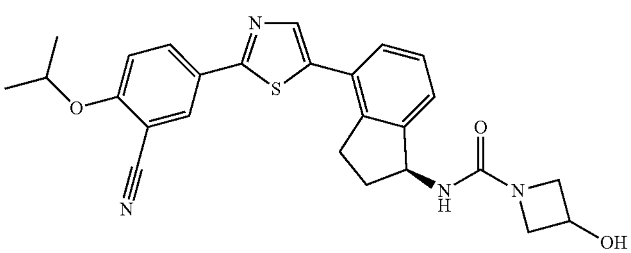 [SMILES: CC(C)Oc1ccc(-c2ncc(-c3cccc4c3CC[C@@H]4NC(=O)N3CC(O)C3)s2)cc1C#N] | 170 | 7.95 |
| 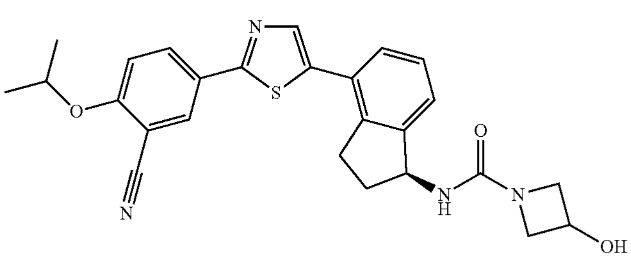 [SMILES: CC(C)Oc1ccc(-c2ncc(-c3cccc4c3CC[C@@H]4NC(=O)N3CC(O)C3)s2)cc1C#N] | 171 | 7.93 |

TABLE 1-continued

| STRUCTURE | COMPOUND NUMBER | LCMS RETENTION TIME (min) |
|---|---|---|
| 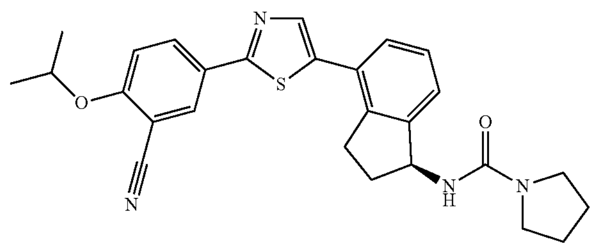 [SMILES: CC(C)Oc1ccc(-c2ncc(-c3cccc4c3CC[C@@H]4NC(=O)N3CCCC3)s2)cc1C#N] | 172 | 9.40 |
| 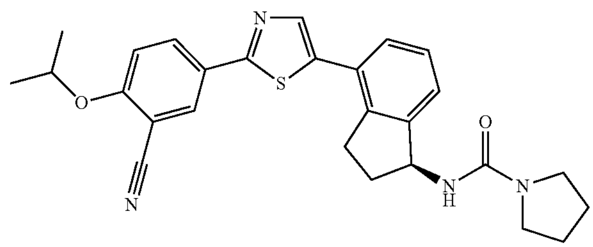 [SMILES: CC(C)Oc1ccc(-c2ncc(-c3cccc4c3CC[C@@H]4NC(=O)N3CCCC3)s2)cc1C#N] | 173 | 9.41 |
| 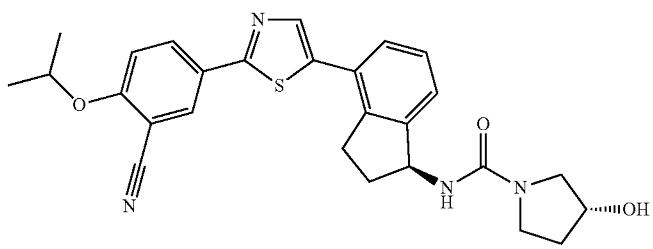 [SMILES: CC(C)Oc1ccc(-c2ncc(-c3cccc4c3CC[C@@H]4NC(=O)N3CC[C@@H](O)C3)s2)cc1C#N] | 174 | 8.01 |
| 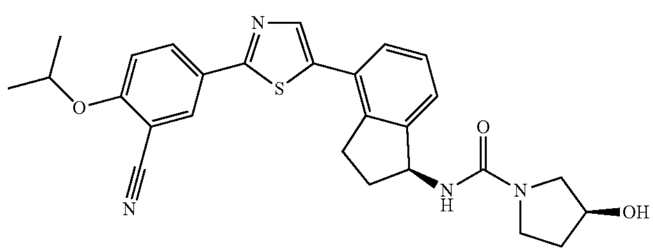 [SMILES: CC(C)Oc1ccc(-c2ncc(-c3cccc4c3CC[C@@H]4NC(=O)N3CC[C@H](O)C3)s2)cc1C#N] | 175 | 7.99 |
| 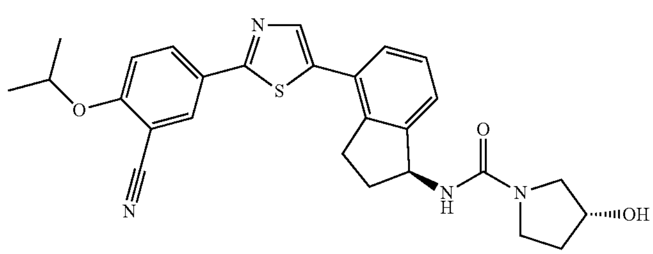 [SMILES: CC(C)Oc1ccc(-c2ncc(-c3cccc4c3CC[C@@H]4NC(=O)N3CC[C@@H](O)C3)s2)cc1C#N] | 176 | 8.02 |
| 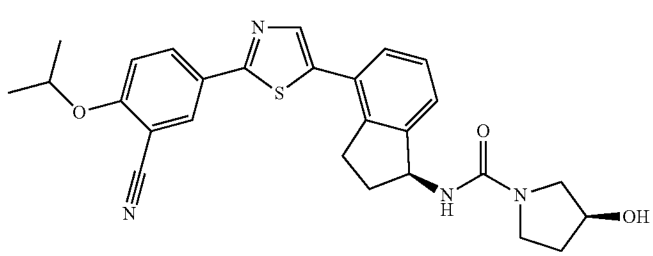 [SMILES: CC(C)Oc1ccc(-c2ncc(-c3cccc4c3CC[C@@H]4NC(=O)N3CC[C@H](O)C3)s2)cc1C#N] | 177 | 8.02 |

TABLE 1-continued
| STRUCTURE | COMPOUND NUMBER | LCMS RETENTION TIME (min) |
|---|---|---|
| 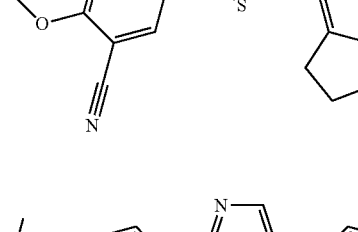 | 178 | 6.53 |
| 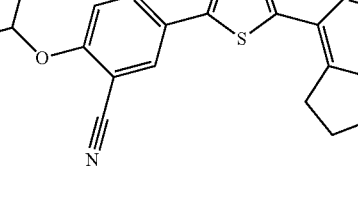 | 179 | 6.54 |
| 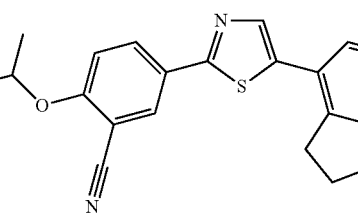 | 180 | 6.42 |
| 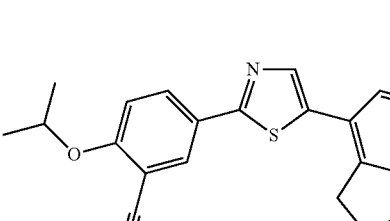 | 181 | 6.45 |
| 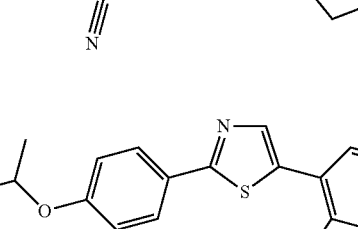 | 182 | 6.51 |
| 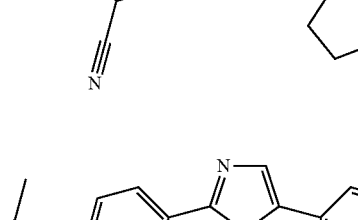 | 183 | 6.62 |

TABLE 1-continued

| STRUCTURE | COMPOUND NUMBER | LCMS RETENTION TIME (min) |
|---|---|---|
| 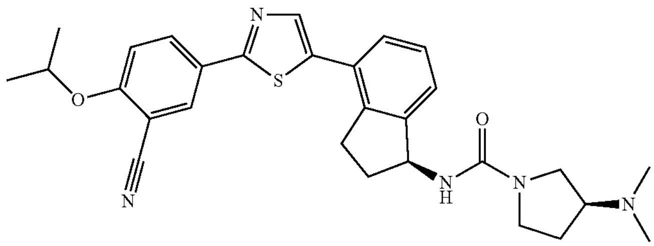 [SMILES: CC(C)Oc1ccc(-c2ncc(-c3cccc4c3CC[C@@H]4NC(=O)N3CC[C@H](N(C)C)C3)s2)cc1C#N] | 184 | 6.55 |
| 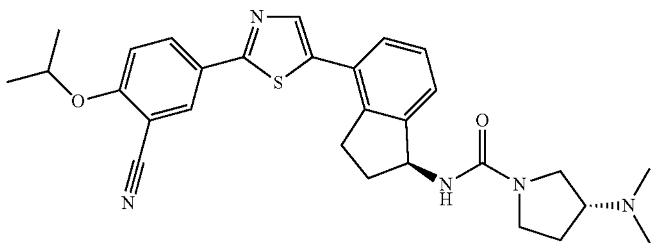 [SMILES: CC(C)Oc1ccc(-c2ncc(-c3cccc4c3CC[C@@H]4NC(=O)N3CC[C@@H](N(C)C)C3)s2)cc1C#N] | 185 | 6.57 |
| 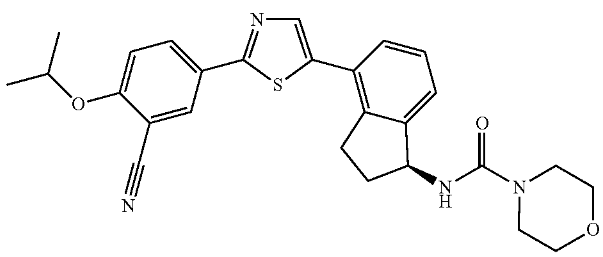 [SMILES: CC(C)Oc1ccc(-c2ncc(-c3cccc4c3CC[C@@H]4NC(=O)N3CCOCC3)s2)cc1C#N] | 186 | 8.87 |
| 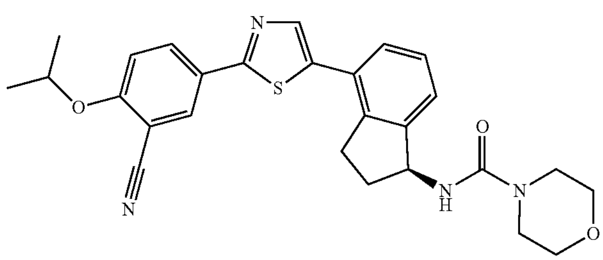 [SMILES: CC(C)Oc1ccc(-c2ncc(-c3cccc4c3CC[C@@H]4NC(=O)N3CCOCC3)s2)cc1C#N] | 187 | 8.87 |
| 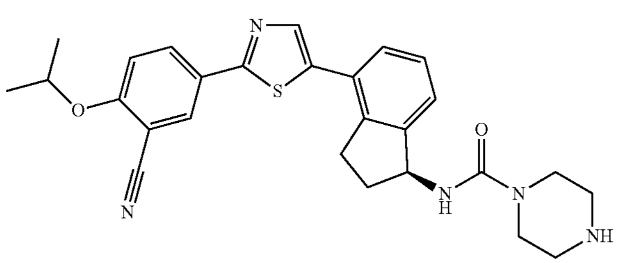 [SMILES: CC(C)Oc1ccc(-c2ncc(-c3cccc4c3CC[C@@H]4NC(=O)N3CCNCC3)s2)cc1C#N] | 188 | 6.42 |
| 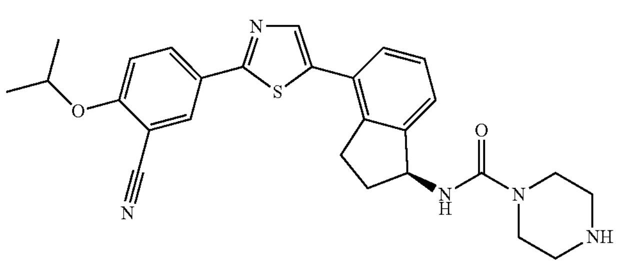 [SMILES: CC(C)Oc1ccc(-c2ncc(-c3cccc4c3CC[C@@H]4NC(=O)N3CCNCC3)s2)cc1C#N] | 189 | 6.39 |

TABLE 1-continued
| STRUCTURE | COMPOUND NUMBER | LCMS RETENTION TIME (min) |
|---|---|---|
| 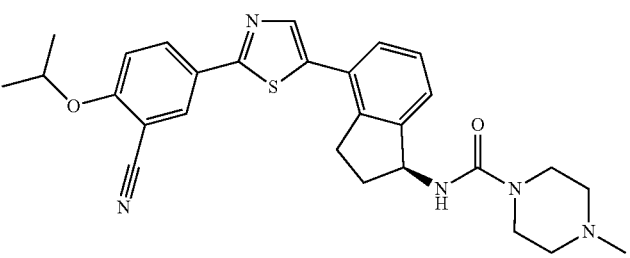 [SMILES: CC(C)Oc1ccc(-c2ncc(-c3cccc4c3CC[C@@H]4NC(=O)N3CCN(C)CC3)s2)cc1C#N] | 190 | 6.60 |
| 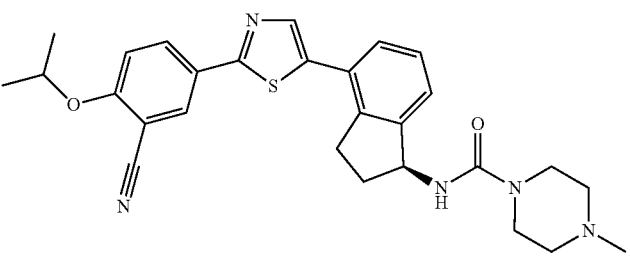 [SMILES: CC(C)Oc1ccc(-c2ncc(-c3cccc4c3CC[C@@H]4NC(=O)N3CCN(C)CC3)s2)cc1C#N] | 191 | 6.57 |
| 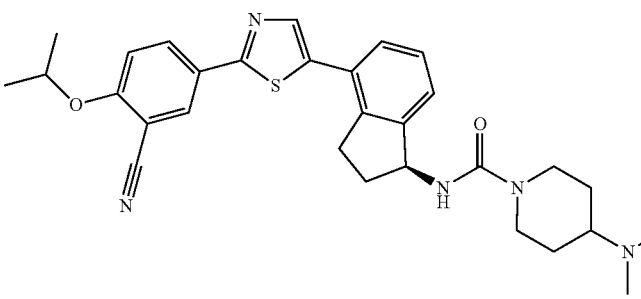 | 192 | 6.65 |
| 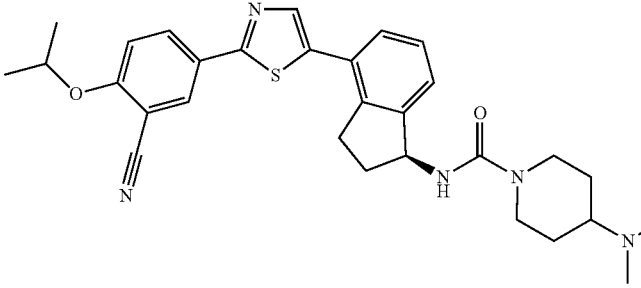 | 193 | 6.66 |
| 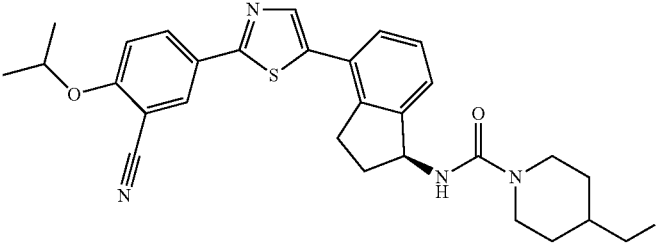 | 194 | 8.41 |

TABLE 1-continued

| STRUCTURE | COMPOUND NUMBER | LCMS RETENTION TIME (min) |
|---|---|---|
| 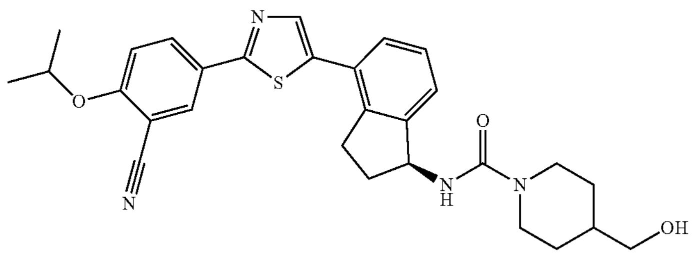 [SMILES: CC(C)Oc1ccc(-c2ncc(-c3cccc4c3CC[C@@H]4NC(=O)N3CCC(CO)CC3)s2)cc1C#N] | 195 | 8.41 |
| 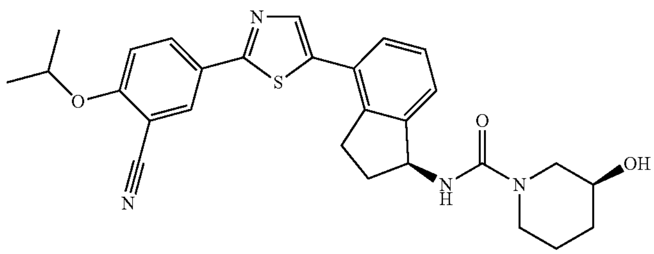 [SMILES: CC(C)Oc1ccc(-c2ncc(-c3cccc4c3CC[C@@H]4NC(=O)N3CCC[C@H](O)C3)s2)cc1C#N] | 196 | 8.39 |
| 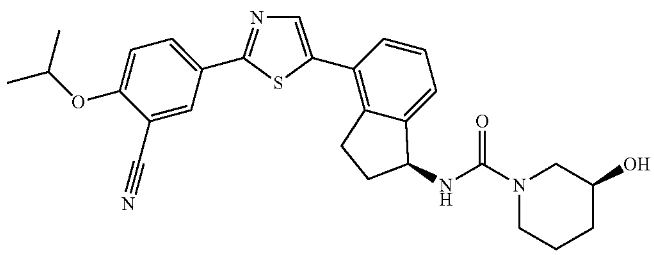 [SMILES: CC(C)Oc1ccc(-c2ncc(-c3cccc4c3CC[C@@H]4NC(=O)N3CCC[C@H](O)C3)s2)cc1C#N] | 197 | 8.42 |
| 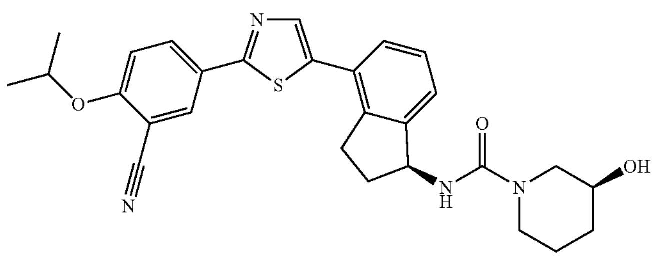 [SMILES: CC(C)Oc1ccc(-c2ncc(-c3cccc4c3CC[C@@H]4NC(=O)N3CCC[C@H](O)C3)s2)cc1C#N] | 198 | 8.45 |
| 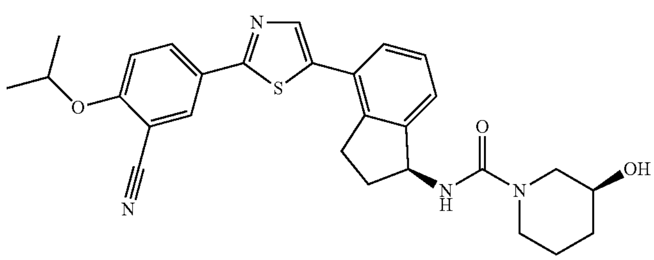 [SMILES: CC(C)Oc1ccc(-c2ncc(-c3cccc4c3CC[C@@H]4NC(=O)N3CCC[C@H](O)C3)s2)cc1C#N] | 199 | 8.43 |
| 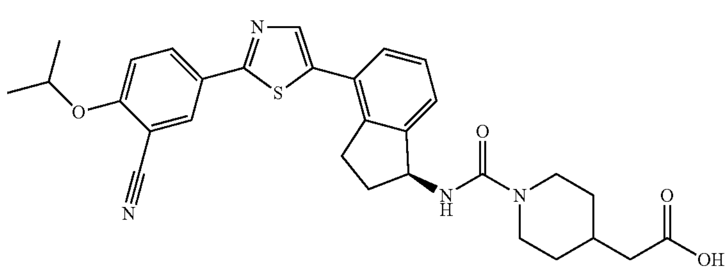 [SMILES: CC(C)Oc1ccc(-c2ncc(-c3cccc4c3CC[C@@H]4NC(=O)N3CCC(CC(=O)O)CC3)s2)cc1C#N] | 200 | 8.59 |

TABLE 1-continued
| STRUCTURE | COMPOUND NUMBER | LCMS RETENTION TIME (min) |
|---|---|---|
| 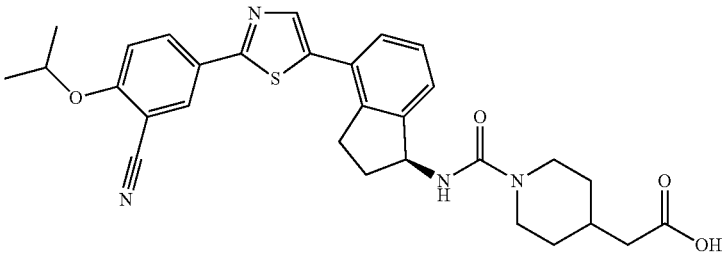 [SMILES: CC(C)Oc1ccc(-c2ncc(-c3cccc4c3CC[C@@H]4NC(=O)N3CCC(CC(=O)O)CC3)s2)cc1C#N] | 201 | 8.61 |
| 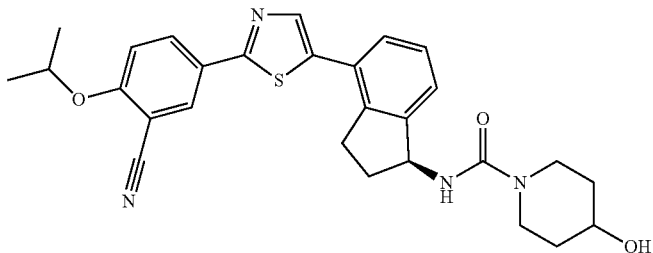 [SMILES: CC(C)Oc1ccc(-c2ncc(-c3cccc4c3CC[C@@H]4NC(=O)N3CCC(O)CC3)s2)cc1C#N] | 202 | 8.17 |
| 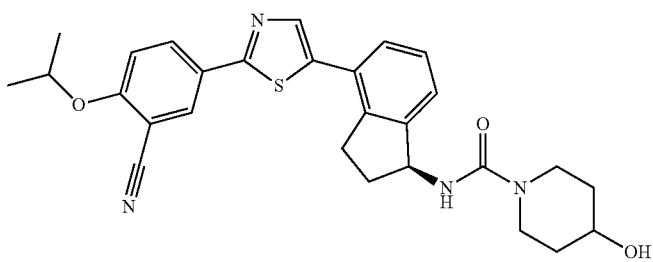 [SMILES: CC(C)Oc1ccc(-c2ncc(-c3cccc4c3CC[C@@H]4NC(=O)N3CCC(O)CC3)s2)cc1C#N] | 203 | 8.15 |
| 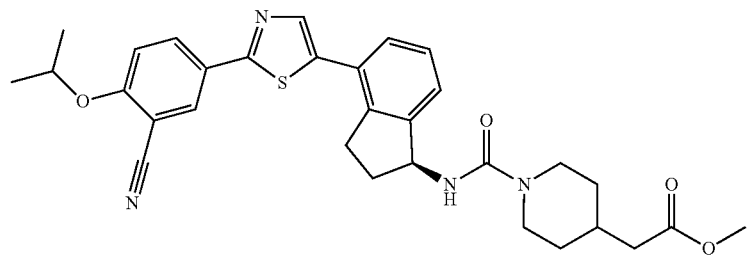 [SMILES: COC(=O)CC1CCN(C(=O)N[C@H]2CCc3c(-c4cnc(-c5ccc(OC(C)C)c(C#N)c5)s4)cccc32)CC1] | 204 | 9.61 |
| 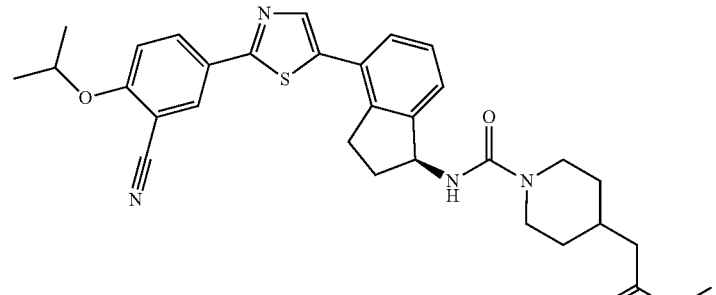 | 205 | 9.62 |

TABLE 1-continued

| STRUCTURE | COMPOUND NUMBER | LCMS RETENTION TIME (min) |
|---|---|---|
| 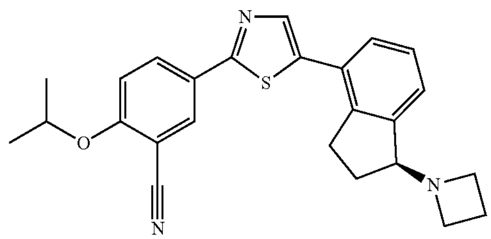 [SMILES: CC(C)Oc1ccc(-c2ncc(-c3cccc4c3CC[C@@H]4N3CCC3)s2)cc1C#N] | 206 | 6.80 |
| 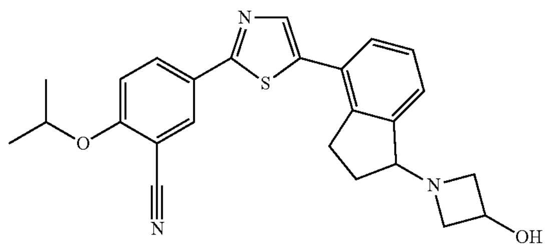 [SMILES: CC(C)Oc1ccc(-c2ncc(-c3cccc4c3CCC4N3CC(O)C3)s2)cc1C#N] | 207 | 6.47 |
| 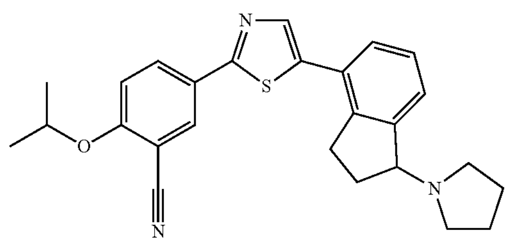 [SMILES: CC(C)Oc1ccc(-c2ncc(-c3cccc4c3CCC4N3CCCC3)s2)cc1C#N] | 208 | 6.93 |
| 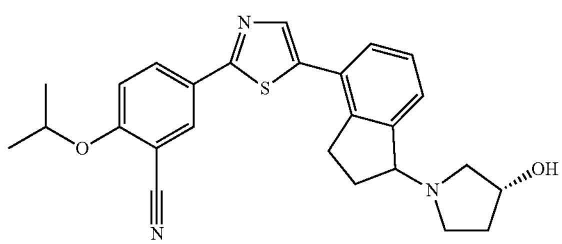 [SMILES: CC(C)Oc1ccc(-c2ncc(-c3cccc4c3CCC4N3CC[C@@H](O)C3)s2)cc1C#N] | 209 | 6.53 |
| 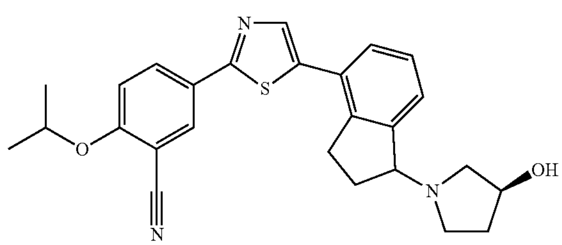 [SMILES: CC(C)Oc1ccc(-c2ncc(-c3cccc4c3CCC4N3CC[C@H](O)C3)s2)cc1C#N] | 210 | 6.57 |
| 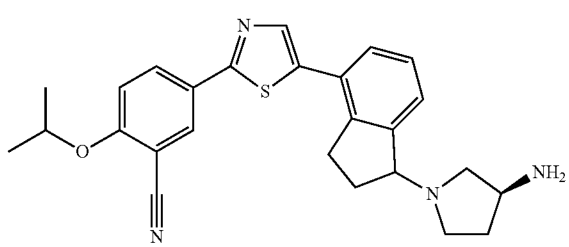 [SMILES: CC(C)Oc1ccc(-c2ncc(-c3cccc4c3CCC4N3CC[C@H](N)C3)s2)cc1C#N] | 211 | 5.76 |

TABLE 1-continued

| STRUCTURE | COMPOUND NUMBER | LCMS RETENTION TIME (min) |
| --- | --- | --- |
| 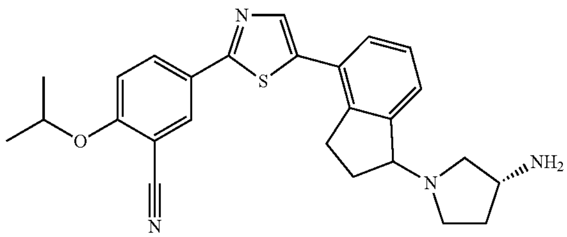 [SMILES: CC(C)Oc1ccc(-c2ncc(-c3cccc4c3CCC4N3CC[C@@H](N)C3)s2)cc1C#N] | 212 | 5.82 |
| 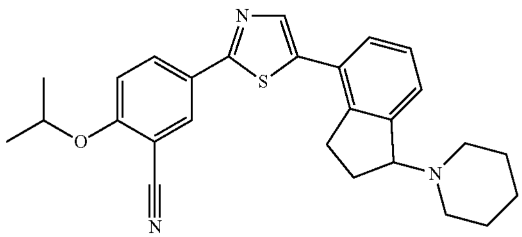 [SMILES: CC(C)Oc1ccc(-c2ncc(-c3cccc4c3CCC4N3CCCCC3)s2)cc1C#N] | 213 | 6.96 |
| 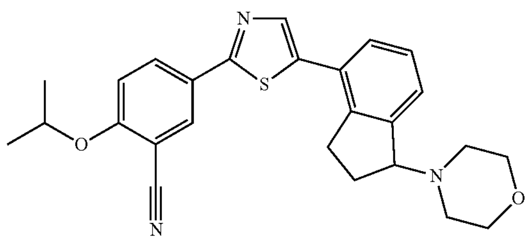 [SMILES: CC(C)Oc1ccc(-c2ncc(-c3cccc4c3CCC4N3CCOCC3)s2)cc1C#N] | 214 | 6.62 |
| 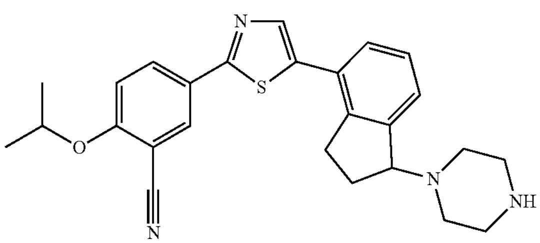 [SMILES: CC(C)Oc1ccc(-c2ncc(-c3cccc4c3CCC4N3CCNCC3)s2)cc1C#N] | 215 | 7.45 |
| 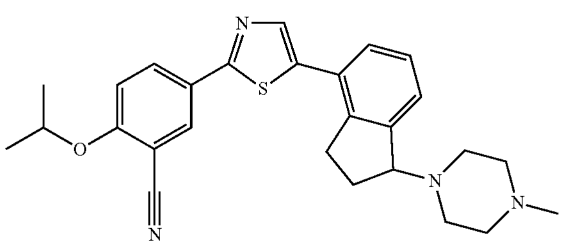 [SMILES: CC(C)Oc1ccc(-c2ncc(-c3cccc4c3CCC4N3CCN(C)CC3)s2)cc1C#N] | 216 | 6.78 |
| 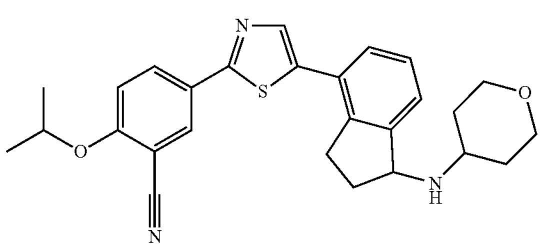 [SMILES: CC(C)Oc1ccc(-c2ncc(-c3cccc4c3CCC4NC3CCOCC3)s2)cc1C#N] | 217 | 6.65 |

TABLE 1-continued

| STRUCTURE | COMPOUND NUMBER | LCMS RETENTION TIME (min) |
|---|---|---|
| 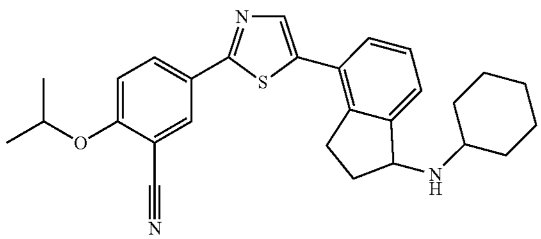 [SMILES: CC(C)Oc1ccc(-c2ncc(-c3cccc4c3CCC4NC3CCCCC3)s2)cc1C#N] | 218 | 7.45 |
| 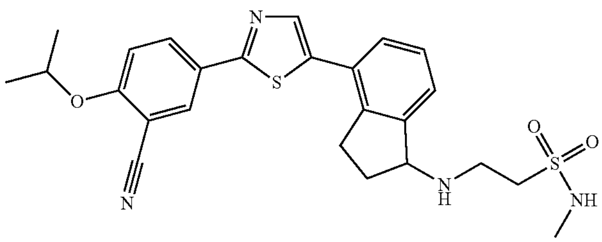 [SMILES: CNS(=O)(=O)CCNC1CCc2c(-c3cnc(-c4ccc(OC(C)C)c(C#N)c4)s3)cccc21] | 219 | 6.67 |
| 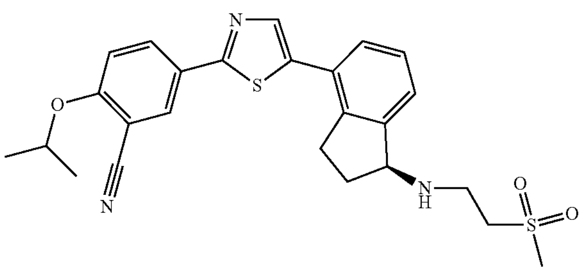 [SMILES: CC(C)Oc1ccc(-c2ncc(-c3cccc4c3CC[C@@H]4NCCS(C)(=O)=O)s2)cc1C#N] | 220 | 6.65 |
| 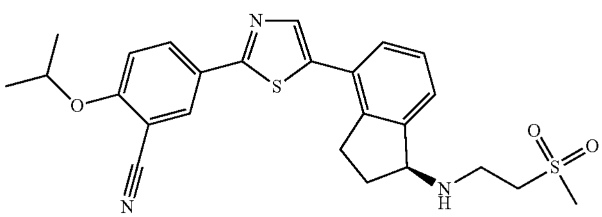 [SMILES: CC(C)Oc1ccc(-c2ncc(-c3cccc4c3CC[C@@H]4NCCS(C)(=O)=O)s2)cc1C#N] | 221 | 6.58 |
| 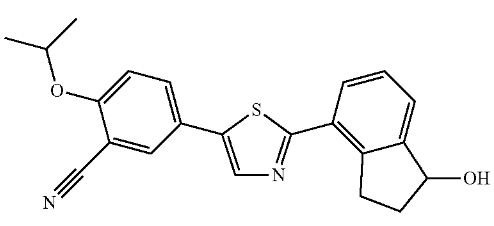 [SMILES: CC(C)Oc1ccc(-c2cnc(-c3cccc4c3CCC4O)s2)cc1C#N] | 222 | 8.16 |
| 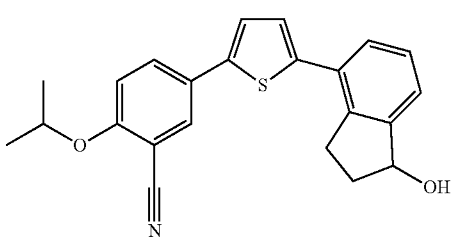 [SMILES: CC(C)Oc1ccc(-c2ccc(-c3cccc4c3CCC4O)s2)cc1C#N] | 223 | 9.88 |

TABLE 1-continued

| STRUCTURE | COMPOUND NUMBER | LCMS RETENTION TIME (min) |
|---|---|---|
| 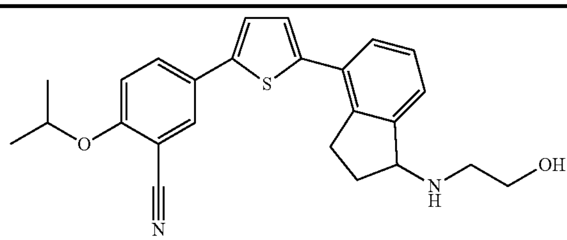 | 224 | 6.88 |
| 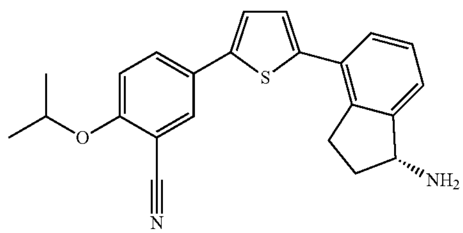 [SMILES: CC(C)Oc1ccc(-c2ccc(-c3cccc4c3CC[C@H]4N)s2)cc1C#N] | 225 | 6.83 |
| 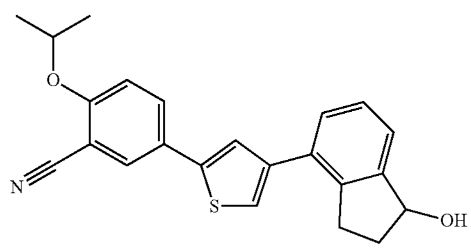 [SMILES: CC(C)Oc1ccc(-c2cc(-c3cccc4c3CCC4O)cs2)cc1C#N] | 226 | 9.68 |
| 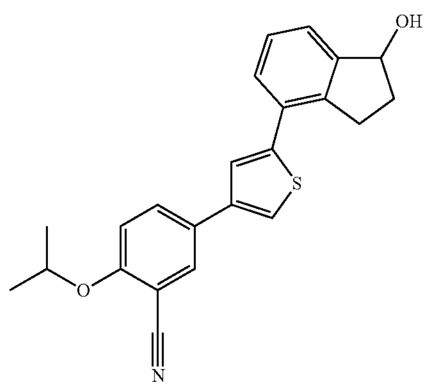 [SMILES: CC(C)Oc1ccc(-c2csc(-c3cccc4c3CCC4O)c2)cc1C#N] | 227 | 9.68 |

Biological Assays

Assay Procedures

Generation of $S1P_1$-mediated Inhibition of cAMP Reporter Assay

A mammalian expression plasmid containing $S1P_1$/EDG1 cloned into pcDNA3.1 was purchased from Missouri S&T cDNA Resource Centre. The nucleotide and amino acid sequence of human $S1P_1$/EDG1 are published in Hla and Maciag (J Biol Chem, 265(1990), 9308-9313). $S1P_1$/pcDNA3.1 was transfected into the CRE-bla CHO K1 (Invitrogen) cell line, and stable single cell clones were selected using standard techniques. Expression of functional $S1P_1$/EDG1 receptor was confirmed by cell surface FACS with a $S1P_1$ antibody (R&D Systems, clone 218713) and S1P-mediated inhibition of Forskolin induced cAMP.

$S1P_1$ CRE-bla CHOK1 Reporter Assay—Characterization of $S1P_1$ Agonists

Cells were seeded into 384-well black wall/clear bottom plates at $10^4$ cells/well/19.5 μl assay media (DMEM-phenol free, 0.5% charcoal/dextran stripped serum, 2 mM glutamine, 0.1 mM NEAA, 1 mM Na-Pyruvate, 25 mM Hepes) and incubated for 18 hrs at 37° C. in 5% $CO_2$. Dose response curves (10-point) were generated in 10 mM Hepes, 0.1% Pluronic F127, in the presence of Forskolin. Cells were treated with 0.5 μl compound in the presence of 2 μM Forskolin for 4 hrs at 37° C. The FRET-based β-lactamase fluorescent substrate (LiveBLAzer™ FRET B/G Loading Kit CC4-AM; Invitrogen) was prepared according to manufacturer's directions, and incubated with cells for 2 hrs at room temperature. Plates were read at Ex:410/Em:458 and Ex:410/Em:522, and the response ratio determined. Data was analyzed by non-linear regression to determine the EC50 for inhibition of Forskolin induced cAMP.

Specificity Over Other S1P Receptors

To assess compound specificity on other S1P receptors the following cell lines were used: $S1P_2$ CRE-bla CHOK1, $S1P_3$-G$\alpha$15 NFAT-bla HEK293T (Invitrogen), $S1P_4$-bla TANGO U2OS (Invitrogen), $S1P_5$-bla TANGO U2OS (Invitrogen). The same assay set up for $S1P_1$ was used but without Forskolin. $S1P_4$ and $S1P_5$ assays were performed in FreeStyle Expression medium (Invitrogen). $S1P_5$ cells were incubated for 48 hrs in prior to treatment with compound.

Reported $S1P_1$ Activity

Activity data for selected $S1P_1$ agonists is displayed in Table 2. The activity range is denoted as follows: ++++ denotes agonist activity <0.05 nM. +++ denotes agonist activity between 0.05 to 0.50 nM, and ++ denotes agonist activity between 0.50-5.00 nM, and + denotes agonist activity >5.00 nM. N/A denotes not available.

TABLE 2

| COMPOUND NUMBER | $S1P_1$ ACTIVITY |
|---|---|
| 1 | +++ |
| 2 | +++ |
| 3 | ++ |
| 4 | ++ |
| 5 | ++ |
| 6 | ++ |
| 7 | ++++ |
| 8 | +++ |
| 9 | +++ |
| 10 | +++ |
| 11 | +++ |
| 12 | ++ |
| 13 | ++ |
| 14 | +++ |
| 15 | +++ |
| 16 | ++ |
| 17 | +++ |
| 18 | ++ |
| 19 | ++ |
| 20 | ++ |
| 21 | ++ |
| 22 | +++ |
| 23 | ++ |
| 24 | ++ |
| 25 | +++ |
| 26 | +++ |
| 27 | +++ |
| 28 | +++ |
| 29 | +++ |
| 30 | ++ |
| 31 | +++ |
| 32 | ++++ |
| 33 | +++ |
| 34 | +++ |
| 35 | +++ |
| 36 | +++ |
| 37 | ++ |
| 38 | ++ |
| 39 | +++ |
| 40 | +++ |
| 41 | ++++ |
| 42 | +++ |
| 43 | +++ |
| 44 | ++++ |
| 45 | +++ |
| 46 | +++ |
| 47 | ++++ |
| 48 | ++++ |
| 49 | ++ |
| 50 | +++ |
| 51 | +++ |
| 52 | +++ |
| 53 | ++ |
| 54 | +++ |
| 55 | ++ |
| 56 | +++ |
| 57 | ++ |
| 58 | +++ |
| 59 | ++ |
| 60 | ++ |
| 61 | +++ |
| 62 | ++ |
| 63 | ++ |
| 64 | ++ |
| 65 | +++ |
| 66 | +++ |
| 67 | ++ |
| 68 | +++ |
| 69 | +++ |
| 70 | ++ |
| 71 | ++ |
| 72 | ++ |
| 73 | +++ |
| 74 | +++ |
| 75 | +++ |
| 76 | ++ |
| 77 | +++ |
| 78 | ++ |
| 79 | +++ |
| 80 | +++ |
| 81 | ++ |
| 82 | ++ |
| 83 | + |
| 84 | + |
| 85 | + |
| 86 | + |
| 87 | +++ |
| 88 | ++ |
| 89 | ++ |
| 90 | ++ |
| 91 | ++ |
| 92 | ++ |
| 93 | ++ |
| 94 | ++ |
| 95 | ++ |
| 96 | +++ |
| 97 | +++ |
| 98 | ++ |
| 99 | ++ |
| 100 | +++ |
| 101 | + |
| 102 | +++ |
| 103 | +++ |
| 104 | ++ |
| 105 | + |
| 106 | + |
| 107 | ++ |
| 108 | + |
| 109 | ++ |
| 110 | ++ |
| 111 | +++ |
| 112 | +++ |
| 113 | +++ |
| 114 | +++ |
| 115 | +++ |
| 116 | ++ |
| 117 | +++ |
| 118 | +++ |
| 119 | +++ |
| 120 | ++ |
| 121 | ++ |
| 122 | ++ |
| 123 | ++ |
| 124 | ++ |
| 125 | ++ |
| 126 | ++ |
| 127 | ++ |
| 128 | + |
| 129 | + |
| 130 | ++ |

TABLE 2-continued

| COMPOUND NUMBER | S1P$_1$ ACTIVITY |
|---|---|
| 131 | ++ |
| 132 | ++ |
| 133 | ++ |
| 134 | ++ |
| 135 | + |
| 136 | + |
| 137 | + |
| 138 | + |
| 139 | + |
| 140 | + |
| 141 | ++ |
| 142 | ++ |
| 143 | ++ |
| 144 | ++ |
| 145 | + |
| 146 | ++ |
| 147 | ++ |
| 148 | ++ |
| 149 | ++ |
| 150 | ++ |
| 151 | + |
| 152 | + |
| 153 | + |
| 154 | +++ |
| 155 | ++ |
| 156 | +++ |
| 157 | +++ |
| 158 | ++++ |
| 159 | +++ |
| 160 | ++++ |
| 161 | +++ |
| 162 | +++ |
| 163 | +++ |
| 164 | +++ |
| 165 | ++ |
| 166 | +++ |
| 167 | +++ |
| 168 | +++ |
| 169 | ++ |
| 170 | ++ |
| 171 | +++ |
| 172 | +++ |
| 173 | ++ |
| 174 | +++ |
| 175 | ++ |
| 176 | ++ |
| 177 | +++ |
| 178 | +++ |
| 179 | ++ |
| 180 | + |
| 181 | + |
| 182 | ++ |
| 183 | ++ |
| 184 | + |
| 185 | + |
| 186 | +++ |
| 187 | ++ |
| 188 | ++ |
| 189 | + |
| 190 | ++ |
| 191 | + |
| 192 | + |
| 193 | + |
| 194 | ++ |
| 195 | ++ |
| 196 | ++ |
| 197 | ++ |
| 198 | +++ |
| 199 | +++ |
| 200 | +++ |
| 201 | +++ |
| 202 | ++ |
| 203 | ++ |
| 204 | ++ |
| 205 | ++ |
| 206 | +++ |
| 207 | ++ |
| 208 | ++ |
| 209 | ++ |
| 210 | ++ |
| 211 | ++ |
| 212 | + |
| 213 | ++ |
| 214 | ++ |
| 215 | ++ |
| 216 | ++ |
| 217 | + |
| 218 | + |
| 219 | +++ |
| 220 | +++ |
| 221 | +++ |
| 222 | + |
| 223 | ++ |
| 224 | + |
| 225 | + |
| 226 | ++ |
| 227 | + |

S1P$_1$-S1P$_5$ data for specific compounds is presented in Table 3. The agonist values (EC$_{50}$) are reported in nM.

TABLE 3

| COMPOUND NUMBER | S1P$_1$ | S1P$_2$ | S1P$_3$ | S1P$_4$ | S1P$_5$ |
|---|---|---|---|---|---|
| 43 | 0.07 | >10000 | >10000 | >10000 | 444 |
| 46 | 0.25 | >10000 | >10000 | 2171 | 194 |
| 47 | 0.03 | >10000 | >10000 | >10000 | 22 |
| 56 | 0.32 | >10000 | >10000 | >10000 | 139 |
| 58 | 0.29 | >10000 | >10000 | >10000 | 47 |
| 166 | 0.14 | 8448 | >10000 | 743 | 64 |
| 172 | 0.19 | >10000 | >10000 | >10000 | 203 |
| 186 | 0.41 | >10000 | >10000 | >10000 | 126 |

In Vivo Assays

Determination of Absolute Oral Bioavailability in Rats.

All pharmacokinetic studies were conducted in non-fasted female Sprague-Dawely rats (Simonsen Laboratories or Harlan Laboratories). Rats were housed in an ALAAC accredited facility and the research was approved by the facilities Institutional Animal Care and Use Committee (IACUC). The animals were acclimated to the laboratory for at least 48 h prior to initiation of experiments.

Compounds were formulated in 5% DMSO/5% Tween20 and 90% purified water (intravenous infusion) or 5% DMSO/5% Tween20 and 90% 0.1N HCL (oral gavage). Depending upon the solubility properties of the compound, alternate oral formulations were used (e.g. 0.5% carboxymethylcellulose). The concentration of the dosing solutions was verified by HPLC-UV. For intravenous dosing, compounds were administered by an infusion pump into the jugular vein over one minute to manually restrained animals (n=4 rats/compound). Oral dosing was by gavage using a standard stainless steel gavage needle (n=2-4 rats/compound). For both routes of administration, blood was collected at eight time-points after dosing with the final sample drawn 24 h post dose. Aliquots of the blood and/or plasma samples were transferred to polypropylene 96-well plate and frozen at −20° C. until analysis.

After thawing the blood and/or plasma samples at room temperature, 5 μL of DMSO was added to each well. Proteins were precipitated by adding 150 μL acetonitrile containing 200 nM internal standard (4-hydroxy-3-(alpha-iminobenzyl)-1-methyl-6-phenylpyridin-2-(1H)-one) and 0.1% formic acid. Plates were mixed for 1 min on a plate shaker to facilitate protein precipitation and then centrifuged at 3,000 rpm for 10 min to pellet protein. The supernatant was transferred to a clean plate and centrifuged at 3,000 rpm for 10 min to pellet any remaining solid material prior to LC/MS/MS analysis. Calibration curve standards were prepared by spiking 5 µL compound stock in DMSO into freshly collected EDTA rat blood. An eight point standard curve spanning a range of 5 nM to 10,000 nM was included with each bioanalytical run. The standards were processed identically to the rat pharmacokinetic samples.

Concentrations in the rat pharmacokinetic samples were determined using a standardized HPLC-LC/MS/MS method relative to the eight point standard curve. The system consisted of a Leap CTC Pal injector, Agilent 1200 HPLC with binary pump coupled with an Applied Biosystems 3200 QTrap. Compounds were chromatographed on a Phenomenex Synergy Fusion RP 20×2 mm 2 um Mercury Cartridge with Security Guard. A gradient method was used with mobile phase A consisting of 0.1% formic acid in water and mobile phase B consisting of 0.1% formic acid in acetonitrile at flow rates varying from 0.7 to 0.8 mL/min. Ions were generated in positive ionization mode using an electrospray ionization (ESI) interface. Multiple reaction monitoring (MRM) methods were developed specific to each compound. The heated nebulizer was set at 325° C. with a nebulizer current of 4.8 µA. Collision energies used to generate daughter ions ranged between 29 and 39 V. Peak area ratios obtained from MRM of the mass transitions specific for each compound were used for quantification. The limit of quantification of the method was typically 5 nM. Data were collected and analyzed using Analyst software version 1.4.2.

Blood and/or plasma concentration versus time data were analyzed using non-compartmental methods (WinNonlin version 5.2; model 200 for oral dosing and model 202 for intravenous infusion). Absolute oral bioavailability (%) was calculated using the following expression: (Oral AUC×IV Dose)/(IV AUC×Oral Dose)×100.

Lymphopenia

In mice: Female C57BL6 mice (Simonsen Laboratories, Gilroy Calif.) were housed in an ALAAC accredited facility and the research was approved by the facilities Institutional Animal Care and Use Committee (IACUC). The animals were acclimated to the laboratory for at least 5 days prior to initiation of experiments. Mice (n=3/compound/time-point) were dosed by oral gavage with 1 mg/kg compound formulated in a vehicle consisting of 5% DMSO/5% Tween 20 and 90% 0.1N HCl. Control mice were dosed PO with the vehicle. Terminal whole blood samples were collected from isoflurane anesthetized mice by cardiac puncture into EDTA. Whole blood was incubated with rat anti-mouse CD16/CD32 (Mouse BD Fc Block, #553141), PE-Rat anti-mouse CD45R/B220 (BD #553089), APC-Cy7-Rat anti-mouse CD8a (BD #557654), and Alexa Fluor647-Rat anti-mouse CD4 (BD #557681) for 30 min on ice. Red blood cells were lysed using BD Pharm Lyse Lysing buffer (#555899) and white blood cells were analyzed by FACS. Lymphopenia was expressed as the % of white blood cells that were CD4 or CD8 positive T cells. The overall lymphopenia response over 24 h was estimated by calculating the area under the effect curve (AUEC) using the linear trapezoidal rule.

In rats: Female rats (Simonsen Laboratories, Gilroy Calif.) were housed in an ALAAC accredited facility and the research was approved by the facilities Institutional Animal Care and Use Committee (IACUC). The animals were acclimated to the laboratory for at least 5 days prior to initiation of experiments. Rats (n=3/compound/time-point) were dosed by oral gavage with 1 mg/kg compound formulated in a vehicle consisting of 5% DMSO/5% Tween 20 and 90% 0.1N HCL. Control rats were dosed PO with the vehicle. Whole blood was collected from isoflurane anesthetized rats via the retro-orbital sinus and terminal samples were collected by cardiac puncture into EDTA. Whole blood was incubated with mouse anti-rat CD32 (BD #550271), PE-mouse anti-rat CD45R/B220 (BD #554881), PECy5-mouse anti-rat CD4 (BD #554839), and APC-mouse anti-rat CD8a (eBioscience #17-0084) for 30 minutes on ice. Red blood cells were lysed using BD Pharm. Lyse Lysing buffer (#555899) and white blood cells were analyzed with a BD FACSArray. Lymphopenia was expressed as the % of white blood cells that were CD4 or CD8 positive T cells. The overall lymphopenia response over 24 h was estimated by calculating the area under the effect curve (AUEC) using the linear trapezoidal rule. In some experiments, total lymphocyte counts were determined using a standard impedance based veterinary hematology analyzer (IDEXX Preclinical Research Services, Sacramento, Calif.).

Rat lymphopenia data for specific compounds is presented in Table 4. The percentage of lymphopenia at 24 h after a 0.2 mg/kg single dose regiment is reported. The estimated dose needed to produce 50% lymphopenia ($ED_{50}$) at 24 h after a 3-5 day dosing regimen is also reported. N/A is not available.

TABLE 4

| Compound Number | % Lymphopenia after 24 h (0.2 mg/kg) | $ED_{50}$ (mg/kg) |
|---|---|---|
| 43 | 40 | N/A |
| 46 | 39 | N/A |
| 47 | 17 | N/A |
| 56 | 52 | N/A |
| 58 | 49 | N/A |
| 166 | 47 | 0.07 |
| 172 | 22 | 0.20 |
| 186 | 25 | 0.20 |

Evaluation of Therapeutic Index in Rats

Studies may be conducted in non-fasted male and female Sprague-Dawely rats (Simonsen Laboratories). Rats may be housed in an AAALAC accredited facility and the research can be approved by the facilities Institutional Animal Care and Use Committee (IACUC). The animals should be acclimated to the laboratory for at least 5 days prior to initiation of experiments.

The compounds may be formulated as suspensions in a vehicle consisting of 0.5% carboxymethyl cellulose (Acros Organics) in purified water (pH adjusted to ~2.2 with hydrochloric acid). The same formulation is used in the rat lymphopenia and toxicology studies described below. The concentration of each compound in suspension should be verified to be within ±10% of the target concentration by HPLC-UV.

Prior to the conduct of toxicology studies, the effect of three to five daily doses of each compound on peripheral T-cell counts of female rats may be determined (see lymphopenia measurements in rats above). In these lymphopenia studies, blood samples are collected onto EDTA at intervals after the final study dose. The collection times need not be identical for each study, however, all studies may include a sample collected 24 hours after the final dose. The lymphopenia data is used as a biomarker to select equally pharmacologically active doses for the subsequent toxicology study. The low dose for the toxicology study is the dose of each compound that resulted in a 50% reduction of T-cell count 24 h after the final dose in the lymphopenia study relative to vehicle treated rats.

In the toxicology studies, three male and three female rats per group are assigned to dosing groups using body weight based randomization. A control group in each study receives vehicle. All animals are dosed orally by gavage on 5 or 14-consecutive days at a dose volume of 5 mL/kg/day. The animals are observed daily for any manifestations of adverse effect. Twenty-four hours after the final study dose, the rats are anesthetized with isoflurane and a terminal blood sample is taken by intra-cardiac puncture for hematology and clinical chemistry evaluation (IDEXX Laboratories, Sacramento, Calif.). The lungs with trachea are collected, weighed, and then prepared for histology by perfusion with 10% neutral buffered formalin via the trachea. The internally fixed lungs are then preserved in 10% neutral buffered formalin and submitted for histological examination (IDEXX).

The dose of each compound resulting in a 10% increase in the lung to terminal body weight ratio can be estimated for each compound by linear interpolation. The therapeutic index can then be estimated as the ratio of the dose producing 10% lung weight increase to the dose producing 50% T-Cell depletion.

Description of the TNBS Crohn's Colitis Model in Rats

Male Sprague-Dawley rats (180-200 g) are acclimatized for seven days and then assigned to 8 rats per group so that each group has approximately the same mean weight. Twenty-four hours prior to disease initiation, rats are deprived of food. Rats are anaesthetized and weighed, then 80 mg/kg TNBS solution (50% TNBS: 50% 200 proof ethanol) is instilled into colon via a 20 g feeding needle inserted into the anus. The rats are maintained in head down position until recovery from anesthesia. Daily oral dosing is initiated 2 h post TNBS-instillation for six days. Prednisolone serves as a positive control and is administered orally daily at 10 mg/kg. Body weights are monitored daily and 24 h after the last dose, all groups are terminated. The colon is removed, flushed of fecal matter and examined for gross changes including strictures, adhesions and ulcers. The colon length, weight of the distal 2 cm, and wall thickness is recorded.

Description of Influenza A H1M1 Model in Mice

Male C57B1/6 (6-8 weeks of age) may be acclimatized for seven days and then assigned to 5-8 mice per group so that each group has approximately the same mean weight. Mice may be infected with $10^4$ PFUs mouse-adapted influenza A virus (A/WSN/33) via the intra-tracheal route. Mice may then be treated with 0.2-1.5 mg/kg compound p.o. 1 hr post-infection. Forty eight hours after infection mice may be euthanized by cervical dislocation and bronchoalveolar lavage fluid can be collected. Quantitative cytokine analysis may be performed via ELISA. In some experiments whole body perfusion can be performed and lungs can be collected for cellular enumeration of inflammatory cells. Longevity studies may be performed by infection with 3-10×$10^4$ PFUs mouse-adapted influenza A virus over 14 days.

We claim:

1. A compound of Formula (I) or a pharmaceutically acceptable salt, ester, prodrug, homolog, tautomer, stereoisomer, or hydrate, or solvate thereof:

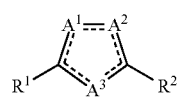

(I)

wherein
    a dashed line signifies that a single bond or a double bond can be present, provided that there are two double bonds and three single bonds in the ring comprising $A^1$, $A^2$, and $A^3$;

$A^1$, $A^2$, and $A^3$ each independently is CH or S or N; provided that one of $A^1$, $A^2$, and $A^3$ is S;

$R^1$ is di-substituted phenyl or di-substituted pyridinyl where the phenyl and pyridinyl substituents are each independently selected from the group consisting of halo, nitro, cyano, perfluromethyl, fluorinated methyl, and $C_{1-4}$-alkoxy; provided that if $R^1$ is di-substituted phenyl, such phenyl is para-substituted with $C_{1-4}$-alkoxy;

$R^2$ is

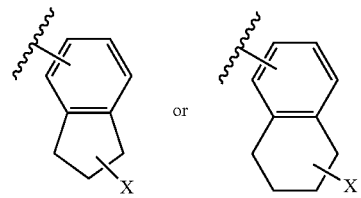

wherein a wavy line indicates a point of attachment;

X is —NR'R'' or —OR''';

R' is H, $C_{1-4}$ alkyl, n-hydroxy $C_{1-4}$ alkyl, —$SO_2$—$R^3$, or —CO—$R^3$;

R'' is H, —$SO_2$—$R^5$, $C_{1-4}$ alkyl optionally substituted with 1 or more $R^4$, or a ring moiety optionally substituted with $R^6$ wherein such ring moiety is piperidinyl, cyclohexyl, morpholinyl, thiazolyl, pyrazolyl, pyrrolidinyl, imidazolyl, or phenyl;

R''' is H, $C_{1-4}$ alkyl, or —CO—$R^3$ or R' and R'' taken together with the nitrogen atom to which they are bound form a 4, 5, or 6 membered saturated heterocyclic ring containing 0 or 1 additional heteroatoms where such additional heteroatom is O or N wherein such heterocycle is optionally singly or multiply substituted with substituents independently selected from the group consisting of —OH, oxo, —$NH_2$, n-hydroxy-$C_{1-4}$ alkyl, —COOH, —$(CH_2)_m$—COOH, —$(CH_2)_m$—$COOR^3$, —$N(R^3R^3)$, and —$(CH_2)_m$—CO—$N(R^7R^7)$;

each $R^3$ is independently $C_{1-4}$ alkyl or H;

each $R^4$ is independently H, halo, OH, oxo, =NH, $NH_2$, —COOH, F, —$NHR^3$, —$N(R^7R^7)$, —$SO_2$—$R^3$, —$SO_2$—$N(R^7R^7)$, —$N(R^3)$—$SO_2$—$R^3$, —$COOR^3$, —$OCO$—$R^3$, —CO—$N(R^7R^7)$, —$N(R^3)$—$COR^3$, $C_{1-3}$ alkyl, $C_{1-3}$ alkoxy, and a ring moiety optionally substituted with $R^6$ wherein such ring moiety is piperazinyl, piperidinyl, morpholinyl, pyrrolidinyl, pyrazolyl, imidazolyl, benzimidazolyl, azetidinyl, cyclobutinyl, or phenyl;

each $R^5$ is independently $R^4$, $C_{1-4}$ alkyl, $C_{3-6}$ cycloalkyl, or $C_{1-4}$ alkyl optionally substituted with 1 or more $R^4$;

each $R^6$ is independently halo, OH, —$NH_2$, —$NHR^3$, —$N(R^3R^3)$, —COOH, —$COOR^3$, —NHCO—$R^3$, each $R^7$ is independently $C_{1-4}$ alkyl or H, or two $R^7$ taken together with the nitrogen atom to which they are bound form a 4, 5, or 6 membered saturated heterocyclic ring containing 0 or 1 additional heteroatoms where such additional heteroatom is O or N wherein such heterocycle is optionally substituted with —OH, —$NH_2$, —$N(R^3R^3)$, n-hydroxy $C_{1-4}$ alkyl, —$(CH_2)_m$—COOH, or —$(CH_2)_m$—$COOR^3$;

each m is independently 0, 1, 2, or 3.

2. The compound of claim 1 wherein the structure of Formula I is selected from the group consisting of formulas a-i through a-x:

a-i
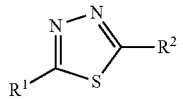

a-ii
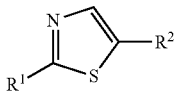

a-iii
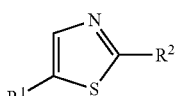

a-iv
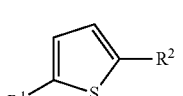

a-v
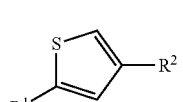

a-vi
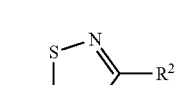

a-vii
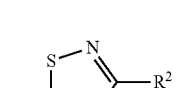

a-viii
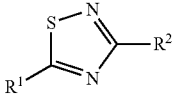

a-ix
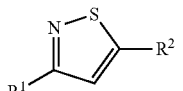

a-x
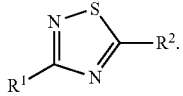

3. The compound of claim 1 wherein $A^1$ is S.

4. The compound of claim 1 wherein $A^2$ is S.

5. The compound of claim 1 wherein $A^3$ is S.

6. The compound of claim 5 wherein $A^1$ is N and $A^2$ is CH or N.

7. The compound of claim 6 wherein $A^2$ is CH.

8. The compound of claim 6 wherein $A^2$ is N.

9. The compound of claim 1 wherein $R^1$ is

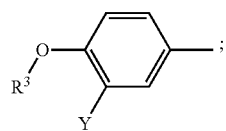

$R^3$ is $C_{2-4}$ alkyl; and Y is —CN, —Cl, —O—$R^3$, or —$CF_3$.

10. The compound of claim 9 wherein $R^3$ is isopropyl or ethyl.

11. The compound of claim 9 wherein Y is —CN or —O—$C_2H_5$.

12. The compound of claim 1 wherein $R^2$ is

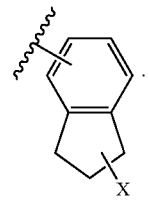

13. The compound of claim 1 wherein $R^2$ is

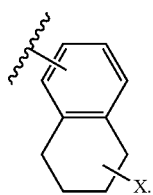

14. The compound of claim 12 wherein $R^2$ is

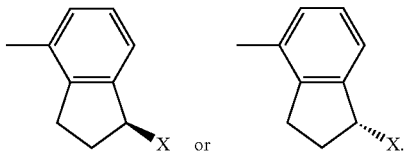

15. The compound of claim 13 wherein $R^2$ is

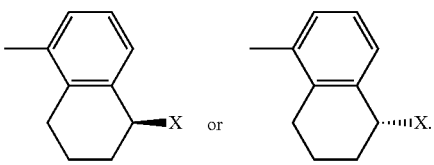

16. The compound of claim 14 wherein $R^2$ is

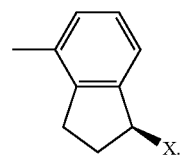

17. The compound of claim 14 wherein $R^2$ is

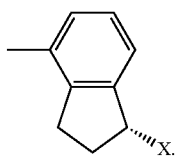

18. The compound of claim 15 wherein $R^2$ is

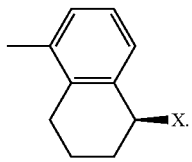

19. The compound of claim 15 wherein $R^2$ is

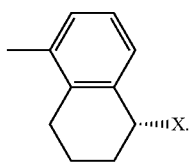

20. The compound of claim 14 wherein the compound is substantially enantiomerically pure.

21. The compound of claim 1 wherein the compound has an $EC_{50}$ as an S1P receptor subtype 1 agonist which is at least ten times smaller than its $EC_{50}$ as an agonist of a mutant S1P receptor subtype 1 having a single mutation with respect to wild type S1P receptor subtype 1 such that the $101^{st}$ amino acid residue is changed from asparagine to alanine.

22. The compound of claim 21 wherein the compound has an $EC_{50}$ as an S1P receptor subtype 1 agonist which is at least twenty times smaller than its $EC_{50}$ as an agonist of a mutant form of S1P receptor subtype 1 having a single mutation with respect to wild type S1P receptor subtype 1 such that the $101^{st}$ amino acid residue is changed from asparagine to alanine.

23. The compound of claim 1 wherein the compound has a therapeutic index of at least 5 as measured in rats following 5 or 14 days of dosing with the compound where the therapeutic index is the ratio of the dose achieving less than or equal to 10% increase in lung to terminal body weight at the conclusion of such 5 or 14 days and the dose achieving 50% lymphopenia.

24. The compound of claim 23 wherein the therapeutic index is at least 10.

25. The compound of claim 23 wherein the therapeutic index is at least 20.

26. The compound of claim 23 wherein the therapeutic index for the compound is greater than the therapeutic index for the enantiomer of the compound.

27. The compound of claim 26 wherein the therapeutic index for the compound is at least 150% of the therapeutic index for the enantiomer of the compound.

28. The compound of claim 9 wherein Y is Cl.
29. The compound of claim 9 wherein Y is $CF_3$.
30. The compound of claim 9 wherein Y is CN.
31. The compound of claim 1 wherein X is —NR'R".
32. The compound of claim 1 wherein X is —OR'''.
33. The compound of claim 32 wherein X is —OH.
34. The compound of claim 32 wherein X is —OCO—$R^3$.
35. The compound of claim 34 wherein $R^3$ is $C_{1-3}$ alkyl.
36. The compound of claim 31 wherein R' is H.
37. The compound of claim 31 wherein R' is —$COR^3$.
38. The compound of claim 31 wherein R' is —$SO_2$—$R^3$.
39. The compound of claim 31 wherein R" is H.
40. The compound of claim 31 wherein R" is —$SO_2$—$R^5$.
41. The compound of claim 31 wherein R" is $C_{1-4}$ alkyl optionally substituted with 1 or more $R^4$.
42. The compound of claim 31 wherein R" is —$(CR^a R^b)_n$—$R^4$; each $R^a$ and each $R^b$ is independently selected from the group consisting of H, hydroxyl and methyl or $R^a$ and $R^b$ bound to the same carbon taken together are oxo; and n is 0, 1, 2, or 3.
43. The compound of claim 42 wherein n is 2.
44. The compound of claim 43 wherein $R^4$ is —OH, —$NH_2$, —$NHR^3$, —$N(R^7R^7)$, or —COOH.
45. The compound of claim 40 wherein $R^5$ is $C_{1-4}$ alkyl optionally substituted with 1 or more $R^4$.
46. The compound of claim 9 wherein Y is CN.
47. The compound of claim 45 wherein $R^5$ is —$C_2H_5$—$N(R^7R^7)$ or —$CH_2$—CO—$N(R^7R^7)$.
48. The compound of claim 46 wherein $R^5$ is $C_2H_5$—O—$R^3$.
49. The compound of claim 31 wherein X is —NH—CO—$N(R^7R^7)$.
50. The compound of claim 1 wherein the compound is selected from:

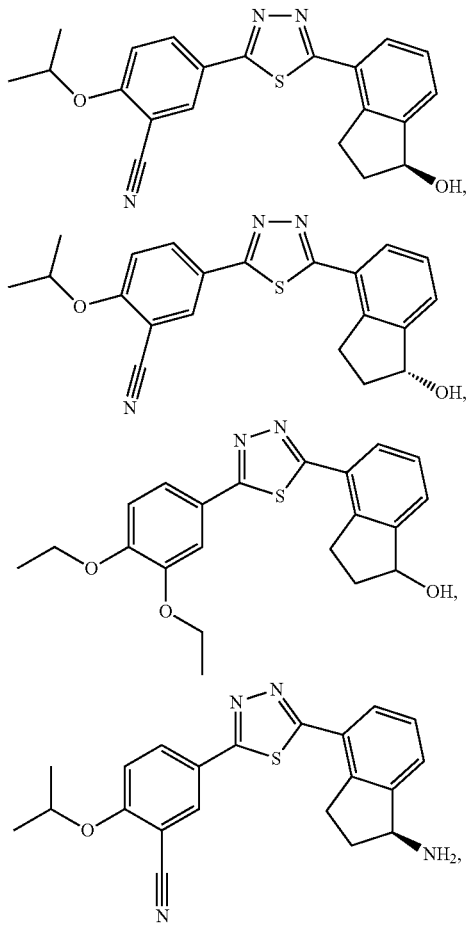

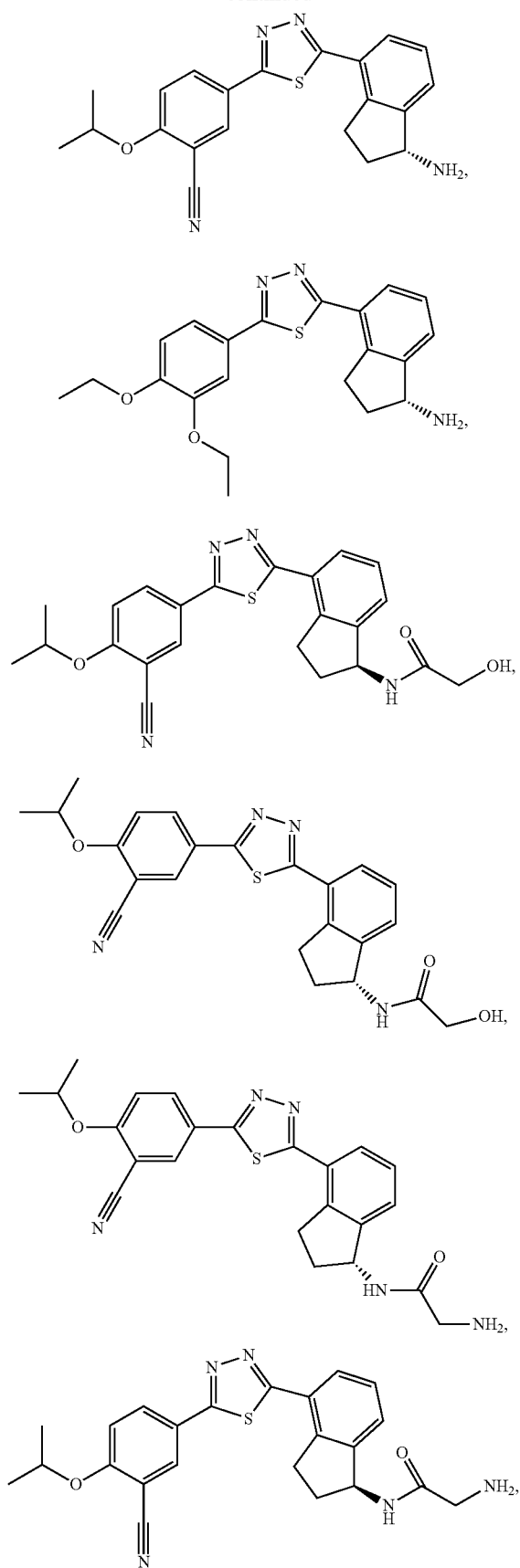
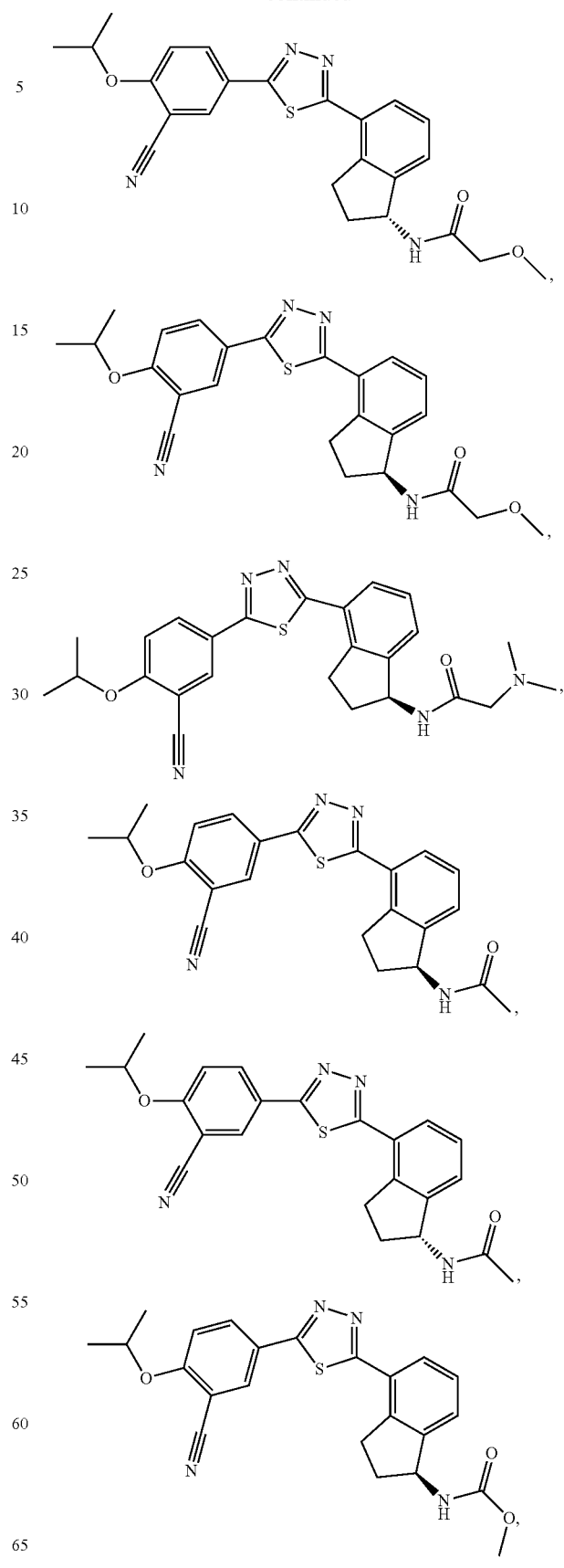

237
-continued
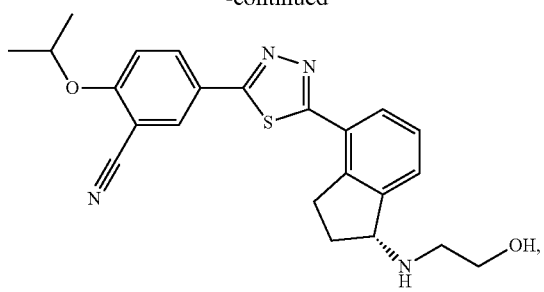
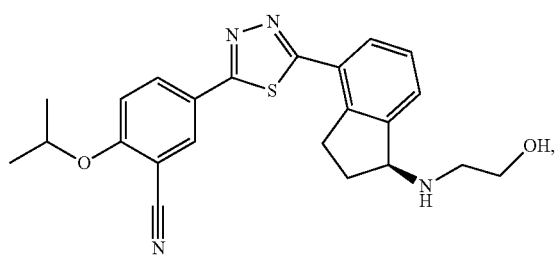
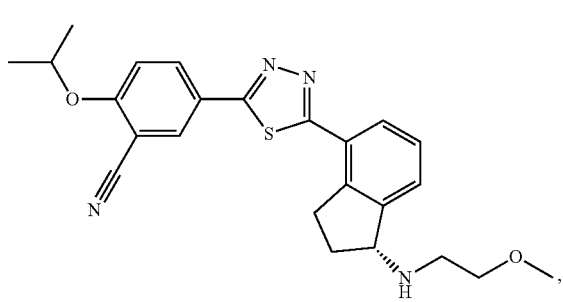
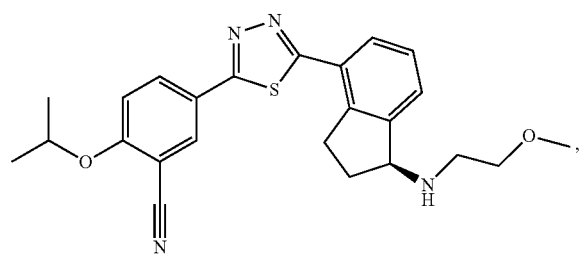
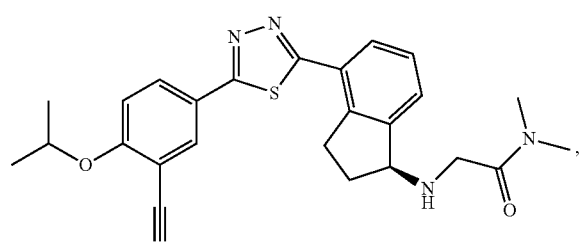
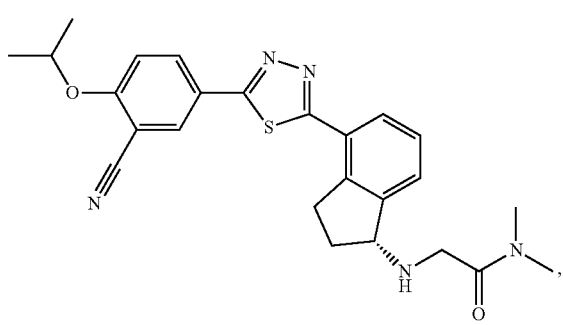
238
-continued
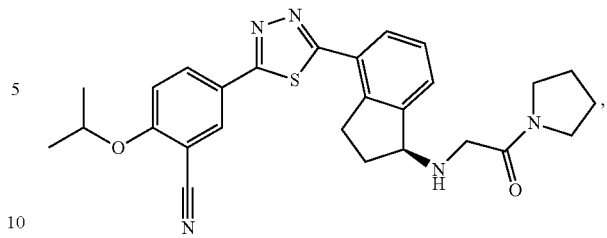
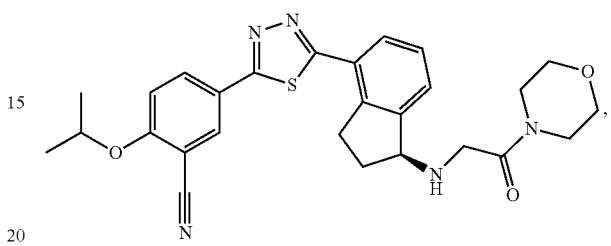
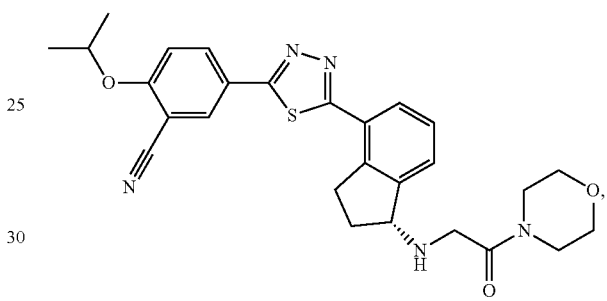
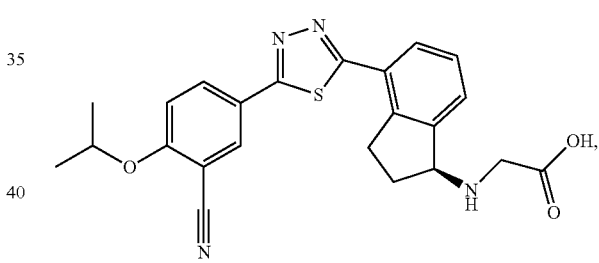
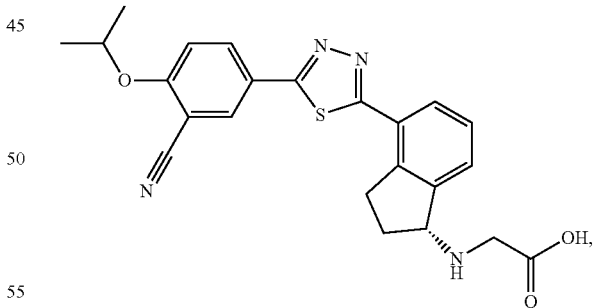
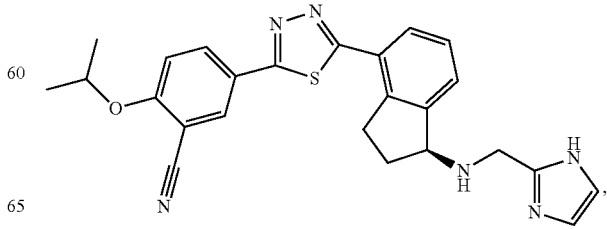

239
-continued
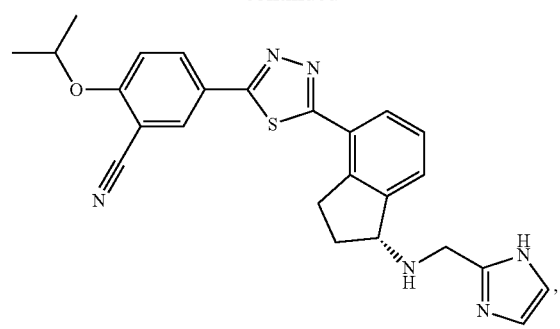
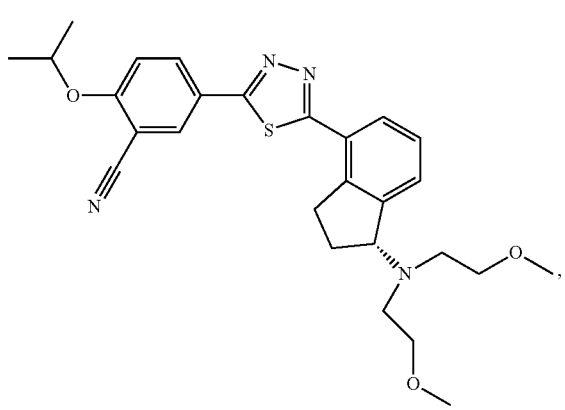
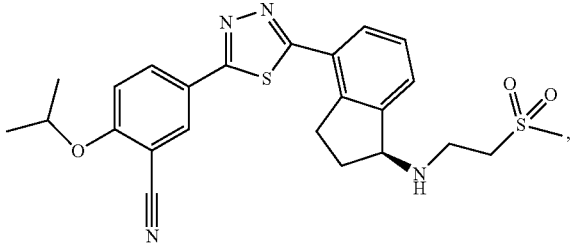
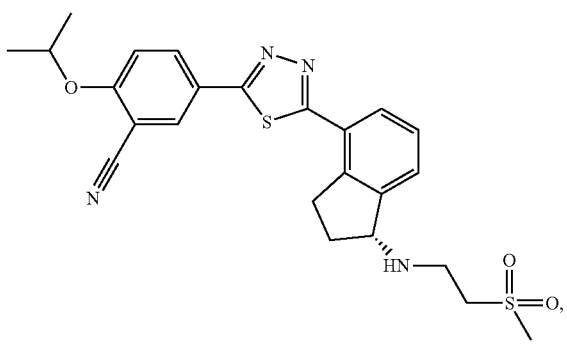
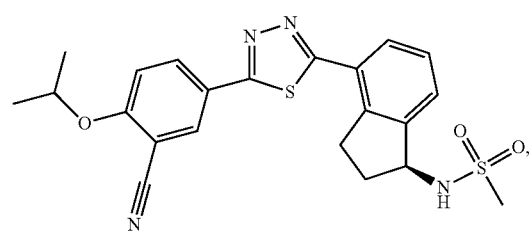
240
-continued
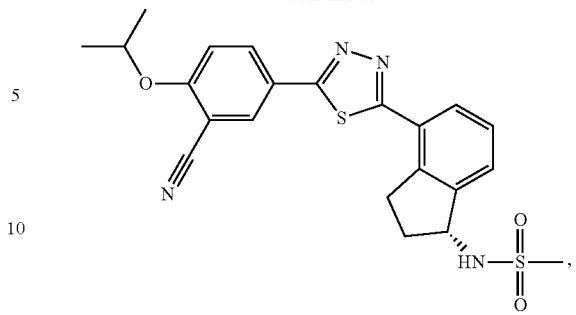
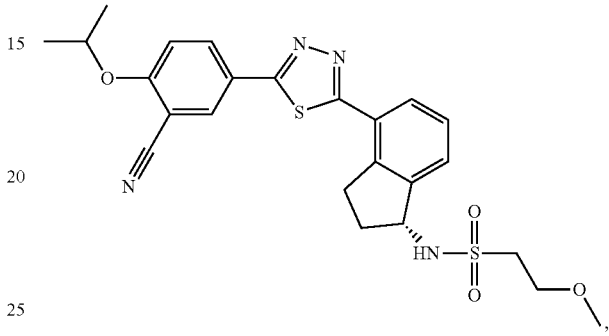
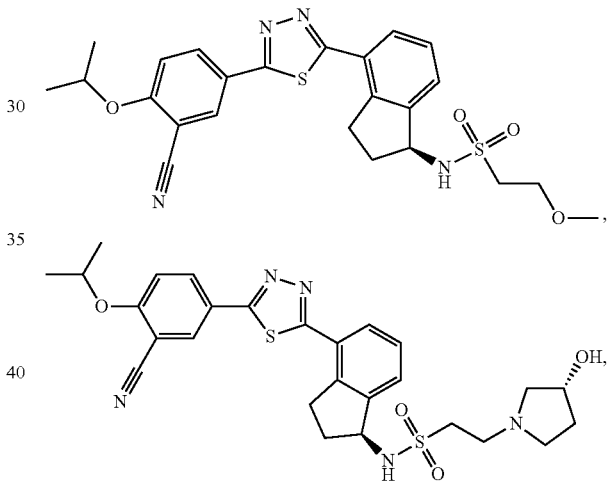
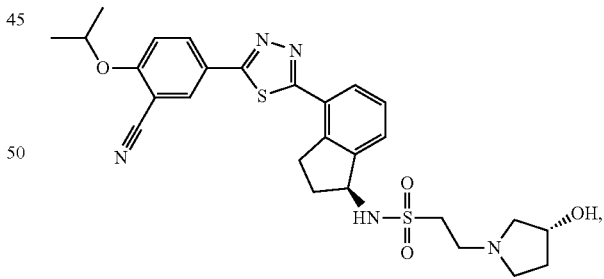
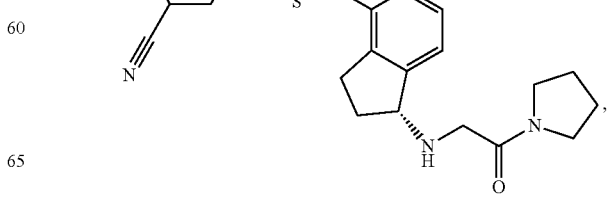

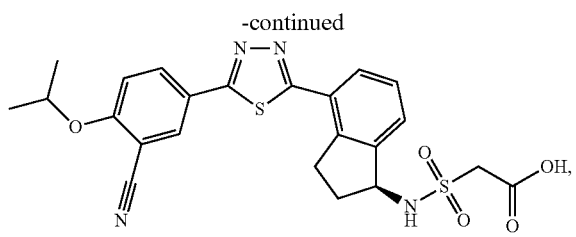
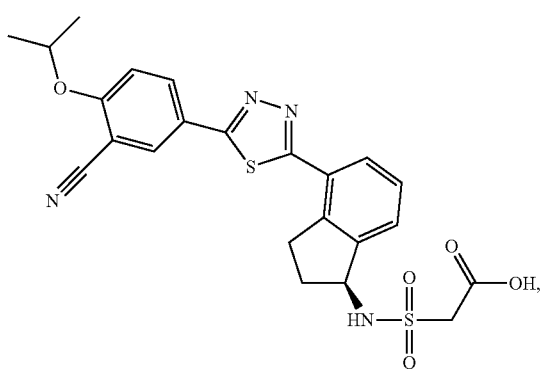
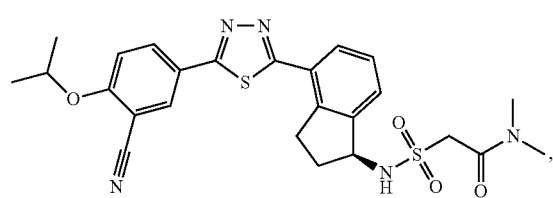
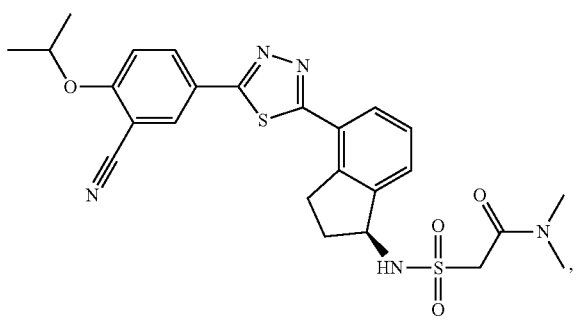
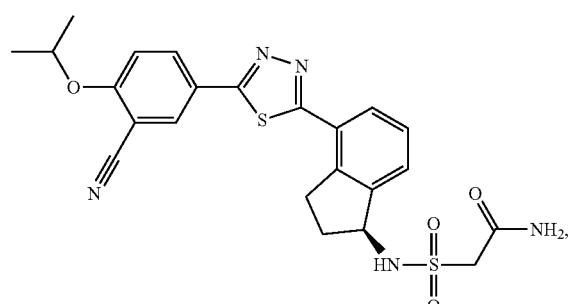
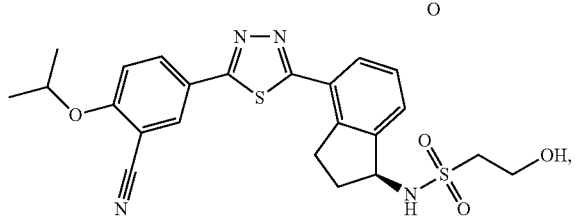
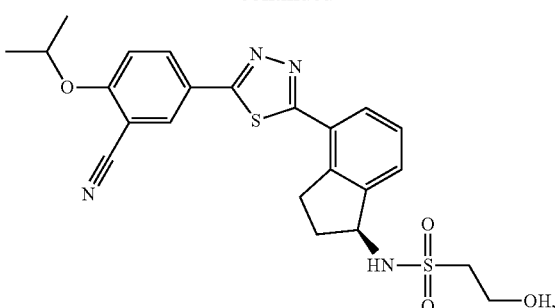
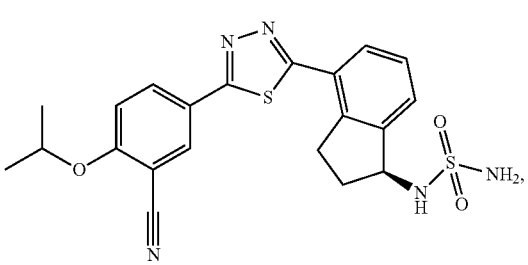
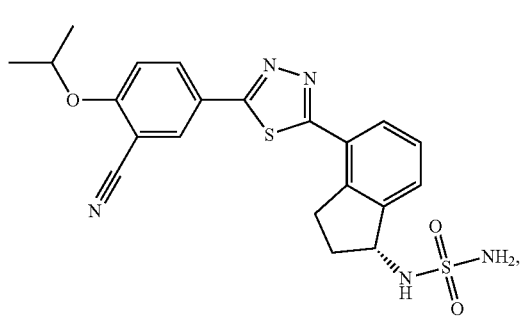
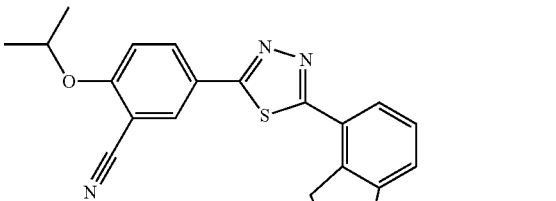
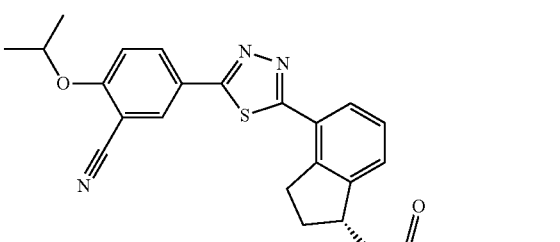

243
-continued
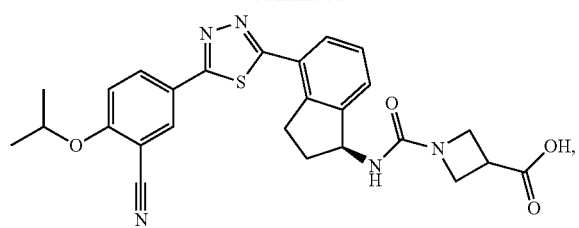
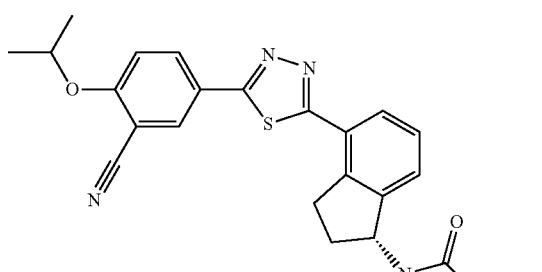
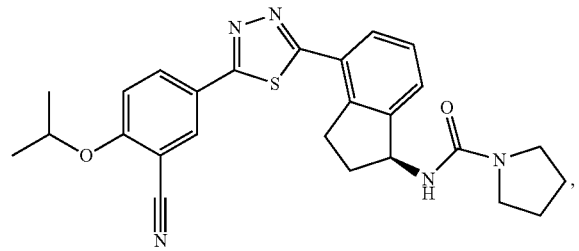
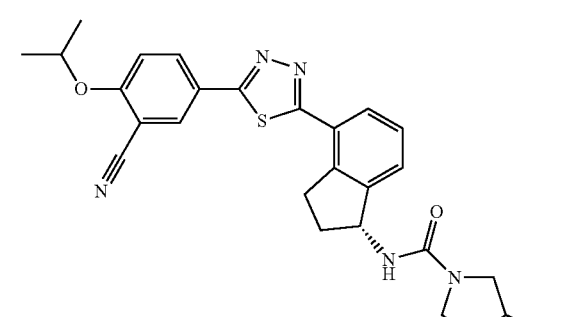
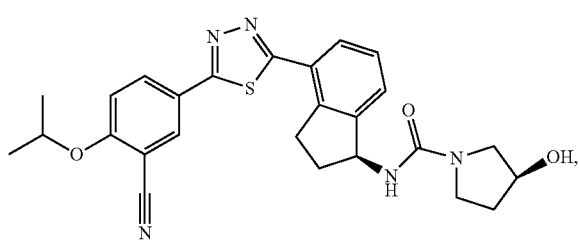
244
-continued
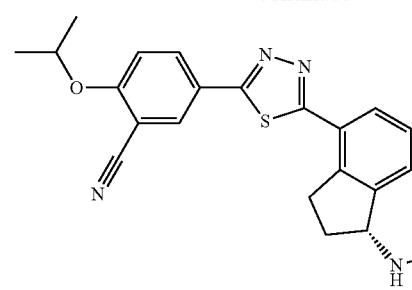
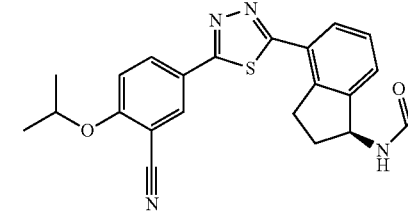
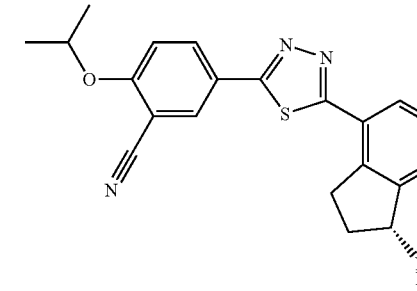
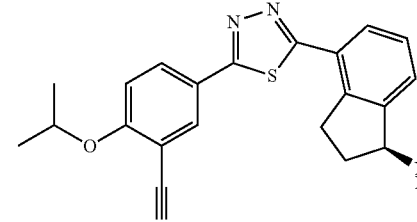
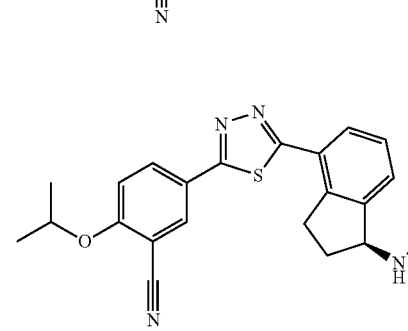

245
-continued
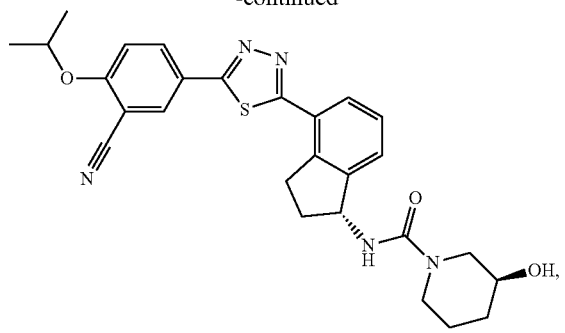
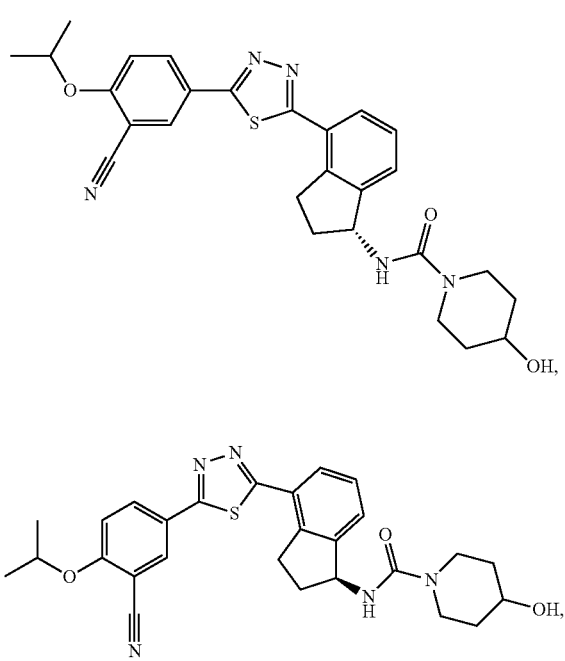
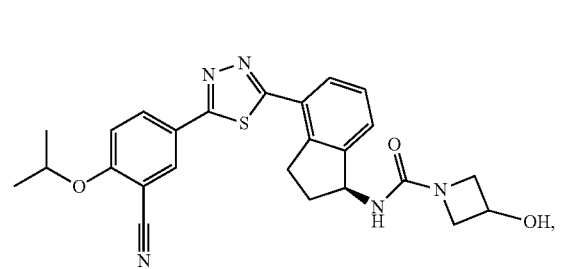
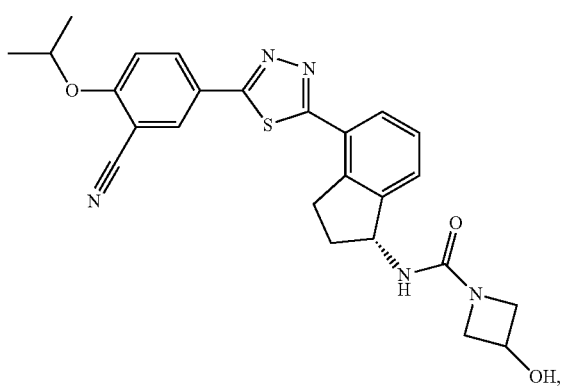
246
-continued
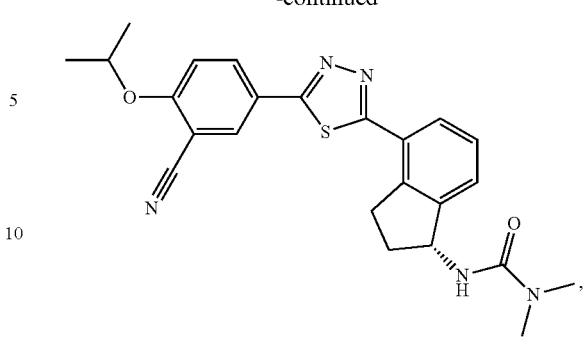
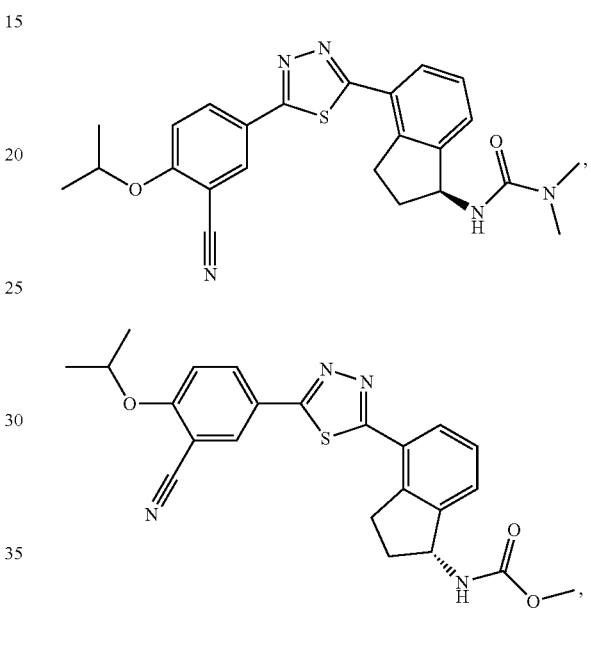
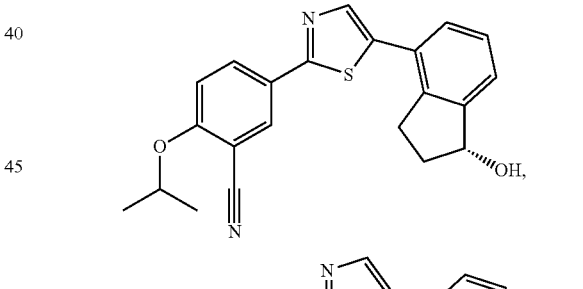
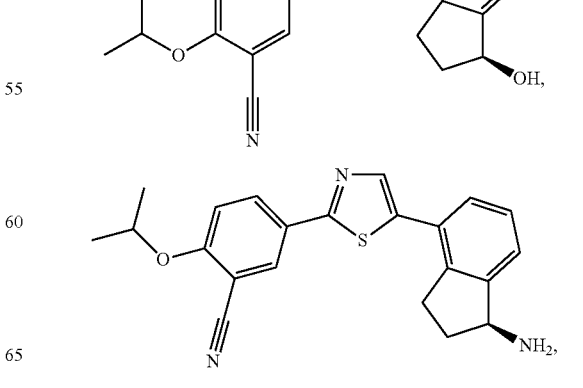

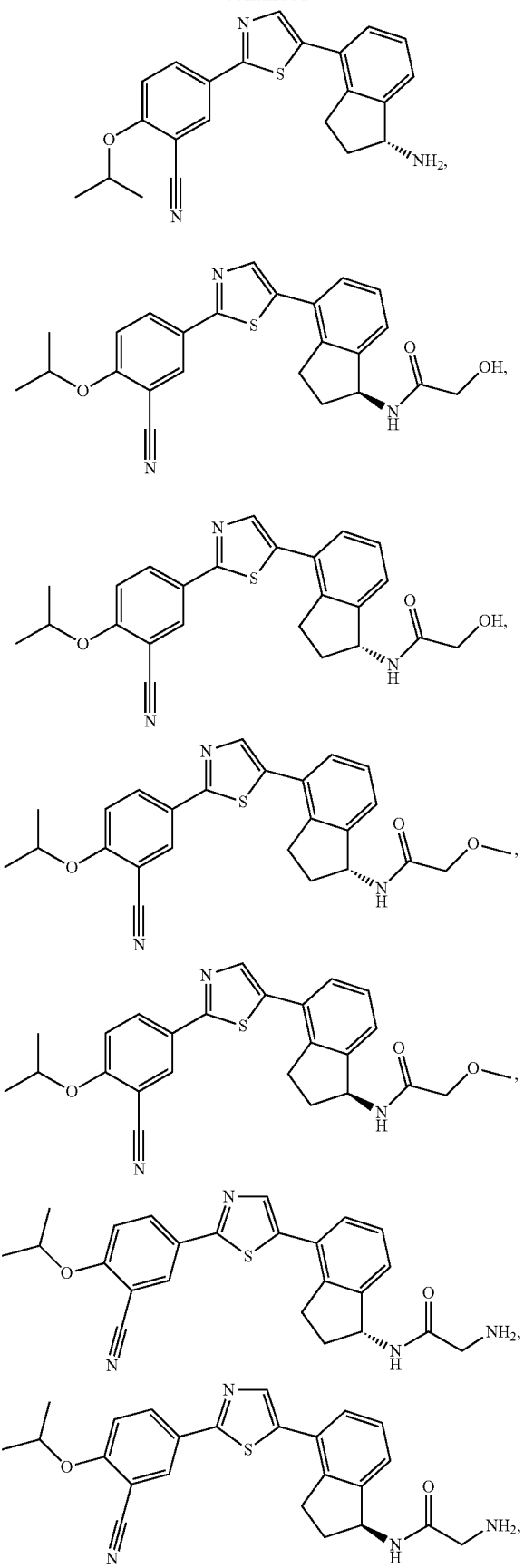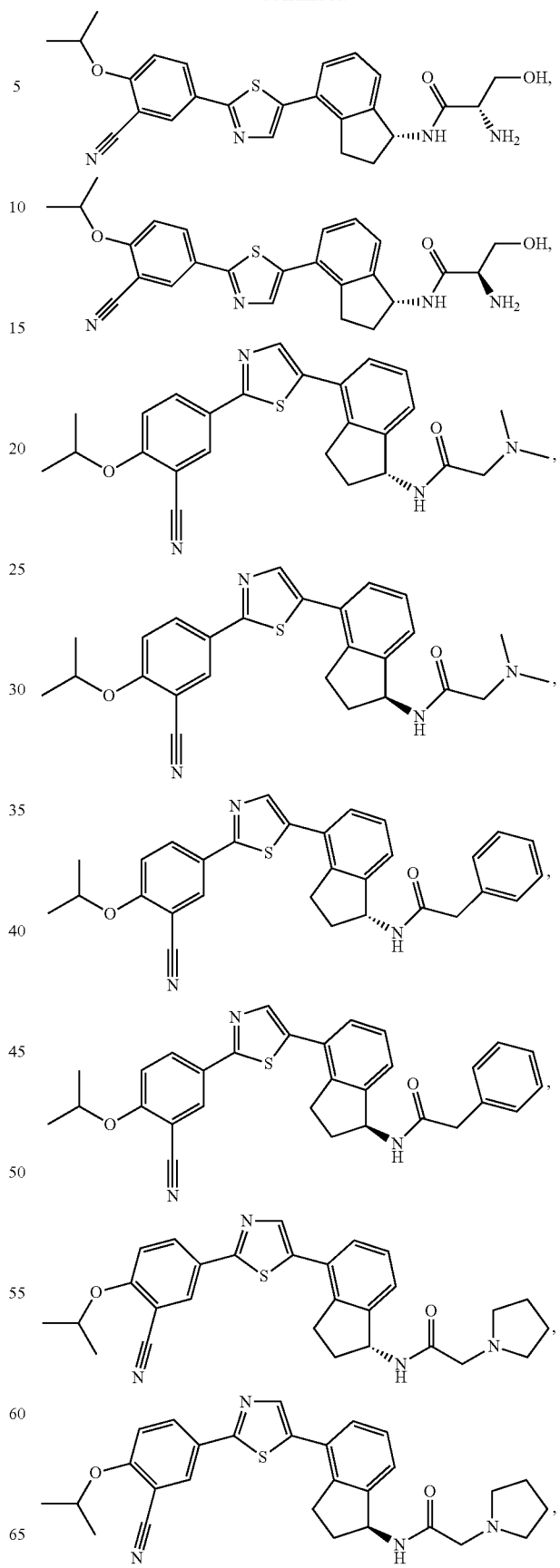

249
-continued
250
-continued
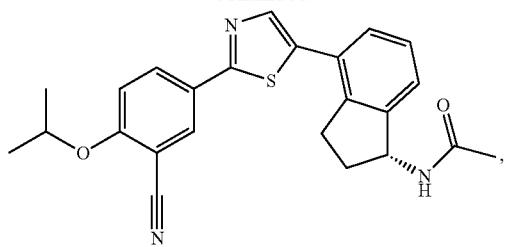
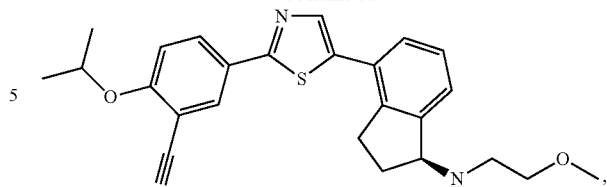
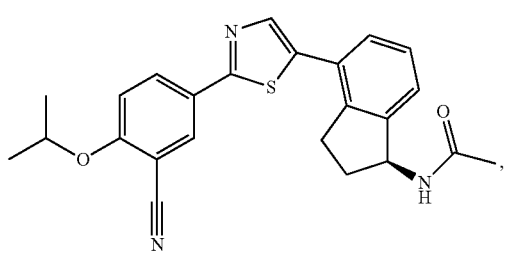
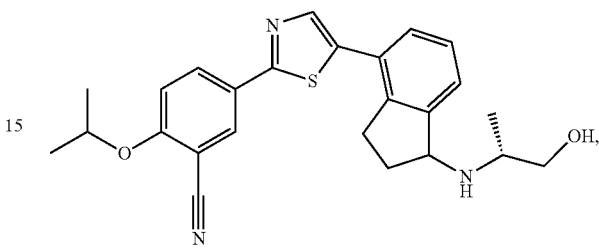
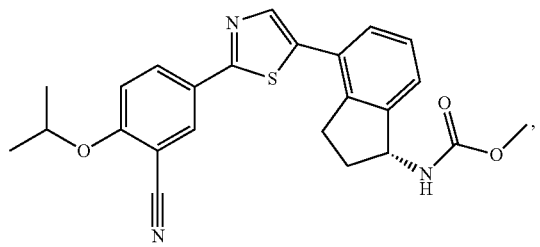
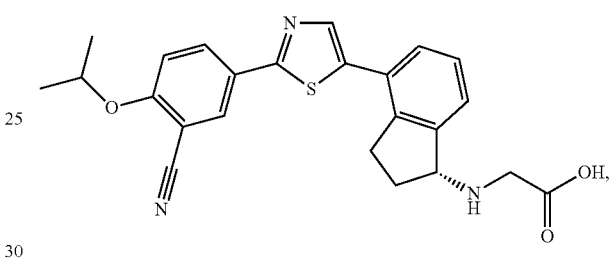
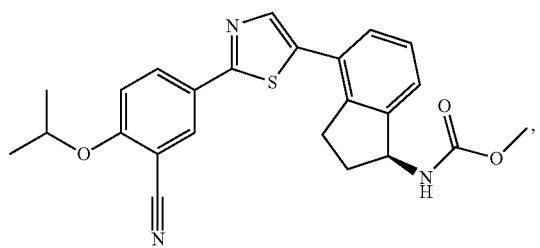
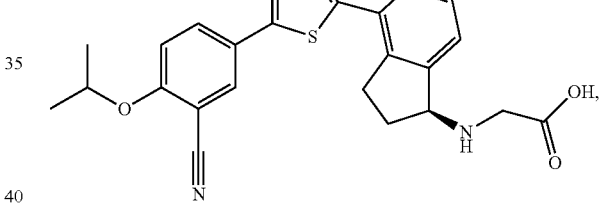
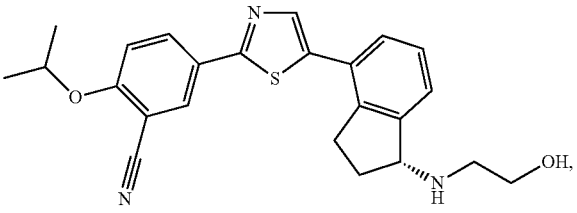
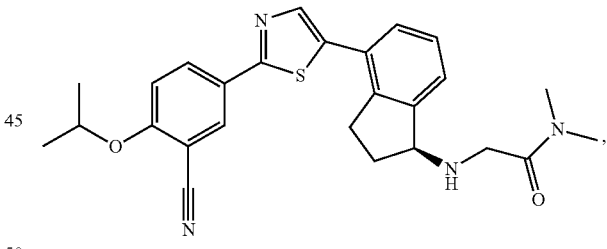
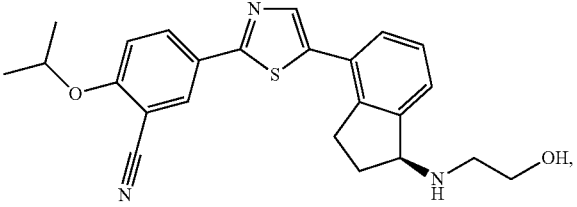
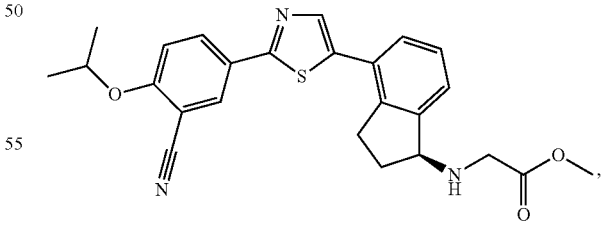
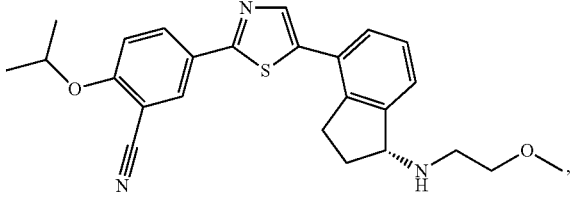
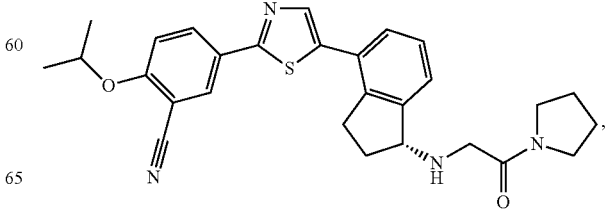

251
-continued
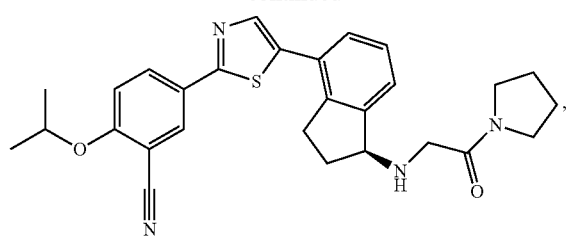
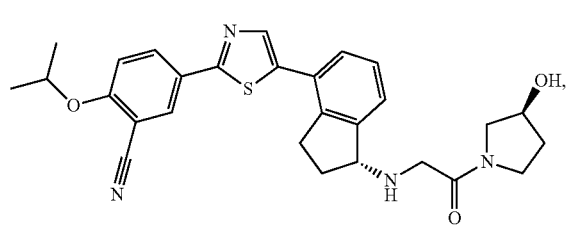
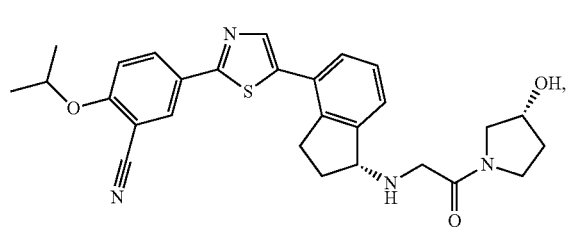
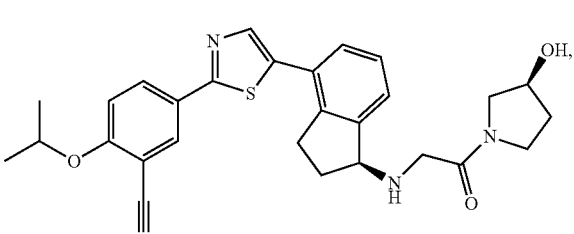
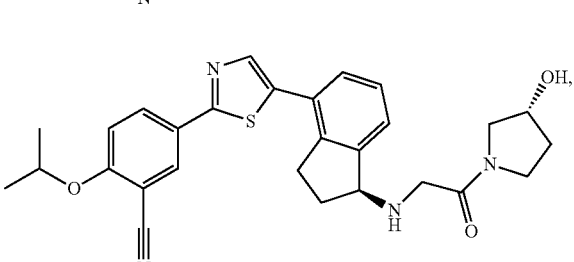
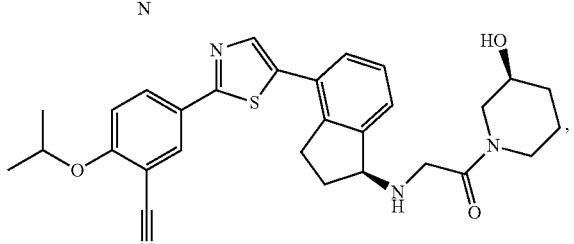
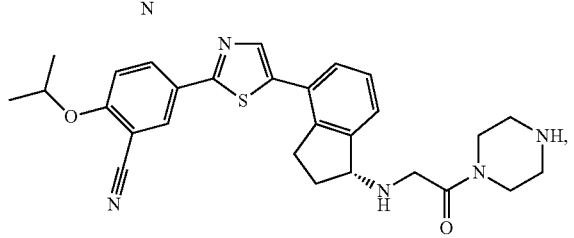
252
-continued
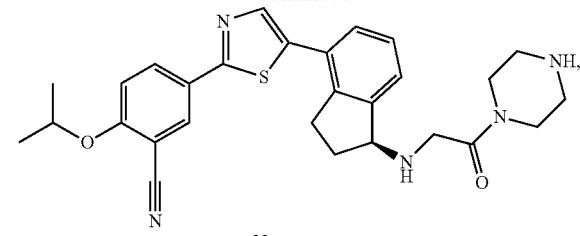
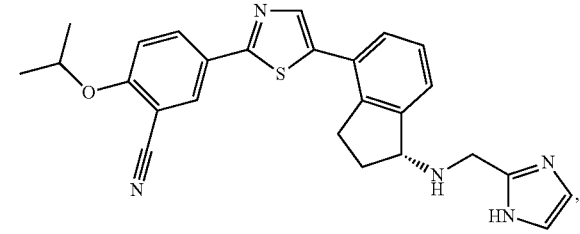
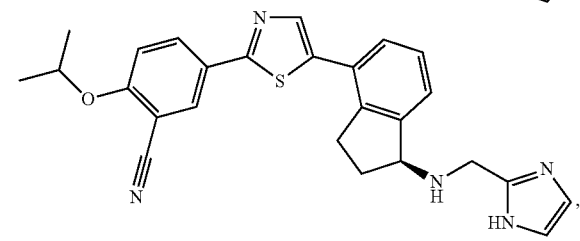
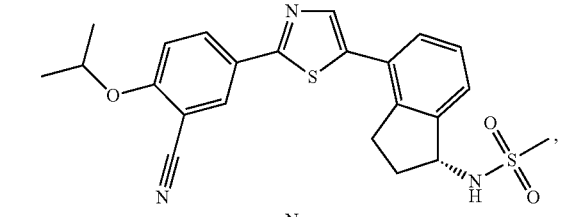
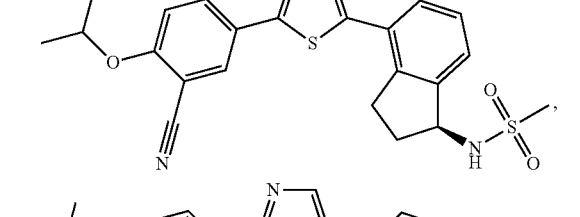
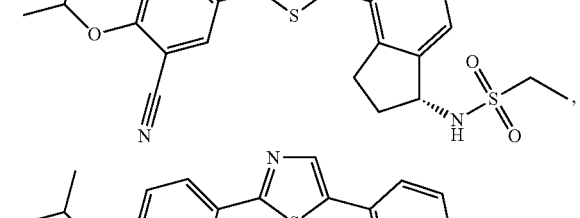
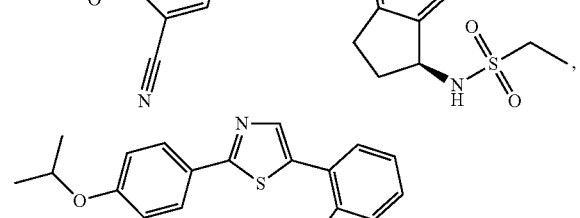

-continued

255
-continued
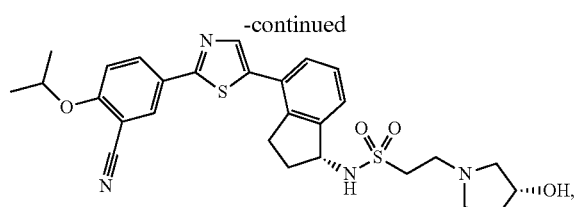
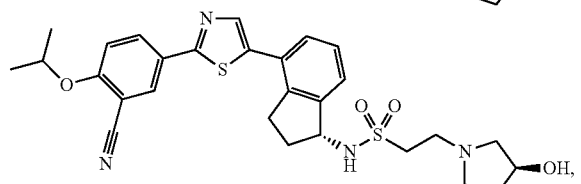
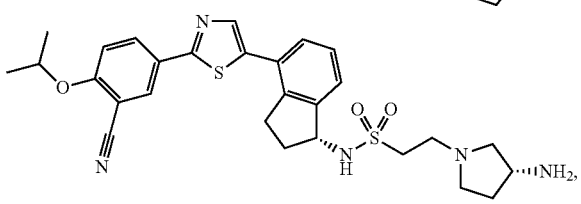
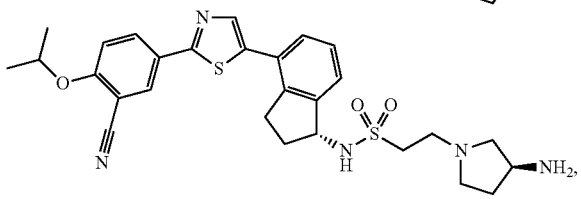
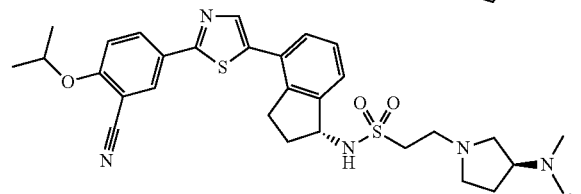
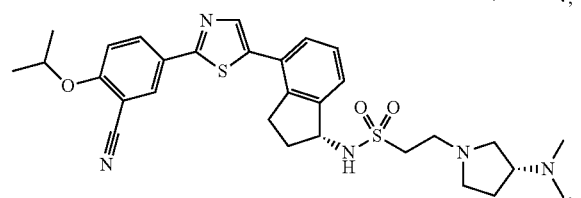
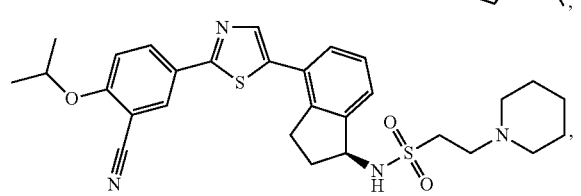
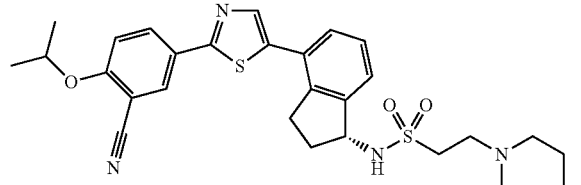
256
-continued
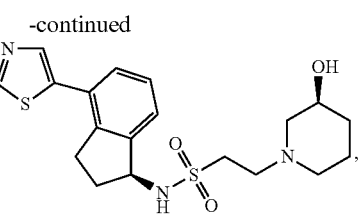
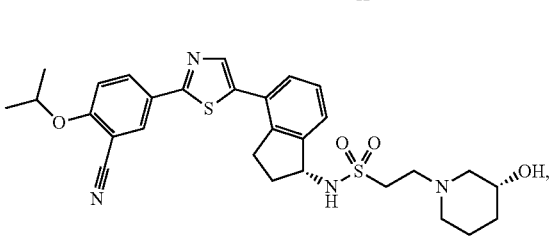
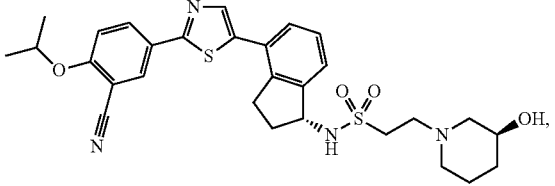
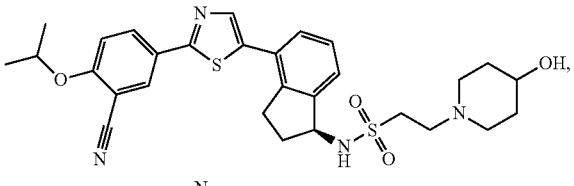
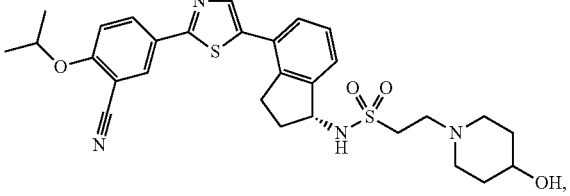
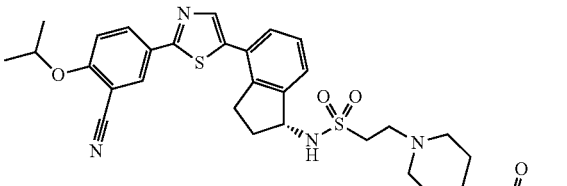
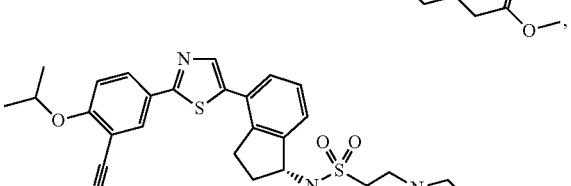
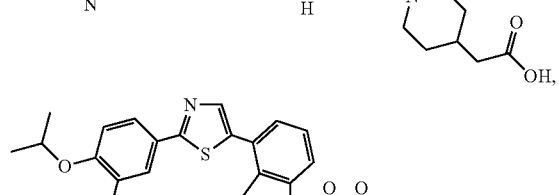
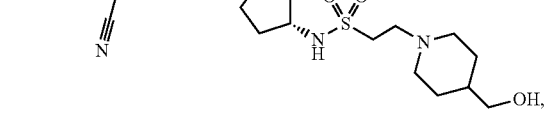

257
-continued
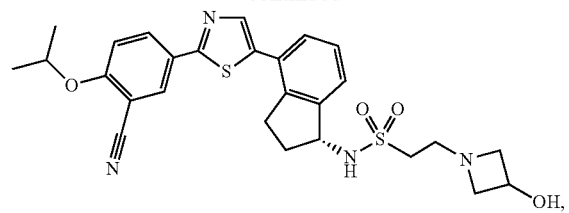
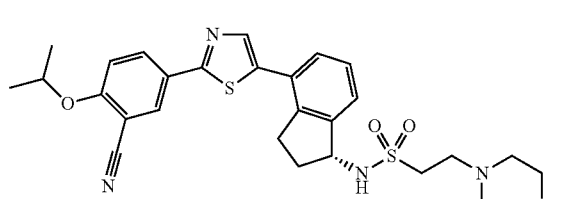
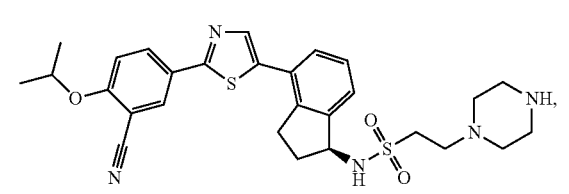
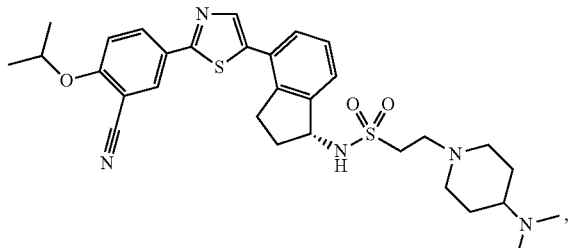
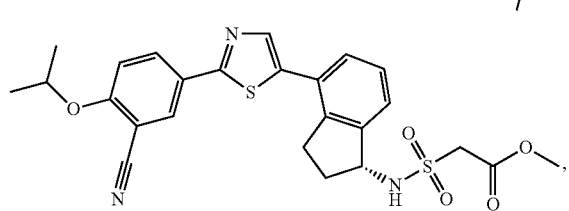
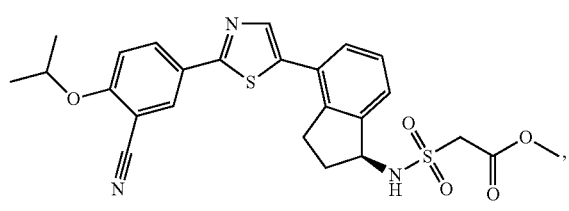
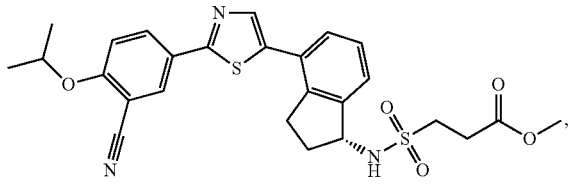
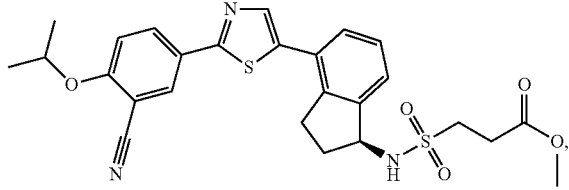
258
-continued
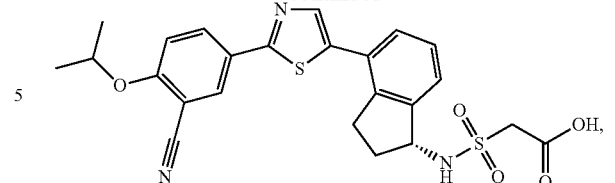
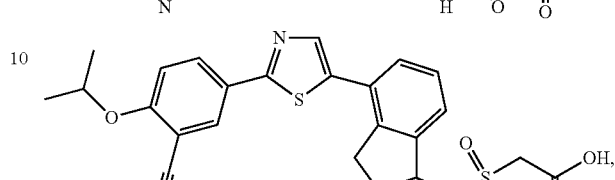
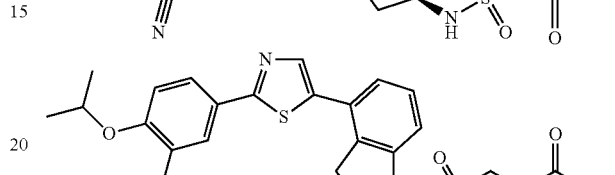
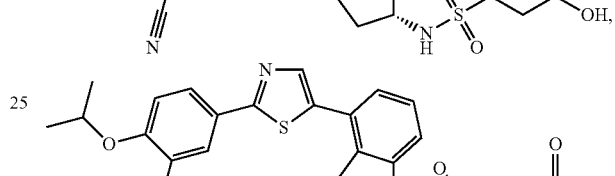
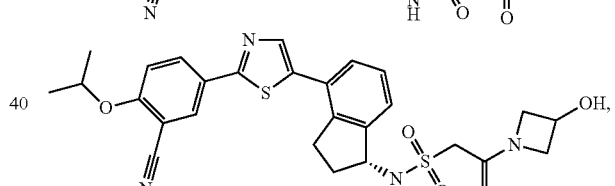
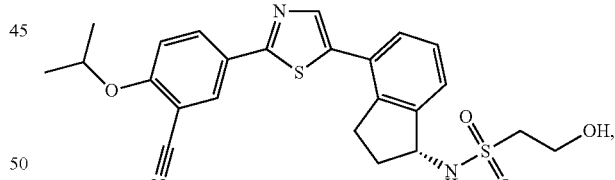
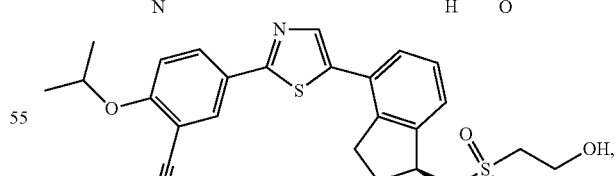
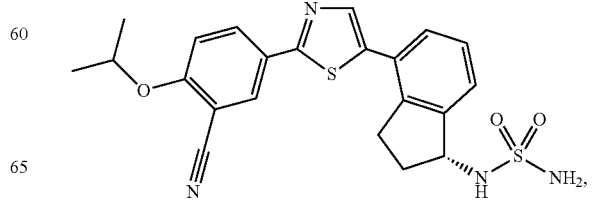

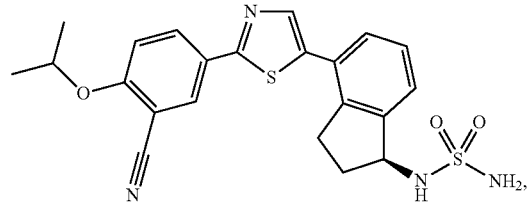
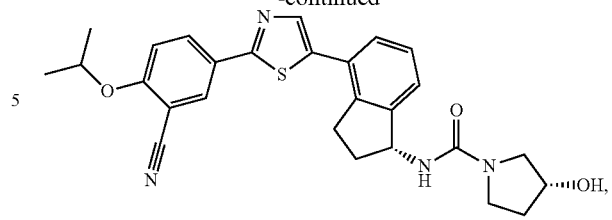
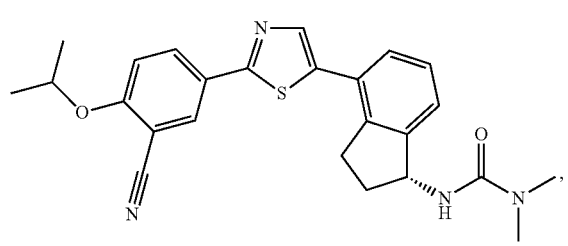
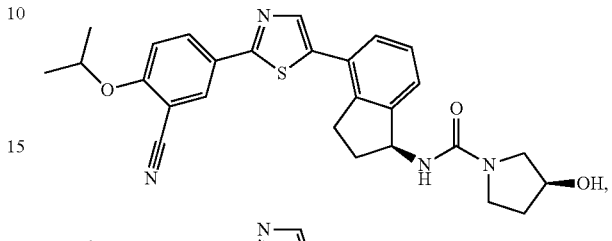
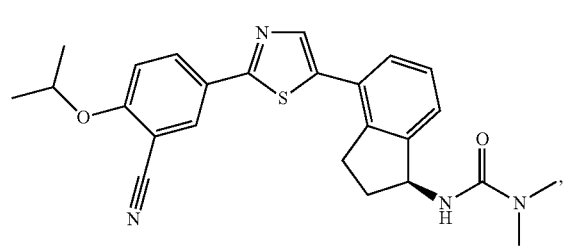
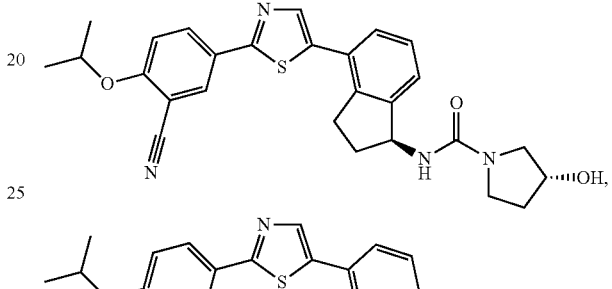
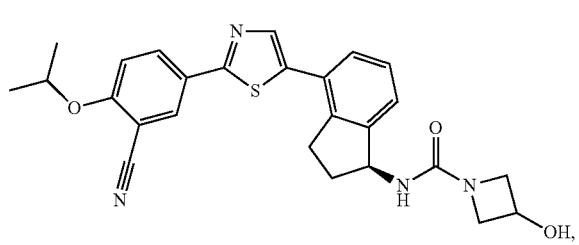
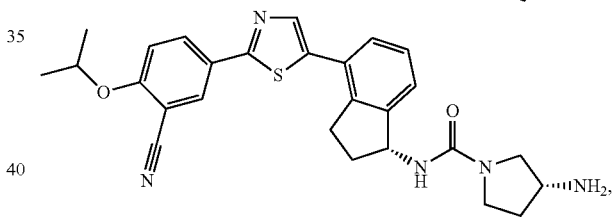
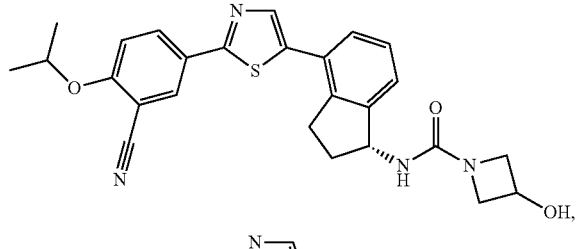
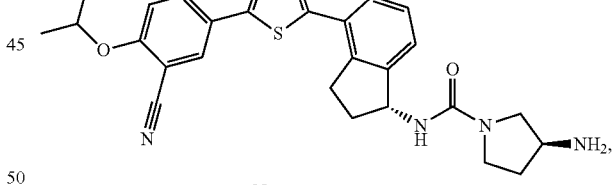
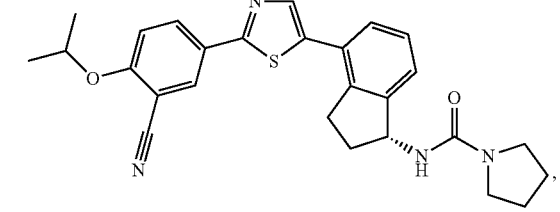
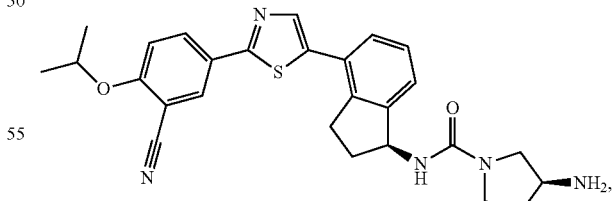
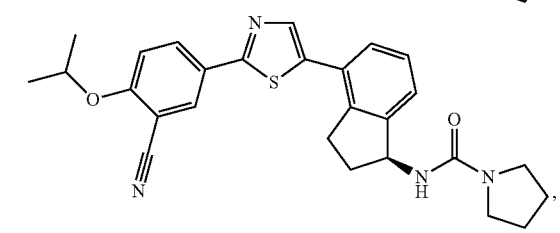
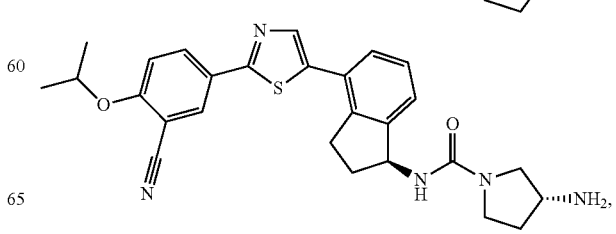

261
-continued
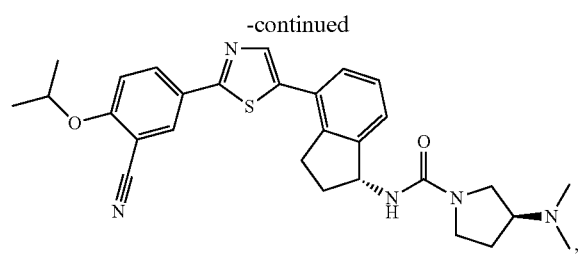
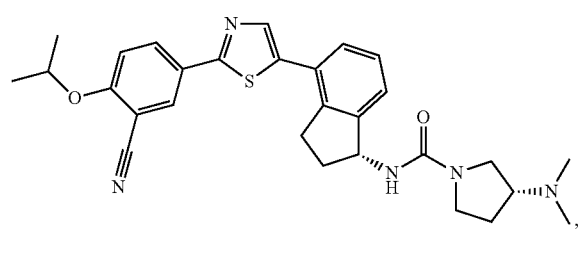
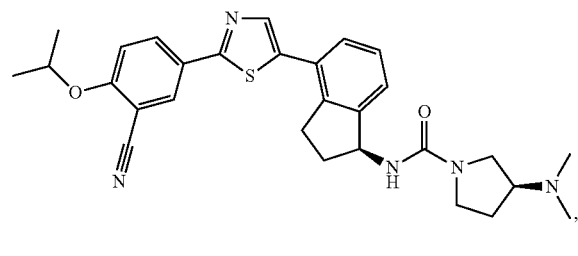
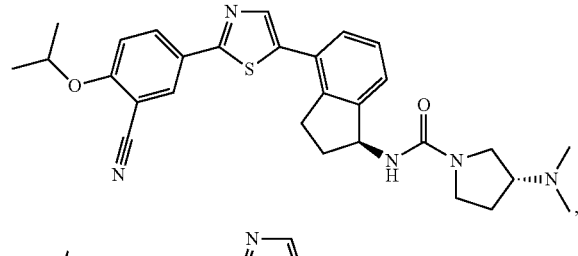
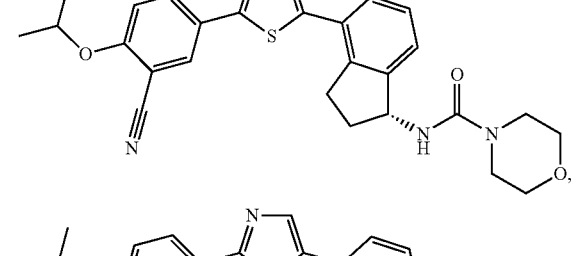
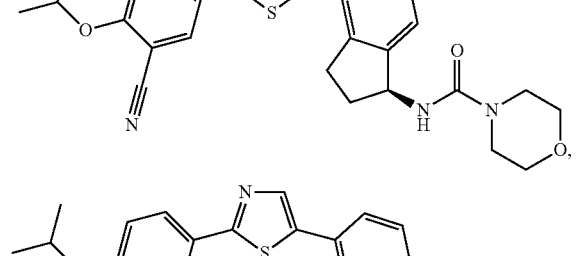
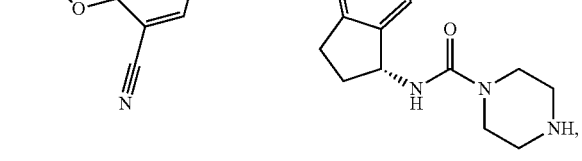
262
-continued
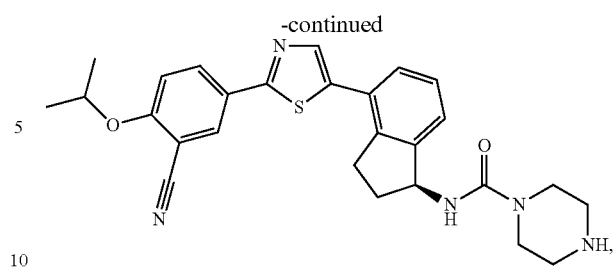
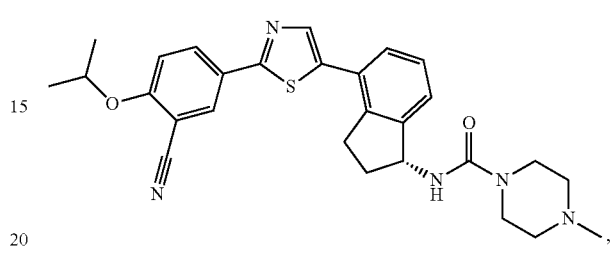
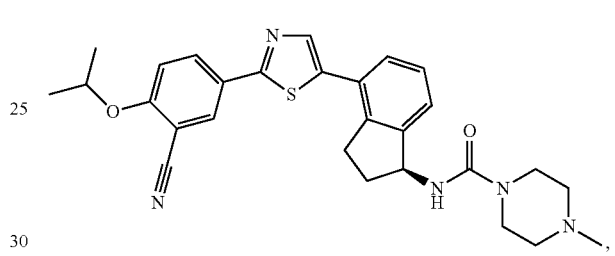
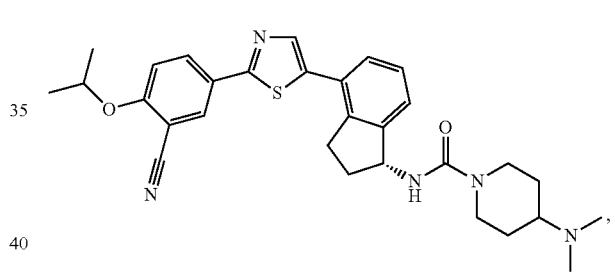
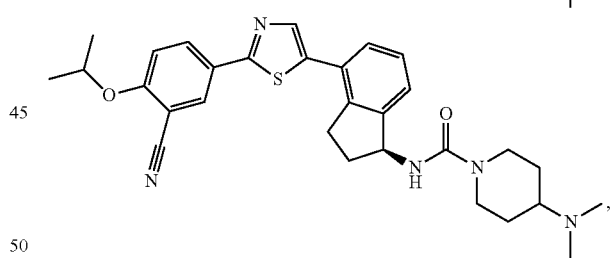
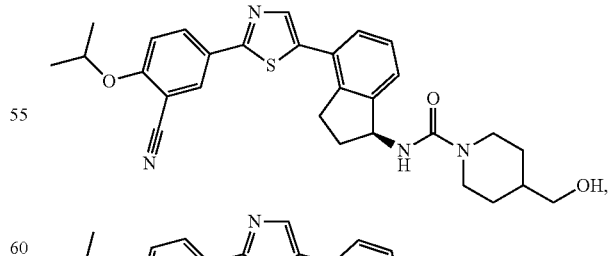
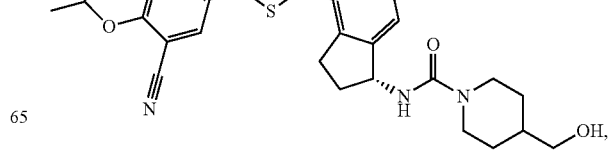

263
-continued
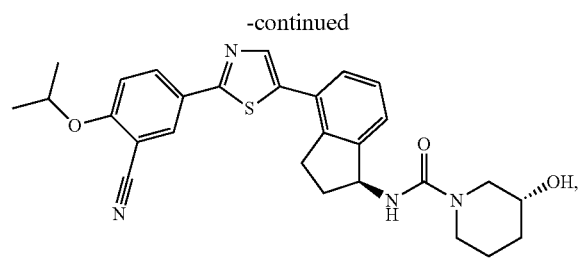
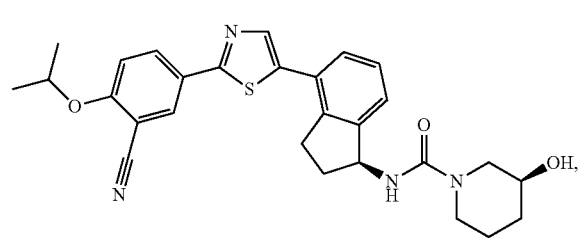
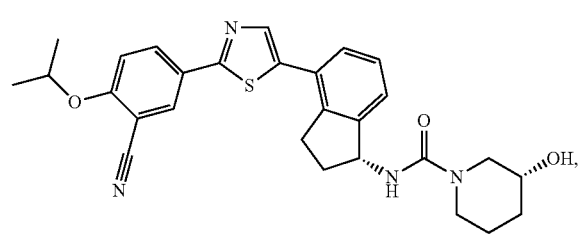
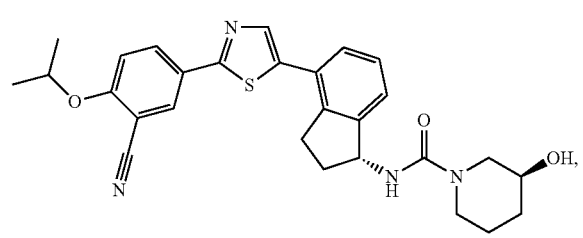
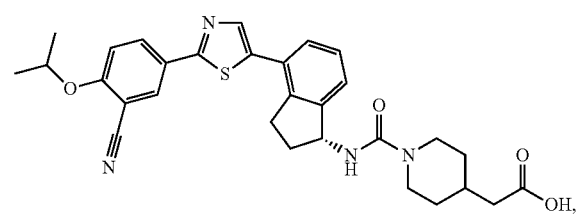
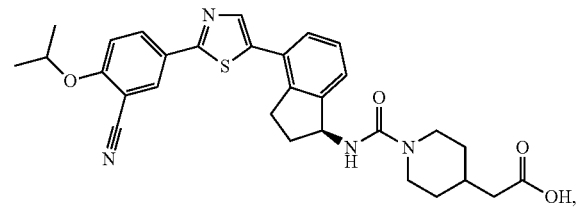
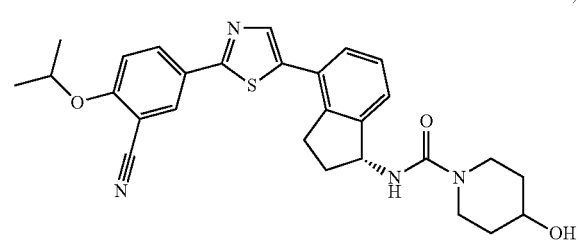
264
-continued
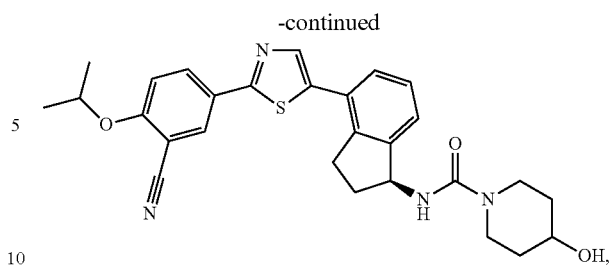
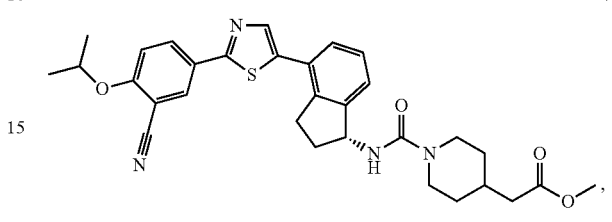
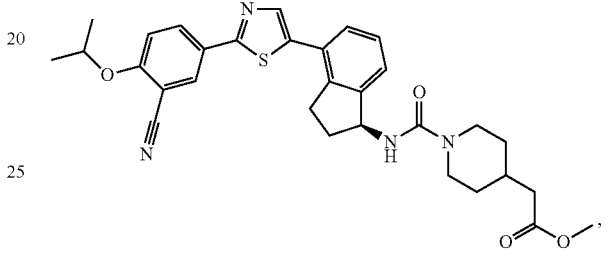
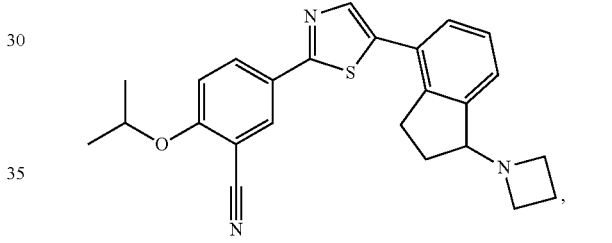
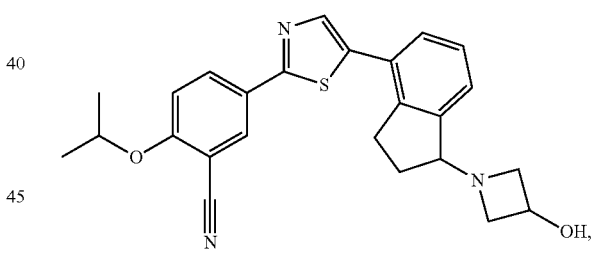
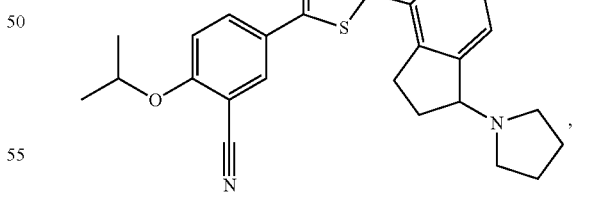
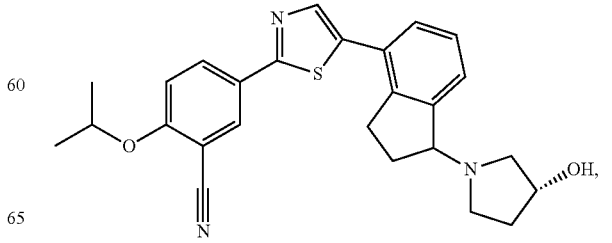

265
-continued
266
-continued
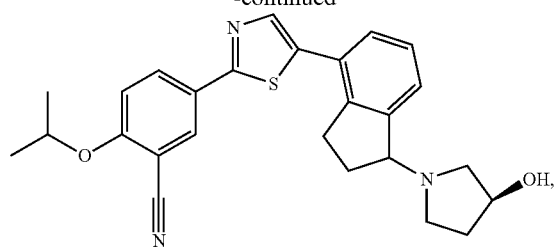
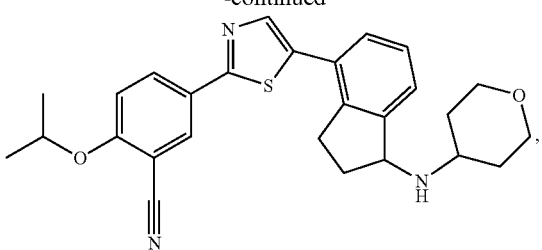

267

-continued

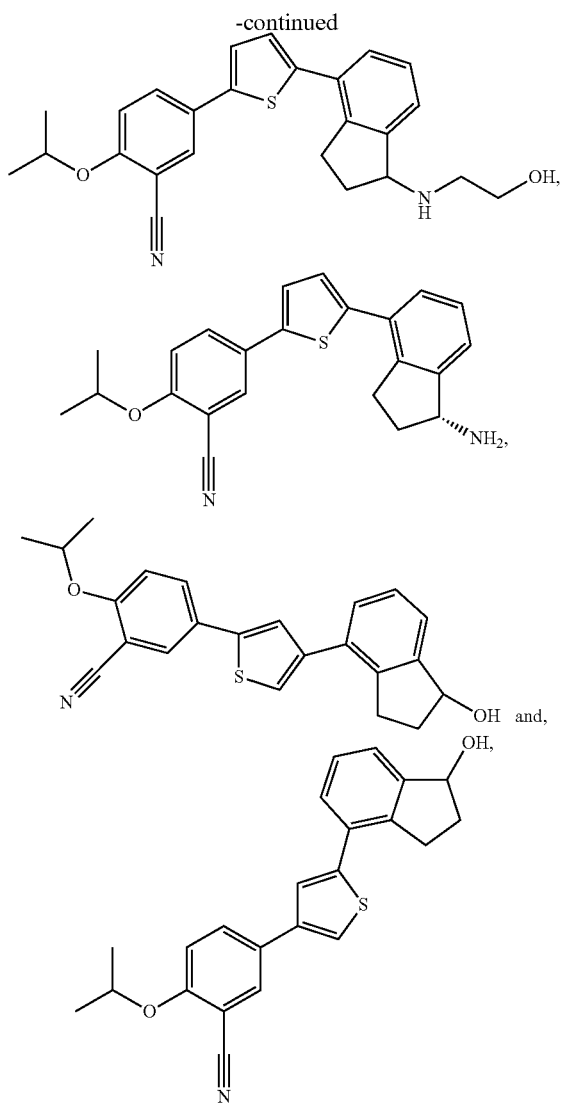

or any pharmaceutically acceptable salt, ester, prodrug, homolog, tautomer, stereoisomer, or hydrate, or solvate thereof.

51. The compound of claim 50 wherein the compound is selected from compounds:

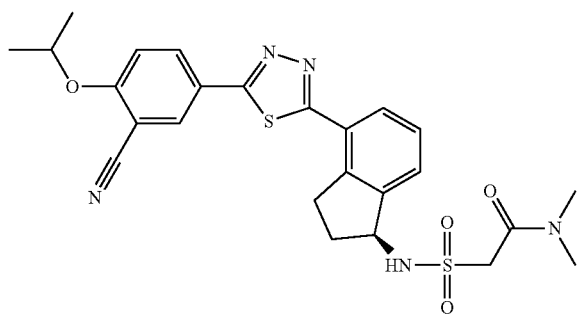

268

-continued

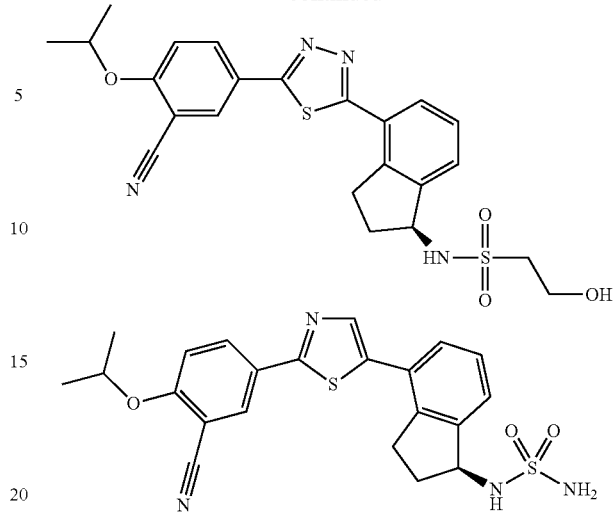

or any pharmaceutically acceptable salt, ester, prodrug, homolog, tautomer, stereoisomer, or hydrate, or solvate thereof.

52. A pharmaceutical composition comprising the compound as in any one of claims 1-51 and suitable excipient.

53. A pharmaceutical composition comprising the compound as in any one of claims 1-51 and a second medicament.

54. The composition of claim 53 wherein the second medicament is medically indicated for the treatment of multiple sclerosis, transplant rejection, or acute respiratory distress syndrome.

55. A method of activation or agonism of a sphingosine-1-phosphate receptor subtype 1 comprising contacting the receptor subtype 1 with an effective amount of the compound as any in one of claims 1-51 or the composition of claims 52 or 53.

56. The method of claim 55 wherein the compound activates or agonizes the sphingosine-1-phosphate receptor subtype 1 to a greater extent than the compound activates or agonizes a sphingosine-1-phosphate receptor subtype 3.

57. The method of claim 56 wherein the sphingosine-1-phosphate receptor subtype 1 is disposed within a living mammal.

58. A method of treatment of a malcondition in a patient for which activation or agonism of an sphingosine-1-phosphate receptor subtype 1 is medically indicated, comprising administering an effective amount of the compound as in any one of claims 1-51 to the patient at a frequency and for a duration of time sufficient to provide a beneficial effect to the patient wherein the malcondition is selected from multiple sclerosis, transplant rejection, acute respiratory distress syndrome, ulcerative colitis, influenza, Crohn's disease and adult respiratory distress syndrome.

59. The compound of claim 15 wherein the compound is substantially enantiomerically pure.

\* \* \* \* \*

UNITED STATES PATENT AND TRADEMARK OFFICE
CERTIFICATE OF CORRECTION

PATENT NO. : 8,507,538 B2  
APPLICATION NO. : 12/946828  
DATED : August 13, 2013  
INVENTOR(S) : Marcus F. Boehm et al.

Page 1 of 1

It is certified that error appears in the above-identified patent and that said Letters Patent is hereby corrected as shown below:

In The Claims

Column 230, Line 56:
"-N($R^3R^3$), -COOH, -COOR$^3$, NHCO-R$^3$, each" should read, --N($R^3R^3$), -COOH, -COOR$^3$, NHCO-R$^3$; each--.

Column 267, Line 47:
"51. The compound of claim 50 wherein the compound is selected from compounds:" should read, --51. The compound of claim 50 wherein the compound is selected from:--.

Column 268, Lines 26-27:
"52. A pharmaceutical composition comprising the compound as in any one of claims 1-51 and suitable excipient" should read, --52. A pharmaceutical composition comprising the compound as in any one of claims 1-51 and a suitable excipient--.

Column 268, Lines 39-40:
"as any in one of claims 1-51 or the composition of claims 52 or 53." should read, --as any in one of claims 1 -51 or the composition of claim 52 or 53--.

Signed and Sealed this  
Twenty-sixth Day of July, 2016

Michelle K. Lee  
*Director of the United States Patent and Trademark Office*